(12) United States Patent
Knust et al.

(10) Patent No.: US 9,226,916 B2
(45) Date of Patent: *Jan. 5, 2016

(54) PYRROLIDINE DERIVATIVES

(71) Applicants: Henner Knust, Rheinfelden (DE);
Andreas Koblet, Bottmingen (CH);
Matthias Nettekoven, Grenzach-Wyhlen (DE); Hasane Ratni, Habsheim (FR);
Claus Riemer, Freiburg (DE); Walter Vifian, Gelterkinden (CH)

(72) Inventors: Henner Knust, Rheinfelden (DE);
Andreas Koblet, Bottmingen (CH);
Matthias Nettekoven, Grenzach-Wyhlen (DE); Hasane Ratni, Habsheim (FR);
Claus Riemer, Freiburg (DE); Walter Vifian, Gelterkinden (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,780

(22) Filed: Feb. 28, 2013

(65) Prior Publication Data
US 2013/0184249 A1    Jul. 18, 2013

Related U.S. Application Data

(63) Continuation of application No. 12/961,536, filed on Dec. 7, 2010, now abandoned.

(30) Foreign Application Priority Data

Dec. 15, 2009 (EP) .................. 09179228

(51) Int. Cl.
| | |
|---|---|
| *A61K 31/445* | (2006.01) |
| *C07D 401/06* | (2006.01) |
| *A61K 31/40* | (2006.01) |
| *C07D 207/14* | (2006.01) |
| *C07D 403/06* | (2006.01) |
| *C07D 405/06* | (2006.01) |
| *C07D 407/04* | (2006.01) |
| *C07D 413/06* | (2006.01) |
| *C07D 417/14* | (2006.01) |
| *A61K 31/4025* | (2006.01) |
| *A61K 31/454* | (2006.01) |
| *A61K 31/4545* | (2006.01) |
| *A61K 31/497* | (2006.01) |
| *A61K 31/501* | (2006.01) |
| *A61K 31/506* | (2006.01) |
| *A61K 31/5377* | (2006.01) |

(52) U.S. Cl.
CPC ............ *A61K 31/40* (2013.01); *A61K 31/4025* (2013.01); *A61K 31/454* (2013.01); *A61K 31/4545* (2013.01); *A61K 31/497* (2013.01); *A61K 31/501* (2013.01); *A61K 31/506* (2013.01); *A61K 31/5377* (2013.01); *C07D 207/14* (2013.01); *C07D 401/06* (2013.01); *C07D 403/06* (2013.01); *C07D 405/06* (2013.01); *C07D 407/04* (2013.01); *C07D 413/06* (2013.01); *C07D 417/14* (2013.01)

(58) Field of Classification Search
CPC .......................... A61K 31/445; C07D 401/06
USPC ........... 546/184, 192, 208; 514/315, 317, 326
See application file for complete search history.

(56) References Cited

U.S. PATENT DOCUMENTS

| | | | |
|---|---|---|---|
| 6,465,489 B1 | 10/2002 | Aulombard et al. | |
| 7,834,008 B2 | 11/2010 | Kehler et al. | |
| 7,893,062 B2 | 2/2011 | Bissantz et al. | |
| 8,022,099 B2 * | 9/2011 | Bissantz et al. | 514/426 |
| 8,618,303 B2 * | 12/2013 | Knust et al. | 546/208 |

FOREIGN PATENT DOCUMENTS

| | | |
|---|---|---|
| JP | 2007-277231 | 10/2007 |
| WO | 2008/128891 | 10/2008 |
| WO | 2009/024502 | 2/2009 |
| WO | 2009/153179 | 12/2009 |
| WO | 2010/032856 | 3/2010 |

(Continued)

OTHER PUBLICATIONS

The English translation of the Japanese Office Action, issued on Feb. 12, 2014, in the corresponding Japanese Application No. 2012-543636.

Marco et al., "Neuropeptides" 32:481-488 ( 1998).

(Continued)

*Primary Examiner* — Golam M M Shameem

(57) ABSTRACT

The present invention relates to compounds of formula

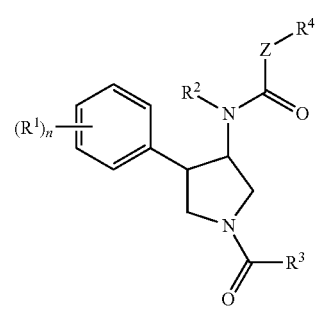

wherein $R^1$, $R^2$, $R^3$, $R^4$, Z, and n are as defined herein or to a pharmaceutically active salt thereof. Compounds of the invention are high potential NK-3 receptor antagonists for the treatment of depression, pain, psychosis, Parkinson's disease, schizophrenia, anxiety and attention deficit hyperactivity disorder (ADHD).

34 Claims, No Drawings

(56) References Cited

FOREIGN PATENT DOCUMENTS

| WO | 2010/040663 | 4/2010 |
|----|-------------|--------|
| WO | 2011/073160 | 6/2011 |

OTHER PUBLICATIONS

Jung et al., "Neuroscience" 74:403-414 (1996).
"Current Opinion in Investigational Drugs" 2(7):950-956 (2001).
(International Search Report PCT/EP2010/069434 dated May 30, 2011).
Accession No. 2010:384388 (Shirai et al STN International HCAPLUS database2010).
Accession No. 2009:1566297 (Bissantz et al: STN International HCAPLUS database2009).
Giardina et al., "Exp. Opinion on Therapeutic Patents" 10(6):939-960 (2000).
Tooney et al., "Neurosci. Letters" 293:185-188 (2000).

* cited by examiner

PYRROLIDINE DERIVATIVES

PRIORITY TO RELATED APPLICATION(S)

This application is a Continuation application of application Ser. No. 12/961,536, filed Dec. 7, 2010, now pending which claims the benefit of European Patent Application No. 09179228.3, filed Dec. 15, 2009, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 *and Psychiatric Disorders Study* 4, *Schizophrenia, June* 2003, Decision Resources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 *and Current Opinion in Investigational Drugs,* 2001, 2(7), 950-956 956 and Psychiatric Disorders Study 4, *Schizophrenia,* June 2003, Decision Resources, Inc., Waltham, Mass.).

SUMMARY OF THE INVENTION

The present invention provides compounds of formula I

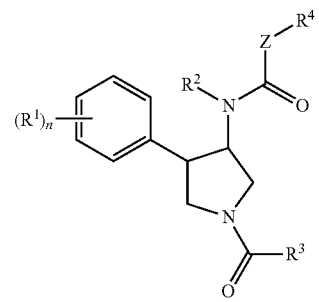

wherein
R$^1$ is hydrogen, halogen, cyano, lower alkyl or lower alkyl substituted by halogen;
n is 1, 2 or 3, wherein when n is 2 or 3, each R$^1$ is the same or different;
R$^2$ is hydrogen or methyl;
R$^3$ is (CH$_2$)$_r$—C(O)NH$_2$ or (CH$_2$)$_r$—CN, wherein r is 1 or 2, or
is a non aromatic heterocyclic group

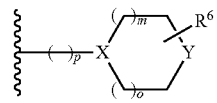

wherein
X is N or CH;
Y is C(R)(R$^7$)—; —N(R$^7$)—, —S(O)$_2$ or O;
R$^6$ is hydrogen, di-lower alkyl or =O;
o and m are each independently 0, 1 or 2;
p is 0, 1 or 2;
R is hydrogen, halogen, or lower alkyl;
R$^7$ is hydrogen, halogen, hydroxy, lower alkyl substituted by hydroxy, cyano, or lower alkoxy;

$R^{7'}$ is hydrogen,
—C(O)-lower alkyl,
—C(O)O-lower alkyl,
—C(O)CH$_2$O-lower alkyl,
—C(O)CH$_2$CN, or is
—C(O)-cycloalkyl, cycloalkyl or —CH$_2$-cycloalkyl,
wherein the cycloalkyl groups are optionally substituted by halogen, lower alkoxy, lower alkyl substituted by halogen, cyano, —CH$_2$O-lower alkyl, or lower alkyl, or is
—C(O)-heterocycloalkyl, heterocycloalkyl, —C(O)-heteroaryl or heteroaryl,
which heterocycloalkyl or heteroaryl groups are optionally substituted by halogen, lower alkyl, =O, lower alkoxy, lower alkyl substituted by halogen, C(O)NH-lower alkyl, C(O)NH$_2$, C(O)-lower alkyl, S(O)$_2$— lower alkyl or cyano;
Z is —O—, NH— or —N(lower alkyl)-;
$R^4$ is lower alkyl,
lower alkyl substituted by halogen,
lower alkyl substituted by hydroxy,
lower alkyl substituted by cycloalkyl,
(CH$_2$)$_s$—O-lower alkyl, wherein s is 2 or 3,
CH(CH$_3$)CH$_2$—O-lower alkyl,
(CH$_2$)$_q$CN, bicyclo[2.2.1]heptanyl,
(CH$_2$)$_q$-cycloalkyl optionally substituted by lower alkyl, lower alkyl substituted by halogen, lower alkoxy or by halogen, or is
(CH$_2$)$_q$-heterocycloalkyl, (CH$_2$)$_q$-aryl, CH(lower alkyl)-aryl, CH(cycloalkyl)-aryl, or (CH$_2$)$_q$-heteroaryl,
which heterocycloalkyl, aryl or heteroaryl rings are optionally substituted by halogen, hydroxy, lower alkyl, lower alkyl substituted by halogen, S(O)$_2$-lower alkyl, cyano or by lower alkoxy;
q is 0, 1 or 2;
or a pharmaceutically active salt thereof.

The invention includes all stereoisomeric forms, including individual diastereoisomers and enantiomers of the compound of formula (I) as well as racemic and non-racemic mixtures thereof.

The present invention provides novel compounds of formula I and pharmaceutical compositions containing them. The invention also provides methods for making such compounds and compositions.

Compounds of the present invention are high potential NK-3 receptor antagonists for the treatment of depression, pain, biplolar disorders, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF INVENTION

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

As used herein, the term "lower alkoxy" denotes a lower alkyl group as defined above which is connected via an oxygen atom.

The term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —C(CH$_3$)$_2$CF$_3$, —CH(CH$_3$)CH$_2$CF$_3$, —CH(CH$_3$)CF$_3$, —CH$_2$CH$_2$CF$_3$, —CH$_2$CH$_2$CH$_2$CF$_3$, —CH$_2$CH$_2$CF$_2$CF$_3$, —CH$_2$CH$_2$CH$_2$CF$_2$CF$_3$, —CH$_2$CF$_2$CF$_3$ and the like. Preferred lower alkyl substituted by halogen groups are groups having 1-5 carbon atoms.

The term "lower alkyl substituted by hydroxy" denotes a lower alkyl group as defined above, wherein at least one hydrogen atom is replaced by hydroxy.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, naphthyl, 1,2,3,4-tetrahydronaphthalenyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazinyl, pyrazolyl, 2,4-dihydro-pyrazol-3-one, pyridinyl, isoxazolyl, benzo[1,3]dioxol, [1.3.4]thiadiazol, pyridazinyl, pyrimidinyl, benzotriazol-5-yl, benzoimidazol-5-yl, [1,3,4]-oxadiazol-2-yl, [1,2.4]triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred heteroaryl group is pyridine-2, 3 or 4-yl.

The term "heterocycloalkyl" denotes a non aromatic ring, wherein one or two of the ring atoms are N, S or O, for example the following groups: tetrahydropyranyl, 1,1-dioxohexahydro-1$\lambda^6$-thiopyranyl, 1,1-dioxo-tetrahydro-1$\lambda^6$-thiophenyl, oxetanyl, morpholinyl, [1,4]diazepam-1-yl, piperazinyl, pyrrolidinyl, piperidinyl, tetrahydrofuranyl, tetrahydrothiophenyl, piperidin-4-yl or 1,1-dioxo-$\lambda^6$-thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following structures are encompassed by formula I of the present invention:

Compounds of formula Ia:

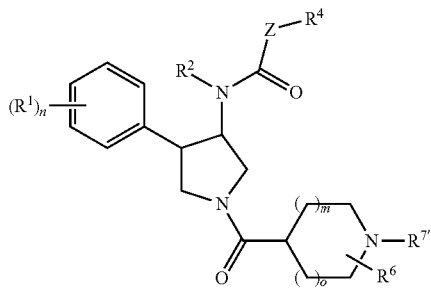

wherein
R¹ is hydrogen, halogen, cyano, lower alkyl or lower alkyl substituted by halogen;
n is 1, 2 or 3, wherein when n is 2 or 3, each R¹ is the same or different;
R² is hydrogen or methyl;
R⁶ is hydrogen, di-lower alkyl or =O;
o and m are each independently 0, 1 or 2;
R⁷ is hydrogen,
—C(O)-lower alkyl,
—C(O)O-lower alkyl,
—C(O)CH₂O-lower alkyl,
—C(O)CH₂CN, or is
—C(O)-cycloalkyl, cycloalkyl or —CH₂-cycloalkyl,
wherein the cycloalkyl groups are optionally substituted by halogen, lower alkoxy, lower alkyl substituted by halogen, cyano, —CH₂O-lower alkyl, or lower alkyl, or is
—C(O)-heterocycloalkyl, heterocycloalkyl, —C(O)-heteroaryl or heteroaryl,
which heterocycloalkyl or heteroaryl groups are optionally substituted by halogen, lower alkyl, =O, lower alkoxy, lower alkyl substituted by halogen, C(O)NH-lower alkyl, C(O)NH₂, C(O)-lower alkyl, S(O)₂— lower alkyl or cyano;
Z is —O—, NH— or —N(lower alkyl)-;
R⁴ is lower alkyl,
lower alkyl substituted by halogen,
lower alkyl substituted by hydroxy,
lower alkyl substituted by cycloalkyl,
(CH₂)ₛO-lower alkyl, wherein s is 2 or 3,
CH(CH₃)CH₂—O-lower alkyl,
(CH₂)qCN, bicyclo[2.2.1]heptanyl,
(CH₂)q-cycloalkyl optionally substituted by lower alkyl, lower alkyl substituted by halogen, lower alkoxy or by halogen, or is
(CH₂)q-heterocycloalkyl, (CH₂)q-aryl, CH(lower alkyl)-aryl, CH(cycloalkyl)-aryl, or (CH₂)q-heteroaryl,
which heterocycloalkyl, aryl or heteroaryl rings are optionally substituted by halogen, hydroxy, lower alkyl, lower alkyl substituted by halogen, S(O)₂-lower alkyl, cyano or by lower alkoxy;
q is 0, 1 or 2;
or a pharmaceutically active salt thereof.
Compounds of formula Ia are the followings:
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid 4-fluoro-phenyl ester;
{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;
{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid phenyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid p-tolyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid 4-chloro-phenyl ester;
rac-[(3R,4S)-1-(1-Cyclopropylmethyl-piperidine-4-carbonyl)-4-(3,4-dichloro-phenyl)-pyrrolidin-3-yl]-methyl-carbamic acid butyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chloro-phenyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid phenyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-methoxyphenyl ester;
{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;
{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;
{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester;
{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester;
[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester;
[(3S,4R)-1-(1-Cyclopropylmethyl-piperidine-4-carbonyl)-4-(3,4-dichloro-phenyl)-pyrrolidin-3-yl]-methyl-carbamic acid 4-methoxy-phenyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 2,2-dimethyl-propyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid prop-2-ynyl ester;
rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopropylmethyl ester;
rac-{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3-dimethyl-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tetrahydro-pyran-4-ylmethyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentylmethyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-methyl-oxetan-3-ylmethyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester;

{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

{(3S,4R)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid 4-fluoro-phenyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-methyl-cyclohexyl ester;

rac-1-{(3R,4S)-4-(4-Chloro-phenyl)-1-[1-(1-methyl-cyclopropanecarbonyl)-piperidine-4-carbonyl]-pyrrolidin-3-yl}-3-(2-cyclopropyl-ethyl)-1-methyl-urea;

{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3S,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester;

rac-[(3R,4S)-1-(1-Acetyl-piperidine-4-carbonyl)-4-(3,4-dichloro-phenyl)-pyrrolidin-3-yl]-methyl-carbamic acid 4-fluoro-phenyl ester;

rac-4-{(3S,4R)-3-(3,4-Dichloro-phenyl)-4-[(4-fluoro-phenoxycarbonyl)-methyl-amino]-pyrrolidine-1-carbonyl}-piperidine-1-carboxylic acid tert-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester;

rac-{(3R,4S)-4-(3-Chloro-4-methyl-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(4-Chloro-3-methyl-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-[(3R,4S)-4-(3,4-Dichloro-phenyl)-1-(piperidine-4-carbonyl)-pyrrolidin-3-yl]-methyl-carbamic acid 4-fluoro-phenyl ester;

rac-[(3R,4S)-4-(3,4-Dichloro-phenyl)-1-(1-propionyl-piperidine-4-carbonyl)-pyrrolidin-3-yl]-methyl-carbamic acid 4-fluoro-phenyl ester;

rac-[(3R,4S)-1-(1-Cyclopropanecarbonyl-piperidine-4-carbonyl)-4-(3,4-dichloro-phenyl)-pyrrolidin-3-yl]-methyl-carbamic acid 4-fluoro-phenyl ester;

rac-{(3R,4S)-4-(3,4-Dichloro-phenyl)-1-[1-(2-methoxy-acetyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(tetrahydro-pyran-4-carbonyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(tetrahydro-pyran-4-yl)-piperidine-4-carbonyl]-pyrrolidin-3-yl}-methyl-carbamic acid 4-fluoro-phenyl ester;

rac-[(3R,4S)-4-(3,4-Dichloro-phenyl)-1-(1-[1,3,4]thiadiazol-2-yl-piperidine-4-carbonyl)-pyrrolidin-3-yl]-methyl-carbamic acid 4-fluoro-phenyl ester;

rac-[(3R,4S)-1-[1-(6-Chloro-pyridazin-3-yl)-piperidine-4-carbonyl]-4-(3,4-dichloro-phenyl)-pyrrolidin-3-yl]-methyl-carbamic acid 4-fluoro-phenyl ester;

rac-[(3R,4S)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,4,4,4-pentafluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-2-yl) methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-2-yl) methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-3-yl) methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-3-yl) methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,5,5,5-pentafluoro-pentyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 2-methyl-cyclopropylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-benzyl ester;

rac-1-{(3R,4S)-4-(4-Chloro-phenyl)-1-[1-(1-methyl-cyclopropanecarbonyl)-piperidine-4-carbonyl]-pyrrolidin-3-yl}-3-(4-fluoro-phenyl)-1-methyl-urea;

rac-1-(2-Cyclopropyl-ethyl)-3-{(3R,4S)-4-(3,4-dichloro-phenyl)-1-[1-(1-methyl-cyclopropanecarbonyl)-piperidine-4-carbonyl]-pyrrolidin-3-yl}-1,3-dimethyl-urea;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-hydroxy-3-methyl-butyl ester;

rac {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexylmethyl ester;

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester;

{(3S,4R)-4-(4-Chloro-phenyl)-1-[1-(1,1-dioxo-hexahydro-1$\lambda^6$-thiopyran-4-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(6-chloro-pyridazin-3-yl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3-difluoro-cyclopentylmethyl ester;

{(3S,4R)-4-(4-Chloro-phenyl)-1-[1-(tetrahydro-pyran-4-yl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 3-bromo-4-fluoro-phenyl ester;

{(3S,4R)-4-(4-Chloro-phenyl)-1-[1-(1,1-dioxo-tetrahydro-1$\lambda^6$-thiophen-3-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(6-methyl-pyridazin-3-yl)-piperidine-4-carbonyl]-pyrrolidin-3-yl}-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester;

rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester;

rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-trifluoromethyl-cyclohexyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester;

{(3S,4R)-4-(3,4-Dichloro-phenyl)-1-[1-(tetrahydro-pyran-4-yl)-piperidine-4-carbonyl]-pyrrolidin-3-yl}-methyl-carbamic acid 4-trifluoromethyl-cyclohexyl ester;

rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4,4,4-trifluoro-butyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester;

{(3S,4R)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester;

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester;

[(3R,4S)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester;

4-{(3R,4S)-3-(4-Chloro-phenyl)-4-[(4-fluoro-phenoxycarbonyl)-methyl-amino]-pyrrolidine-1-carbonyl}-piperidine-1-carboxylic acid tert-butyl ester;

{(3S,4R)-4-(4-Chloro-phenyl)-1-[1-(5-methyl-[1,3,4]oxadiazol-2-yl)-piperidine-4-carbonyl]-pyrrolidin-3-yl}-methyl-carbamic acid 4-fluoro-phenyl ester;

[(3S,4R)-4-(4-Chloro-phenyl)-1-(piperidine-4-carbonyl)-pyrrolidin-3-yl]-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid isopropyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid isobutyl ester;

{(3S,4R)-4-(4-Chloro-phenyl)-1-[1-(6-cyano-pyridazin-3-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-methyl-cyclopropane carbonyl)-piperidine-4-carbonyl]-pyrrolidin-3-yl}-methyl-carbamic acid isobutyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester;

[(3S,4R)-4-(4-Chloro-phenyl)-1-(1-cyclopropyl-piperidine-4-carbonyl)-pyrrolidin-3-yl]-methyl-carbamic acid 4-fluoro-phenyl ester;

3-{(3R,4S)-3-(4-Chloro-phenyl)-4-[(4-fluoro-phenoxycarbonyl)-methyl-amino]-pyrrolidine-1-carbonyl}-pyrrolidine-1-carboxylic acid tert-butyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-cyclopropyl-ethyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 1-cyclopropyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid oxetan-3-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid sec-butyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-ethyl ester;

[(3S,4R)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-trifluoromethyl-cyclohexyl ester;

{(3S,4R)-4-(3,4-Dichloro-phenyl)-1-[1-(6-methyl-pyridazin-3-yl)-piperidine-4-carbonyl]-pyrrolidin-3-yl}-methyl-carbamic acid 4-trifluoromethyl-cyclohexyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid tetrahydro-pyran-4-yl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid sec-butyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro ethyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro-1-methyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1-methyl-ethyl ester;

{(3S,4R)-4-(4-Chloro-phenyl)-1-[1-(4-methyl-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(pyrrolidine-3-carbonyl)-pyrrolidin-3-yl]-methyl-carbamic acid 4-fluoro-phenyl ester;

{(3S,4R)-4-(4-Chloro-phenyl)-1-[1-(5-fluoro-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(1-propionyl-pyrrolidine-3-carbonyl)-pyrrolidin-3-yl]-methyl-carbamic acid 4-fluoro-phenyl ester;

[(3S,4R)-4-(4-Chloro-phenyl)-1-(1-cyclopropanecarbonyl-pyrrolidine-3-carbonyl)-pyrrolidin-3-yl]-methyl-carbamic acid 4-fluoro-phenyl ester;

{(3S,4R)-4-(4-Chloro-phenyl)-1-[1-(2-methoxy-acetyl)-pyrrolidine-3-carbonyl]-pyrrolidin-3-yl}-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclobutyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclobutyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,3,3-tetrafluorocyclobutyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,3,3-tetrafluorocyclobutyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-1-methyl-propyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 3,3,3-trifluoro-1-methyl-propyl ester;

{(3S,4R)-4-(4-Chloro-phenyl)-1-[1-(tetrahydro-pyran-4-yl)-pyrrolidine-3-carbonyl]-pyrrolidin-3-yl}-methyl-carbamic acid 4-fluoro-phenyl ester;

[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester;

[(3S,4R)-4-(4-Chloro-phenyl)-1-(1-pyrimidin-2-yl-piperidine-4-carbonyl)-pyrrolidin-3-yl]-methyl-carbamic acid 4-fluoro-phenyl ester;

{(3S,4R)-4-(4-Chloro-phenyl)-1-[1-(5-chloro-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(4'-cyano-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(3'-cyano-3,4,5,6-tetrahydro-2H-[1,2']bipyridinyl-4-carbonyl)-pyrrolidin-3-yl]-methyl-carbamic acid 4-fluoro-phenyl ester;

{(3S,4R)-4-(4-Chloro-phenyl)-1-[1-(6-cyano-pyrazin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(3'-chloro-5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(6'-cyano-3,4,5,6-tetrahydro-2H-[1,2']bipyridinyl-4-carbonyl)-pyrrolidin-3-yl]-methyl-carbamic acid 4-fluoro-phenyl ester;

{(3S,4R)-4-(4-Chloro-phenyl)-1-[1-(5-methoxy-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(1-pyrimidin-4-yl-piperidine-4-carbonyl)-pyrrolidin-3-yl]-methyl-carbamic acid 4-fluoro-phenyl ester;

{(3S,4R)-4-(4-Chloro-phenyl)-1-[1-(5-cyano-pyrimidin-2-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester;

{(3S,4R)-4-(4-Chloro-phenyl)-1-[1-(6-methoxy-pyridazin-3-yl)-piperidine-4-carbonyl]-pyrrolidin-3-yl}-methyl-carbamic acid 4-fluoro-phenyl ester;

[(3S,4R)-4-(4-Chloro-phenyl)-1-(6'-cyano-3,4,5,6-tetrahydro-2H-[1,3]bipyridinyl-4-carbonyl)-pyrrolidin-3-yl]-methyl-carbamic acid 4-fluoro-phenyl ester;

[(3S,4R)-4-(4-Chloro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid p-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-chloro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopentyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2-dimethyl-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,4-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,4-difluoro-phenyl ester;

[(3S,4R)-4-(4-Chloro-phenyl)-1-(6'-cyano-3,4,5,6-tetrahydro-2H-[1,3]bipyridinyl-4-carbonyl)-pyrrolidin-3-yl]-methyl-carbamic acid 3,5-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,3-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-chloro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-fluoro-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methoxy-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopropylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methyl-oxetan-3-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-cyclopropyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-1-methyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methanesulfonyl-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-cyano-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-1-fluoromethyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid o-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid m-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-2-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-3-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,1-dimethyl-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1,1-dimethyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-2-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropyl-(4-fluoro-phenyl)-methyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-1-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopentyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 5-chloro-pyridin-2-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-3-fluoro-phenyl ester;

[(3S,4R)-1-(1-Acetyl-piperidine-4-carbonyl)-4-(4-chloro-phenyl)-pyrrolidin-3-yl]-methyl-carbamic acid 4-fluoro-phenyl ester;

[(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester;

{(3S,4R)-4-(4-Chloro-phenyl)-1-[1-(3-methyl-oxetane-3-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3-fluoro-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3,3-difluoro-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3-methoxy-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2-cyano-acetyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-cyano-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(tetrahydro-pyran-4-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl) 1-[1-(2,2-dimethyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-fluoro-pyridine-2-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester;

[(3S,4R)-1-(1-Cyclobutanecarbonyl-piperidine-4-carbonyl)-4-(3,4-dichloro-phenyl)-pyrrolidin-3-yl]-methyl-carbamic acid 4-fluoro-phenyl ester;

{(3S,4R)-4-(3,4-Dichloro-phenyl)-1-[1-(3-methyl-oxetane-3-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(3-fluoro-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(3,3-difluoro-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(3-methoxy-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

[(3S,4R)-1-[1-(2-Cyano-acetyl)-piperidine-4-carbonyl]-4-(3,4-dichloro-phenyl)-pyrrolidin-3-yl]-methyl-carbamic acid 4-fluoro-phenyl ester;

[(3S,4R)-1-[1-(1-Cyano-cyclopropanecarbonyl)-piperidine-4-carbonyl]-4-(3,4-dichloro-phenyl)-pyrrolidin-3-yl]-methyl-carbamic acid 4-fluoro-phenyl ester;

{(3S,4R)-4-(3,4-Dichloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(tetrahydro-pyran-4-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(2,2-dimethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(5-fluoro-pyridine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester;

[(3S,4R)-1-(1-Acetyl-piperidine-4-carbonyl)-4-(3,4-dichloro-phenyl)-pyrrolidin-3-yl]-methyl-carbamic acid 4-fluoro-phenyl ester;

[(3S,4R)-1-[1-(2-Cyano-acetyl)-piperidine-4-carbonyl]-4-(4-fluoro-phenyl)-pyrrolidin-3-yl]-methyl-carbamic acid 4-fluoro-phenyl ester;

[(3S,4R)-1-(1-Acetyl-piperidine-4-carbonyl)-4-(4-fluoro-phenyl)-pyrrolidin-3-yl]-methyl-carbamic acid 4-fluoro-phenyl ester;

{(3S,4R)-4-(4-Fluoro-phenyl)-1-[1-(3-methyl-oxetane-3-carbonyl)-piperidine-4-carbonyl]-pyrrolidin-3-yl}-methyl-carbamic acid 4-fluoro-phenyl ester;

[(3S,4R)-1-[1-(3-Fluoro-cyclobutanecarbonyl)-piperidine-4-carbonyl]-4-(4-fluoro-phenyl)-pyrrolidin-3-yl]-methyl-carbamic acid 4-fluoro-phenyl ester;

[(3S,4R)-1-[1-(1-Cyano-cyclopropanecarbonyl)-piperidine-4-carbonyl]-4-(4-fluoro-phenyl)-pyrrolidin-3-yl]-methyl-carbamic acid 4-fluoro-phenyl ester;

{(3S,4R)-4-(4-Fluoro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

{(3S,4R)-4-(4-Fluoro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(4-Fluoro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-4-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-methyl-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-4-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 5-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-5-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-cyano-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-6-methyl-pyridin-3-yl ester;

[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-methyl-carbamic acid 4-fluoro-phenyl ester;

[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(3-Chloro-4-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-methyl-carbamic acid 4-fluoro-phenyl ester;

{(3S,4R)-4-(4-Chloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester;

[(3S,4R)-4-(4-Chloro-phenyl)-1-(5'-hydroxy-3,4,5,6-tetrahydro-2H-[1,2']bipyridinyl-4-carbonyl)-pyrrolidin-3-yl]-methyl-carbamic acid 4-fluoro-phenyl ester; and Acetic acid 4-{(3R,4S)-3-(4-chloro-phenyl)-4-[(4-fluoro-phenoxycarbonyl)-methyl-amino]-pyrrolidine-1-carbonyl}-3,4,5,6-tetrahydro-2H-[1,2']bipyridinyl-5'-yl ester.

Compounds of formula Ib:

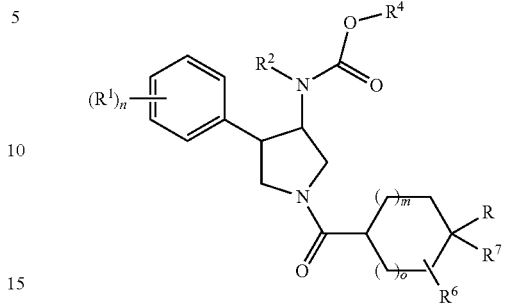

wherein
R¹ is hydrogen, halogen, cyano, lower alkyl or lower alkyl substituted by halogen;
n is 1, 2 or 3, wherein when n is 2 or 3, R¹ is the same or different;
R² is hydrogen or methyl;
R⁶ is hydrogen, di-lower alkyl or =O;
o and m are each independently 0, 1 or 2;
R is hydrogen, halogen, or lower alkyl;
R⁷ is hydrogen, halogen, hydroxy, lower alkyl substituted by hydroxy, cyano, or lower alkoxy;
R⁴ is lower alkyl,
lower alkyl substituted by halogen,
lower alkyl substituted by hydroxy,
lower alkyl substituted by cycloalkyl,
(CH₂)ₛ—O-lower alkyl, wherein s is 2 or 3,
CH(CH₃)CH₂—O-lower alkyl,
(CH₂)qCN, bicyclo[2.2.1]heptanyl,
(CH₂)q-cycloalkyl optionally substituted by lower alkyl, lower alkyl substituted by halogen, lower alkoxy or by halogen, or is
(CH₂)q-heterocycloalkyl, (CH₂)q-aryl, CH(lower alkyl)-aryl, CH(cycloalkyl)-aryl, or (CH₂)q-heteroaryl,
which heterocycloalkyl, aryl or heteroaryl rings are optionally substituted by halogen, hydroxy, lower alkyl, lower alkyl substituted by halogen, S(O)₂-lower alkyl, cyano or by lower alkoxy;
q is 0, 1 or 2;
or a pharmaceutically active salt thereof.

Compounds of formula Ib are the followings:
[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester;

[(3S,4R)-4-(3,4-Dichloro-phenyl)-1-(trans-4-hydroxy-cyclohexanecarbonyl)-pyrrolidin-3-yl]-methyl-carbamic acid 4-fluoro-phenyl ester;

rac-[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester;

rac-[(3R,4S)-4-(3,4-Dichloro-phenyl)-1-(cis-4-methoxy-cyclohexanecarbonyl)-pyrrolidin-3-yl]-methyl-carbamic acid 4-fluoro-phenyl ester;

rac-[(3R,4S)-4-(3,4-Dichloro-phenyl)-1-(trans-4-hydroxy-4-methyl-cyclohexanecarbonyl)-pyrrolidin-3-yl]-methyl-carbamic acid 4-fluoro-phenyl ester;

rac-[(3R,4S)-4-(3,4-Dichloro-phenyl)-1-(cis-4-hydroxy-4-methyl-cyclohexanecarbonyl)-pyrrolidin-3-yl]-methyl-carbamic acid 4-fluoro-phenyl ester;

[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester;

[(3S,4R)-4-(3,4-Dichloro-phenyl)-1-(cis-4-hydroxy-cyclohexanecarbonyl)-pyrrolidin-3-yl]-methyl-carbamic acid 4-fluoro-phenyl ester;
[(3S,4R)-4-(4-Chloro-phenyl)-1-(4-hydroxy-cyclohexanecarbonyl)-pyrrolidin-3-yl]-methyl-carbamic acid 4-fluoro-phenyl ester;
[(3S,4R)-4-(4-Chloro-phenyl)-1-(4-cyano-cyclohexanecarbonyl)-pyrrolidin-3-yl]-methyl-carbamic acid 4-fluoro-phenyl ester;
[(3S,4R)-4-(4-Chloro-phenyl)-1-(4-hydroxymethyl-cyclohexanecarbonyl)-pyrrolidin-3-yl]-methyl-carbamic acid 4-fluoro-phenyl ester;
[(3S,4R)-4-(4-Chloro-phenyl)-1-(4,4-difluoro-cyclohexanecarbonyl)-pyrrolidin-3-yl]-methyl-carbamic acid 4-fluoro-phenyl ester; and
[(3S,4R)-4-(4-Chloro-phenyl)-1-(3-methoxy-cyclobutanecarbonyl)-pyrrolidin-3-yl]-methyl-carbamic acid 4-fluoro-phenyl ester.

Compounds of formula Ic:

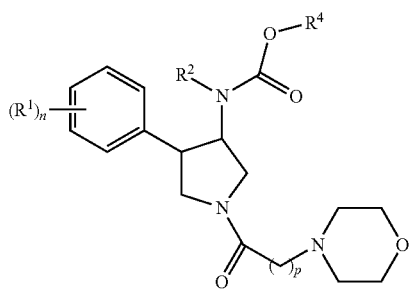

wherein
$R^1$ is hydrogen, halogen, cyano, lower alkyl or lower alkyl substituted by halogen;
n is 1, 2 or 3, wherein when n is 2 or 3, each $R^1$ is the same or different;
$R^2$ is hydrogen or methyl;
P is 0, 1 or 2;
$R^4$ is lower alkyl,
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q CN$, bicyclo[2.2.1]heptanyl,
$(CH_2)_q$-cycloalkyl optionally substituted by lower alkyl, lower alkyl substituted by halogen, lower alkoxy or by halogen, or is
$(CH_2)_q$-heterocycloalkyl, $(CH_2)_q$-aryl, CH(lower alkyl)-aryl, CH(cycloalkyl)-aryl, or $(CH_2)_q$ heteroaryl,
which heterocycloalkyl, aryl or heteroaryl rings are optionally substituted by halogen, hydroxy, lower alkyl, lower alkyl substituted by halogen, $S(O)_2$-lower alkyl, cyano or by lower alkoxy;
q is 0, 1 or 2;
or a pharmaceutically active salt thereof.

Compounds of formula Ic are the followings:
rac-[(3R,4S)-4-(3,4-Dichloro-phenyl)-1-(morpholine-4-carbonyl)-pyrrolidin-3-yl]-methyl-carbamic acid 4-fluoro-phenyl ester;
[(3S,4R)-4-(4-Chloro-phenyl)-1-(3-morpholin-4-yl-propionyl)-pyrrolidin-3-yl]-methyl-carbamic acid 4-fluoro-phenyl ester;

Compounds of formula Id:

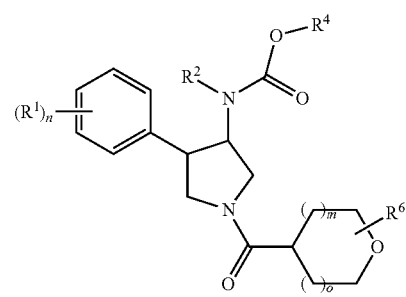

wherein
$R^1$ is hydrogen, halogen, cyano, lower alkyl or lower alkyl substituted by halogen;
n is 1, 2 or 3, wherein when n is 2 or 3, each $R^1$ is the same or different;
$R^2$ is hydrogen or methyl;
$R^6$ is hydrogen, di-lower alkyl or =O;
o and m are each independently 0, 1 or 2;
$R^4$ is lower alkyl,
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q CN$, bicyclo[2.2.1]heptanyl,
$(CH_2)_q$-cycloalkyl optionally substituted by lower alkyl, lower alkyl substituted by halogen, lower alkoxy or by halogen, or is
$(CH_2)_q$-heterocycloalkyl, $(CH_2)_q$-aryl, CH(lower alkyl)-aryl, CH(cycloalkyl)-aryl, or $(CH_2)_q$ heteroaryl,
which heterocycloalkyl, aryl or heteroaryl rings are optionally substituted by halogen, hydroxy, lower alkyl, lower alkyl substituted by halogen, $S(O)_2$-lower alkyl, cyano or by lower alkoxy;
q is 0, 1 or 2;
or a pharmaceutically active salt thereof.

Compounds of formula Id are the followings:
rac-[(3R,4S)-4-(3,4-Dichloro-phenyl)-1-(tetrahydro-pyran-4-carbonyl)-pyrrolidin-3-yl]-methyl-carbamic acid 4-fluoro-phenyl ester;
[(3R,4S)-4-(3,4-Dichloro-phenyl)-1-(tetrahydro-pyran-4-carbonyl)-pyrrolidin-3-yl]-methyl-carbamic acid 4-fluoro-phenyl ester;
[(3S,4R)-4-(3,4-Dichloro-phenyl)-1-(tetrahydro-pyran-4-carbonyl)-pyrrolidin-3-yl]-methyl-carbamic acid 4-fluoro-phenyl ester;
[(3S,4R)-4-(4-Chloro-phenyl)-1-(tetrahydro-pyran-4-carbonyl)-pyrrolidin-3-yl]-methyl-carbamic acid 4-fluoro-phenyl ester;
[(3S,4R)-4-(4-Chloro-phenyl)-1-(2,2-dimethyl-tetrahydro-pyran-4-carbonyl)-pyrrolidin-3-yl]-methyl-carbamic acid 4-fluoro-phenyl ester;
[(3S,4R)-4-(4-Chloro-phenyl)-1-(tetrahydro-pyran-3-carbonyl)-pyrrolidin-3-yl]-methyl-carbamic acid 4-fluoro-phenyl ester;
[(3S,4R)-4-(4-Chloro-phenyl)-1-(tetrahydro-furan-3-carbonyl)-pyrrolidin-3-yl]-methyl-carbamic acid 4-fluoro-phenyl ester;
[(3S,4R)-4-(3,4-Dichloro-phenyl)-1-(tetrahydro-pyran-4-carbonyl)-pyrrolidin-3-yl]-methyl-carbamic acid 4-trifluoromethyl-cyclohexyl ester;

Compounds of formula Ie

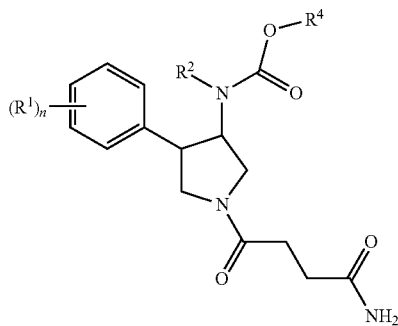

wherein
R[1] is hydrogen, halogen, cyano, lower alkyl or lower alkyl substituted by halogen;
n is 1, 2 or 3, wherein when n is 2 or 3, each R[1] is the same or different;
R[2] is hydrogen or methyl;
R[4] is lower alkyl,
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q CN$, bicyclo[2.2.1]heptanyl,
$(CH_2)_q$-cycloalkyl optionally substituted by lower alkyl, lower alkyl substituted by halogen, lower alkoxy or by halogen, or is
$(CH_2)_q$-heterocycloalkyl, $(CH_2)_q$-aryl, CH(lower alkyl)-aryl, CH(cycloalkyl)-aryl, or $(CH_2)_q$ heteroaryl,
which heterocycloalkyl, aryl or heteroaryl rings are optionally substituted by halogen, hydroxy, lower alkyl, lower alkyl substituted by halogen, $S(O)_2$-lower alkyl, cyano or by lower alkoxy;
q is 0, 1 or 2;
or a pharmaceutically active salt thereof.
A compound of formula Ie is the following:
rac-[(3R,4S)-1-(3-Carbamoyl-propionyl)-4-(3,4-dichloro-phenyl)-pyrrolidin-3-yl]-methyl-carbamic acid 4-fluoro-phenyl ester.

Compounds of formula If

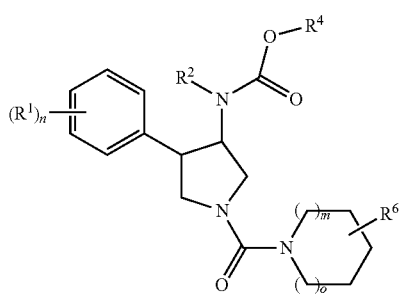

wherein
R[1] is hydrogen, halogen, cyano, lower alkyl or lower alkyl substituted by halogen;
n is 1, 2 or 3, wherein when n is 2 or 3, each R[1] is the same or different;
R[2] is hydrogen or methyl;
R[6] is hydrogen, di-lower alkyl or =O;
o and m are each independently 0, 1 or 2;
R[4] is lower alkyl,
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q CN$, bicyclo[2.2.1]heptanyl,
$(CH_2)_q$-cycloalkyl optionally substituted by lower alkyl, lower alkyl substituted by halogen, lower alkoxy or by halogen, or is
$(CH_2)_q$-heterocycloalkyl, $(CH_2)_q$-aryl, CH(lower alkyl)-aryl, CH(cycloalkyl)-aryl, or $(CH_2)_q$ heteroaryl,
which heterocycloalkyl, aryl or heteroaryl rings are optionally substituted by halogen, hydroxy, lower alkyl, lower alkyl substituted by halogen, $S(O)_2$-lower alkyl, cyano or by lower alkoxy;
q is 0, 1 or 2;
or a pharmaceutically active salt thereof.
A compound of formula If is the following:
[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester.

Compounds of formula Ig

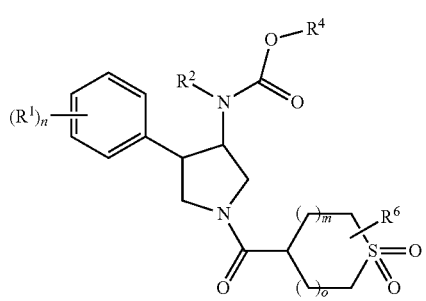

wherein
R[1] is hydrogen, halogen, cyano, lower alkyl or lower alkyl substituted by halogen;
n is 1, 2 or 3, wherein when n is 2 or 3, each R[1] is the same or different;
R[2] is hydrogen or methyl;
R[6] is hydrogen, di-lower alkyl or =O;
o and m are each independently 0, 1 or 2;
R[4] is lower alkyl,
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q CN$, bicyclo[2.2.1]heptanyl,
$(CH_2)_q$-cycloalkyl optionally substituted by lower alkyl, lower alkyl substituted by halogen, lower alkoxy or by halogen, or is (CH$_2$)$_q$-heterocycloalkyl, (CH$_2$)$_q$-aryl, CH(lower alkyl)-aryl, CH(cycloalkyl)-aryl, or (CH$_2$)$_q$-heteroaryl, which heterocycloalkyl, aryl or heteroaryl rings are optionally substituted by halogen, hydroxy, lower alkyl, lower alkyl substituted by halogen, S(O)$_2$-lower alkyl, cyano or by lower alkoxy;

q is 0, 1 or 2;

or a pharmaceutically active salt thereof.

A compound of formula Ig is the following:

[(3S,4R)-4-(4-Chloro-phenyl)-1-(1,1-dioxo-hexahydro-1λ$^6$-thiopyran-4-carbonyl)-pyrrolidin-3-yl]-methyl-carbamic acid 4-fluoro-phenyl ester.

A further embodiment of the invention are compounds of formula

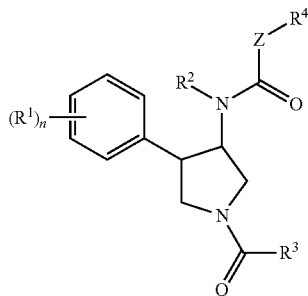

II wherein
R$^1$ is hydrogen, halogen, cyano, lower alkyl or lower alkyl substituted by halogen;
n is 1, 2 or 3, wherein when n is 2 or 3, each R$^1$ is the same or different;
R$^2$ is hydrogen or methyl;
R$^3$ is (CH$_2$)$_r$—C(O)NH$_2$ wherein r is 1 or 2 or

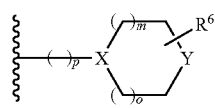

is a non aromatic heterocyclic group
wherein
X is N or CH;
Y is C(R)(R$^7$)—; —N(R$^7$')—, —S(O)$_2$ or O;
R$^6$ is hydrogen, di-lower alkyl or =O;
o and m are each independently 0, 1 or 2;
p is 0, 1 or 2;
R is hydrogen, halogen, or lower alkyl;
R$^7$ is hydrogen, halogen, hydroxy, lower alkyl substituted by hydroxy, cyano, or lower alkoxy;
R$^7$' is hydrogen, —C(O)-lower alkyl, —C(O)O-lower alkyl, —C(O)CH$_2$O-lower alkyl, or is cycloalkyl, —CH$_2$-cycloalkyl or —C(O)-cycloalkyl, wherein the cycloalkyl groups are optionally substituted by lower alkyl, or is —C(O)-heterocycloalkyl or heterocycloalkyl, or is heteroaryl, which heterocycloalkyl or heteroaryl groups are optionally substituted by halogen, lower alkyl, lower alkoxy, lower alkyl substituted by halogen, C(O)NH-lower alkyl, C(O)NH$_2$, C(O)-lower alkyl, S(O)$_2$— lower alkyl or cyano;

Z is —O—, NH— or —N(lower alkyl)-;

R$^4$ is lower alkyl, lower alkyl substituted by halogen, lower alkyl substituted by hydroxy, lower alkyl substituted by cycloalkyl, (CH$_2$)$_s$—O-lower alkyl, wherein s is 2 or 3, CH(CH$_3$)CH$_2$—O-lower alkyl, (CH$_2$)$_q$CN, bicyclo[2.2.1]heptanyl, (CH$_2$)$_q$-cycloalkyl optionally substituted by lower alkyl, lower alkyl substituted by halogen, lower alkoxy or by halogen, or is (CH$_2$)$_q$-heterocycloalkyl, (CH$_2$)$_q$-aryl, CH(lower alkyl)-aryl, CH(cycloalkyl)-aryl, or (CH$_2$)$_q$-heteroaryl, which heterocycloalkyl, aryl or heteroaryl rings are optionally substituted by halogen, hydroxy, lower alkyl, lower alkyl substituted by halogen, S(O)$_2$-lower alkyl, cyano or by lower alkoxy;

q is 0, 1 or 2;

or a pharmaceutically active salt thereof.

Preferred compounds of formula I are those, wherein R$^2$ is methyl.

The present compounds of formula I

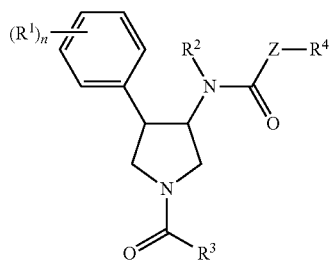

I and their pharmaceutically acceptable salts can be prepared by processes described below, which process comprises a) coupling a compound of formula II

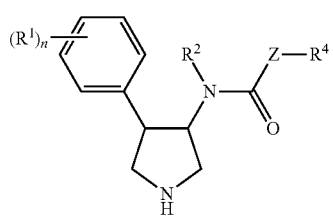

II with a suitable carbamoyl chloride, acid chloride or carboxylic acid to afford a compound of formula I

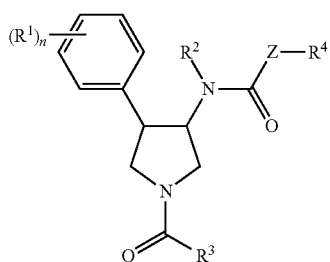

wherein the substituents R¹, R², R³, R⁴ and Z and n are as defined above
and if desired, converting the compounds obtained into pharmaceutically acceptable acid addition salts;
or
b) coupling a compound with formula III

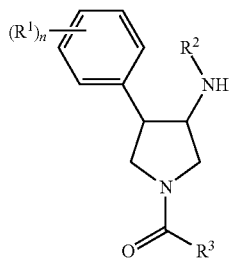

with a corresponding chloroformate, acid anhydride or a mixture of triphosgene and corresponding alcohol or amine to afford a compound of formula I

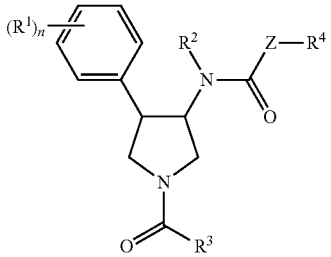

wherein the substituents $R^1$, $R^2$, $R^3$, $R^4$ and Z and n are as defined above and if desired, converting the compounds obtained into pharmaceutically acceptable acid addition salts.

The following schemes 1 and 2 describe the processes for the preparation of compounds of formula I in more detail. The starting material of formula II is a known compound and can be prepared according to methods known in the art.

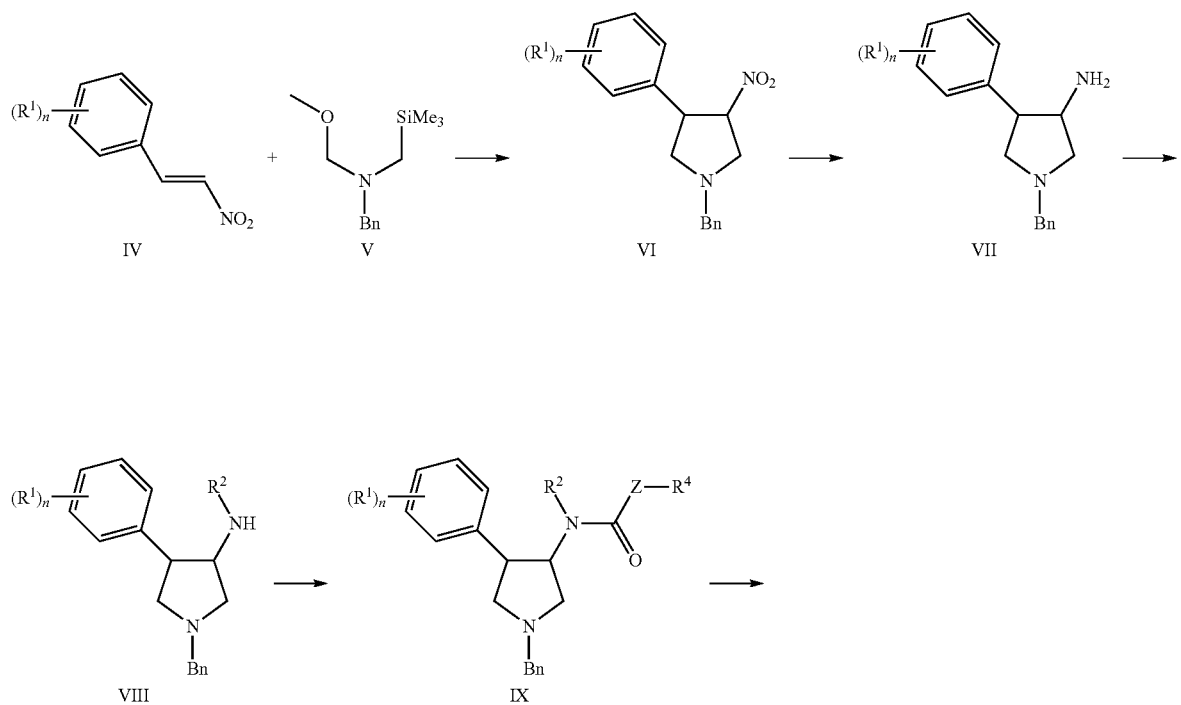

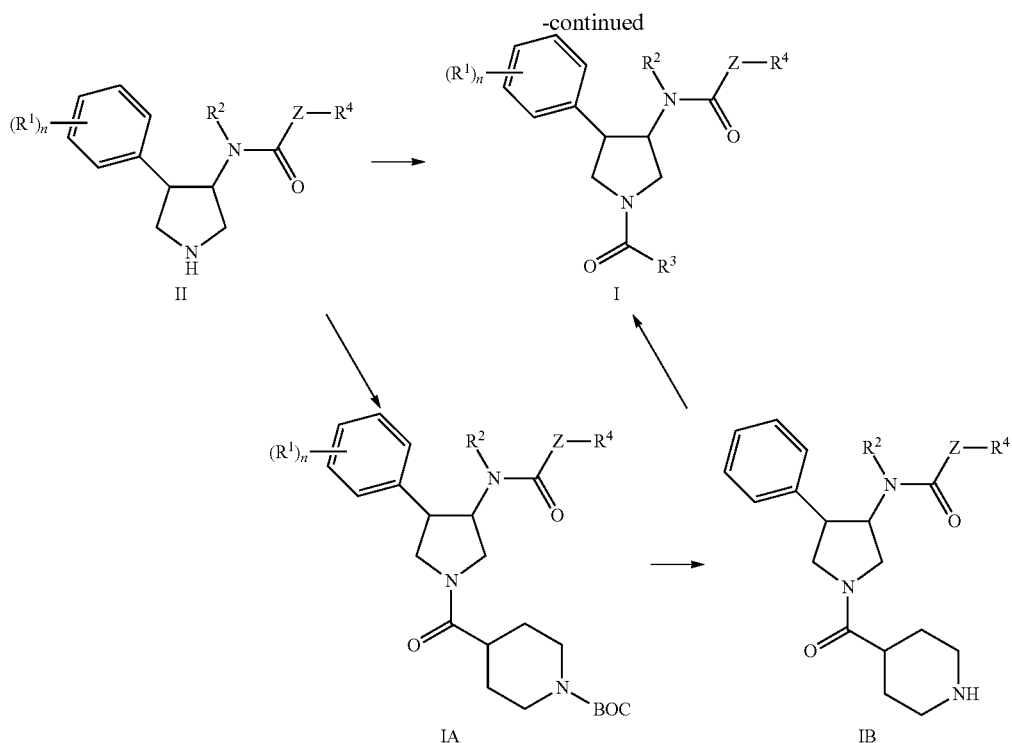

wherein the substituents R', R², R³, R⁴ and Z are as defined above

According to scheme 1, the 3,4-disubstituted pyrrolidine VI is prepared via a stereo specific 1,3-dipolar cycloaddition between the 2-nitrostyrene derivative IV and the azomethine ylide generated in situ from the N-(methoxymethyl)-N-(phenylmethyl)-N-(trimethylsilyl) methylamine V in the presence of a catalytic amount of acid, such as TFA. Reduction of the nitro moiety of VI using standard conditions for example $SnCl_2 \cdot H_2O$ yields VII. The amino moiety of VII is subsequently alkylated to produce VIII. Reaction of VIII with an acid anhydride, chloroformate or a mixture of triphosgene and an alcohol or amine in the presence of a base affords IX. Selective N-debenzylation is then carried out using several known procedures which are compatible with the substitution patterns of the aromatic rings to afford II. Finally, derivatives I are prepared via a coupling with a suitable carbamoyl chloride, acid chloride or carboxylic acid. Alternatively, pyrrolidine II is coupled with the corresponding acid to afford a compound of formula IA which can be deprotected to afford the piperidine of formula IB which might be further derivatised to obtain final compounds of formula I.

Scheme 2

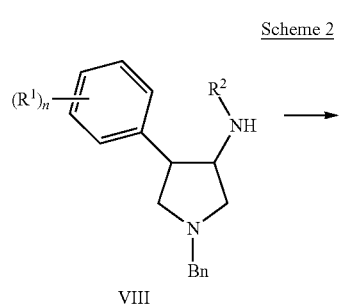

VIII

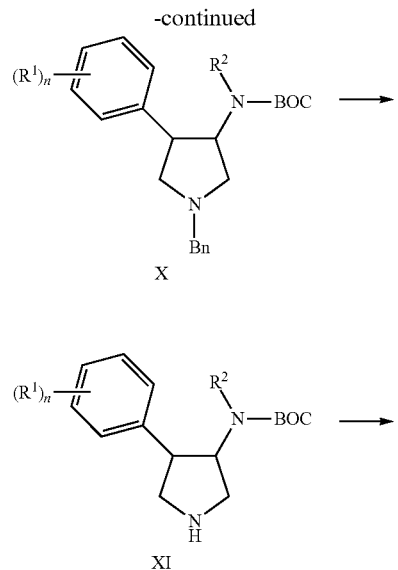

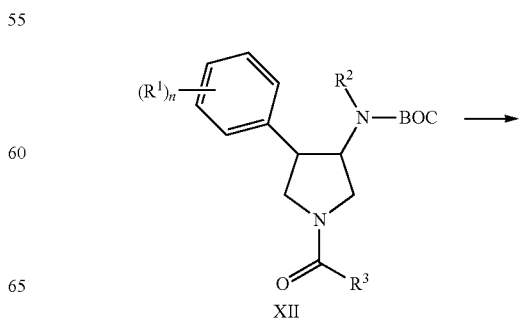

-continued

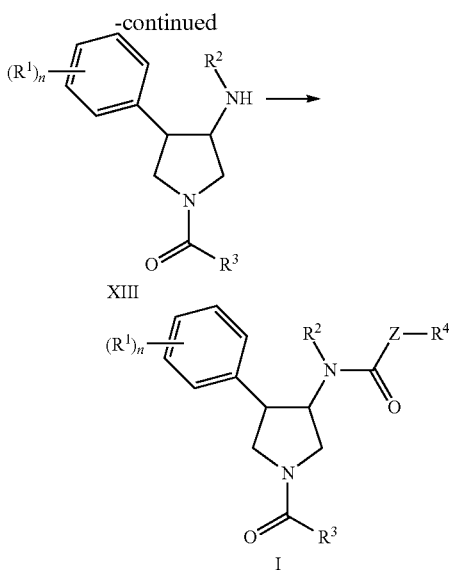

wherein the substituents $R^1$, $R^2$, $R^3$, $R^4$ and Z are as defined above

According to scheme 2, the secondary amine of the intermediates VII can be protected, for instance with a Boc group to afford a compound of formula X, followed by a selective debenzylation to produce XI. Then a coupling with a suitable carbamoyl chloride, acid chloride or carboxylic acid gives XII. Deprotection with TFA affords the free amine XIII, which after reaction with an acid anhydride, chloroformate or a mixture of triphosgene and an alcohol or amine in the presence of a base affords derivatives of formula I.

EXAMPLE 1 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester

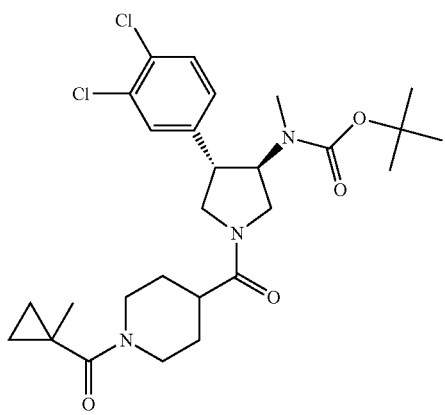 [SMILES: CN(C(=O)OC(C)(C)C)[C@H]1CN(C(=O)C2CCN(C(=O)C3(C)CC3)CC2)C[C@@H]1c1ccc(Cl)c(Cl)c1]

a) rac-(3R,4S)-1-Benzyl-3-(3,4-dichloro-phenyl)-4-nitro-pyrrolidine

A solution of N-(methoxymethyl)-N-(phenylmethyl)-N-(trimethylsilyl)methylamine (32.50 g, 0.135 mol) in $CH_2Cl_2$ (70 mL) was added drop wise, over a 30 minutes period, to a stirred solution of 1,2-dichloro-4-((E)-2-nitro-vinyl)-benzene (19.60 g, 0.09 mol) and trifluoroacetic acid (1.54 mL, 0.013 mol) in $CH_2Cl_2$ (160 mL) at 0° C. The ice bath was removed, and the solution was stirred at 25° C. for an additional 48 h. It was then concentrated and purification by flash chromatography ($SiO_2$, EtOAc/H 1:6) afforded 25.0 g (79%) of the title compound as a yellow oil. ES-MS m/e: 351.0 $(M+H^+)$.

b) rac-(3S,4R)-1-Benzyl-4-(3,4-dichloro-phenyl)-pyrrolidin-3-ylamine

To a stirred solution of rac-(3R,4S)-1-benzyl-3-(3,4-dichloro-phenyl)-4-nitro-pyrrolidine (11.60 g, 33.0 mmol) in EtOAc (200 mL) was added in one portion 5 $nCl_2.2H_2O$ (37.26 g, 0.165 mol). The reaction mixture was then heated at reflux for 4 hours, cooled down to ambient temperature and a saturated aqueous solution of $NaHCO_3$ was added. The salts were filtered off and the product extracted with EtOAc. The organic phases were then dried over $Na_2SO_4$, and concentration under vacuum gave 5.7 g (54%) of rac-(3S,4R)-1-benzyl-4-(3,4-dichloro-phenyl)-pyrrolidin-3-ylamine as a yellow oil. The product was then used in the next step without further purification. ES-MS m/e: 321.2 $(M+H^+)$.

c) rac-[(3S,4R)-1-Benzyl-4-(3,4-dichloro-phenyl)-pyrrolidin-3-yl]-methyl-amine

To a solution of rac-(3S,4R)-1-benzyl-4-(3,4-dichloro-phenyl)-pyrrolidin-3-ylamine (0.54 g, 1.68 mmol) in THF (5 mL) was added a solution of $K_2CO_3$ (0.46 g, 3.36 mmol) in $H_2O$ (3 mL). After 10 minutes, ethyl chloroformate (0.18 mL, 1.85 mmol) was added and stirring was continued at ambient temperature for an additional 2 h. The intermediate carbamate was then extracted with $Et_2O$, dried over $Na_2SO_4$ and concentrated under vacuo to give viscous oil. The oil was taken up in THF (5 mL) and a solution of borane in THF (1M) was added (6.7 mL). The reaction mixture was then heated at 65° C. over night, cooled to ambient temperature and carefully quenched with conc. HCl (5 mL). The mixture was then heated at 80° C. for 2 h, cooled to ambient temperature, concentrated under vacuo, diluted with $Et_2O$ (20 mL) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 0.29 g (51%) of rac-[(3S,4R)-1-benzyl-4-(3,4-dichloro-phenyl)-pyrrolidin-3-yl]-methyl-amine as a colorless oil. ES-MS m/e: 335.3 $(M+H^+)$.

d) rac-[(3R,4S)-1-Benzyl-4-(3,4-dichloro-phenyl)-pyrrolidin-3-yl]-methyl-carbamic acid tert-butyl ester To a solution of rac-[(3S,4R)-1-benzyl-4-(3,4-dichloro-phenyl)-pyrrolidin-3-yl]-methyl-amine (2.85 g, 8.50 mmol) in dichloromethane (29 mL) was added at ambient temperature triethylamine (2.4 mL, 17.0 mmol), 4-dimethylaminopyridine (0.10 g, 0.85 mmol) and di-tert.-butyl-dicarbonate (2.04 g, 9.35 mmol). The solution was stirred for 2 h at ambient temperature. The solution was diluted with water (30 mL). The organic layer was washed with water (30 mL), the aqueous layers were extracted with dichloromethane (20 mL), dried over sodium sulfate and concentrated. Purification by chromatography ($SiO_2$, heptane:ethyl acetate=100:0 to e) rac-[(3R,4S)-4-(3,4-Dichloro-phenyl)-pyrrolidin-3-yl]-methyl-carbamic acid tert-butyl ester To a solution of rac-[(3R,4S)-1-benzyl-4-(3,4-dichloro-phenyl)-pyrrolidin-3-yl]-methyl-carbamic acid tert-butyl ester (3.50 g, 8.04 mmol) in toluene (50 mL) was added under an atmosphere of nitrogen N,N-diisopropyl ethyl amine (1.86 mL, 10.9 mmol). The flask was cooled with a water bath and 1-chloroethyl chloroformate (1.14 mL, 10.5 mmol) was added during 2 min. After stirring for 2 h at ambient temperature the solution stood over night at 5° C. The reaction mixture was concentrated in vacuo. After the addition of methanol (50 mL) it was stirred for 4 h at ambient temperature. Concentration afforded the title compound (2.95 g, 99%) as a light brown oil. MS m/e: 345.1 [M+H]$^+$.

f) rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester To a solution of rac-[(3R,4S)-4-(3,4-dichloro-phenyl)-pyrrolidin-3-yl]-methyl-carbamic acid tert-butyl ester (2.78 g, 7.56 mmol) in DMF (28 mL) were added at 0° C. N,N-diisopropyl ethyl amine (8.26 mL, 48.2 mmol), 1-(1-methyl-cyclopropanecarbonyl)-piperidine-4-carboxylic acid (2.78 g, 8.04 mmol), O-(7-azabenzotriazol-1-yl)-N,N,N',N'-tetramethyluronium hexafluorophosphate (3.67 g, 9.65 mmol). The resulting solution was stirred for 6 h at ambient temperature. After diluting with EtOAc (50 mL) the solution was washed twice with water (50 mL) and brine (50 mL). The aqueous layers were extracted with EtOAc (50 mL) and dried over sodium sulfate. Concentration and purification by chromatography (SiO$_2$, heptane:ethyl acetate:methanol=80:20:0 to 0:90:10) afforded the title compound (3.06 g, 75%) as a light brown foam. MS m/e: 538.3 [M+H]$^+$.

EXAMPLE 2 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

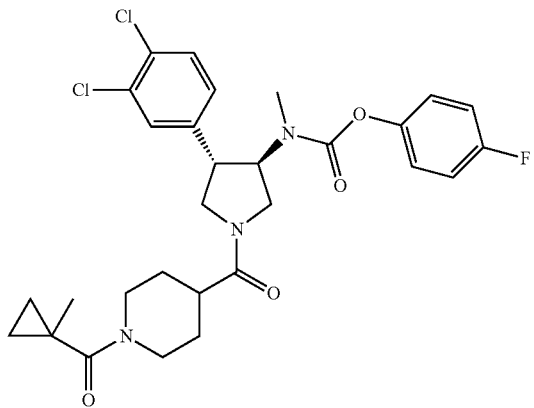 [SMILES: CN(C(=O)Oc1ccc(F)cc1)[C@H]1CN(C(=O)C2CCN(C(=O)C3(C)CC3)CC2)C[C@@H]1c1ccc(Cl)c(Cl)c1]

a) rac-{4-[(3S,4R)-3-(3,4-Dichloro-phenyl)-4-methylamino-pyrrolidine-1-carbonyl]-piperidin-1-yl}-(1-methyl-cyclopropyl)-methanone Under an atmosphere of nitrogen to a solution of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester (3.02 g, 5.61 mmol) in dichloromethane (30 mL) was added at ambient temperature trifluoroacetic acid (4.3 mL, 56 mmol) and stirred for 20 h at this temperature. The reaction mixture was added slowly onto an aqueous solution of sodium carbonate (1M, 60 mL). The organic layer was separated and washed with brine (50 mL). The aqueous layers were extracted with dichloromethane (30 mL), dried over sodium sulfate and concentrated. Purification by chromatography (SiO$_2$, heptane:ethyl acetate:methanol=50:50:0 to 0:90:10) afforded the title compound (1.79 g, 73%) as a light brown oil. MS m/e: 338.3 [M+H]$^+$.

b) rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester To a solution of rac-{4-[(3S,4R)-3-(3,4-dichloro-phenyl)-4-methylamino-pyrrolidine-1-carbonyl]-piperidin-1-yl}-(1-methyl-cyclopropyl)-methanone (50 mg, 0.11 mmol) in dichloromethane (1 mL) were added N,N-diisopropyl ethyl amine (29 µl, 0.17 mmol), 4-fluorophenyl chloroformate (19 µl, 0.15 mmol) and the resulting mixture was stirred for 18 h at ambient temperature. It was diluted with EtOAc (15 mL) and washed with an aqueous solution of sodium carbonate (1M, 10 mL). The aqueous layers were extracted with dichloromethane (30 mL), dried over sodium sulfate and concentrated. Purification by chromatography (SiO$_2$, heptane:ethyl acetate=100:0 to 90:10) afforded the title compound (45 mg, 68%) as a light brown oil. MS m/e: 576.3 [M+H]$^+$.

EXAMPLE 3 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentyl ester

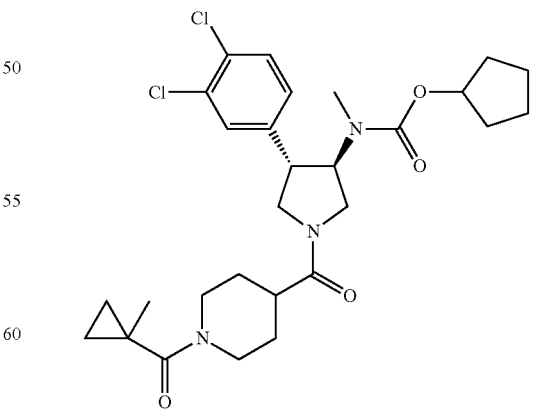

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid cyclopentyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using cyclopentyl chloroformate instead of 4-fluorophenyl chloroformate and was obtained as a white solid. MS m/e: 550.3 [M+H]+.

EXAMPLE 4 rac-[(3R,4S)-1-(1-Cyclopropylmethyl-piperidine-4-carbonyl)-4-(3,4-dichloro-phenyl)-pyrrolidin-3-yl]-methyl-carbamic acid 4-fluoro-phenyl ester

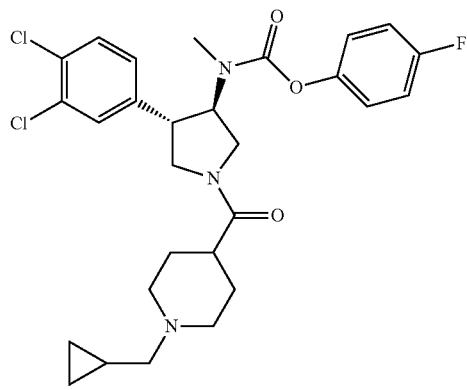 [SMILES: CN(C(=O)Oc1ccc(F)cc1)[C@H]1CN(C(=O)C2CCN(CC3CC3)CC2)C[C@@H]1c1ccc(Cl)c(Cl)c1]

a) rac-[(3R,4S)-1-(1-Cyclopropylmethyl-piperidine-4-carbonyl)-4-(3,4-dichloro-phenyl)-pyrrolidin-3-yl]-methyl-carbamic acid tert-butyl ester In analogy to the procedure described for the synthesis of example 1 (step f), the title compound rac-[(3R,4S)-1-(1-cyclopropylmethyl-piperidine-4-carbonyl)-4-(3,4-dichloro-phenyl)-pyrrolidin-3-yl]-methyl-carbamic acid tert-butyl ester was prepared from rac-[(3R,4S)-4-(3,4-dichloro-phenyl)-pyrrolidin-3-yl]-methyl-carbamic acid tert-butyl ester using 1-(1-cyclopropylmethyl)-piperidine-4-carboxylic acid instead of 1-(1-methyl-cyclopropanecarbonyl)-piperidine-4-carboxylic acid and was obtained as a brown oil which was directly used in the next step without purification.

b) rac-(1-Cyclopropylmethyl-piperidin-4-yl)-[(3S,4R)-3-(3,4-dichloro-phenyl)-4-methylamino-pyrrolidin-1-yl]-methanone In analogy to the procedure described for the synthesis of example 2 (step a), the title compound rac-(1-Cyclopropylmethyl-piperidin-4-yl)-[(3S,4R)-3-(3,4-dichloro-phenyl)-4-methylamino-pyrrolidin-1-yl]-methanone was prepared from rac-[(3R,4S)-1-(1-cyclopropylmethyl-piperidine-4-carbonyl)-4-(3,4-dichloro-phenyl)-pyrrolidin-3-yl]-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a brown oil. MS m/e: 410.2 [M+H]+.

c) rac-[(3R,4S)-1-(1-Cyclopropylmethyl-piperidine-4-carbonyl)-4-(3,4-dichloro-phenyl)-pyrrolidin-3-yl]-methyl-carbamic acid 4-fluoro-phenyl ester In analogy to the procedure described for the synthesis of example 2 (step b), the title compound rac-[(3R,4S)-1-(1-Cyclopropylmethyl-piperidine-4-carbonyl)-4-(3,4-dichloro-phenyl)-pyrrolidin-3-yl]-methyl-carbamic acid 4-fluoro-phenyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a light yellow oil. MS m/e: 548.2 [M+H]+.

EXAMPLE 5

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

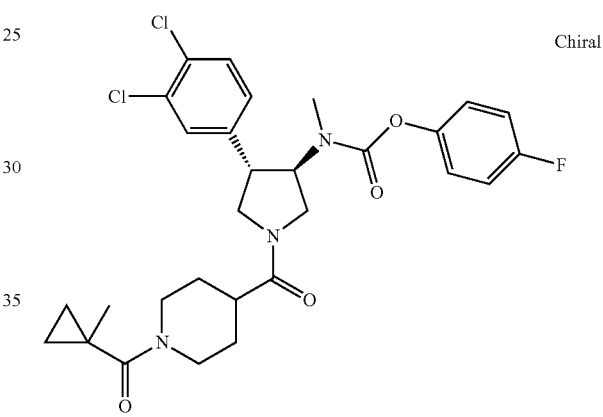

and

EXAMPLE 6

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

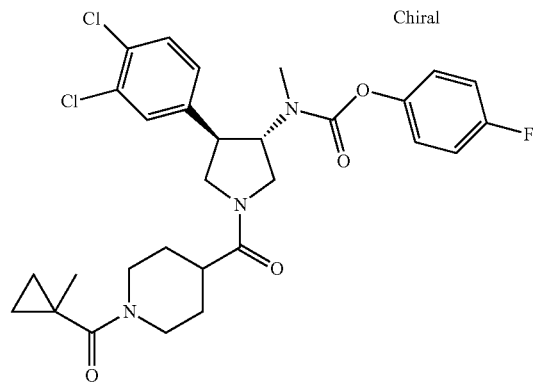 [SMILES: CN(C(=O)Oc1ccc(F)cc1)[C@@H]1CN(C(=O)C2CCN(C(=O)C3(C)CC3)CC2)C[C@H]1c1ccc(Cl)c(Cl)c1]

Rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-phenyl ester was subjected to column chromatography on chiral phase to yield {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 576.2 [M+H]$^+$) as a white foam and {(3S,4R)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 576.2 [M+H]$^+$) as a white foam.

EXAMPLE 7 rac-[(3R,4S)-1-(1-Cyclopropylmethyl-piperidine-4-carbonyl)-4-(3,4-dichloro-phenyl)-pyrrolidin-3-yl]-methyl-carbamic acid phenyl ester

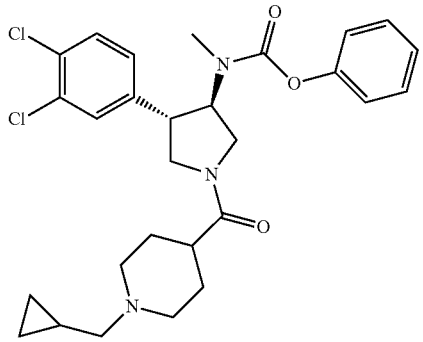 [SMILES: CN(C(=O)Oc1ccccc1)[C@H]1CN(C(=O)C2CCN(CC3CC3)CC2)C[C@@H]1c1ccc(Cl)c(Cl)c1]

In analogy to the procedure described for the synthesis of example 2 (step b), the title compound rac-[(3R,4S)-1-(1-cyclopropylmethyl-piperidine-4-carbonyl)-4-(3,4-dichloro-phenyl)-pyrrolidin-3-yl]-methyl-carbamic acid phenyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using phenyl chloroformate instead of fluorophenyl chloroformate and was obtained as a colorless oil. MS m/e: 530.2 [M]$^+$.

EXAMPLE 8 rac-[(3R,4S)-1-(1-Cyclopropylmethyl-piperidine-4-carbonyl)-4-(3,4-dichloro-phenyl)-pyrrolidin-3-yl]-methyl-carbamic acid p-tolyl ester

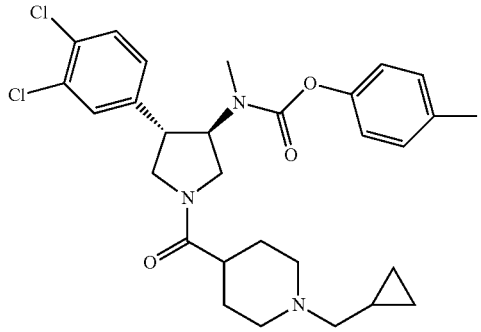 [SMILES: Cc1ccc(OC(=O)N(C)[C@H]2CN(C(=O)C3CCN(CC4CC4)CC3)C[C@@H]2c2ccc(Cl)c(Cl)c2)cc1]

In analogy to the procedure described for the synthesis of example 2 (step b), the title compound rac-[(3R,4S)-1-(1-cyclopropylmethyl-piperidine-4-carbonyl)-4-(3,4-dichloro-phenyl)-pyrrolidin-3-yl]-methyl-carbamic acid p-tolyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using p-tolyl chloroformate instead of fluorophenyl chloroformate and was obtained as a colorless oil. MS m/e: 544.2 [M]$^+$.

EXAMPLE 9 rac-[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester

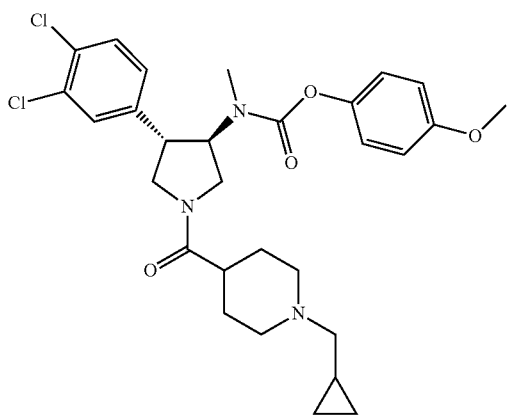 [SMILES: COc1ccc(OC(=O)N(C)[C@H]2CN(C(=O)C3CCN(CC4CC4)CC3)C[C@@H]2c2ccc(Cl)c(Cl)c2)cc1]

In analogy to the procedure described for the synthesis of example 2 (step b), the title compound rac-[(3R,4S)-1-(1-cyclopropylmethyl-piperidine-4-carbonyl)-4-(3,4-dichloro-phenyl)-pyrrolidin-3-yl]-methyl-carbamic acid 4-methoxy-phenyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-methoxy-phenyl chloroformate instead of fluorophenyl chloroformate and was obtained as a colorless oil. MS m/e: 560.2 [M]$^+$.

EXAMPLE 10 rac-[(3R,4S)-1-(1-Cyclopropylmethyl-piperidine-4-carbonyl)-4-(3,4-dichloro-phenyl)-pyrrolidin-3-yl]-methyl-carbamic acid 4-chloro-phenyl ester

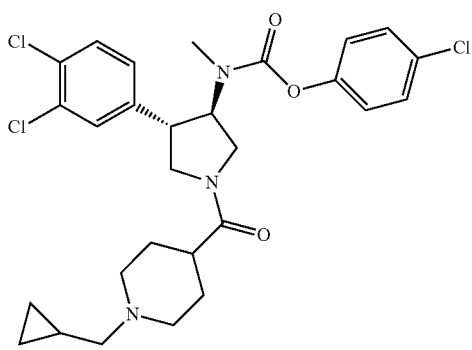 [SMILES: CN(C(=O)Oc1ccc(Cl)cc1)[C@H]1CN(C(=O)C2CCN(CC3CC3)CC2)C[C@@H]1c1ccc(Cl)c(Cl)c1]

In analogy to the procedure described for the synthesis of example 2 (step b), the title compound rac-[(3R,4S)-1-(1-cyclopropylmethyl-piperidine-4-carbonyl)-4-(3,4-dichlorophenyl)-pyrrolidin-3-yl]-methyl-carbamic acid 4-chlorophenyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-chloro-phenyl chloroformate instead of fluorophenyl chloroformate and was obtained as a colorless oil. MS m/e: 564.2 [M]+.

EXAMPLE 11 rac-[(3R,4S)-1-(1-Cyclopropylmethyl-piperidine-4-carbonyl)-4-(3,4-dichloro-phenyl)-pyrrolidin-3-yl]-methyl-carbamic acid butyl ester

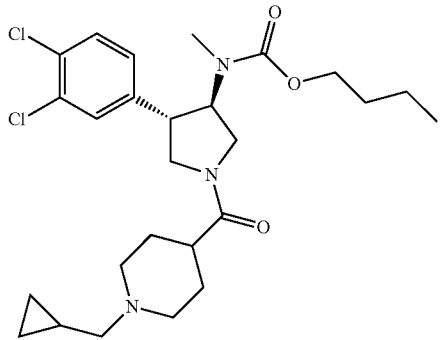 [SMILES: CCCCOC(=O)N(C)[C@H]1CN(C(=O)C2CCN(CC3CC3)CC2)C[C@@H]1c1ccc(Cl)c(Cl)c1]

In analogy to the procedure described for the synthesis of example 2 (step b), the title compound rac-[(3R,4S)-1-(1-cyclopropylmethyl-piperidine-4-carbonyl)-4-(3,4-dichloro-phenyl)-pyrrolidin-3-yl]-methyl-carbamic acid butyl ester was prepared from rac-(1-cyclopropylmethyl-piperidin-4-yl)-[(3S,4R)-3-(3,4-dichloro-phenyl)-4-methylamino-pyrrolidin-1-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using butyl chloroformate instead of fluorophenyl chloroformate and was obtained as a colorless oil. MS m/e: 510.4 [M]+.

EXAMPLE 12 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester

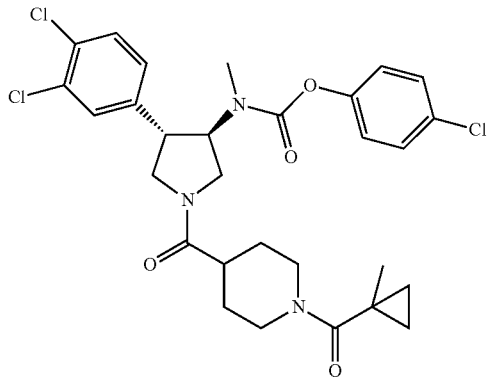 [SMILES: CN(C(=O)Oc1ccc(Cl)cc1)[C@H]1CN(C(=O)C2CCN(C(=O)C3(C)CC3)CC2)C[C@@H]1c1ccc(Cl)c(Cl)c1]

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-chloro-phenyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-chlorophenyl-chloroformate instead of 4-fluorophenyl chloroformate and was obtained as a white foam. MS m/e: 592.3 [M]+.

EXAMPLE 13 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid phenyl ester

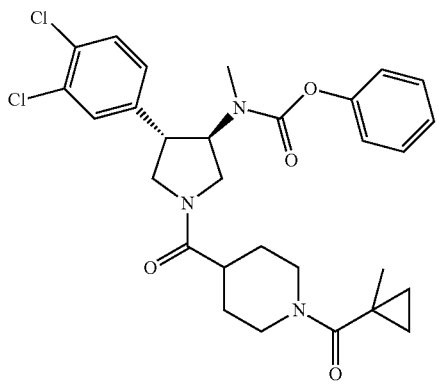 [SMILES: CN(C(=O)Oc1ccccc1)[C@H]1CN(C(=O)C2CCN(C(=O)C3(C)CC3)CC2)C[C@@H]1c1ccc(Cl)c(Cl)c1]

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid phenyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using phenyl chloroformate instead of 4-fluorophenyl chloroformate and was obtained as a light brown foam. MS m/e: 558.0 [M]+.

EXAMPLE 14 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester

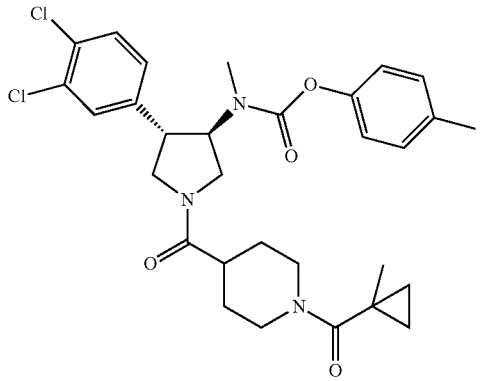 [SMILES: Cc1ccc(OC(=O)N(C)[C@H]2CN(C(=O)C3CCN(C(=O)C4(C)CC4)CC3)C[C@@H]2c2ccc(Cl)c(Cl)c2)cc1]

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid p-tolyl-phenyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using p-tolyl chloroformate instead of 4-fluorophenyl chloroformate and was obtained as a light brown foam. MS m/e: 572.2 [M]⁺.

EXAMPLE 15 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-methoxyphenyl ester

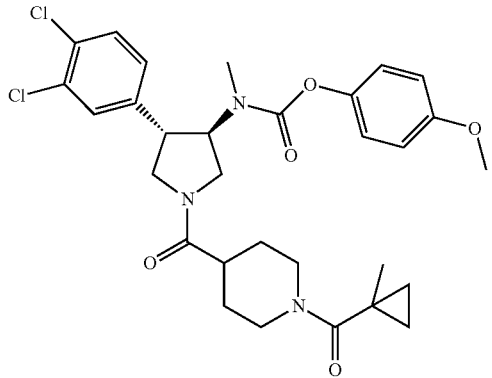 [SMILES: COc1ccc(OC(=O)N(C)[C@H]2CN(C(=O)C3CCN(C(=O)C4(C)CC4)CC3)C[C@@H]2c2ccc(Cl)c(Cl)c2)cc1]

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid p-methoxy-phenyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using p-methoxyphenyl chloroformate instead of 4-fluorophenyl chloroformate and was obtained as a light brown foam. MS m/e: 588.2 [M]⁺.

EXAMPLE 16

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester

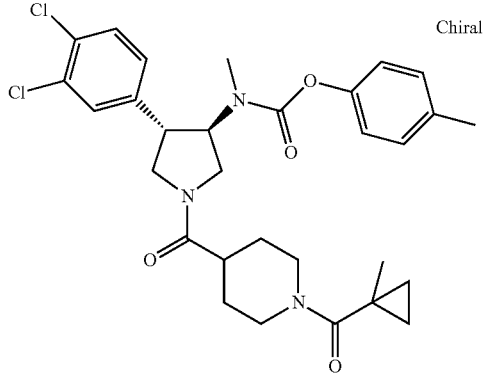 [SMILES: Cc1ccc(OC(=O)N(C)[C@H]2CN(C(=O)C3CCN(C(=O)C4(C)CC4)CC3)C[C@@H]2c2ccc(Cl)c(Cl)c2)cc1]

and

EXAMPLE 17

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester

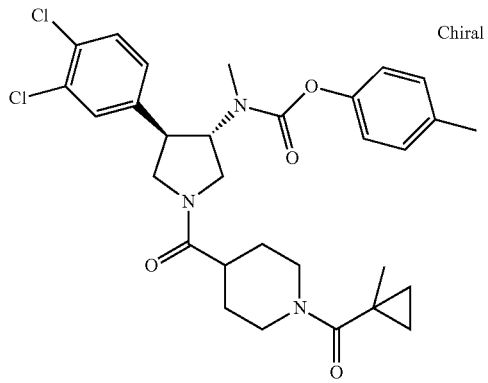 [SMILES: Cc1ccc(OC(=O)N(C)[C@@H]2CN(C(=O)C3CCN(C(=O)C4(C)CC4)CC3)C[C@H]2c2ccc(Cl)c(Cl)c2)cc1]

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester was subjected to column chromatography on chiral phase to yield {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid p-tolyl ester (MS (m/e): 572.3 [M]⁺) as an off-white foam and {(3S,4R)-4-(3,4-dichloro-phenyl)-1-[1-(1-methyl-cyclopropanecarbonyl)-piperidine-4-carbonyl]-pyrrolidin-3-yl}-methyl-carbamic acid p-tolyl ester (MS (m/e): 572.3 [M]⁺) as a colorless oil.

EXAMPLE 18

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester

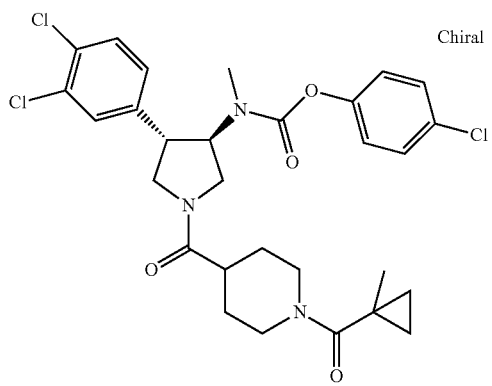 [SMILES: CN(C(=O)Oc1ccc(Cl)cc1)[C@H]1CN(C(=O)C2CCN(C(=O)C3(C)CC3)CC2)C[C@@H]1c1ccc(Cl)c(Cl)c1]

and

EXAMPLE 19

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester

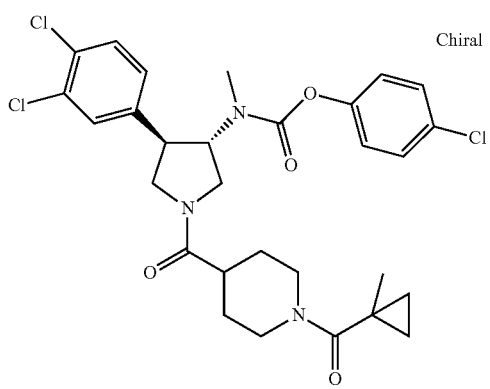 [SMILES: CN(C(=O)Oc1ccc(Cl)cc1)[C@@H]1CN(C(=O)C2CCN(C(=O)C3(C)CC3)CC2)C[C@H]1c1ccc(Cl)c(Cl)c1]

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester was subjected to column chromatography on chiral phase to yield {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-chlorophenyl ester (MS (m/e): 592.3 [M]$^+$) as an off-white foam and {(3S,4R)-4-(3,4-dichloro-phenyl)-1-[1-(1-methyl-cyclopropanecarbonyl)-piperidine-4-carbonyl]-pyrrolidin-3-yl}-methyl-carbamic acid 4-chlorophenyl ester (MS (m/e): 592.3 [M]$^+$) as an off-white foam.

EXAMPLE 20

[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester

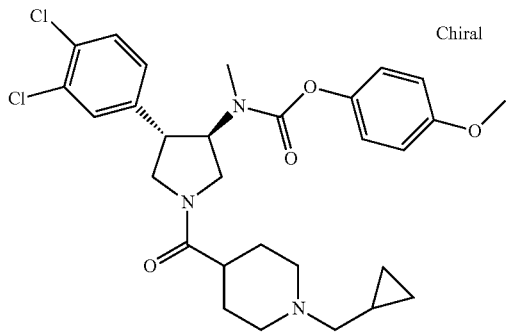 [SMILES: COc1ccc(OC(=O)N(C)[C@H]2CN(C(=O)C3CCN(CC4CC4)CC3)C[C@@H]2c2ccc(Cl)c(Cl)c2)cc1]

and

EXAMPLE 21

[(3S,4R)-1-(1-Cyclopropylmethyl-piperidine-4-carbonyl)-4-(3,4-dichloro-phenyl)-pyrrolidin-3-yl]-methyl-carbamic acid 4-methoxy-phenyl ester

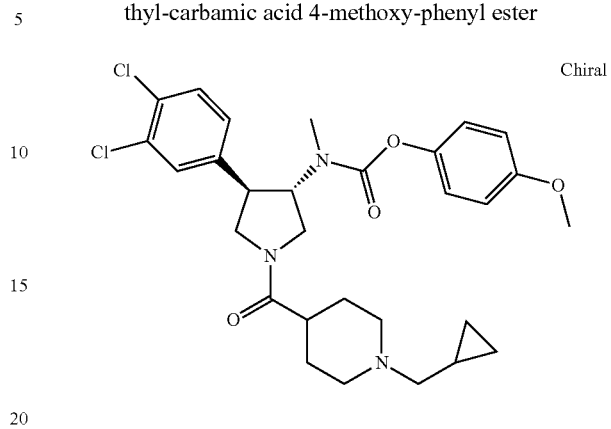

rac-[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester was subjected to column chromatography on chiral phase to yield [(3R,4S)-1-(1-cyclopropylmethyl-piperidine-4-carbonyl)-4-(3,4-dichloro-phenyl)-pyrrolidin-3-yl]-methyl-carbamic acid 4-methoxy-phenyl ester (MS (m/e): 560.2 [M]$^+$) as a colorless oil and [(3S,4R)-1-(1-cyclopropylmethyl-piperidine-4-carbonyl)-4-(3,4-dichloro-phenyl)-pyrrolidin-3-yl]-methyl-carbamic acid 4-methoxy-phenyl ester (MS (m/e): 560.2 [M]$^+$) as a colorless oil.

EXAMPLE 22 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 2,2-dimethyl-propyl ester

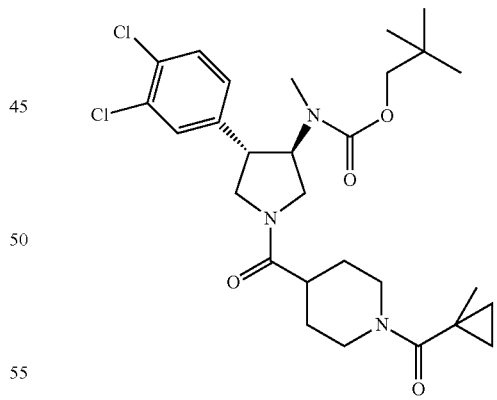

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 2,2-dimethyl-propyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using neopentyl chloroformate instead of 4-fluorophenyl chloroformate and was obtained as a yellow foam. MS m/e: 552.3 [M]$^+$.

EXAMPLE 23 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid prop-2-ynyl ester

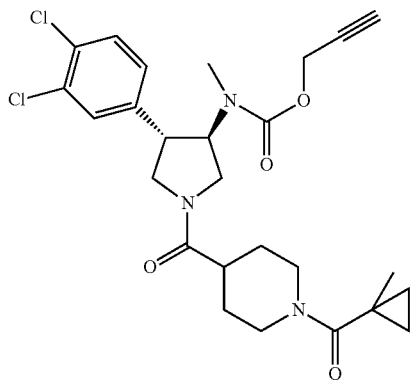 [SMILES: C#CCOC(=O)N(C)[C@H]1CN(C(=O)C2CCN(C(=O)C3(C)CC3)CC2)C[C@@H]1c1ccc(Cl)c(Cl)c1]

In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid prop-2-ynyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using propargyl chloroformate instead of 4-fluorophenyl chloroformate and was obtained as a yellow foam. MS m/e: 552.3 [M]+.

EXAMPLE 24 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopropyl-methyl ester

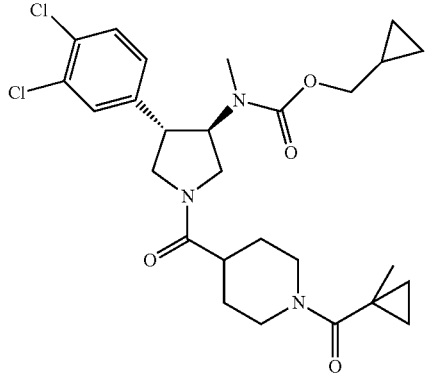 [SMILES: CN(C(=O)OCC1CC1)[C@H]1CN(C(=O)C2CCN(C(=O)C3(C)CC3)CC2)C[C@@H]1c1ccc(Cl)c(Cl)c1]

To a solution of 1,1'-carbonyl-diimidazole (102 mg, 0.627 mmol) in dioxane (1 mL) was added hydroxymethylcyclopropane (55 µl, 0.68 mmol). After stirring for 15 min at ambient temperature rac-{4-[(3S,4R)-3-(3,4-dichloro-phenyl)-4-methylamino-pyrrolidine-1-carbonyl]-piperidin-1-yl}-(1-methyl-cyclopropyl)-methanone (50 mg, 0.11 mmol) was added and the solution was irradiated in the microwave for 900 s at 170° C. and 1800 s at 200° C. The reaction mixture was diluted with ethyl acetate (15 mL) and washed with water (15 mL) and brine (15 mL). The organic layers were extracted with ethyl acetate, dried over sodium sulfate and concentrated. Purification by chromatography (SiO₂, ethyl acetate:methanol=100:0 to 85:15) afforded the title compound (21 mg, 34%) as a light brown oil. MS m/e: 536.4 [M]+.

EXAMPLE 25 rac-{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester

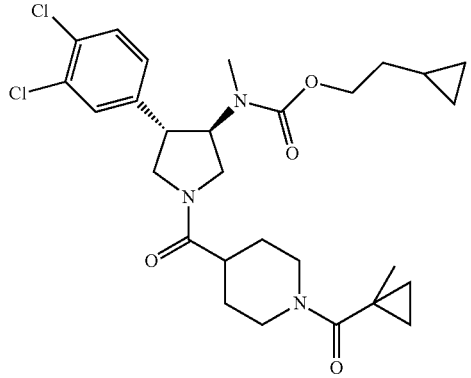 [SMILES: CN(C(=O)OCCC1CC1)[C@H]1CN(C(=O)C2CCN(C(=O)C3(C)CC3)CC2)C[C@@H]1c1ccc(Cl)c(Cl)c1]

To a solution of triphosgene (68 mg, 0.23 mmol) in dichloromethane (0.5 mL) was added 2-cyclopropylethanol (69 mg, 0.80 mmol). After the solution was stirred for 45 min at ambient temperature N,N-diisopropyl ethyl amine (156 µl, 0.912 mmol) and rac-{4-[(3S,4R)-3-(3,4-dichloro-phenyl)-4-methylamino-pyrrolidine-1-carbonyl]-piperidin-1-yl}-(1-methyl-cyclopropyl)-methanone (50 mg, 0.11 mmol) were added and the solution was stirred for 3 d at ambient temperature. It was diluted with ethyl acetate (15 mL) and washed with aqueous sodium carbonate (1 M, 15 mL) and brine (15 mL). The aqueous layers were extracted with ethyl acetate, dried over sodium sulfate and concentrated. Purification by chromatography (SiO₂, ethyl acetate:methanol=100:0 to 80:20) afforded the title compound (59 mg, 94%) as an off-white foam. MS m/e: 550.3 [M]+.

EXAMPLE 26 rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester

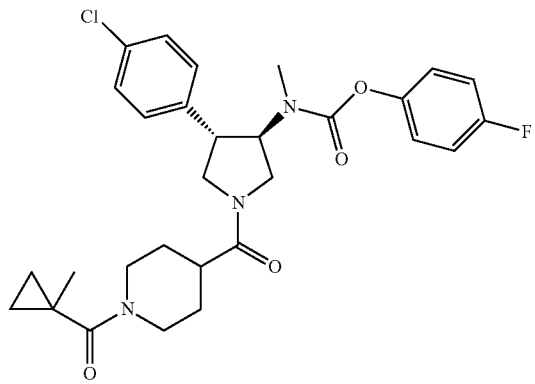 [SMILES: CN(C(=O)Oc1ccc(F)cc1)[C@H]1CN(C(=O)C2CCN(C(=O)C3(C)CC3)CC2)C[C@@H]1c1ccc(Cl)cc1]

a) rac-(3S,4R)-1-Benzyl-3-(4-chloro-phenyl)-4-nitro-pyrrolidine

In analogy to the procedure described for the synthesis of example 1 (step a), the title compound rac-(3S,4R)-1-benzyl-3-(4-chloro-phenyl)-4-nitro-pyrrolidine was prepared from 1-chloro-4-((E)-2-nitro-vinyl)-benzene instead of 1,2-dichloro-4-((E)-2-nitro-vinyl)-benzene and was obtained as a light pink oil. MS m/e: 317.1 [M]$^+$.

b) rac-(3R,4S)-1-Benzyl-4-(4-chloro-phenyl)-pyrrolidin-3-ylamine

In analogy to the procedure described for the synthesis of example 1 (step b), the title compound rac-(3R,4S)-1-benzyl-4-(4-chloro-phenyl)-pyrrolidin-3-ylamine was prepared from rac-(3S,4R)-1-benzyl-3-(4-chloro-phenyl)-4-nitro-pyrrolidine instead of rac-(3S,4R)-1-Benzyl-3-(3,4-dichloro-phenyl)-4-nitro-pyrrolidine and was obtained as a light brown oil. MS m/e: 287.1 [M+H]$^+$.

c) rac-[(3R,4S)-1-Benzyl-4-(4-chloro-phenyl)-pyrrolidin-3-yl]-methyl-amine

In analogy to the procedure described for the synthesis of example 1 (step c), the title compound rac-[(3R,4S)-1-benzyl-4-(4-chloro-phenyl)-pyrrolidin-3-yl]-methyl-amine was prepared from rac-(3R,4S)-1-benzyl-4-(4-chloro-phenyl)-pyrrolidin-3-ylamine instead of rac-(3S,4R)-1-benzyl-4-(3,4-dichloro-phenyl)-pyrrolidin-3-ylamine and was obtained as a colorless oil. MS m/e: 301.2 [M+H]$^+$.

d) rac-[(3R,4S)-1-Benzyl-4-(4-chloro-phenyl)-pyrrolidin-3-yl]-methyl-carbamic acid tert-butyl ester In analogy to the procedure described for the synthesis of example 1 (step d), the title compound rac-[(3R,4S)-1-benzyl-4-(4-chloro-phenyl)-pyrrolidin-3-yl]-methyl-carbamic acid tert-butyl ester was prepared from rac-[(3R,4S)-1-benzyl-4-(4-chloro-phenyl)-pyrrolidin-3-yl]-methyl-amine instead of rac-[(3R,4S)-1-benzyl-4-(3,4-dichloro-phenyl)-pyrrolidin-3-yl]-methyl-amine and was obtained as a white foam. MS m/e: 401.3 [M+H]$^+$.

e) rac-[(3R,4S)-4-(4-Chloro-phenyl)-pyrrolidin-3-yl]-methyl-carbamic acid tert-butyl ester In analogy to the procedure described for the synthesis of example 1 (step e), the title compound rac-[(3R,4S)-4-(4-chloro-phenyl)-pyrrolidin-3-yl]-methyl-carbamic acid tert-butyl ester was prepared from rac-[(3R,4S)-1-benzyl-4-(4-chloro-phenyl)-pyrrolidin-3-yl]-methyl-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as a brown oil. MS m/e: 311.2 [M+H]$^+$.

f) rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid tert-butyl ester In analogy to the procedure described for the synthesis of example 1 (step f), the title compound rac-{(3R,4S)-4-(4-chloro-phenyl)-1-[1-(1-methyl-cyclopropanecarbonyl)-piperidine-4-carbonyl]-pyrrolidin-3-yl}-methyl-carbamic acid tert-butyl ester was prepared from rac-[(3R,4S)-4-(4-chloro-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester and was obtained as a light brown foam. MS m/e: 504.3 [M]$^+$.

g) rac-{4-[(3S,4R)-3-(4-Chloro-phenyl)-4-methylamino-pyrrolidine-1-carbonyl]-piperidin-1-yl}-(1-methyl-cyclopropyl)-methanone In analogy to the procedure described for the synthesis of example 2 (step a), the title compound rac-{4-[(3S,4R)-3-(4-chloro-phenyl)-4-methylamino-pyrrolidine-1-carbonyl]-piperidin-1-yl}-(1-methyl-cyclopropyl)-methanone was prepared from rac-{(3R,4S)-4-(4-chloro-phenyl)-1-[1-(1-methyl-cyclopropanecarbonyl)-piperidine-4-carbonyl]-pyrrolidin-3-yl}-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light brown foam. MS m/e: 404.4 [M+H]$^+$.

h) rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester In analogy to the procedure described for the synthesis of example 2 (step b), the title compound rac-{(3R,4S)-4-(4-chloro-phenyl)-1-[1-(1-methyl-cyclopropanecarbonyl)-piperidine-4-carbonyl]-pyrrolidin-3-yl}-methyl-carbamic acid 4-fluoro-phenyl ester was prepared from rac-{4-[(3S,4R)-3-(4-chloro-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a light yellow foam. MS m/e: 542.3 [M]$^+$.

EXAMPLE 27 rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid butyl ester

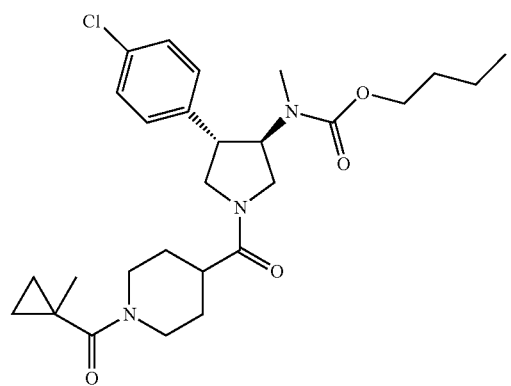 [SMILES: CCCCOC(=O)N(C)[C@H]1CN(C(=O)C2CCN(C(=O)C3(C)CC3)CC2)C[C@@H]1c1ccc(Cl)cc1]

In analogy to the procedure described for the synthesis of example 2 (step b), the title compound rac-{(3R,4S)-4-(4-chloro-phenyl)-1-[1-(1-methyl-cyclopropanecarbonyl)-piperidine-4-carbonyl]-pyrrolidin-3-yl}-methyl-carbamic acid butyl ester was prepared from rac-{4-[(3S,4R)-3-(4-chloro-phenyl)-4-methylamino-pyrrolidine-1-carbonyl]-piperidin- 1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using butyl chloroformate instead of 4-fluoro-phenyl chloroformate and was obtained as a light yellow foam. MS m/e: 504.2 [M]+.

EXAMPLE 28 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester

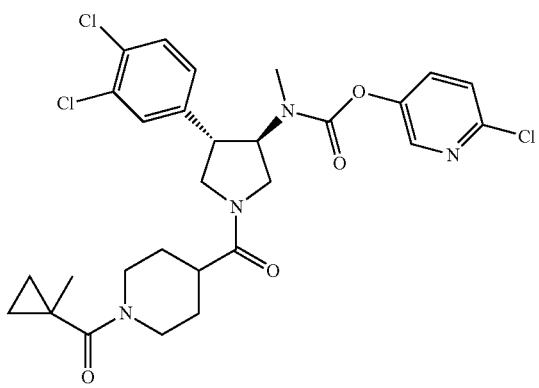 [SMILES: CN(C(=O)Oc1ccc(Cl)nc1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2-chloro-5-hydroxypyridine instead of 2-cyclopropylethanol and was obtained as a light brown foam. MS m/e: 593.2 [M]+.

EXAMPLE 29 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester

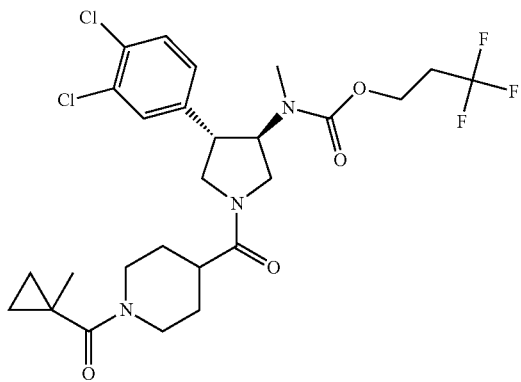 [SMILES: CN(C(=O)OCCC(F)(F)F)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3,3,3-trifluoro-1-propanol instead of 2-cyclopropylethanol and was obtained as a yellow foam. MS m/e: 578.2 [M]+.

EXAMPLE 30 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3-dimethyl-butyl ester

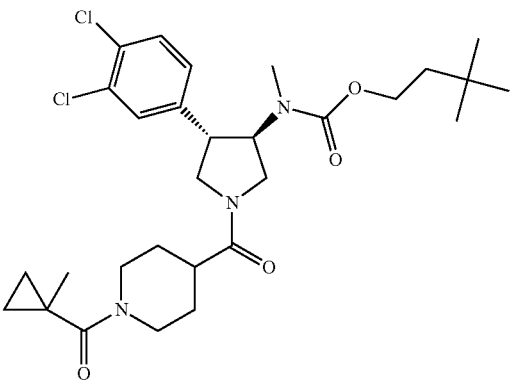 [SMILES: CN(C(=O)OCCC(C)(C)C)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3,3-dimethyl-butyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3,3-dimethyl-1-butanol instead of 2-cyclopropylethanol and was obtained as a light yellow foam. MS m/e: 566.3 [M]+.

EXAMPLE 31 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tetrahydro-pyran-4-ylmethyl ester

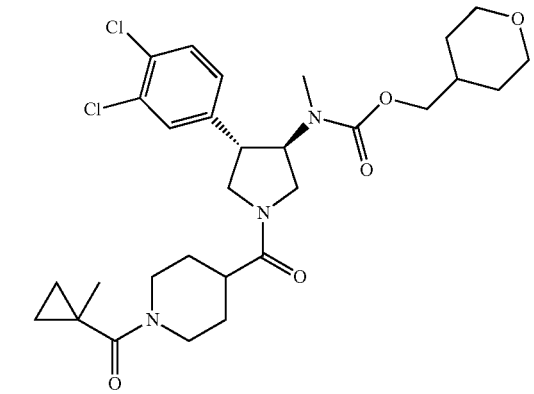 [SMILES: CN(C(=O)OCC1CCOCC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4- dichloro-phenyl)-1-[1-(1-methyl-cyclopropanecarbonyl)-piperidine-4-carbonyl]-pyrrolidin-3-yl}-methyl-carbamic acid tetrahydro-pyran-4-ylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using tetrahydro-2H-pyran-4-ylmethanol instead of 2-cyclopropylethanol and was obtained as a light yellow foam. MS m/e: 580.2 [M]+.

EXAMPLE 32 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentylmethyl ester

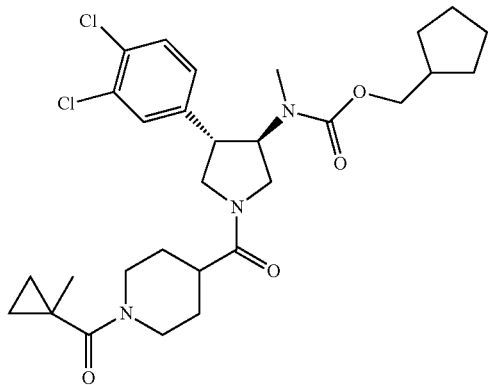 [SMILES: CN(C(=O)OCC1CCCC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid cyclopentylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using cyclopentanemethanol instead of 2-cyclopropylethanol and was obtained as a light yellow foam. MS m/e: 566.3 [M]+.

EXAMPLE 33 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-methyl-oxetan-3-ylmethyl ester

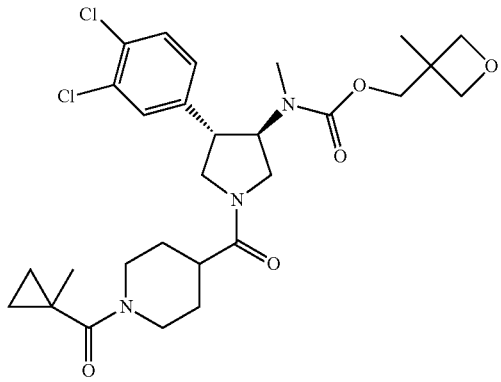 [SMILES: CN(C(=O)OCC1(C)COC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3-methyl-oxetan-3-ylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3-methyl-3-oxetanemethanol instead of 2-cyclopropylethanol and was obtained as a light yellow foam. MS m/e: 566.5 [M]+.

EXAMPLE 34 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester

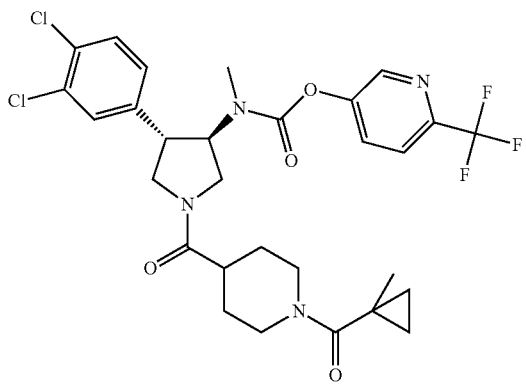 [SMILES: CN(C(=O)Oc1ccc(C(F)(F)F)nc1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 6-(trifluoromethyl)pyridin-3-ol instead of 2-cyclopropylethanol and was obtained as a light brown oil. MS m/e: 627.2 [M]+.

EXAMPLE 35

{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester

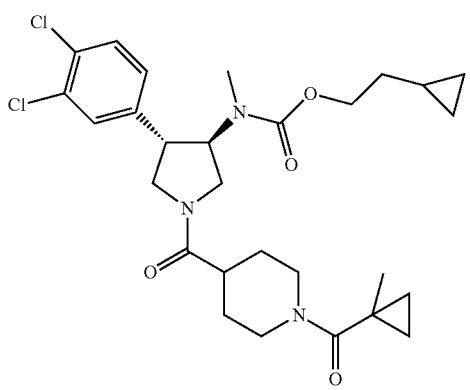

and

EXAMPLE 36

{(3S,4R)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester

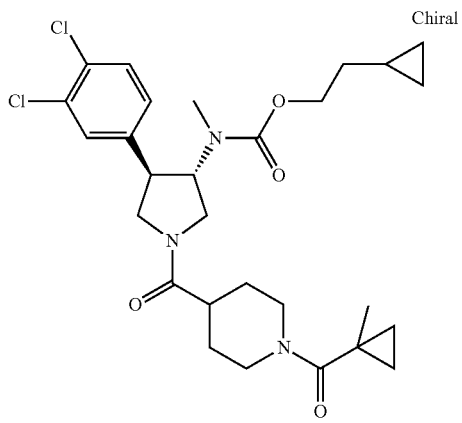 [SMILES: CN(C(=O)OCCC1CC1)[C@@H]1CN(C(=O)C2CCN(C(=O)C3(C)CC3)CC2)C[C@H]1c1ccc(Cl)c(Cl)c1]

rac-[(3R,4S)-1-(1-Cyclopropylmethyl-piperidine-4-carbonyl)-4-(3,4-dichloro-phenyl)-pyrrolidin-3-yl]-methyl-carbamic acid 2-cyclopropyl-ethyl ester was subjected to column chromatography on chiral phase to yield [(3R,4S)-1-(1-cyclopropylmethyl-piperidine-4-carbonyl)-4-(3,4-dichloro-phenyl)-pyrrolidin-3-yl]-methyl-carbamic acid 2-cyclopropyl-ethyl ester (MS (m/e): 550.3 [M]$^+$) as a light brown oil and [(3S,4R)-1-(1-cyclopropylmethyl-piperidine-4-carbonyl)-4-(3,4-dichloro-phenyl)-pyrrolidin-3-yl]-methyl-carbamic acid 2-cyclopropyl-ethyl ester (MS (m/e): 550.3 [M]$^+$) as a light brown oil.

EXAMPLE 37 rac-[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester

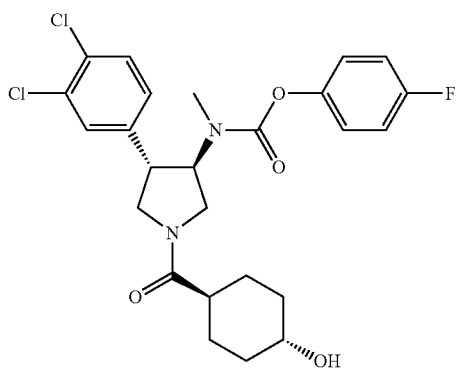 [SMILES: CN(C(=O)Oc1ccc(F)cc1)[C@H]1CN(C(=O)[C@H]2CC[C@H](O)CC2)C[C@@H]1c1ccc(Cl)c(Cl)c1]

a) rac-[(3R,4S)-1-Benzyl-4-(3,4-dichloro-phenyl)-pyrrolidin-3-yl]-methyl-carbamic acid 4-fluoro-phenyl ester In analogy to the procedure described for the synthesis of example 2 (step b), the title compound rac-[(3R,4S)-1-Benzyl-4-(3,4-dichloro-phenyl)-pyrrolidin-3-yl]-methyl-carbamic acid 4-fluoro-phenyl ester was prepared from rac-[(3S,4R)-1-benzyl-4-(3,4-dichloro-phenyl)-pyrrolidin-3-yl]-methyl-amine instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a colorless oil. MS m/e: 473.1 [MH]$^+$.

b) rac-[(3R,4S)-4-(3,4-dichloro-phenyl)-pyrrolidin-3-yl]-methyl-carbamic acid 4-fluoro-phenyl ester In analogy to the procedure described for the synthesis of example 1 (step e), the title compound rac-[(3R,4S)-4-(3,4-dichloro-phenyl)-pyrrolidin-3-yl]-methyl-carbamic acid 4-fluoro-phenyl ester was prepared from rac-[(3R,4S)-1-benzyl-4-(3,4-dichloro-phenyl)-pyrrolidin-3-yl]-methyl-carbamic acid 4-fluoro-phenyl ester instead of rac-[(3R,4S)-1-benzyl-4-(3,4-dichloro-phenyl)-pyrrolidin-3-yl]-methyl-carbamic acid tert-butyl ester and was obtained as a light brown foam. MS m/e: 383.1 [M]$^+$.

c) rac-[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester In analogy to the procedure described for the synthesis of example 1 (step f), the title compound rac-[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-[(3R,4S)-4-(3,4-dichloro-phenyl)-pyrrolidin-3-yl]-methyl-carbamic acid tert-butyl ester using trans-4-hydroxycyclohexanecarboxylic acid instead of 1-(1-methyl-cyclopropanecarbonyl)-piperidine-4-carboxylic acid and was obtained as a light brown oil. MS m/e: 509.3 [M]$^+$.

EXAMPLE 38

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester

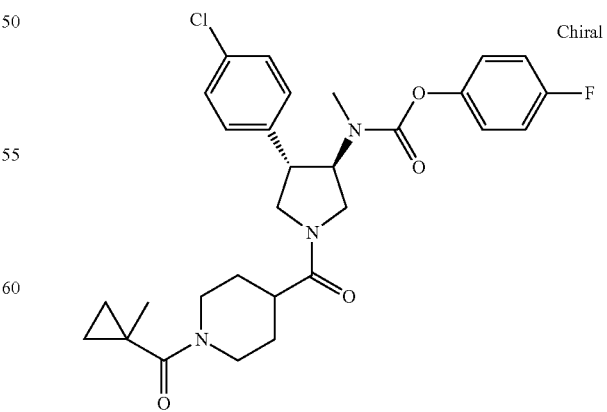

and

EXAMPLE 39

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester

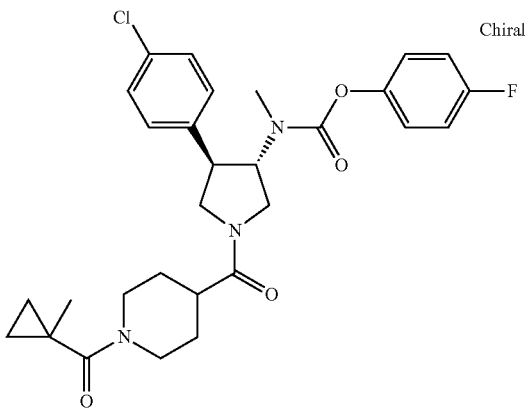 [SMILES: CN(C(=O)Oc1ccc(F)cc1)[C@@H]1CN(C(=O)C2CCN(C(=O)C3(C)CC3)CC2)C[C@H]1c1ccc(Cl)cc1]

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester was subjected to column chromatography on chiral phase to yield {(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 542.2 [M]$^+$) as a white foam and {(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 542.2 [M]$^+$) as a white foam.

EXAMPLE 40 rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

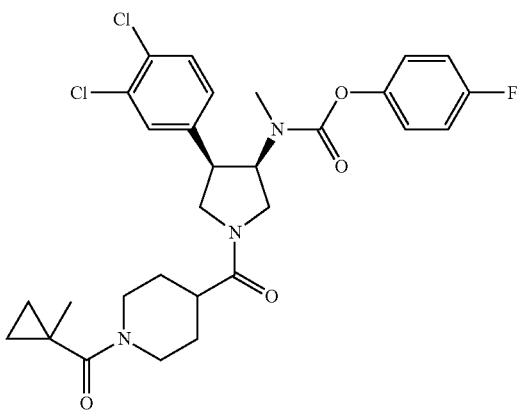 [SMILES: CN(C(=O)Oc1ccc(F)cc1)[C@H]1CN(C(=O)C2CCN(C(=O)C3(C)CC3)CC2)C[C@H]1c1ccc(Cl)c(Cl)c1]

rac-[(3R,4R)-1-Benzyl-4-(3,4-dichloro-phenyl)-pyrrolidin-3-yl]-methyl-amine

In analogy to the procedure described for the synthesis of example 1 (step c), the title compound rac-[(3R,4R)-1-benzyl-4-(3,4-dichloro-phenyl)-pyrrolidin-3-yl]-methyl-amine was prepared from rac-(3R,4R)-1-benzyl-4-(3,4-dichloro-phenyl)-pyrrolidin-3-ylamine instead of rac-(3S,4R)-1-benzyl-4-(3,4-dichloro-phenyl)-pyrrolidin-3-ylamine and was obtained as a light brown oil. MS m/e: 335.2 [M]$^+$.

b) rac-[(3R,4R)-1-Benzyl-4-(3,4-dichloro-phenyl)-pyrrolidin-3-yl]-methyl-carbamic acid tert-butyl ester In analogy to the procedure described for the synthesis of example 1 (step d), the title compound rac-[(3R,4R)-1-benzyl-4-(3,4-dichloro-phenyl)-pyrrolidin-3-yl]-methyl-carbamic acid tert-butyl ester was prepared from rac-[(3R,4R)-1-benzyl-4-(3,4-dichloro-phenyl)-pyrrolidin-3-yl]-methyl-amine instead of rac-[(3R,4S)-1-benzyl-4-(3,4-dichloro-phenyl)-pyrrolidin-3-yl]-methyl-amine and was obtained as a light brown oil. MS m/e: 435.2 [M]$^+$.

c) rac-[(3R,4R)-4-(3,4-Dichloro-phenyl)-pyrrolidin-3-yl]-methyl-carbamic acid tert-butyl ester In analogy to the procedure described for the synthesis of example 1 (step e), the title compound rac-[(3R,4R)-4-(3,4-dichloro-phenyl)-pyrrolidin-3-yl]-methyl-carbamic acid tert-butyl ester was prepared from of rac-[(3R,4R)-1-benzyl-4-(3,4-dichloro-phenyl)-pyrrolidin-3-yl]-methyl-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as a brown oil. MS m/e: 345.1 [M]$^+$.

d) rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester In analogy to the procedure described for the synthesis of example 1 (step f), the title compound rac-{(3R,4R)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester was prepared from rac-[(3R,4RS)-4-(3,4-dichloro-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester and was obtained as a brown oil. MS m/e: 538.3 [M]$^+$.

e) rac-{4-[(3R,4R)-3-(3,4-Dichloro-phenyl)-4-methylamino-pyrrolidine-1-carbonyl]-piperidin-1-yl}-(1-methyl-cyclopropyl)-methanone In analogy to the procedure described for the synthesis of example 2 (step a), the title compound rac-{4-[(3R,4R)-3-(3,4-dichloro-phenyl)-4-methylamino-pyrrolidine-1-carbonyl]-piperidin-1-yl}-(1-methyl-cyclopropyl)-methanone was prepared from rac-{(3R,4R)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a brown oil. MS m/e: 438.2 [M]+.

f) rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester In analogy to the procedure described for the synthesis of example 2 (step b), the title compound rac-{(3R,4R)-4-(3,4- dichloro-phenyl)-1-[1-(1-methyl-cyclopropanecarbonyl)-piperidine-4-carbonyl]-pyrrolidin-3-yl}-methyl-carbamic acid 4-fluoro-phenyl ester was prepared from rac-{4-[(3R,4R)-3-(3,4-dichloro-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a brown oil. MS m/e: 576.3 [M+H]$^+$.

EXAMPLE 41

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester

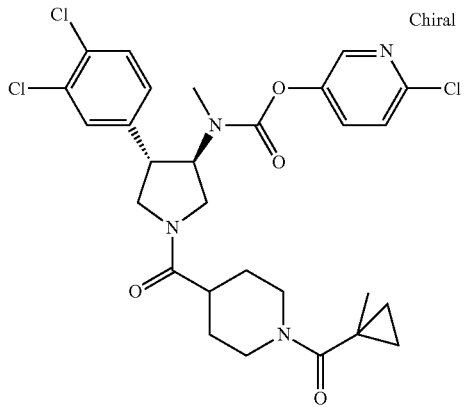 [SMILES: CN(C(=O)Oc1ccc(Cl)nc1)[C@H]1CN(C(=O)C2CCN(C(=O)C3(C)CC3)CC2)C[C@@H]1c1ccc(Cl)c(Cl)c1]

and

EXAMPLE 42

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester

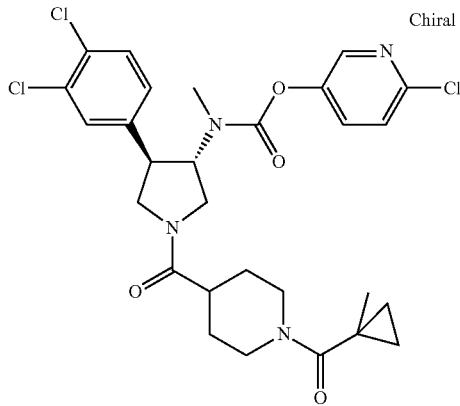 [SMILES: CN(C(=O)Oc1ccc(Cl)nc1)[C@@H]1CN(C(=O)C2CCN(C(=O)C3(C)CC3)CC2)C[C@H]1c1ccc(Cl)c(Cl)c1]

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester was subjected to column chromatography on chiral phase to yield {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester (MS (m/e): 593.2 [M]$^+$) as an off-white foam and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester (MS (m/e): 593.2 [M]$^+$) as an off-white foam.

EXAMPLE 43 rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid 4-fluoro-phenyl ester

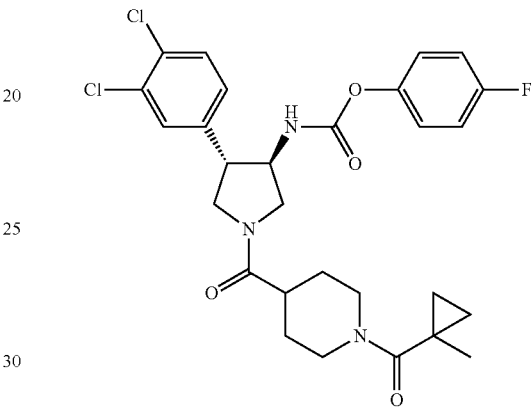

a) rac-[(3R,4S)-1-Benzyl-4-(3,4-dichloro-phenyl)-pyrrolidin-3-yl]-carbamic acid tert-butyl ester To a solution of rac-(3S,4R)-1-benzyl-4-(3,4-dichloro-phenyl)-pyrrolidin-3-ylamine (30.64 g, 0.095 mol) in dichloromethane (300 mL) was added N,N-diisopropyl ethyl amine (32.65 mL, 0.191 mol) and 4-dimethylaminopyridine (1.17 g, 0.010 mol). The reaction mixture was cooled to 0° C. and di-tert.-butyl-dicarbonate (24.98 g; 0.114 mol) was added in 2 portions. After stirring 2 h at this temperature the solution was stirred at ambient temperature for 18 h. The resulting mixture was concentrated and purification by chromatography (SiO$_2$, heptane:ethyl acetate=75:25) afforded the title compound (5.82 g, 14%) as a light yellow solid. MS m/e: 421.1 [M]$^+$.

b) rac-[(3R,4S)-4-(3,4-Dichloro-phenyl)-pyrrolidin-3-yl]-carbamic acid tert-butyl ester In analogy to the procedure described for the synthesis of example 1 (step e), the title compound rac-[(3R,4S)-4-(3,4-dichloro-phenyl)-pyrrolidin-3-yl]-carbamic acid tert-butyl ester was prepared from rac-[(3R,4S)-1-benzyl-4-(3,4-dichloro-phenyl)-pyrrolidin-3-yl]-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as a light brown solid. MS m/e: 331.1 [M+H]$^+$.

c) rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid tert-butyl ester In analogy to the procedure described for the synthesis of example 1 (step f), the title compound rac-{(3R,4S)-4-(3,4-

Dichloro-phenyl)-1-[1-(1-methyl-cyclopropanecarbonyl)-piperidine-4-carbonyl]-pyrrolidin-3-yl}-carbamic acid tert-butyl ester was prepared from rac-[(3R,4S)-4-(3,4-dichloro-phenyl)-pyrrolidin-3-yl]-carbamic acid tert-butyl ester instead of rac-[(3R,4S)-4-(3,4-dichloro-phenyl)-pyrrolidin-3-yl]-methyl-carbamic acid tert-butyl ester and was obtained as a light brown foam. MS m/e: 524.1 [M]+.

d) rac-{4-[(3R,4S)-3-Amino-4-(3,4-dichloro-phenyl)-pyrrolidine-1-carbonyl]-piperidin-1-yl}-(1-methyl-cyclopropyl)-methanone In analogy to the procedure described for the synthesis of example 2 (step a), the title compound rac-{4-[(3R,4S)-3-Amino-4-(3,4-dichloro-phenyl)-pyrrolidine-1-carbonyl]-piperidin-1-yl}-(1-methyl-cyclopropyl)-methanone was prepared from rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light brown foam. MS m/e: 424.2 [M+H]+.

e) rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid 4-fluoro-phenyl ester In analogy to the procedure described for the synthesis of example 2 (step b), the title compound rac-{(3R,4S)-4-(3,4-dichloro-phenyl)-1-[1-(1-methyl-cyclopropanecarbonyl)-piperidine-4-carbonyl]-pyrrolidin-3-yl}-carbamic acid 4-fluoro-phenyl ester was prepared from rac-{4-[(3R,4S)-3-Amino-4-(3,4-dichloro-phenyl)-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a light yellow foam. MS m/e: 562.0 [M]+.

EXAMPLE 44 rac-[(3R,4S)-4-(3,4-Dichloro-phenyl)-1-(tetrahydro-pyran-4-carbonyl)-pyrrolidin-3-yl]-methyl-carbamic acid 4-fluoro-phenyl ester

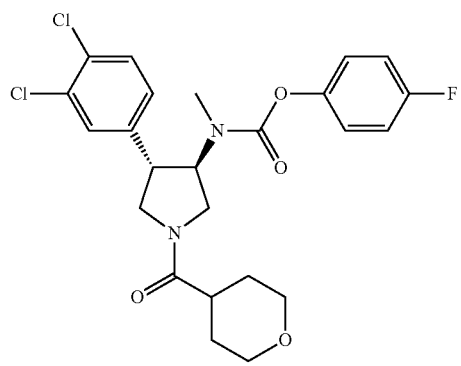 [SMILES: CN(C(=O)Oc1ccc(F)cc1)[C@H]1CN(C(=O)C2CCOCC2)C[C@@H]1c1ccc(Cl)c(Cl)c1]

a) rac-(3R,4S)-1-Benzyl-4-(3,4-dichloro-phenyl)-pyrrolidin-3-yl]-methyl-carbamic acid 4-fluoro-phenyl ester In analogy to the procedure described for the synthesis of example 2 (step b), the title compound rac-(3R,4S)-1-benzyl-4-(3,4-dichloro-phenyl)-pyrrolidin-3-yl]-methyl-carbamic acid 4-fluoro-phenyl ester was prepared from rac-[(3S,4R)-1-benzyl-4-(3,4-dichloro-phenyl)-pyrrolidin-3-yl]-methyl-amine instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a colorless oil. MS m/e: 473.1 [M]+.

b) rac-[(3R,4S)-4-(3,4-Dichloro-phenyl)-pyrrolidin-3-yl]-methyl-carbamic acid 4-fluoro-phenyl ester In analogy to the procedure described for the synthesis of example 1 (step e), the title compound rac-[(3R,4S)-4-(3,4-dichloro-phenyl)-pyrrolidin-3-yl]-methyl-carbamic acid 4-fluoro-phenyl ester was prepared from rac-(3R,4S)-1-benzyl-4-(3,4-dichloro-phenyl)-pyrrolidin-3-yl]-methyl-carbamic acid 4-fluoro-phenyl ester instead of rac-[(3R,4S)-1-benzyl-4-(3,4-dichloro-phenyl)-pyrrolidin-3-yl]-methyl-carbamic acid tert-butyl ester and was obtained as a light brown foam. MS m/e: 383.1 [M]+.

c) rac-[(3R,4S)-4-(3,4-Dichloro-phenyl)-1-(tetrahydro-pyran-4-carbonyl)-pyrrolidin-3-yl]-methyl-carbamic acid 4-fluoro-phenyl ester To a solution of tetrahydropyran-4-yl-carboxylic acid (51 mg, 0.39 mmol) in DMF (1 mL) was added ambient temperature 2-(1H-benzotriazole-1-yl)-1,1,3,3-tetramethyluronium tetrafluoroborate (114 mg, 0.36 mmol) and N,N-diisopropyl ethyl amine (125 mg, 0.97 mmol). After stirring for 15 min at this temperature a solution of rac-[(3R,4S)-4-(3,4-dichloro-phenyl)-pyrrolidin-3-yl]-methyl-carbamic acid 4-fluoro-phenyl ester (124 mg, 0.32 mol) in DMF (1 mL) was added and stirred for 20 h at ambient temperature. The reaction mixture was diluted with ethyl acetate (10 mL) and washed with aqueous sodium carbonate (1 M, 10 mL), water (10 mL) and brine (10 mL). The aqueous layers were extracted with ethyl acetate (10 mL) and the combined organic layers were dried over sodium sulfate and concentrated. Purification by chromatography (SiO$_2$, ethyl acetate:methanol=98:2 to 85:15) afforded the title compound (92 mg, 57%) as a white oil. MS m/e: 495.3 [M]+.

EXAMPLE 45

[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester

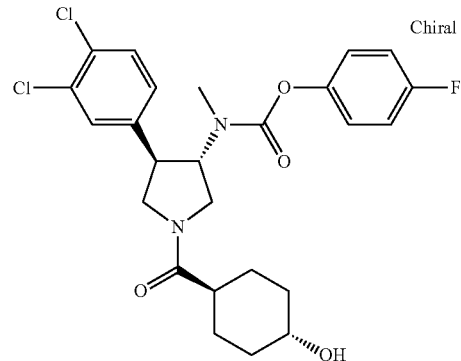 [SMILES: CN(C(=O)Oc1ccc(F)cc1)[C@@H]1CN(C(=O)[C@H]2CC[C@H](O)CC2)C[C@H]1c1ccc(Cl)c(Cl)c1]

and

EXAMPLE 46

[(3S,4R)-4-(3,4-Dichloro-phenyl)-1-(trans-4-hydroxy-cyclohexanecarbonyl)-pyrrolidin-3-yl]-methyl-carbamic acid 4-fluoro-phenyl ester

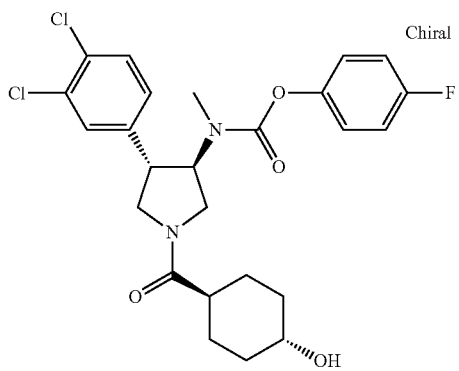 [SMILES: CN(C(=O)Oc1ccc(F)cc1)[C@H]1CN(C(=O)[C@H]2CC[C@H](O)CC2)C[C@@H]1c1ccc(Cl)c(Cl)c1]

rac-[(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester was subjected to column chromatography on chiral phase to yield [(3R,4S)-4-(3,4-Dichloro-phenyl)-1-(trans-4-hydroxy-cyclohexanecarbonyl)-pyrrolidin-3-yl]-methyl-carbamic acid 4-fluoro-phenyl ester (MS (m/e): 509.3 [M]$^+$) as an off-white foam and [(3S,4R)-4-(3,4-Dichloro-phenyl)-1-(trans-4-hydroxy-cyclohexanecarbonyl)-pyrrolidin-3-yl]-methyl-carbamic acid 4-fluoro-phenyl ester (MS (m/e): 509.3 [M]$^+$) as an off-white foam.

EXAMPLE 47 rac-[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester

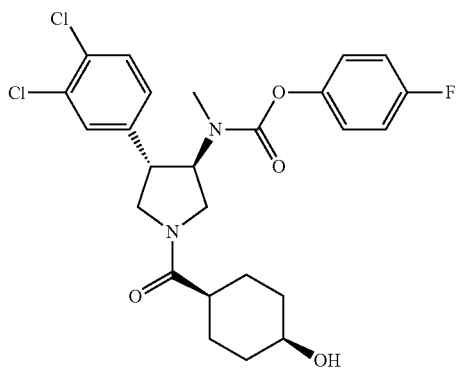 [SMILES: CN(C(=O)Oc1ccc(F)cc1)[C@H]1CN(C(=O)[C@H]2CC[C@@H](O)CC2)C[C@@H]1c1ccc(Cl)c(Cl)c1]

In analogy to the procedure described for the synthesis of example 44 (step c), the title compound rac-[(3R,4S)-4-(3,4-dichloro-phenyl)-1-(cis-4-hydroxy-cyclohexanecarbonyl)-pyrrolidin-3-yl]-methyl-carbamic acid 4-fluoro-phenyl ester was prepared from rac-[(3R,4S)-4-(3,4-Dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cis-4-hydroxycyclohexanecarboxylic acid instead of 1-methylcyclopropane-1-carboxylic acid and was obtained as a an off-white foam. MS m/e: 509.2 [M]$^+$.

EXAMPLE 48 rac-[(3R,4S)-4-(3,4-Dichloro-phenyl)-1-(morpholine-4-carbonyl)-pyrrolidin-3-yl]-methyl-carbamic acid 4-fluoro-phenyl ester

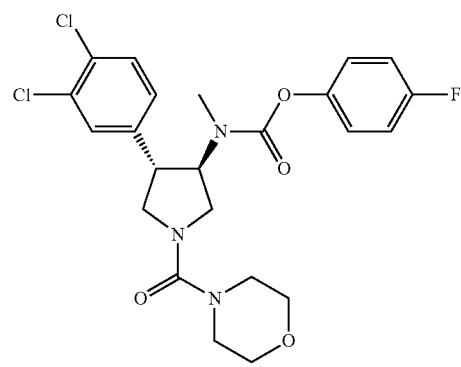 [SMILES: CN(C(=O)Oc1ccc(F)cc1)[C@H]1CN(C(=O)N2CCOCC2)C[C@@H]1c1ccc(Cl)c(Cl)c1]

In analogy to the procedure described for the synthesis of example 2 (step b), the title compound rac-[(3R,4S)-4-(3,4-dichloro-phenyl)-1-(morpholine-4-carbonyl)-pyrrolidin-3-yl]-methyl-carbamic acid 4-fluoro-phenyl ester was prepared from rac-[(3R,4S)-4-(3,4-Dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using morpholin-4-carbonyl chloride instead of fluorophenyl chloroformate and was obtained as a colorless oil. MS m/e: 496.2 [M]$^+$.

EXAMPLE 49 rac-[(3R,4S)-4-(3,4-Dichloro-phenyl)-1-(cis-4-methoxy-cyclohexanecarbonyl)-pyrrolidin-3-yl]-methyl-carbamic acid 4-fluoro-phenyl ester

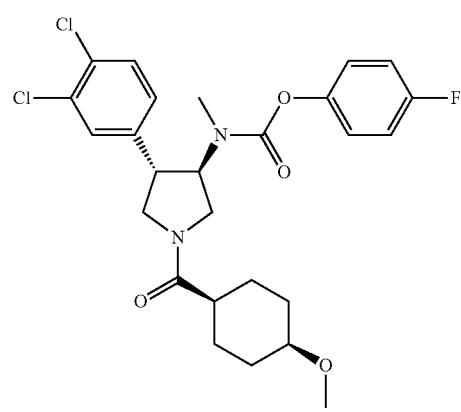 [SMILES: CO[C@H]1CC[C@@H](C(=O)N2C[C@H](c3ccc(Cl)c(Cl)c3)[C@@H](N(C)C(=O)Oc3ccc(F)cc3)C2)CC1]

In analogy to the procedure described for the synthesis of example 44 (step c), the title compound rac-[(3R,4S)-4-(3,4-dichloro-phenyl)-1-(cis-4-methoxy-cyclohexanecarbonyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cis-4-methoxycyclohexanecarboxylic acid instead of 1-methylcyclopropane-1-carboxylic acid and was obtained as a light yellow oil. MS m/e: 523.4 [M]+.

EXAMPLE 50

[(3R,4S)-4-(3,4-Dichloro-phenyl)-1-(tetrahydro-pyran-4-carbonyl)-pyrrolidin-3-yl]-methyl-carbamic acid 4-fluoro-phenyl ester

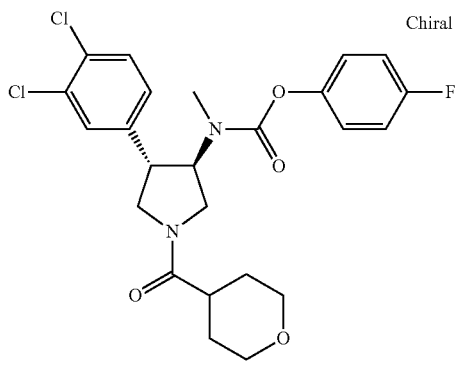 [SMILES: CN(C(=O)Oc1ccc(F)cc1)[C@H]1CN(C(=O)C2CCOCC2)C[C@@H]1c1ccc(Cl)c(Cl)c1]

and

EXAMPLE 51

[(3S,4R)-4-(3,4-Dichloro-phenyl)-1-(tetrahydro-pyran-4-carbonyl)-pyrrolidin-3-yl]-methyl-carbamic acid 4-fluoro-phenyl ester

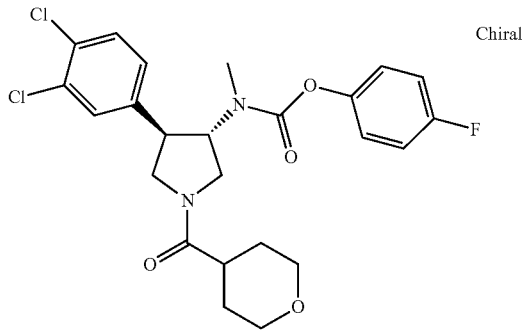 [SMILES: CN(C(=O)Oc1ccc(F)cc1)[C@@H]1CN(C(=O)C2CCOCC2)C[C@H]1c1ccc(Cl)c(Cl)c1]

rac-[(3R,4S)-4-(3,4-Dichloro-phenyl)-1-(tetrahydro-pyran-4-carbonyl)-pyrrolidin-3-yl]-methyl-carbamic acid 4-fluoro-phenyl ester was subjected to column chromatography on chiral phase to yield [(3R,4S)-4-(3,4-dichloro-phenyl)-1-(tetrahydro-pyran-4-carbonyl)-pyrrolidin-3-yl]-methyl-carbamic acid 4-fluoro-phenyl ester (MS (m/e): 495.2 [M]+) as an off-white foam and [(3S,4R)-4-(3,4-dichloro-phenyl)-1-(tetrahydro-pyran-4-carbonyl)-pyrrolidin-3-yl]-methyl-carbamic acid 4-fluoro-phenyl ester (MS (m/e): 495.2 [M]+) as an off-white foam.

EXAMPLE 52 rac-[(3R,4S)-4-(3,4-Dichloro-phenyl)-1-(trans-4-hydroxy-4-methyl-cyclohexanecarbonyl)-pyrrolidin-3-yl]-methyl-carbamic acid 4-fluoro-phenyl ester

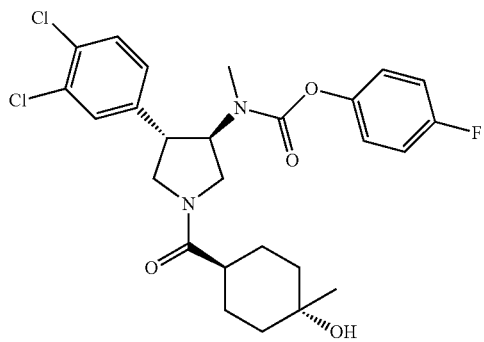 [SMILES: CN(C(=O)Oc1ccc(F)cc1)[C@H]1CN(C(=O)[C@H]2CC[C@](C)(O)CC2)C[C@@H]1c1ccc(Cl)c(Cl)c1]

In analogy to the procedure described for the synthesis of example 44 (step c), the title compound rac-[(3R,4S)-4-(3,4-dichloro-phenyl)-1-(trans-4-hydroxy-4-methyl-cyclohexanecarbonyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using trans-4-hydroxy-4-methyl-cyclohexanecarboxylic acid instead of 1-methylcyclopropane-1-carboxylic acid and was obtained as an off-white foam. MS m/e: 523.3 [M]+.

EXAMPLE 53 rac-[(3R,4S)-4-(3,4-Dichloro-phenyl)-1-(cis-4-hydroxy-4-methyl-cyclohexanecarbonyl)-pyrrolidin-3-yl]-methyl-carbamic acid 4-fluoro-phenyl ester

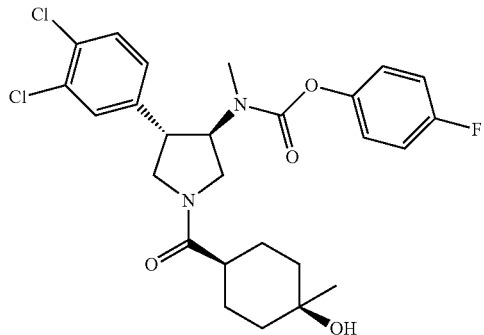 [SMILES: CN(C(=O)Oc1ccc(F)cc1)[C@H]1CN(C(=O)[C@H]2CC[C@@](C)(O)CC2)C[C@@H]1c1ccc(Cl)c(Cl)c1]

In analogy to the procedure described for the synthesis of example 44 (step c), the title compound rac-[(3R,4S)-4-(3,4-dichloro-phenyl)-1-(ciss-4-hydroxy-4-methyl-cyclohexanecarbonyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cis-4-hydroxy-4-methyl-cyclohexanecarboxylic acid instead

EXAMPLE 54 rac-{(3R,4S)-4-(4-Chloro-phenyl)-1-[1-(1-methyl-cyclopropane carbonyl)-piperidine-4-carbonyl]-pyrrolidin-3-yl}-methyl-carbamic acid 2-cyclopropyl-ethyl ester In analogy to the procedure described for the synthesis of example 25, the title compound rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester was prepared from rac-{4-[(3S,4R)-3-(4-chloro-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as an off-white foam. MS m/e: 516.3 [M]+.

EXAMPLE 55 rac-[(3R,4S)-1-(3-Carbamoyl-propionyl)-4-(3,4-dichloro-phenyl)-pyrrolidin-3-yl]-methyl-carbamic acid 4-fluoro-phenyl ester

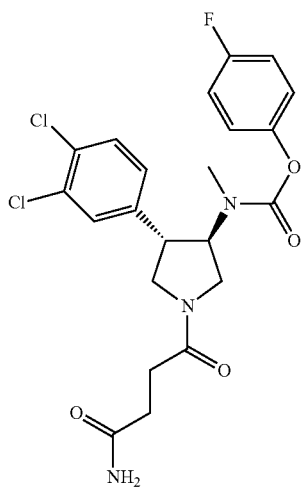 [SMILES: CN(C(=O)Oc1ccc(F)cc1)[C@H]1CN(C(=O)CCC(N)=O)C[C@@H]1c1ccc(Cl)c(Cl)c1]

In analogy to the procedure described for the synthesis of example 44 (step c), the title compound rac-[(3R,4S)-1-(3-carbamoyl-propionyl)-4-(3,4-dichloro-phenyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using succinamic acid instead of 1-methylcyclopropane-1-carboxylic acid and was obtained as a colorless oil. MS m/e: 465.1 [M]+.

EXAMPLE 56 rac-{(3R,4S)-4-(3,4-Dichloro-phenyl)-1-[3-(2-oxo-pyrrolidin-1-yl)-propionyl]-pyrrolidin-3-yl}-methyl-carbamic acid 4-fluoro-phenyl ester

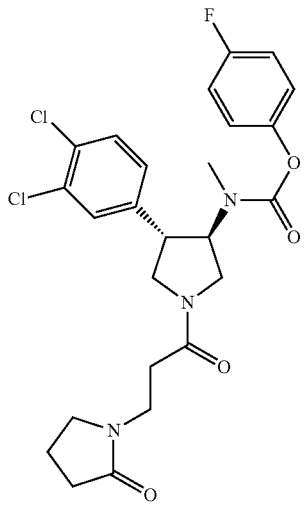 [SMILES: CN(C(=O)Oc1ccc(F)cc1)[C@H]1CN(C(=O)CCN2CCCC2=O)C[C@@H]1c1ccc(Cl)c(Cl)c1]

In analogy to the procedure described for the synthesis of example 44 (step c), the title compound rac-{(3R,4S)-4-(3,4-dichloro-phenyl)-1-[3-(2-oxo-pyrrolidin-1-yl)-propionyl]-pyrrolidin-3-yl}-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3-(2-oxo-pyrrolidin-1-yl)-propionic acid instead of 1-methylcyclopropane-1-carboxylic acid and was obtained as a colorless oil. MS m/e: 522.2 [M]+.

EXAMPLE 57 rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-methyl-cyclohexyl ester

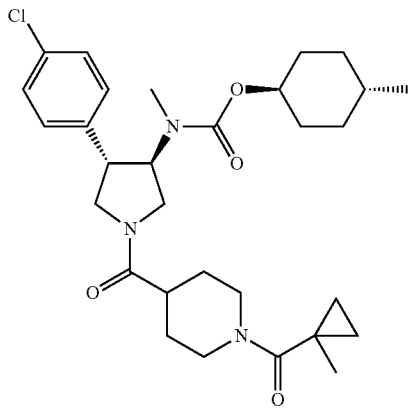 [SMILES: CN(C(=O)O[C@H]1CC[C@H](C)CC1)[C@H]1CN(C(=O)C2CCN(C(=O)C3(C)CC3)CC2)C[C@@H]1c1ccc(Cl)cc1]

In analogy to the procedure described for the synthesis of example 25, the title compound rac-{(3R,4S)-4-(4-chloro-phenyl)-1-[1-(1-methyl-cyclopropanecarbonyl)-piperidine-4-carbonyl]-pyrrolidin-3-yl}-methyl-carbamic acid 4-methyl-cyclohexyl ester was prepared from rac-{4-[(3S,4R)-3-(4-chloro-phenyl)-4-methylamino-pyrrolidine-1-carbonyl]- piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using trans-4-methylcyclohexanol instead of 2-cyclopropylethanol and was obtained as an off-white foam. MS m/e: 544.3 [M]⁺.

EXAMPLE 58 rac-1-{(3R,4S)-4-(4-Chloro-phenyl)-1-[1-(1-methyl-cyclopropanecarbonyl)-piperidine-4-carbonyl]-pyrrolidin-3-yl}-3-(2-cyclopropyl-ethyl)-1-methyl-urea

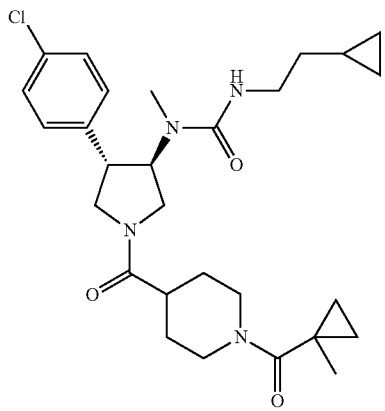 [SMILES: CN(C(=O)NCCC1CC1)[C@H]1CN(C(=O)C2CCN(C(=O)C3(C)CC3)CC2)C[C@@H]1c1ccc(Cl)cc1]

In analogy to the procedure described for the synthesis of example 25, the title compound rac-1-{(3R,4S)-4-(4-chloro-phenyl)-1-[1-(1-methyl-cyclopropanecarbonyl)-piperidine-4-carbonyl]-pyrrolidin-3-yl}-3-(2-cyclopropyl-ethyl)-1-methyl-urea was prepared from rac-{4-[(3S,4R)-3-(4-chloro-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2-cyclopropyl ethyl amine instead of 2-cyclopropylethanol and was obtained as an off-white foam. MS m/e: 515.4 [M]⁺.

EXAMPLE 59

[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester

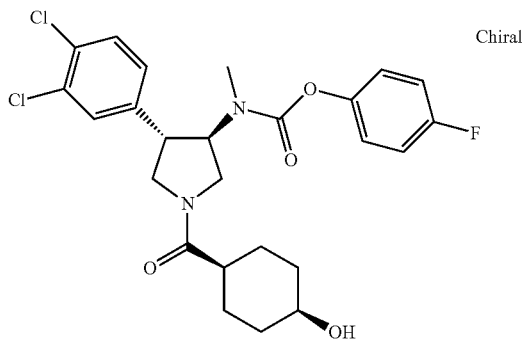 [SMILES: CN(C(=O)Oc1ccc(F)cc1)[C@H]1CN(C(=O)[C@H]2CC[C@@H](O)CC2)C[C@@H]1c1ccc(Cl)c(Cl)c1]

and

EXAMPLE 60

[(3S,4R)-4-(3,4-Dichloro-phenyl)-1-(cis-4-hydroxy-cyclohexanecarbonyl)-pyrrolidin-3-yl]-methyl-carbamic acid 4-fluoro-phenyl ester

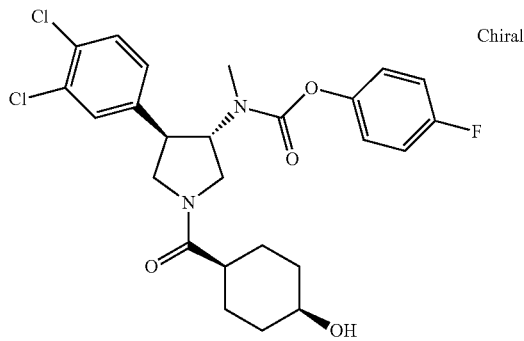 [SMILES: CN(C(=O)Oc1ccc(F)cc1)[C@@H]1CN(C(=O)[C@H]2CC[C@@H](O)CC2)C[C@H]1c1ccc(Cl)c(Cl)c1]

rac-[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester was subjected to column chromatography on chiral phase to yield [(3R,4S)-4-(3,4-dichloro-phenyl)-1-(cis-4-hydroxy-cyclohexanecarbonyl)-pyrrolidin-3-yl]-methyl-carbamic acid 4-fluoro-phenyl ester (MS (m/e): 509.3 [M]⁺) as an off-white foam and [(3S,4R)-4-(3,4-dichloro-phenyl)-1-(cis-4-hydroxy-cyclohexanecarbonyl)-pyrrolidin-3-yl]-methyl-carbamic acid 4-fluoro-phenyl ester (MS (m/e): 509.3 [M]⁺) as an off-white foam.

EXAMPLE 61

{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

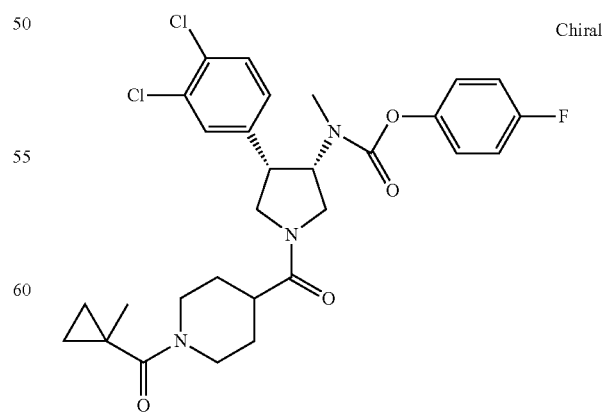

and

EXAMPLE 62

{(3S,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester

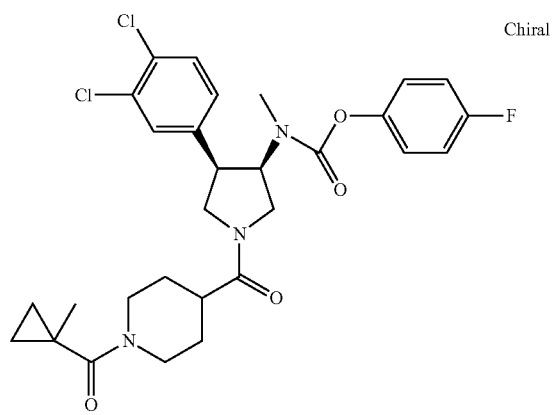 [SMILES: CN(C(=O)Oc1ccc(F)cc1)[C@H]1CN(C(=O)C2CCN(C(=O)C3(C)CC3)CC2)C[C@H]1c1ccc(Cl)c(Cl)c1]

rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester was subjected to column chromatography on chiral phase to yield {(3R,4R)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 576.2 [M]$^+$) as a light brown oil and {(3S,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 576.2 [M]$^+$) as a light brown oil.

EXAMPLE 63 rac-{(3R,4S)-4-(4-Chloro-phenyl)-1-[1-(1-methyl-cyclopropane carbonyl)-piperidine-4-carbonyl]-pyrrolidin-3-yl}-methyl-carbamic acid 2-cyclopropyl-ethyl ester

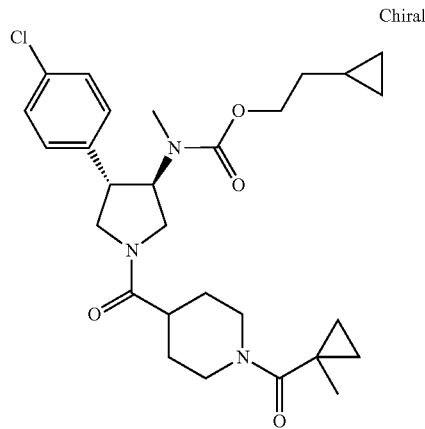 [SMILES: CN(C(=O)OCCC1CC1)[C@H]1CN(C(=O)C2CCN(C(=O)C3(C)CC3)CC2)C[C@@H]1c1ccc(Cl)cc1]

and

EXAMPLE 64 rac-{(3R,4S)-4-(4-Chloro-phenyl)-1-[1-(1-methyl-cyclopropane carbonyl)-piperidine-4-carbonyl]-pyrrolidin-3-yl}-methyl-carbamic acid 2-cyclopropyl-ethyl ester

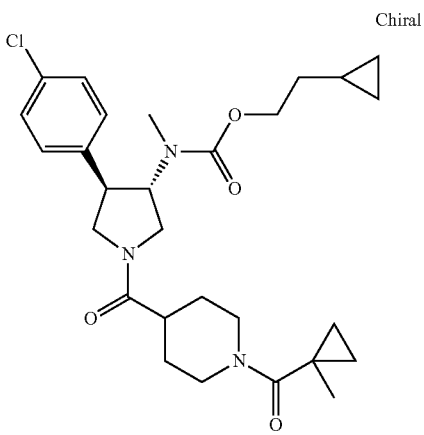 [SMILES: CN(C(=O)OCCC1CC1)[C@@H]1CN(C(=O)C2CCN(C(=O)C3(C)CC3)CC2)C[C@H]1c1ccc(Cl)cc1]

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester was subjected to column chromatography on chiral phase to yield {(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester (MS (m/e): 516.3 [M]$^+$) as an off-white foam and {(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester (MS (m/e): 516.3 [M]$^+$) as an off-white foam.

EXAMPLE 65 rac-[(3R,4S)-1-(1-Acetyl-piperidine-4-carbonyl)-4-(3,4-dichloro-phenyl)-pyrrolidin-3-yl]-methyl-carbamic acid 4-fluoro-phenyl ester

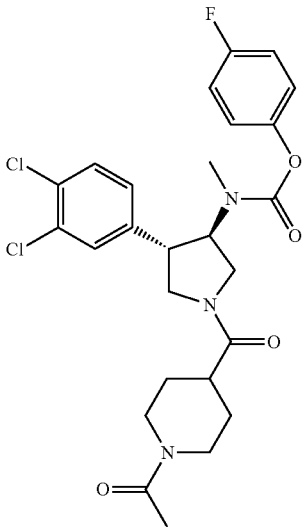 [SMILES: CC(=O)N1CCC(C(=O)N2C[C@H](c3ccc(Cl)c(Cl)c3)[C@@H](N(C)C(=O)Oc3ccc(F)cc3)C2)CC1]

In analogy to the procedure described for the synthesis of example 44 (step c), the title compound rac-[(3R,4S)-1-(1- acetyl-piperidine-4-carbonyl)-4-(3,4-dichloro-phenyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester using 1-acetylpiperidine-4-carboxylic acid instead of 1-methylcyclopropane-1-carboxylic acid and was obtained as a brown oil. MS m/e: 536.1 [M]$^+$.

EXAMPLE 66 rac-4-{(3S,4R)-3-(3,4-Dichloro-phenyl)-4-[(4-fluoro-phenoxycarbonyl)-methyl-amino]-pyrrolidine-1-carbonyl}-piperidine-1-carboxylic acid tert-butyl ester

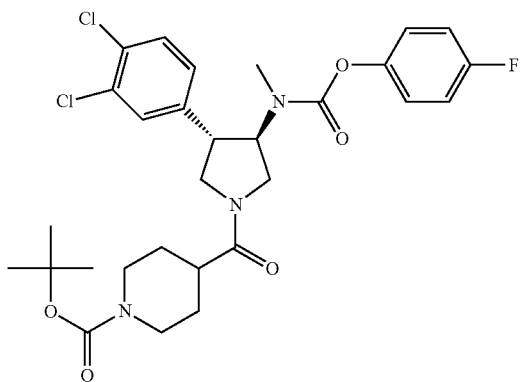 [SMILES: CN(C(=O)Oc1ccc(F)cc1)[C@H]1CN(C(=O)C2CCN(C(=O)OC(C)(C)C)CC2)C[C@@H]1c1ccc(Cl)c(Cl)c1]

In analogy to the procedure described for the synthesis of example 44 (step c), the title compound rac-4-{(3S,4R)-3-(3,4-dichloro-phenyl)-4-[(4-fluoro-phenoxycarbonyl)-methyl-amino]-pyrrolidine-1-carbonyl}-piperidine-1-carboxylic acid tert-butyl ester was prepared from rac-[(3R,4S)-4-(3,4-dichloro-phenyl)-pyrrolidin-3-yl]-methyl-carbamic acid 4-fluoro-phenyl ester using piperidine-1,4-dicarboxylic acid mono-tert-butyl ester instead of 1-methylcyclopropane-1-carboxylic acid and was obtained as a yellow foam. MS m/e: 593.1 [M]$^+$.

EXAMPLE 67 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester

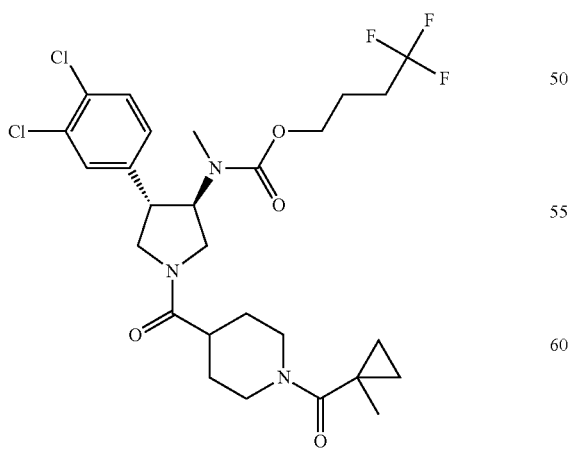

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,4-trifluorobutanol instead of 2-cyclopropylethanol and was obtained as an off-white foam. MS m/e: 592.3 [M]$^+$.

EXAMPLE 68

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester

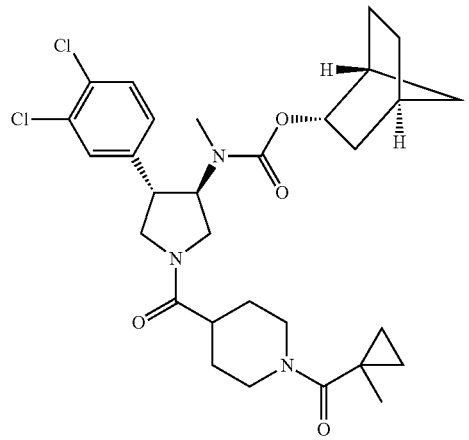 [SMILES: CN(C(=O)O[C@H]1C[C@H]2CC[C@@H]1C2)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compounds {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester and {(3S,4R)-4-(3,4-dichloro-phenyl)-1-[1-(1-methyl-cyclopropane carbonyl)-piperidine-4-carbonyl]-pyrrolidin-3-yl}-methyl-carbamic acid (1R,2S,4S)-bicyclo[2.2.1]hept-2-yl ester were prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using endo-norborneol instead of 2-cyclopropylethanol and were obtained as an off-white foam. MS m/e: 576.3 [M]$^+$.

EXAMPLE 69

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester

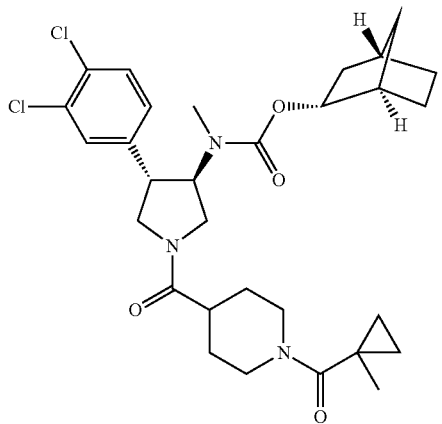 [SMILES: CN(C(=O)O[C@@H]1C[C@H]2CC[C@@H]1C2)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compounds {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester were prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using exo-norborneol instead of 2-cyclopropylethanol and were obtained as an off-white foam. MS m/e: 576.3 [M]$^+$.

EXAMPLE 70 rac-{(3R,4S)-4-(3-Chloro-4-methyl-phenyl)-1-[1-(1-methyl-cyclopropanecarbonyl)-piperidine-4-carbonyl]-pyrrolidin-3-yl}-methyl-carbamic acid 4-fluoro-phenyl ester

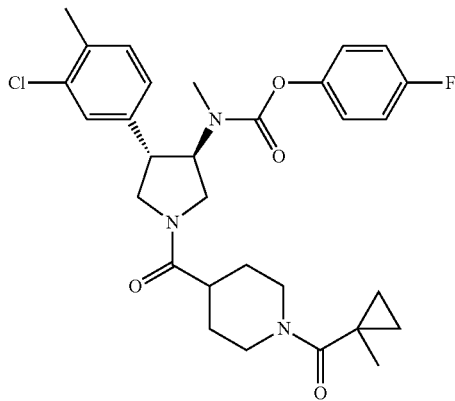 [SMILES: Cc1ccc([C@H]2CN(C(=O)C3CCN(C(=O)C4(C)CC4)CC3)C[C@@H]2N(C)C(=O)Oc2ccc(F)cc2)cc1Cl]

a) rac-(3S,4R)-1-Benzyl-3-(3-chloro-4-methyl-phenyl)-4-nitro-pyrrolidine

In analogy to the procedure described for the synthesis of example 1 (step a), the title compound rac-(3S,4R)-1-benzyl-3-(3-chloro-4-methyl-phenyl)-4-nitro-pyrrolidine was prepared from 2-chloro-1-methyl-4-((E)-2-nitro-vinyl)-benzene instead of 1,2-dichloro-4-((E)-2-nitro-vinyl)-benzene and was obtained as a light green oil. MS m/e: 331.1 [M]$^+$.

b) rac-(3R,4S)-1-Benzyl-4-(3-chloro-4-methyl-phenyl)-pyrrolidin-3-ylamine

In analogy to the procedure described for the synthesis of example 1 (step b), the title compound rac-(3R,4S)-1-benzyl-4-(3-chloro-4-methyl-phenyl)-pyrrolidin-3-ylamine was prepared from rac-(3S,4R)-1-benzyl-3-(3-chloro-4-methyl-phenyl)-4-nitro-pyrrolidine instead of rac-(3R,4S)-1-Benzyl-3-(3,4-dichloro-phenyl)-4-nitro-pyrrolidine and was obtained as a light brown oil. MS m/e: 301.2 [M+H]$^+$.

c) rac-[(3R,4S)-1-Benzyl-4-(3-chloro-4-methyl-phenyl)-pyrrolidin-3-yl]-methyl-amine In analogy to the procedure described for the synthesis of example 1 (step c), the title compound rac-[(3R,4S)-1-benzyl-4-(3-chloro-4-methyl-phenyl)-pyrrolidin-3-yl]-methyl-amine was prepared from rac-(3R,4S)-1-benzyl-4-(3-chloro-4-methyl-phenyl)-pyrrolidin-3-ylamine instead of rac-(3S,4R)-1-benzyl-4-(3,4-dichloro-phenyl)-pyrrolidin-3-ylamine and was obtained as a colorless oil. MS m/e: 315.1 [M+H]$^+$.

d) rac-[(3R,4S)-1-Benzyl-4-(3-chloro-4-methyl-phenyl)-pyrrolidin-3-yl]-methyl-carbamic acid tert-butyl ester In analogy to the procedure described for the synthesis of example 1 (step d), the title compound rac-[(3R,4S)-1-benzyl-4-(3-chloro-4-methyl-phenyl)-pyrrolidin-3-yl]-methyl-carbamic acid tert-butyl ester was prepared from rac-[(3R,4S)-1-benzyl-4-(3-chloro-4-methyl-phenyl)-pyrrolidin-3-yl]-methyl-amine instead of rac-[(3R,4S)-1-benzyl-4-(3,4-dichloro-phenyl)-pyrrolidin-3-yl]-methyl-amine and was obtained as a light yellow oil. MS m/e: 415.3 [M+H]$^+$.

e) rac-[(3R,4S)-4-(3-Chloro-4-methyl-phenyl)-pyrrolidin-3-yl]-methyl-carbamic acid tert-butyl ester In analogy to the procedure described for the synthesis of example 1 (step e), the title compound rac-[(3R,4S)-4-(3-chloro-4-methyl-phenyl)-pyrrolidin-3-yl]-methyl-carbamic acid tert-butyl ester was prepared from rac-[(3R,4S)-1-benzyl-4-(3-chloro-4-methyl-phenyl)-pyrrolidin-3-yl]-methyl-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as a brown foam. MS m/e: 271.3 [M+-tBu+H]$^+$.

f) rac-{(3R,4S)-4-(3-Chloro-4-methyl-phenyl)-1-[1-(1-methyl-cyclopropanecarbonyl)-piperidine-4-carbonyl]-pyrrolidin-3-yl}-methyl-carbamic acid tert-butyl ester In analogy to the procedure described for the synthesis of example 1 (step f), the title compound rac-{(3R,4S)-4-(3-chloro-4-methyl-phenyl)-1-[1-(1-methyl-cyclopropanecarbonyl)-piperidine-4-carbonyl]-pyrrolidin-3-yl}-methyl-carbamic acid tert-butyl ester was prepared from rac-[(3R,4S)-4-(3-chloro-4-methyl-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester and was obtained as a yellow oil. MS m/e: 518.3 [M]⁺.

g) rac-{4-[(3S,4R)-3-(3-Chloro-4-methyl-phenyl)-4-methylamino-pyrrolidine-1-carbonyl]-piperidin-1-yl}-(1-methyl-cyclopropyl)-methanone In analogy to the procedure described for the synthesis of example 2 (step a), the title compound rac-{4-[(3S,4R)-3-(3-chloro-4-methyl-phenyl)-4-methylamino-pyrrolidine-1-carbonyl]-piperidin-1-yl}-(1-methyl-cyclopropyl)-methanone was prepared from rac-{(3R,4S)-4-(3-chloro-4-methylphenyl)-1-[1-(1-methyl-cyclopropanecarbonyl)-piperidine-4-carbonyl]-pyrrolidin-3-yl}-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light brown oil. MS m/e: 418.4 [M+H]⁺.

h) rac-{(3R,4S)-4-(3-Chloro-4-methyl-phenyl)-1-[1-(1-methyl-cyclopropanecarbonyl)-piperidine-4-carbonyl]-pyrrolidin-3-yl}-methyl-carbamic acid 4-fluoro-phenyl ester In analogy to the procedure described for the synthesis of example 2 (step b), the title compound rac-{(3R,4S)-4-(3-chloro-4-methyl-phenyl)-1-[1-(1-methyl-cyclopropanecarbonyl)-piperidine-4-carbonyl]-pyrrolidin-3-yl}-methyl-carbamic acid 4-fluoro-phenyl ester was prepared from rac-{4-[(3S,4R)-3-(3-chloro-4-methyl-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as an off-white foam. MS m/e: 566.2 [M]⁺.

EXAMPLE 71 rac-{(3R,4S)-4-(4-Chloro-3-methyl-phenyl)-1-[1-(1-methyl-cyclopropanecarbonyl)-piperidine-4-carbonyl]-pyrrolidin-3-yl}-methyl-carbamic acid 4-fluoro-phenyl ester

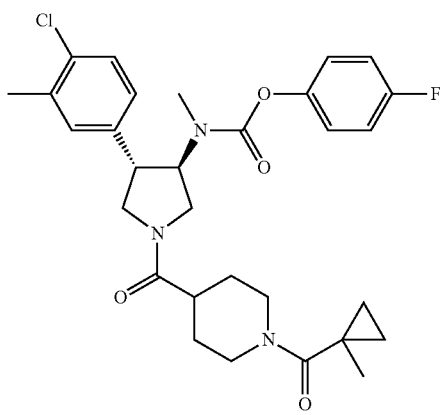 [SMILES: Cc1cc([C@H]2CN(C(=O)C3CCN(C(=O)C4(C)CC4)CC3)C[C@@H]2N(C)C(=O)Oc2ccc(F)cc2)ccc1Cl]

a) rac-(3S,4R)-1-Benzyl-3-(4-chloro-3-methyl-phenyl)-4-nitro-pyrrolidine

In analogy to the procedure described for the synthesis of example 1 (step a), the title compound rac-(3S,4R)-1-benzyl-3-(4-chloro-3-methyl-phenyl)-4-nitro-pyrrolidine was prepared from 1-chloro-2-methyl-4-((E)-2-nitro-vinyl)-benzene instead of 1,2-dichloro-4-((E)-2-nitro-vinyl)-benzene and was obtained as a light green oil. MS m/e: 331.1 [M]⁺.

b) rac-(3R,4S)-1-Benzyl-4-(4-chloro-3-methyl-phenyl)-pyrrolidin-3-ylamine

In analogy to the procedure described for the synthesis of example 1 (step b), the title compound rac-(3R,4S)-1-benzyl-4-(4-chloro-3-methyl-phenyl)-pyrrolidin-3-ylamine was prepared from rac-(3S,4R)-1-benzyl-3-(4-chloro-3-methyl-phenyl)-4-nitro-pyrrolidine instead of rac-(3R,4S)-1-Benzyl-3-(3,4-dichloro-phenyl)-4-nitro-pyrrolidine and was obtained as a dark brown oil. MS m/e: 301.2 [M+H]⁺.

c) rac-[(3R,4S)-1-Benzyl-4-(4-chloro-3-methyl-phenyl)-pyrrolidin-3-yl]-methyl-amine In analogy to the procedure described for the synthesis of example 1 (step c), the title compound rac-[(3R,4S)-1-benzyl-4-(4-chloro-3-methyl-phenyl)-pyrrolidin-3-yl]-methyl-amine was prepared from rac-(3R,4S)-1-benzyl-4-(4-chloro-3-methyl-phenyl)-pyrrolidin-3-ylamine instead of rac-(3S,4R)-1-benzyl-4-(3,4-dichloro-phenyl)-pyrrolidin-3-ylamine and was obtained as a light yellow oil. MS m/e: 315.1 [M+H]⁺.

d) rac-[(3R,4S)-1-Benzyl-4-(4-chloro-3-methyl-phenyl)-pyrrolidin-3-yl]-methyl-carbamic acid tert-butyl ester In analogy to the procedure described for the synthesis of example 1 (step d), the title compound rac-[(3R,4S)-1-benzyl-4-(4-chloro-3-methyl-phenyl)-pyrrolidin-3-yl]-methyl-carbamic acid tert-butyl ester was prepared from rac-[(3R,4S)-1-benzyl-4-(4-chloro-3-methyl-phenyl)-pyrrolidin-3-yl]-methyl-amine instead of rac-[(3R,4S)-1-benzyl-4-(3,4-dichloro-phenyl)-pyrrolidin-3-yl]-methyl-amine and was obtained as a light yellow oil. MS m/e: 415.3 [M+H]⁺.

e) rac-[(3R,4S)-4-(4-Chloro-3-methyl-phenyl)-pyrrolidin-3-yl]-methyl-carbamic acid tert-butyl ester In analogy to the procedure described for the synthesis of example 1 (step e), the title compound rac-[(3R,4S)-4-(4-chloro-3-methyl-phenyl)-pyrrolidin-3-yl]-methyl-carbamic acid tert-butyl ester was prepared from rac-[(3R,4S)-1-benzyl-4-(4-chloro-3-methyl-phenyl)-pyrrolidin-3-yl]-methyl-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as a brown oil. MS m/e: 271.3 [M+-tBu+H]⁺.

f) rac-{(3R,4S)-4-(4-Chloro-3-methyl-phenyl)-1-[1-(1-methyl-cyclopropanecarbonyl)-piperidine-4-carbonyl]-pyrrolidin-3-yl}-methyl-carbamic acid tert-butyl ester In analogy to the procedure described for the synthesis of example 1 (step f), the title compound rac-{(3R,4S)-4-(4-chloro-3-methyl-phenyl)-1-[1-(1-methyl-cyclopropanecarbonyl)-piperidine-4-carbonyl]-pyrrolidin-3-yl}-methyl-carbamic acid tert-butyl ester was prepared from rac-[(3R,4S)-4-(4-chloro-3-methyl-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester and was obtained as a yellow oil. MS m/e: 518.4 [M]+.

g) rac-{4-[(3S,4R)-3-(4-Chloro-3-methyl-phenyl)-4-methylamino-pyrrolidine-1-carbonyl]-piperidin-1-yl}-(1-methyl-cyclopropyl)-methanone In analogy to the procedure described for the synthesis of example 2 (step a), the title compound rac-{4-[(3S,4R)-3-(4-chloro-3-methyl-phenyl)-4-methylamino-pyrrolidine-1-carbonyl]-piperidin-1-yl}-(1-methyl-cyclopropyl)-methanone was prepared from rac-{(3R,4S)-4-(4-chloro-3-methylphenyl)-1-[1-(1-methyl-cyclopropanecarbonyl)-piperidine-4-carbonyl]-pyrrolidin-3-yl}-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light yellow oil. MS m/e: 418.2 [M+H]+.

h) rac-{(3R,4S)-4-(4-Chloro-3-methyl-phenyl)-1-[1-(1-methyl-cyclopropanecarbonyl)-piperidine-4-carbonyl]-pyrrolidin-3-yl}-methyl-carbamic acid 4-fluoro-phenyl ester In analogy to the procedure described for the synthesis of example 2 (step b), the title compound rac-{(3R,4S)-4-(4-chloro-3-methyl-phenyl)-1-[1-(1-methyl-cyclopropanecarbonyl)-piperidine-4-carbonyl]-pyrrolidin-3-yl}-methyl-carbamic acid 4-fluoro-phenyl ester was prepared from rac-{4-[(3S,4R)-3-(4-chloro-3-methyl-phenyl)-4-methylamino-pyrrolidine-1-carbonyl]-piperidin-1-yl}-(1-methyl-cyclopropyl)-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as an off-white foam. MS m/e: 566.2 [M]+.

EXAMPLE 72 rac-[(3R,4S)-4-(3,4-Dichloro-phenyl)-1-(piperidine-4-carbonyl)-pyrrolidin-3-yl]-methyl-carbamic acid 4-fluoro-phenyl ester

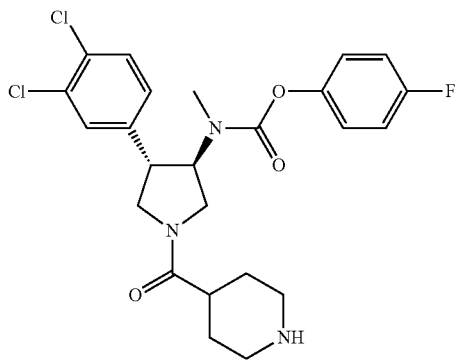 [SMILES: CN(C(=O)Oc1ccc(F)cc1)[C@H]1CN(C(=O)C2CCNCC2)C[C@@H]1c1ccc(Cl)c(Cl)c1]

In analogy to the procedure described for the synthesis of example 2 (step a), the title compound rac-[(3R,4S)-4-(3,4-dichloro-phenyl)-1-(piperidine-4-carbonyl)-pyrrolidin-3-yl]-methyl-carbamic acid 4-fluoro-phenyl ester was prepared from rac-4-{(3S,4R)-3-(3,4-dichloro-phenyl)-4-[(4-fluoro-phenoxycarbonyl)-methyl-amino]-pyrrolidine-1-carbonyl}-piperidine-1-carboxylic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light yellow foam. MS m/e: 494.2 [M]+

EXAMPLE 73 rac-[(3R,4S)-4-(3,4-Dichloro-phenyl)-1-(1-propionyl-piperidine-4-carbonyl)-pyrrolidin-3-yl]-methyl-carbamic acid 4-fluoro-phenyl ester

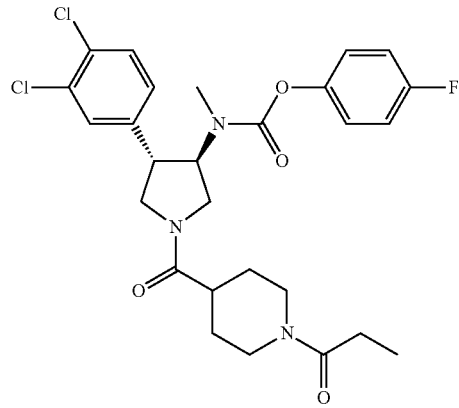 [SMILES: CCC(=O)N1CCC(C(=O)N2C[C@H](c3ccc(Cl)c(Cl)c3)[C@@H](N(C)C(=O)Oc3ccc(F)cc3)C2)CC1]

To a solution of rac-[(3R,4S)-4-(3,4-dichloro-phenyl)-1-(piperidine-4-carbonyl)-pyrrolidin-3-yl]-methyl-carbamic acid 4-fluoro-phenyl ester (200 mg, 0.41 mmol) in THF (2 mL) was added N,N-diisopropyl ethyl amine (208 µl, 1.21 mmol). After stirring for a period of 5 min propionyl chloride (53 µl, 0.61 mmol) was added. After stirring for 3 h at ambient temperature the reaction mixture was treated with an aqueous solution of sodium carbonate (1 M, 10 mL). The organic layer was separated and washed with brine (10 mL) and the aqueous layers were extracted with ethyl acetate (20 mL). The combined organic layers were dried over sodium sulfate and concentrated. Purification by chromatography (SiO$_2$, ethyl acetate:methanol=100:0 to 80:20) afforded the title compound (88 mg, 40%) as a white solid. MS m/e: 550.3 [M]+.

EXAMPLE 74 rac-[(3R,4S)-1-(1-Cyclopropanecarbonyl-piperidine-4-carbonyl)-4-(3,4-dichloro-phenyl)-pyrrolidin-3-yl]-methyl-carbamic acid 4-fluoro-phenyl ester

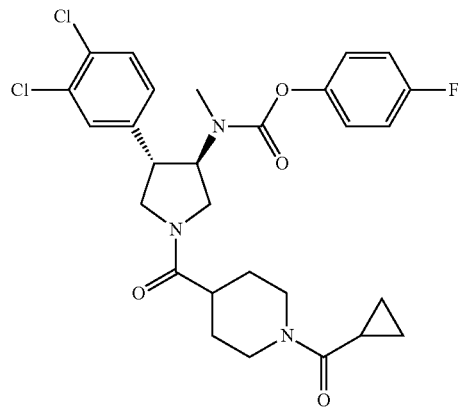 [SMILES: CN(C(=O)Oc1ccc(F)cc1)[C@H]1CN(C(=O)C2CCN(C(=O)C3CC3)CC2)C[C@@H]1c1ccc(Cl)c(Cl)c1]

In analogy to the procedure described for the synthesis of example 73, the title compound rac-[(3R,4S)-1-(1-cyclopropanecarbonyl-piperidine-4-carbonyl)-4-(3,4-dichloro-phenyl)-pyrrolidin-3-yl]-methyl-carbamic acid 4-fluoro-phenyl ester was prepared from rac-[(3R,4S)-4-(3,4-dichloro-phenyl)-1-(piperidine-4-carbonyl)-pyrrolidin-3-yl]-methyl-carbamic acid 4-fluoro-phenyl ester using cyclopropanecarbonyl chloride instead of propionyl chloride and was obtained as a white foam. MS m/e: 562.1 [M]⁺.

EXAMPLE 75 rac-{(3R,4S)-4-(3,4-Dichloro-phenyl)-1-[1-(2-methoxy-acetyl)-piperidine-4-carbonyl]-pyrrolidin-3-yl}-methyl-carbamic acid 4-fluoro-phenyl ester

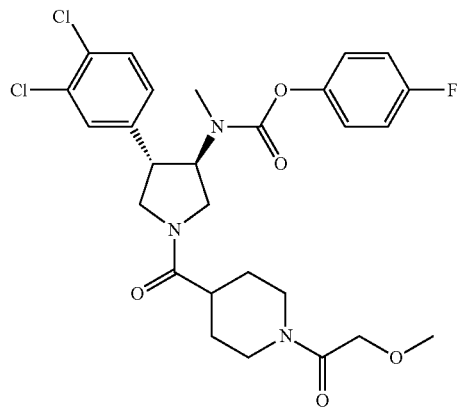 [SMILES: COCC(=O)N1CCC(C(=O)N2C[C@H](c3ccc(Cl)c(Cl)c3)[C@@H](N(C)C(=O)Oc3ccc(F)cc3)C2)CC1]

In analogy to the procedure described for the synthesis of example 73, the title compound rac-{(3R,4S)-4-(3,4-dichloro-phenyl)-1-[1-(2-methoxy-acetyl)-piperidine-4-carbonyl]-pyrrolidin-3-yl}-methyl-carbamic acid 4-fluoro-phenyl ester was prepared from rac-[(3R,4S)-4-(3,4-dichloro-phenyl)-1-(piperidine-4-carbonyl)-pyrrolidin-3-yl]-methyl-carbamic acid 4-fluoro-phenyl ester using methoxyacetyl chloride instead of propionyl chloride and was obtained as a white foam. MS m/e: 566.3 [M]⁺.

EXAMPLE 76 rac-{(3R,4S)-4-(3,4-Dichloro-phenyl)-1-[1-(tetrahydro-pyran-4-carbonyl)-piperidine-4-carbonyl]-pyrrolidin-3-yl}-methyl-carbamic acid 4-fluoro-phenyl ester

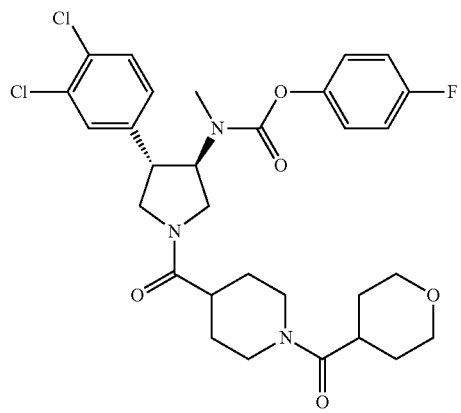 [SMILES: CN(C(=O)Oc1ccc(F)cc1)[C@H]1CN(C(=O)C2CCN(C(=O)C3CCOCC3)CC2)C[C@@H]1c1ccc(Cl)c(Cl)c1]

In analogy to the procedure described for the synthesis of example 73, the title compound rac-{(3R,4S)-4-(3,4-dichloro-phenyl)-1-[1-(tetrahydro-pyran-4-carbonyl)-piperidine-4-carbonyl]-pyrrolidin-3-yl}-methyl-carbamic acid 4-fluoro-phenyl ester was prepared from rac-[(3R,4S)-4-(3,4-dichloro-phenyl)-1-(piperidine-4-carbonyl)-pyrrolidin-3-yl]-methyl-carbamic acid 4-fluoro-phenyl ester using tetrahydro-2H-pyran-4-carbonyl chloride instead of propionyl chloride and was obtained as a white foam. MS m/e: 606.3 [M]⁺.

EXAMPLE 77 rac-{(3R,4S)-4-(3,4-Dichloro-phenyl)-1-[1-(tetrahydro-pyran-4-yl)-piperidine-4-carbonyl]-pyrrolidin-3-yl}-methyl-carbamic acid 4-fluoro-phenyl ester

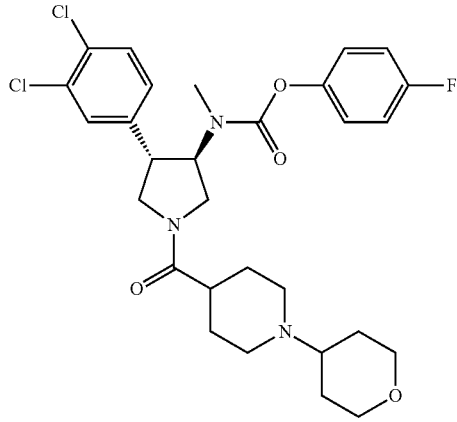 [SMILES: CN(C(=O)Oc1ccc(F)cc1)[C@H]1CN(C(=O)C2CCN(C3CCOCC3)CC2)C[C@@H]1c1ccc(Cl)c(Cl)c1]

In analogy to the procedure described for the synthesis of example 44 (step c), the title compound rac-{(3R,4S)-4-(3,4-Dichloro-phenyl)-1-[1-(tetrahydro-pyran-4-yl)-piperidine-4-carbonyl]-pyrrolidin-3-yl}-methyl-carbamic acid 4-fluoro-phenyl ester was prepared from rac-[(3R,4S)-4-(3,4-dichloro-phenyl)-1-(piperidine-4-carbonyl)-pyrrolidin-3-yl]-methyl-carbamic acid 4-fluoro-phenyl ester using 1-(tetrahydro-pyran-4-yl)-piperidine-4-carboxylic acid instead of 1-methylcyclopropane-1-carboxylic acid and was obtained as an off-white foam. MS m/e: 578.2 [M]⁺.

EXAMPLE 78 rac-[(3R,4S)-4-(3,4-Dichloro-phenyl)-1-(1-[1,3,4]thiadiazol-2-yl-piperidine-4-carbonyl)-pyrrolidin-3-yl]-methyl-carbamic acid 4-fluoro-phenyl ester

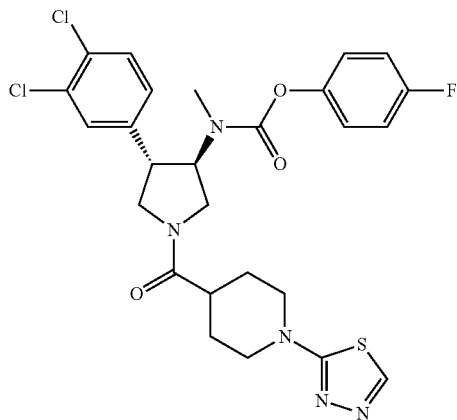 [SMILES: CN(C(=O)Oc1ccc(F)cc1)[C@H]1CN(C(=O)C2CCN(c3nncs3)CC2)C[C@@H]1c1ccc(Cl)c(Cl)c1]

To a solution of rac-[(3R,4S)-4-(3,4-dichloro-phenyl)-1-(piperidine-4-carbonyl)-pyrrolidin-3-yl]-methyl-carbamic acid 4-fluoro-phenyl ester (100 mg, 0.20 mmol) in N-methylpyrrolidinone (1 mL) was added 2-bromo-1,3,4-thiadiazole (50 mg, 0.30 mmol) and N,N-diisopropyl ethyl amine (69 µl, 0.40 mmol). The solution was irradiated in the microwave for 35 min at 150° C. The reaction mixture was diluted with ethyl acetate (15 mL) and washed with an aqueous solution of sodium carbonate (1 M, 15 mL). The organic layer was separated and washed with brine (15 mL) and the aqueous layers were extracted with ethyl acetate (20 mL). The combined organic layers were dried over sodium sulfate and concentrated. Purification by chromatography (SiO$_2$, ethyl acetate:methanol=100:0 to 80:20) afforded the title compound (37 mg, 32%) as an off-white foam. MS m/e: 578.1 [M]$^+$.

EXAMPLE 79 rac-[(3R,4S)-1-[1-(6-Chloro-pyridazin-3-yl)-piperidine-4-carbonyl]-4-(3,4-dichloro-phenyl)-pyrrolidin-3-yl]-methyl-carbamic acid 4-fluoro-phenyl ester

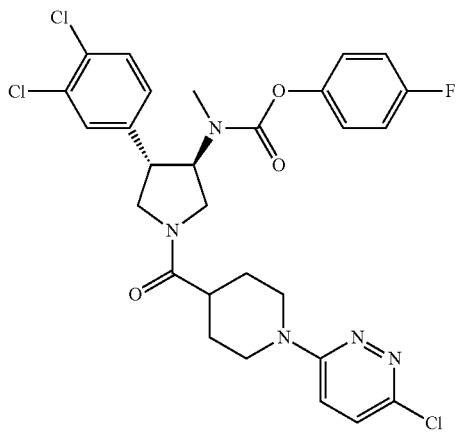 [SMILES: CN(C(=O)Oc1ccc(F)cc1)[C@H]1CN(C(=O)C2CCN(c3ccc(Cl)nn3)CC2)C[C@@H]1c1ccc(Cl)c(Cl)c1]

In analogy to the procedure described for the synthesis of example 44 (step c), the title compound rac-[(3R,4S)-1-[1-(6-Chloro-pyridazin-3-yl)-piperidine-4-carbonyl]-4-(3,4-dichloro-phenyl)-pyrrolidin-3-yl]-methyl-carbamic acid 4-fluoro-phenyl ester was prepared from rac-[(3R,4S)-4-(3,4-dichloro-phenyl)-pyrrolidin-3-yl]-methyl-carbamic acid 4-fluoro-phenyl ester using 1-(6-chloro-3-pyridazinyl)-4-piperidinecarboxylic acid instead of 1-methylcyclopropane-1-carboxylic acid and was obtained as an off-white foam. MS m/e: 608.1 [M+H]$^+$.

EXAMPLE 80 rac-[(3R,4S)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester

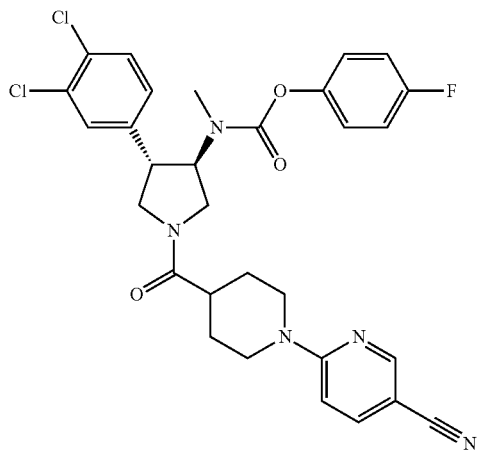 [SMILES: CN(C(=O)Oc1ccc(F)cc1)[C@H]1CN(C(=O)C2CCN(c3ccc(C#N)cn3)CC2)C[C@@H]1c1ccc(Cl)c(Cl)c1]

A solution of [(3R,4S)-4-(3,4-Dichloro-phenyl)-1-(piperidine-4-carbonyl)-pyrrolidin-3-yl]-methyl-carbamic acid 4-fluoro-phenyl ester (50 mg, 0.10 mmol), 6-chloronicotinonitrile (21 mg, 0.15 mmol) in N-methylpyrrolidinone (0.5 mL) was treated with N,N-diisopropyl ethyl amine (52 µl, 0.30 mmol). The solution was stirred for 6 h at ambient temperature before it was diluted with ethyl acetate (15 mL) and washed with an aqueous solution of sodium carbonate (1 M, 15 mL). The organic layer was separated and washed with brine (15 mL) and the aqueous layers were extracted with ethyl acetate (20 mL). The combined organic layers were dried over sodium sulfate and concentrated. Purification by chromatography (SiO$_2$, heptane:ethyl acetate:methanol=80:20:0 to 0:90:10) afforded the title compound (52 mg, 86%) as an off-white foam. MS m/e: 596.2 [M]$^+$.

EXAMPLE 81

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester

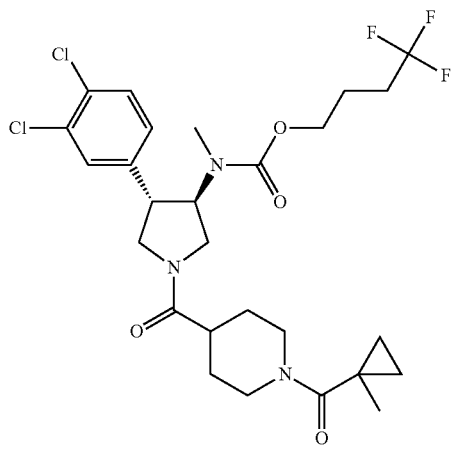 [SMILES: CN(C(=O)OCCCC(F)(F)F)[C@H]1CN(C(=O)C2CCN(C(=O)C3(C)CC3)CC2)C[C@@H]1c1ccc(Cl)c(Cl)c1]

and

EXAMPLE 82

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester

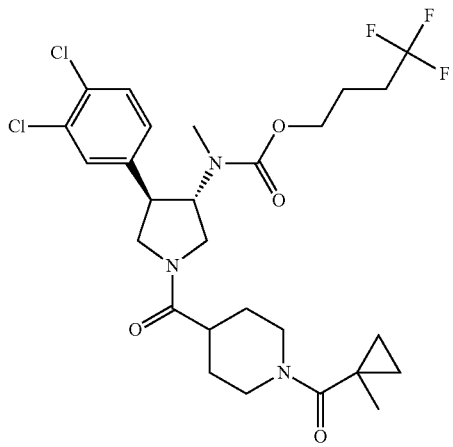 [SMILES: CN(C(=O)OCCCC(F)(F)F)[C@@H]1CN(C(=O)C2CCN(C(=O)C3(C)CC3)CC2)C[C@H]1c1ccc(Cl)c(Cl)c1]

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester was subjected to column chromatography on chiral phase to yield {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester (MS (m/e): 592.3 [M]$^+$) as an off-white foam and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester (MS (m/e): 592.3 [M]$^+$) as an off-white foam.

EXAMPLE 83 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,4,4,4-pentafluoro-butyl ester

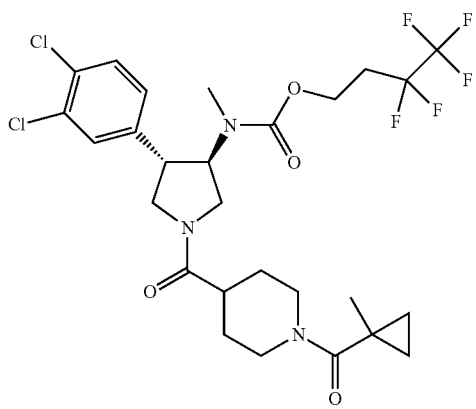 [SMILES: CN(C(=O)OCCC(F)(F)C(F)(F)F)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3,3,4,4,4-pentafluoro-butyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3,3,4,4,4-pentafluorobutan-1-ol instead of 2-cyclopropylethanol and was obtained as a white foam. MS m/e: 628.2 [M]$^+$.

EXAMPLE 84 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-2-yl)methyl ester and rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-2-yl)methyl ester

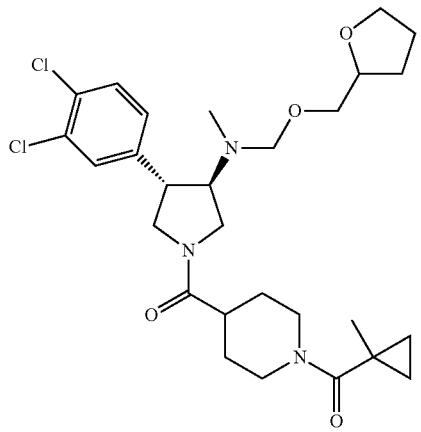 [SMILES: CN(COCC1CCCO1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compounds rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-2-yl)methyl ester and rac-{(3R,4S)-4-(3,4-dichloro-phenyl)-1-[1-(1-methyl-cyclopropane-carbonyl)-piperidine-4-carbonyl]-pyrrolidin-3-yl}-methyl-carbamic acid (R)-1-(tetrahydro-furan-2-yl)methyl ester were prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using rac-tetrahydro-3-furanmethanol instead of 2-cyclopropylethanol and was obtained as an off-white foam. MS m/e: 566.2 [M]$^+$.

EXAMPLE 85 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-3-yl)methyl ester and rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-3-yl)methyl ester

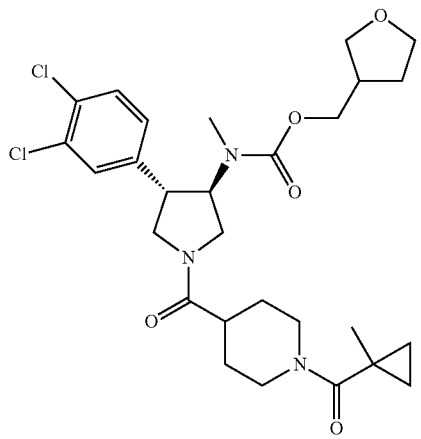 [SMILES: CN(C(=O)OCC1CCOC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compounds rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-3-yl)methyl ester and rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-3-yl)methyl ester were prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using rac-tetrahydrofurfuryl alcohol instead of 2-cyclopropylethanol and was obtained as a white foam. MS m/e: 566.2 [M]+.

EXAMPLE 86 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester

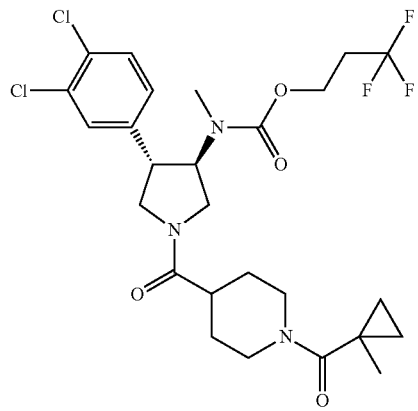 [SMILES: CN(C(=O)OCCC(F)(F)F)[C@H]1CN(C(=O)C2CCN(C(=O)C3(C)CC3)CC2)C[C@@H]1c1ccc(Cl)c(Cl)c1]

and

EXAMPLE 87 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester

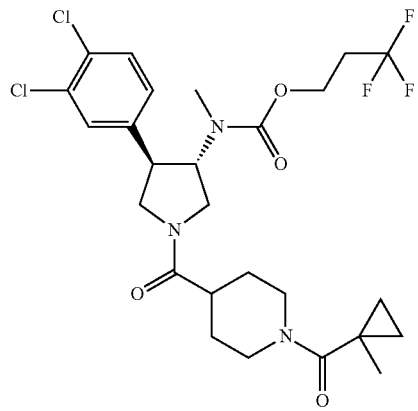 [SMILES: CN(C(=O)OCCC(F)(F)F)[C@@H]1CN(C(=O)C2CCN(C(=O)C3(C)CC3)CC2)C[C@H]1c1ccc(Cl)c(Cl)c1]

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester was subjected to column chromatography on chiral phase to yield {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester (MS (m/e): 578.3 [M]+) as an off-white foam and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester (MS (m/e): 578.3 [M]+) as an off-white foam.

EXAMPLE 88 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,5,5,5-pentafluoro-pentyl ester

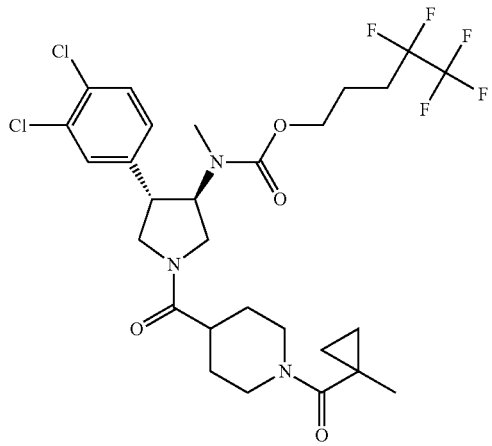 [SMILES: CN(C(=O)OCCCC(F)(F)C(F)(F)F)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4,4,5,5,5-pentafluoro-pentyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,5,5,5-pentafluoropentanol instead of 2-cyclopropylethanol and was obtained as an off-white foam. MS m/e: 642.2 [M]+.

EXAMPLE 89

[(3S,4R)-4-(4-Chloro-phenyl)-1-(4-hydroxy-cyclohexanecarbonyl)-pyrrolidin-3-yl]-methyl-carbamic acid 4-fluoro-phenyl ester

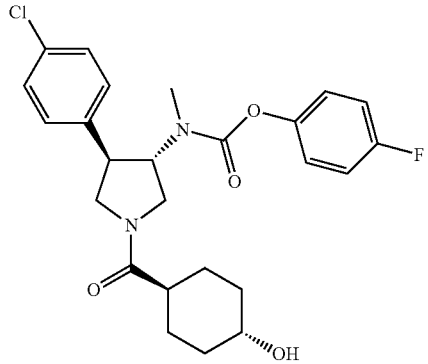 [SMILES: CN(C(=O)Oc1ccc(F)cc1)[C@@H]1CN(C(=O)[C@H]2CC[C@H](O)CC2)C[C@H]1c1ccc(Cl)cc1]

a) (4-Chloro-phenyl)-propynoic acid ethyl ester

A mixture of 1-chloro-4-iodobenzene (120.4 g, 0.50 mol) and cesium carbonate (352.8 g, 1.0 mol) in tetrahydrofuran (1.275 L) was evaporated and flushed with argon. Then cuprous iodide (3.81 g, 20.0 mmol) and bis(triphenylphosphine)palladium(II) chloride (7.02 g, 10.0 mmol) were added and then ethyl propiolate (100 g, 1.01 mol) was added dropwise over a period of 20 min. The resulting dark brown suspension was stirred for 41 h at 35° C., then filtrated over Hyflo® and washed with THF (5 L). The solution was concentrated and treated with toluene/heptane 1:2 (1.5 L) and stirred for 1 h at 45° C. under reduced pressure (250 mbar). The resulting suspension was filtered and the residue was washed with further toluene/heptane 1:2 (1.5 L). The solid was dried affording 181.64 g (MS m/e: 209.0/211.2 [M+H]$^+$) of a dark brown oil as crude product which was used without further purification.

b) 1-Benzyl-4-(4-chloro-phenyl)-2,5-dihydro-1H-pyrrole-3-carboxylic acid

To a solution of (4-chloro-phenyl)-propynoic acid ethyl ester (92.65 g, 444.1 mmol) in dichloromethane (425 mL) was added trifluoroacetic acid (3.4, 44.4 mmol). The reaction mixture was cooled with a water bath and a solution of N-(methoxymethyl)-N-(trimethylsilylmethyl)benzylamine (164.7 g, 666.1 mmol) in dichloromethane (325 mL) was added dropwise over a period of 1.5 h. It was stirred for 22 h at ambient temperature. Further N-(methoxymethyl)-N-(trimethylsilylmethyl)benzylamine (27.5 g, 111.0 mmol) in dichloromethane (50 mL) was added and stirring was continued for 2 h at ambient temperature. The solvent was distilled off and the residue was taken up in dioxane (950 mL). After addition of water (475 mL) and sodium hydroxide (32%, 114.3 mL, 1.23 mol), it was stirred for 67 h at ambient temperature. After concentration the residue was diluted with water (400 mL) and extracted with tert-butylmethylether (400 mL). The organic layers were washed with water (400 mL). The aqueous layers were combined, cooled to 5° C. and set to pH=1.5 with aqueous HCl (25%, 172). After stirring for 1 h at 5° C., the solid was filtered off and was washed with water (1400 mL) and ethanol (400 mL). Drying (50° C., 25 mbar) afforded the title compound (109.85 g, 79%) as an off-white solid. MS m/e: 312.2/314.1 [M−H]$^−$.

c) (3R,4R)-1-Benzyl-4-(4-chloro-phenyl)-pyrrolidine-3-carboxylic acid

An autoclave was charged under argon in a glove box (O$_2$ content<2 ppm) with 1-benzyl-4-(4-chloro-phenyl)-2,5-dihydro-1H-pyrrole-3-carboxylic acid (1.00 g, 3.19 mmol), [Ru(OAc)$_2$((S)-2-furyl-MeOBIPHEP)] (9.72 mg, 0.01 mmol) (2-furyl-MeOBIPHEP=(6,6'-dimethoxybiphenyl-2,2'-diyl)bis(di-2-furylphosphine) and methanol (30 ml). The asymmetric hydrogenation was run for 20 h at 30° C. under 40 bar of hydrogen (>95% conversion, determined by NMR). After the pressure was released, the grey suspension was evaporated to dryness to yield 1.01 g of the crude title compound. The crude product was dissolved in methanol (15 mL) and heated to reflux for 1 h. After cooling to ambient temperature it was stirred for 2 h at 0° C. The resulting suspension was filtered and dried (40° C., 15 mbar) for 2 h. affording the title compound (0.984 g, 95%, e.e. 99.8% R,R (chiral HPLC)) as white solid. MS m/e: 316.1 [M+H]$^+$.

d) (3R,4R)-1-Benzyl-4-(4-chloro-phenyl)-pyrrolidine-3-carboxylic acid methyl ester To a white suspension of (3R,4R)-1-benzyl-4-(4-chlorophenyl)-pyrrolidine-3-carboxylic acid (72.31 g, 229 mmol) in methanol (725 mL) was added slowly sulfuric acid (25.8 ml, 457.9 mmol). The resulting dark brown solution was stirred for 19 h at 60° C. After cooling to 0° C., tert-butylmethylether (1.6 L) was added and the solution was set to pH=9 with aqueous sodium carbonate (1M, 480 mL). The aqueous layer was separated and extracted with further tert-butylmethylether (410 mL). The organic layers were washed with brine (310 mL) and dried over sodium sulfate. Concentration afforded the title compound (74.18 g, 98%) as a light brown oil. MS m/e: 330.3/332.3 [M+H]$^+$.

e) (3S,4R)-1-Benzyl-4-(4-chloro-phenyl)-pyrrolidine-3-carboxylic acid methyl ester To a solution of (3R,4R)-1-benzyl-4-(4-chloro-phenyl)-pyrrolidine-3-carboxylic acid methyl ester (72.74 g, 220.5 mmol) in methanol (730 mL) was added sodium methylate solution (5.4 M methanol, 81.7 mL, 441.1 mmol). The reaction mixture was stirred for 116 h at ambient temperature (after 17.5 h further sodium methylate solution (5.4 M in methanol, 20.4 mL, 110.3 mmol) was added). It was set to pH=1 by addition of sulfuric acid (26.13 mL, 463.1 mmol) and stirred at 60° C. for 19 h. The resulting suspension was cooled to 0° C., tert-butylmethylether (1.6 L) was added and the solution was set to pH=9 with aqueous sodium carbonate (1 M, 440 mL). The aqueous layer was separated and extracted with further tert-butylmethylether (410 mL). The organic layers were washed with brine (310 mL), combined and dried over sodium sulfate. Concentration and filtration over silicagel (heptane: ethyl acetate=80:20) afforded the title compound (62.82 g, 86%) as a light yellow oil. MS m/e: 330.3/332.3 [M+H]$^+$.

f) (3S,4R)-1-Benzyl-4-(4-chloro-phenyl)-pyrrolidine-3-carboxylic acid amide

A solution of (3S,4R)-1-benzyl-4-(4-chloro-phenyl)-pyrrolidine-3-carboxylic acid methyl ester (62.82 g, 190.5 mmol) and formamide (22.7 mL, 571.4 mmol) in DMF (75 mL) was heated to 100° C. Then sodium methylate solution (5.4 M in methanol, 17.6 mL, 95.2 mmol) was added dropwise over a period of 50 min. The solution was stirred for 3 h at 100° C. (after 1 h further formamide (11.4 mL, 285.7 mmol) was added). The reaction mixture was cooled to ambient temperature and the resulting suspension was separated between ethyl acetate (1500 mL) and water (1000 mL). The organic layers were washed with brine (500 mL), combined and dried over sodium sulfate. Concentration and trituration with tert-butylmethylether (500 mL) afforded the tittle compound (51.19 g, 85%) as white crystals. MS m/e: 315.2 and 317.3 [M+H]$^+$).

g) [(3S,4R)-1-Benzyl-4-(4-chloro-phenyl)-pyrrolidin-3-yl]-carbamic acid methyl ester To a solution of potassium hydroxide (25.09 g, 447.2 mmol) in methanol (520 mL) was added a solution of (3S,4R)-1-benzyl-4-(4-chloro-phenyl)-pyrrolidine-3-carboxylic acid amide (51.19 g, 162.6 mmol) in THF (260 mL). After cooling to 0° C., diacetoxyiodosobenzene (57.61 g, 178.9 mmol) was added. The reaction mixture was stirred for 45 min at 0° C. and for 1.5 h at ambient temperature and was then diluted with water (1000 mL). The mixture was separated between dichloromethane (1500 mL) and aqueous sodium carbonate (1M, 1000 mL). The organic layers were washed with brine (750 mL), combined and dried over sodium sulfate. Concentration and trituration with tert-butylmethylether (180 mL) afforded the tittle compound (49.22 g, 88%) as a white solid. MS m/e: 345.3 and 347.2 [M+H]$^+$).

h) [(3S,4R)-1-Benzyl-4-(4-chloro-phenyl)-pyrrolidin-3-yl]-methyl-amine

To a suspension of [(3S,4R)-1-benzyl-4-(4-chloro-phenyl)-pyrrolidin-3-yl]-carbamic acid methyl ester (49.22 g, 142.7 mmol) in THF (520 mL) borane-tetrahydrofurane complex solution (1 M in tetrahydrofurane, 571 mL, 571 mmol) was added slowly over a period of 25 min. The reaction mixture was stirred for 19 h at 60° C. and then quenched with aqueous HCl (1N, 570 mL, dropwise over 60 min). The mixture was stirred for further 21 h at 60° C. After cooling to ambient temperature, tetrahydrofurane was distilled away and the residue was separated between tert-butylmethylether (1500 mL) and aqueous HCl (1N, 1000 mL). The aqueous layer was set to pH=10 with aqueous sodium carbonate (saturated, 2000 mL) and then extracted with tert-butylmethylether (twice 1500 mL). The organic layers were washed with brine (750 mL), combined and was dired over sodium sulfate. Concentration and filtration over silicagel (ethyl acetate: methanol, triethylamine=90:5:5) afforded the title compound (34.38, 80%) as a light yellow liquid. MS m/e: 301.4/303.4 [M+H]$^+$.

i) [(3S,4R)-1-Benzyl-4-(4-chloro-phenyl)-pyrrolidin-3-yl]-methyl-carbamic acid 4-fluoro-phenyl ester In analogy to the procedure described for the synthesis of example 2 (step b), the title compound [(3S,4R)-1-benzyl-4-(4-chloro-phenyl)-pyrrolidin-3-yl]-methyl-carbamic acid 4-fluoro-phenyl ester was prepared from [(3S,4R)-1-benzyl-4-(4-chloro-phenyl)-pyrrolidin-3-yl]-methyl-amine instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using fluorophenyl chloroformate and was obtained as a light brown oil. MS m/e: 439.2 [M+H]$^+$.

j) [(3S,4R)-4-(4-Chloro-phenyl)-pyrrolidin-3-yl]-methyl-carbamic acid 4-fluoro-phenyl ester In analogy to the procedure described for the synthesis of example 1 (step e), the title compound [(3S,4R)-4-(4-chloro-phenyl)-pyrrolidin-3-yl]-methyl-carbamic acid 4-fluoro-phenyl ester was prepared from [(3S,4R)-1-benzyl-4-(4-chloro-phenyl)-pyrrolidin-3-yl]-methyl-carbamic acid 4-fluoro-phenyl ester instead of rac-[(3R,4S)-1-benzyl-4-(3,4-dichloro-phenyl)-pyrrolidin-3-yl]-methyl-carbamic acid tert-butyl ester and was obtained as a light brown oil. MS m/e: 349.2 [M+H]$^+$.

k) [(3S,4R)-4-(4-Chloro-phenyl)-1-(4-hydroxy-cyclohexanecarbonyl)-pyrrolidin-3-yl]-methyl-carbamic acid 4-fluoro-phenyl ester In analogy to the procedure described for the synthesis of example 44 (step c), the title compound [(3S,4R)-4-(4-Chloro-phenyl)-1-(4-hydroxy-cyclohexanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of rac-[(3S,4R)-4-(3,4-dichloro-phenyl)-pyrrolidin-3-yl]-methyl-carbamic acid 4-fluoro-phenyl ester using trans-4-hydroxycyclohexanecarboxylic acid instead of 1-methylcyclopropane-1-carboxylic acid and was obtained as an off-white foam. MS m/e: 475.2 [M+H]$^+$.

EXAMPLE 90

[(3S,4R)-4-(4-Chloro-phenyl)-1-(tetrahydro-pyran-4-carbonyl)-pyrrolidin-3-yl]-methyl-carbamic acid 4-fluoro-phenyl ester

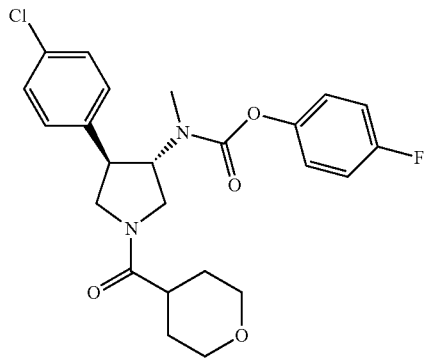 [SMILES: CN(C(=O)Oc1ccc(F)cc1)[C@@H]1CN(C(=O)C2CCOCC2)C[C@H]1c1ccc(Cl)cc1]

In analogy to the procedure described for the synthesis of example 44 (step c), the title compound [(3S,4R)-4-(4-chloro-phenyl)-1-(tetrahydro-pyran-4-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of rac-[(3S,4R)-4-(3,4-dichloro-phenyl)-pyrrolidin-3-yl]-methyl-carbamic acid 4-fluoro-phenyl ester using tetrahydropyran-4-yl-carboxylic acid instead of 1-methylcyclopropane-1-carboxylic acid and was obtained as an off-white foam. MS m/e: 461.2 [M+H]$^+$.

EXAMPLE 91 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester

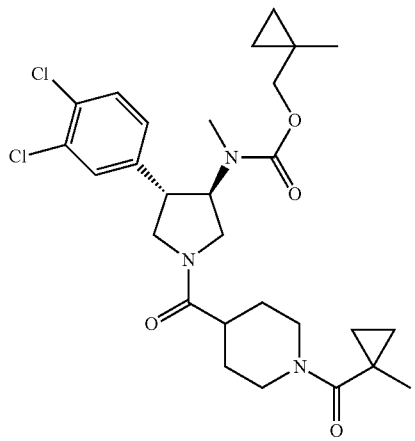 [SMILES: CN(C(=O)OCC1(C)CC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 1-methylcyclopropanemethanol instead of 2-cyclopropylethanol and was obtained as an off-white foam. MS m/e: 550.2 [M]⁺.

EXAMPLE 92 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 2-methyl-cyclopropylmethyl ester

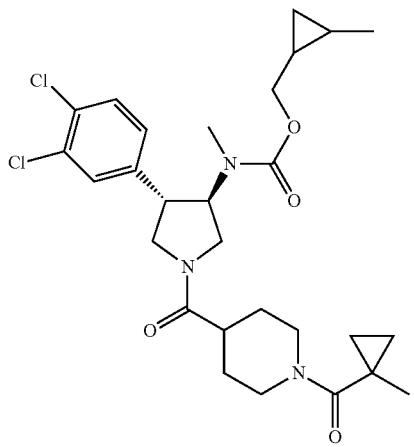 [SMILES: CC1CC1COC(=O)N(C)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 2-methyl-cyclopropylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2-methylcyclopropanemethanol (mixture of cis/trans) instead of 2-cyclopropylethanol and was obtained as an off-white foam. MS m/e: 550.2 [M]⁺.

EXAMPLE 93

[(3S,4R)-4-(4-Chloro-phenyl)-1-(1,1-dioxo-hexahydro-1$\lambda^6$-thiopyran-4-carbonyl)-pyrrolidin-3-yl]-methyl-carbamic acid 4-fluoro-phenyl ester

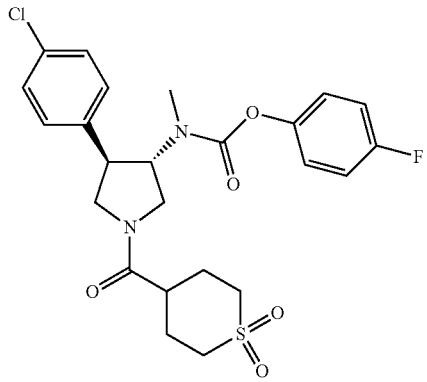 [SMILES: CN(C(=O)Oc1ccc(F)cc1)[C@@H]1CN(C(=O)C2CCS(=O)(=O)CC2)C[C@H]1c1ccc(Cl)cc1]

In analogy to the procedure described for the synthesis of example 44 (step c), the title compound [(3S,4R)-4-(4-chloro-phenyl)-1-(1,1-dioxo-hexahydro-1$\lambda^6$-thiopyran-4-carbonyl)-pyrrolidin-3-yl]-methyl-carbamic acid 4-fluoro-phenyl ester was prepared from [(3S,4R)-4-(3,4-dichloro-phenyl)-pyrrolidin-3-yl]-methyl-carbamic acid 4-fluoro-phenyl ester using 1,1-dioxo-hexahydro-1$\lambda^6$-thiopyran-4-carboxylic acid instead of 1-methylcyclopropane-1-carboxylic acid and was obtained as an off-white foam. MS m/e: 509.1 [M]⁺.

EXAMPLE 94

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester

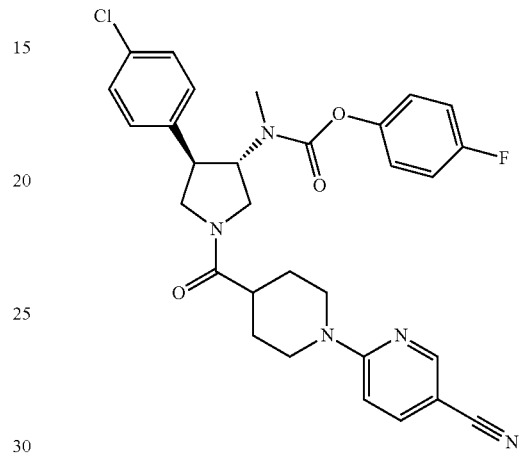

In analogy to the procedure described for the synthesis of example 44 (step c), the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 5'-cyano-3,4,5,6-tetrahydro-2H-[1,2']bipyridinyl-4-carboxylic acid instead of 1-methylcyclopropane-1-carboxylic acid and was obtained as an off-white foam. MS m/e: 562.1 [M]⁺.

EXAMPLE 95 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-benzyl ester

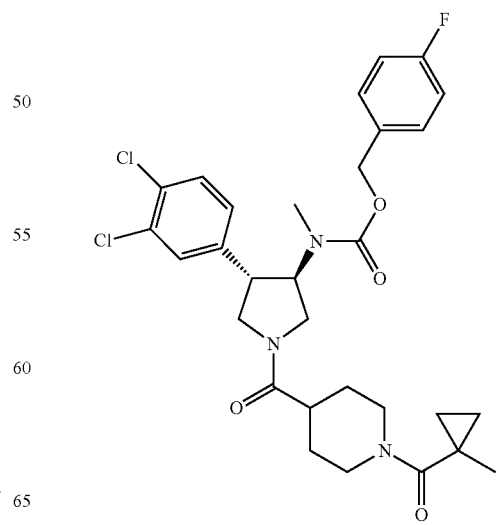

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-fluoro-benzyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-fluorobenzyl alcohol instead of 2-cyclopropylethanol and was obtained as an off-white foam. MS m/e: 590.2 [M]+.

EXAMPLE 96 rac-1-{(3R,4S)-4-(4-Chloro-phenyl)-1-[1-(1-methyl-cyclopropanecarbonyl)-piperidine-4-carbonyl]-pyrrolidin-3-yl}-3-(4-fluoro-phenyl)-1-methyl-urea

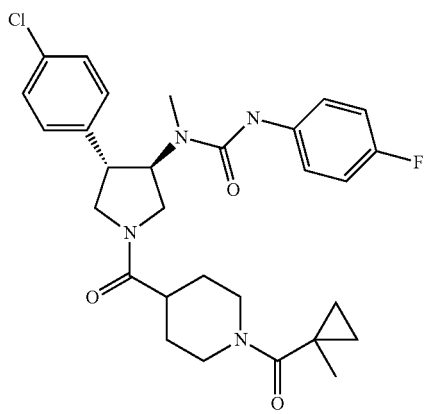 [SMILES: CN(C(=O)Nc1ccc(F)cc1)[C@H]1CN(C(=O)C2CCN(C(=O)C3(C)CC3)CC2)C[C@@H]1c1ccc(Cl)cc1]

To a solution of triphosgene (110 mg, 0.37 mmol) in dichloromethane (2 mL) was added at 0° C. very carefully 4-fluoroaniline (178 µl, 1.86 mmol). After the resulting suspension was stirred for 15 min N,N-diisopropyl ethyl amine (381 µl, 2.23 mmol) was added dropwise. The solution was stirred for 4 h at ambient temperature and then added to rac-{4-[(3S,4R)-3-(4-Chloro-phenyl)-4-methylamino-pyrrolidine-1-carbonyl]-piperidin-1-yl}-(1-methyl-cyclopropyl)-methanone (150 mg, 0.37 mmol). The resulting solution was irradiated in the microwave for 30 min at 80° C. before it was diluted with ethyl acetate (15 mL) and washed with an aqueous solution of sodium carbonate (1 M, 15 mL). The organic layer was separated and washed with brine (15 mL) and the aqueous layers were extracted with ethyl acetate (20 mL). The combined organic layers were dried over sodium sulfate and concentrated. Purification by chromatography (SiO₂, heptane:ethyl acetate:methanol=80:20:0 to 0:90:10) afforded the title compound (190 mg, 95%) as an off-white foam. MS m/e: 541.3 [M]+.

EXAMPLE 97 rac-1-(2-Cyclopropyl-ethyl)-3-{(3R,4S)-4-(3,4-dichloro-phenyl)-1-[1-(1-methyl-cyclopropanecarbonyl)-piperidine-4-carbonyl]-pyrrolidin-3-yl}-1,3-dimethyl-urea

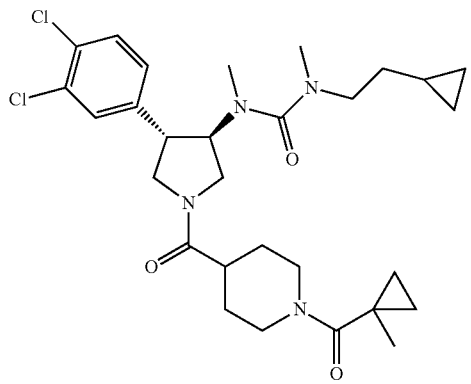 [SMILES: CN(CCC1CC1)C(=O)N(C)[C@H]1CN(C(=O)C2CCN(C(=O)C3(C)CC3)CC2)C[C@@H]1c1ccc(Cl)c(Cl)c1]

To a solution of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid chloride (250 mg, 0.50 mmol) in THF (1 mL) was added (2-cyclopropyl-ethyl)-methyl-amine (99 mg, 1.0 mmol) and N,N-diisopropyl ethyl amine (256, 1.50 mmol). The solution was irradiated in the microwave for 900 sec. at 130° C. before it was diluted with ethyl acetate (15 mL) and washed with an aqueous solution of sodium carbonate (1 M, 15 mL). The organic layer was separated and washed with brine (15 mL) and the aqueous layers were extracted with ethyl acetate (20 mL). The combined organic layers were dried over sodium sulfate and concentrated. Purification by chromatography (SiO₂, ethyl acetate:methanol=100:0 to 85:15) afforded the title compound (202 mg, 72%) as a white foam. MS m/e: 563.4 [M]+.

EXAMPLE 98 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-hydroxy-3-methyl-butyl ester

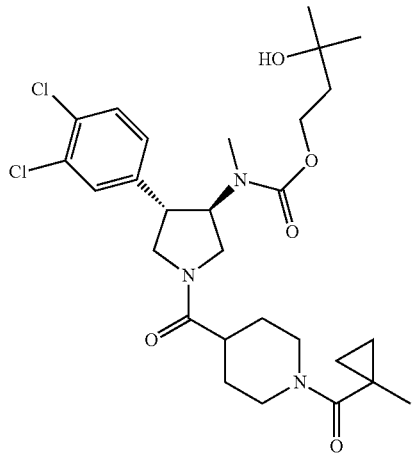 [SMILES: CN(C(=O)OCCC(C)(C)O)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3-hydroxy-3-methyl-butyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)- methanone using 3-methyl-1,3-butanediol instead of 2-cyclopropylethanol and was obtained as an off-white foam. MS m/e: 568.2 [M]⁺.

EXAMPLE 99 rac {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexylmethyl ester

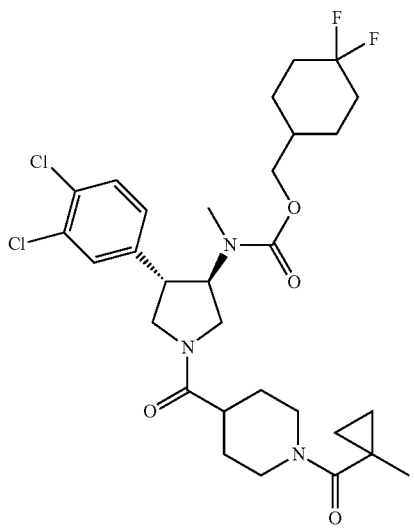 [SMILES: CN(C(=O)OCC1CCC(F)(F)CC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac {(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using (4,4-difluoro-cyclohexyl)-methanol instead of 2-cyclopropylethanol and was obtained as an off-white foam. MS m/e: 614.2 [M]⁺.

EXAMPLE 100

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester

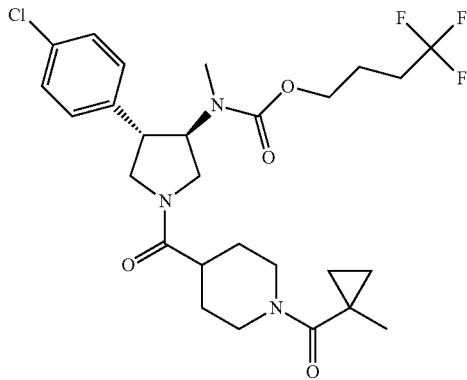 [SMILES: CN(C(=O)OCCCC(F)(F)F)[C@H]1CN(C(=O)C2CCN(C(=O)C3(C)CC3)CC2)C[C@@H]1c1ccc(Cl)cc1]

and

EXAMPLE 101

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester

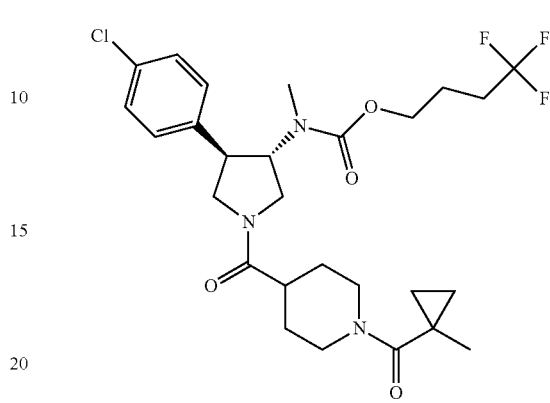

In analogy to the procedure described for the synthesis of example 44 (step c), the title compounds {(3R,4S)-4-(4-chloro-phenyl)-1-[1-(1-methyl-cyclopropane carbonyl)-piperidine-4-carbonyl]-pyrrolidin-3-yl}-methyl-carbamic acid 4,4,4-trifluoro-butyl ester and {(3S,4R)-4-(4-chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester were prepared from [(3R,4S)-4-(4-Chloro-phenyl)-pyrrolidin-3-yl]-methyl-carbamic acid 4,4,4-trifluoro-butyl ester using 1-(1-methyl-cyclopropanecarbonyl)-piperidine-4-carboxylic acid instead of 1-methylcyclopropane-1-carboxylic acid and were obtained as a light brown gum. MS m/e: 558.1 [M]⁺. The racemate was subjected to column chromatography on chiral phase to yield {(3R,4S)-4-(4-chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester (MS (m/e): 558.1 [M]⁺) as an off-white foam and {(3S,4R)-4-(4-chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester (MS (m/e): 558.1 [M]⁺) as an off-white foam.

EXAMPLE 102 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexyl ester

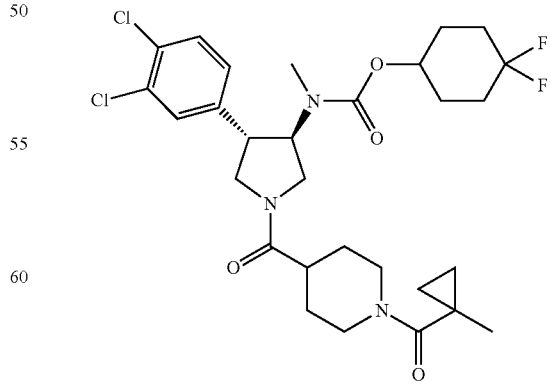

In analogy to the procedure described for the synthesis of example 25, the title compound rac-{(3R,4S)-4-(3,4- dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4-difluoro-cyclohexanol instead of 2-cyclopropylethanol and was obtained as an off-white foam. MS m/e: 600.2 [M]$^+$.

EXAMPLE 103 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester

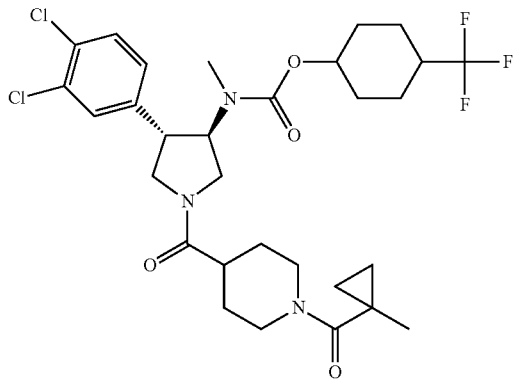 [SMILES: CN(C(=O)OC1CCC(C(F)(F)F)CC1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-trifluoromethyl)cyclohexanol (cis/trans mixture) instead of 2-cyclopropylethanol and was obtained as an off-white foam. MS m/e: 632.2 [M]$^+$.

EXAMPLE 104

[(3S,4R)-4-(4-Chloro-phenyl)-1-(4-cyano-cyclohexanecarbonyl)-pyrrolidin-3-yl]-methyl-carbamic acid 4-fluoro-phenyl ester

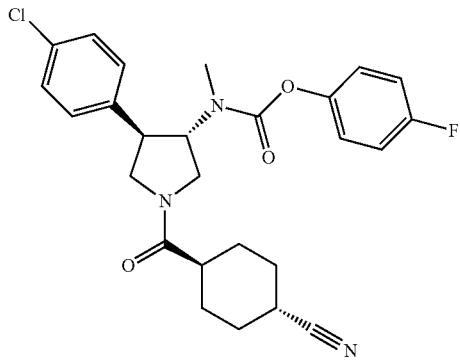 [SMILES: CN(C(=O)Oc1ccc(F)cc1)[C@@H]1CN(C(=O)[C@H]2CC[C@H](C#N)CC2)C[C@H]1c1ccc(Cl)cc1]

In analogy to the procedure described for the synthesis of example 44 (step c), the title compound [(3S,4R)-4-(4-chloro-phenyl)-1-(4-cyano-cyclohexanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 4-cyano-cyclohexanecarboxylic acid instead of 1-methylcyclopropane-1-carboxylic acid and was obtained as an off-white foam. MS m/e: 484.2 [M+H]$^+$.

EXAMPLE 105

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester

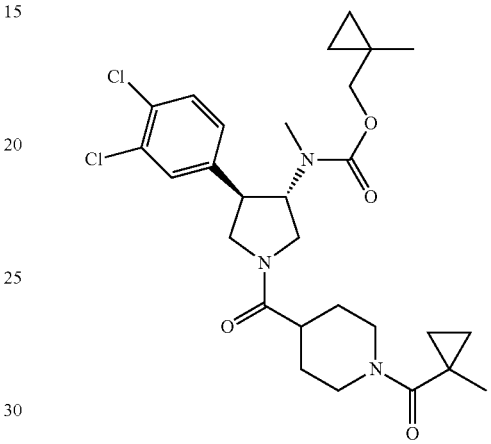

and

EXAMPLE 106

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester

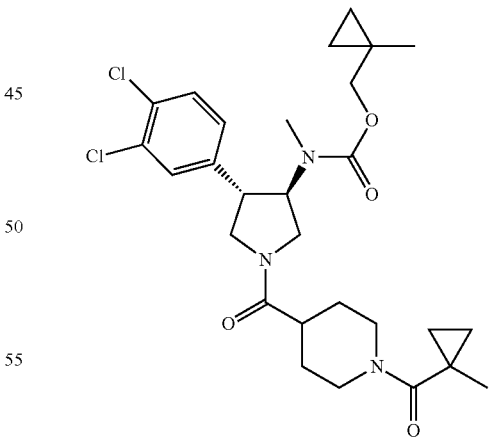

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester was subjected to column chromatography on chiral phase to yield -{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester (MS (m/e): 550.4 [M]$^+$) as a white foam and -{(3S,4R)-4-(3,4-dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester (MS (m/e): 550.4 [M]$^+$) as a white foam.

EXAMPLE 107

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester

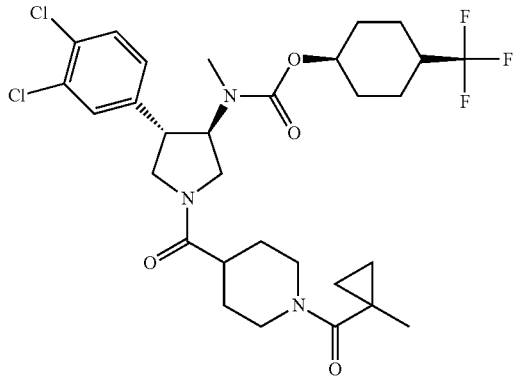

and

EXAMPLE 108

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester

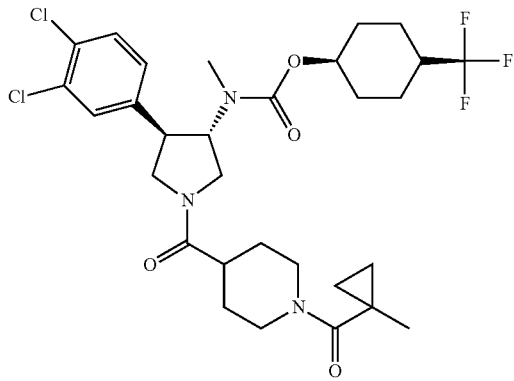

rac-{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester was subjected to column chromatography on chiral phase to yield {(3S,4R)-4-(3,4-dichloro-phenyl)-1-[1-(1-methyl-cyclopropane carbonyl)-piperidine-4-carbonyl]-pyrrolidin-3-yl}-methyl-carbamic acid 4-trifluoromethyl-cyclohexyl ester (MS (m/e): 632.2 [M]$^+$) as an off-white foam and {(3S,4R)-4-(3,4-dichloro-phenyl)-1-[1-(1-methyl-cyclopropane carbonyl)-piperidine-4-carbonyl]-pyrrolidin-3-yl}-methyl-carbamic acid 4-trifluoromethyl-cyclohexyl ester (MS (m/e): 632.2 [M]$^+$) as an off-white foam.

EXAMPLE 109

{(3S,4R)-4-(4-Chloro-phenyl)-1-[1-(1,1-dioxo-hexahydro-1λ$^6$-thiopyran-4-yl)-piperidine-4-carbonyl]-pyrrolidin-3-yl}-methyl-carbamic acid 4-fluoro-phenyl ester

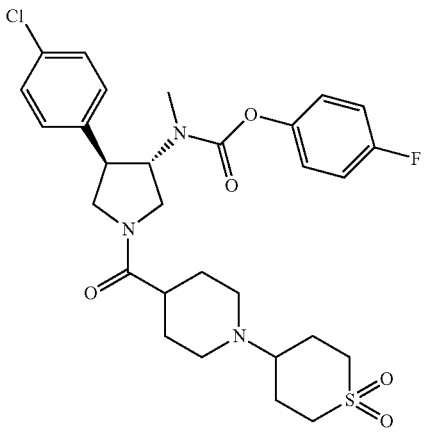 [SMILES: CN(C(=O)Oc1ccc(F)cc1)[C@@H]1CN(C(=O)C2CCN(C3CCS(=O)(=O)CC3)CC2)C[C@H]1c1ccc(Cl)cc1]

In analogy to the procedure described for the synthesis of example 44 (step c), the title compound {(3S,4R)-4-(4-chloro-phenyl)-1-[1-(1,1-dioxo-hexahydro-1λ$^6$-thiopyran-4-yl)-piperidine-4-carbonyl]-pyrrolidin-3-yl}-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 1-(1,1-dioxo-hexahydro-1λ$^6$-thiopyran-4-yl)-piperidine-4-carboxylic acid instead of 1-methylcyclopropane-1-carboxylic acid and was obtained as an off-white foam. MS m/e: 592.2 [M]$^+$.

EXAMPLE 110

{(3S,4R)-4-(4-Chloro-phenyl)-1-[1-(6-chloro-pyridazin-3-yl)-piperidine-4-carbonyl]-pyrrolidin-3-yl}-methyl-carbamic acid 4-fluoro-phenyl ester

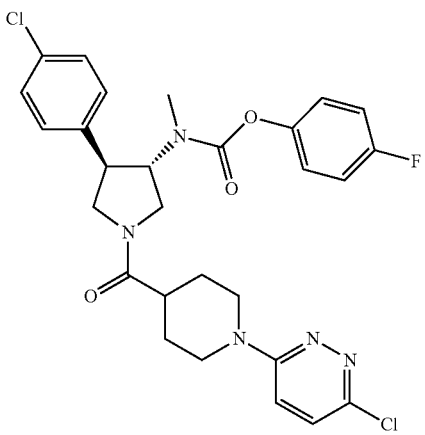 [SMILES: CN(C(=O)Oc1ccc(F)cc1)[C@@H]1CN(C(=O)C2CCN(c3ccc(Cl)nn3)CC2)C[C@H]1c1ccc(Cl)cc1]

In analogy to the procedure described for the synthesis of example 44 (step c), the title compound {(3S,4R)-4-(4-chloro-phenyl)-1-[1-(6-chloro-pyridazin-3-yl)-piperidine-4-carbonyl]-pyrrolidin-3-yl}-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 1-(6-chloro-3-pyridazinyl)-4-piperidinecarboxylic acid instead of 1-methylcyclopropane-1-carboxylic acid and was obtained as an off-white foam. MS m/e: 572.2 [M]$^+$.

EXAMPLE 111 rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3-difluoro-cyclopentylmethyl ester

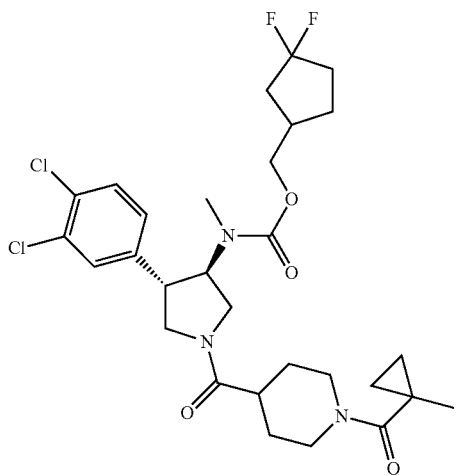 [SMILES: CN(C(=O)OCC1CCC(F)(F)C1)[C@H]1CN(C(=O)C2CCN(C(=O)C3(C)CC3)CC2)C[C@@H]1c1ccc(Cl)c(Cl)c1]

In analogy to the procedure described for the synthesis of example 25, the title compound rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid 3,3-difluoro-cyclopentylmethyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using (3,3-difluoro-cyclopentyl)-methanol instead of 2-cyclopropylethanol and was obtained as a colorless oil. MS m/e: 600.2 [M]$^+$.

EXAMPLE 112

{(3S,4R)-4-(4-Chloro-phenyl)-1-[1-(tetrahydro-pyran-4-yl)-piperidine-4-carbonyl]-pyrrolidin-3-yl}-methyl-carbamic acid 4-fluoro-phenyl ester

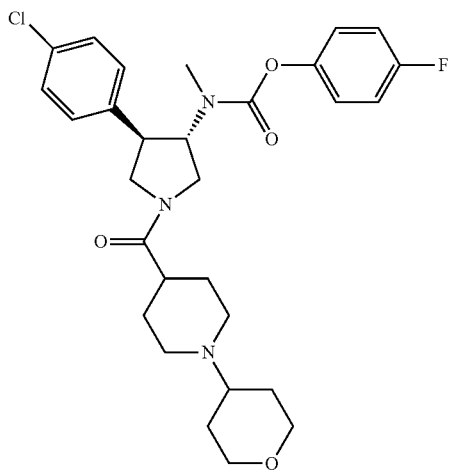 [SMILES: CN(C(=O)Oc1ccc(F)cc1)[C@@H]1CN(C(=O)C2CCN(C3CCOCC3)CC2)C[C@H]1c1ccc(Cl)cc1]

In analogy to the procedure described for the synthesis of example 44 (step c), the title compound {(3S,4R)-4-(4-chloro-phenyl)-1-[1-(tetrahydro-pyran-4-yl)-piperidine-4-carbonyl]-pyrrolidin-3-yl}-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 1-(tetrahydro-pyran-4-yl)-piperidine-4-carboxylic acid instead of 1-methylcyclopropane-1-carboxylic acid and was obtained as a white solid. MS m/e: 544.2 [M]$^+$.

EXAMPLE 113

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 3-bromo-4-fluoro-phenyl ester

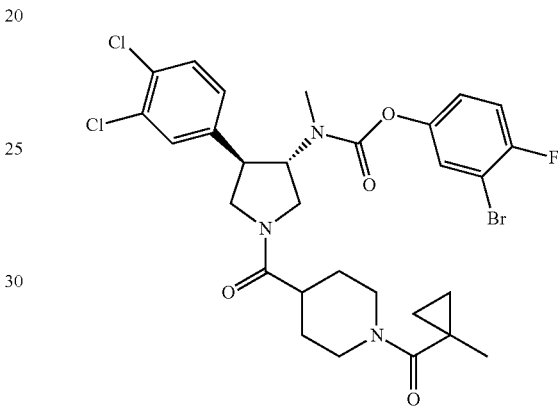

In analogy to the procedure described for the synthesis of example 25, the title compound rac-{(3S,4R)-4-(3,4-dichloro-phenyl)-1-[1-(1-methyl-cyclopropanecarbonyl)-piperidine-4-carbonyl]-pyrrolidin-3-yl}-methyl-carbamic acid 3-bromo-4-fluoro-phenyl ester was prepared from rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3-bromo-4-fluorophenol instead of 2-cyclopropylethanol and was obtained as a colorless oil. MS m/e: 656.2 [M+H]$^+$. It was subjected to column chromatography on chiral phase to yield {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 3-bromo-4-fluoro-phenyl ester (MS (m/e): 656.1 [M+H]$^+$) as an off-white foam.

EXAMPLE 114

[(3S,4R)-4-(4-Chloro-phenyl)-1-(3-morpholin-4-yl-propionyl)-pyrrolidin-3-yl]-methyl-carbamic acid 4-fluoro-phenyl ester

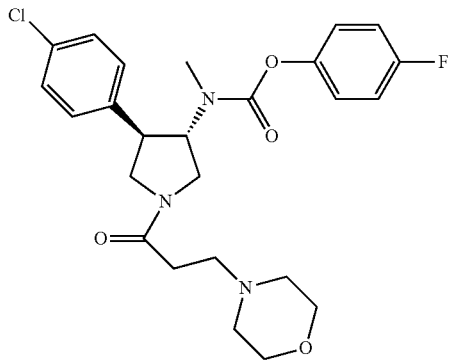 [SMILES: CN(C(=O)Oc1ccc(F)cc1)[C@@H]1CN(C(=O)CCN2CCOCC2)C[C@H]1c1ccc(Cl)cc1]

In analogy to the procedure described for the synthesis of example 44 (step c), the title compound [(3S,4R)-4-(4-chloro-phenyl)-1-(3-morpholin-4-yl-propionyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 3-morpholin-4-yl-propionic acid instead of 1-methylcyclopropane-1-carboxylic acid and was obtained as a white solid. MS m/e: 490.2 [M+H]$^+$.

EXAMPLE 115

{(3S,4R)-4-(4-Chloro-phenyl)-1-[1-(1,1-dioxo-tetrahydro-1λ$^6$-thiophen-3-yl)-piperidine-4-carbonyl]-pyrrolidin-3-yl}-methyl-carbamic acid 4-fluoro-phenyl ester

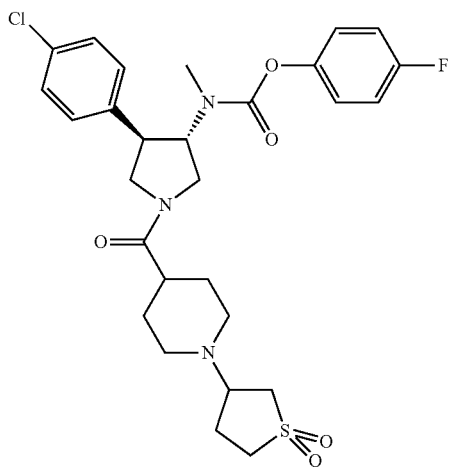 [SMILES: CN(C(=O)Oc1ccc(F)cc1)[C@@H]1CN(C(=O)C2CCN(C3CCS(=O)(=O)C3)CC2)C[C@H]1c1ccc(Cl)cc1]

In analogy to the procedure described for the synthesis of example 44 (step c), the title compound [(3S,4R)-4-(4-chloro-phenyl)-1-(3-morpholin-4-yl-propionyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using rac-1-(1,1-dioxo-tetrahydro-1λ$^6$-thiophen-3-yl)-piperidine-4-carboxylic acid and was obtained as a light yellow solid. MS m/e: 578.2 [M]$^+$.

EXAMPLE 116

[(3S,4R)-4-(4-Chloro-phenyl)-1-(4-hydroxymethyl-cyclohexanecarbonyl)-pyrrolidin-3-yl]-methyl-carbamic acid 4-fluoro-phenyl ester

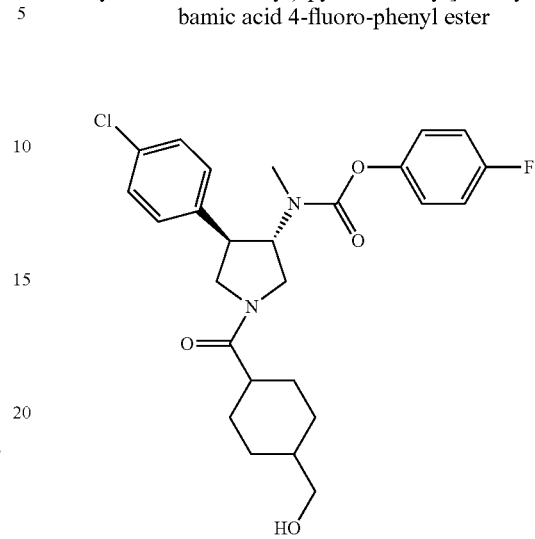

In analogy to the procedure described for the synthesis of example 44 (step c), the title compound [(3S,4R)-4-(4-chloro-phenyl)-1-(4-hydroxymethyl-cyclohexanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 4-hydroxymethyl-1-cyclohexanecarboxylic acid instead of 1-methylcyclopropane-1-carboxylic acid and was obtained as an off-white solid. MS m/e: 489.2 [M+H]$^+$.

EXAMPLE 117

[(3S,4R)-4-(4-Chloro-phenyl)-1-(4,4-di fluoro-cyclohexane carbonyl)-pyrrolidin-3-yl]-methyl-carbamic acid 4-fluoro-phenyl ester

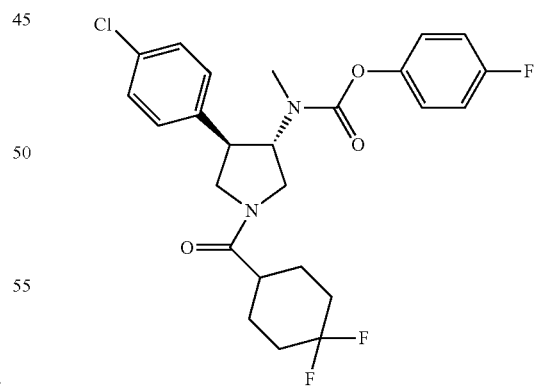

In analogy to the procedure described for the synthesis of example 44 (step c), the title compound [(3S,4R)-4-(4-chloro-phenyl)-1-(4,4-difluoro-cyclohexanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 4,4-Difluoro-cyclohexanecarboxylic acid instead of 1-methylcyclopropane-1-carboxylic acid and was obtained as an off-white solid. MS m/e: 494.2 [M]+.

EXAMPLE 118

{(3S,4R)-4-(4-Chloro-phenyl)-1-[1-(6-methyl-pyridazin-3-yl)-piperidine-4-carbonyl]-pyrrolidin-3-yl}-methyl-carbamic acid 4-fluoro-phenyl ester

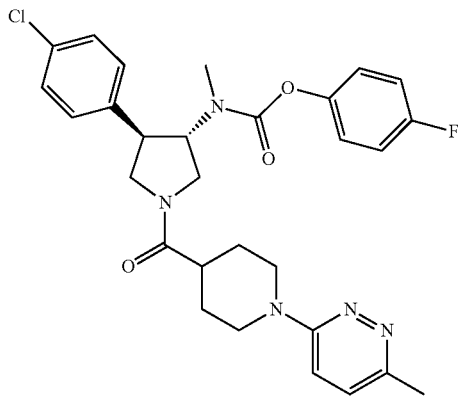 [SMILES: Cc1ccc(N2CCC(C(=O)N3C[C@@H](N(C)C(=O)Oc4ccc(F)cc4)[C@H](c4ccc(Cl)cc4)C3)CC2)nn1]

In analogy to the procedure described for the synthesis of example 44 (step c), the title compound [(3S,4R)-4-(4-chloro-phenyl)-1-(4-hydroxymethyl-cyclohexanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester using 1-(6-methyl-pyridazin-3-yl)-piperidine-4-carboxylic acid instead of 1-methylcyclopropane-1-carboxylic acid and was obtained as an off-white solid. MS m/e: 552.1 [M]+.

EXAMPLE 119

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester

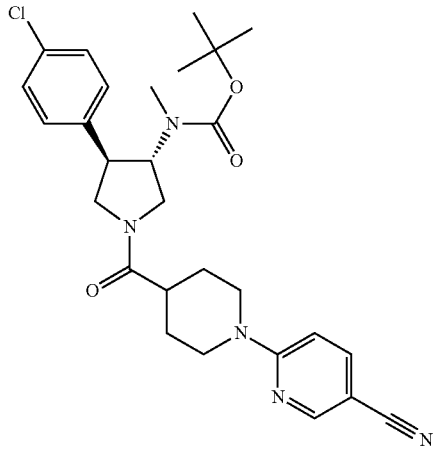 [SMILES: CN(C(=O)OC(C)(C)C)[C@@H]1CN(C(=O)C2CCN(c3ccc(C#N)cn3)CC2)C[C@H]1c1ccc(Cl)cc1]

a) [(3S,4R)-1-Benzyl-4-(4-chloro-phenyl)-pyrrolidin-3-yl]-methyl-carbamic acid tert-butyl ester To a solution of [(3S,4R)-1-benzyl-4-(4-chloro-phenyl)-pyrrolidin-3-yl]-methyl-amine (4.42 g, 13 mmol) in dichloromethane (30 mL) was added at ambient temperature triethylamine (5.72 mL, 41 mmol), 4-dimethylaminopyridine (251 mg, 2 mmol) and di-tert.-butyl-dicarbonate (4.92 g, 23 mmol). The resulting solution was stirred for 20 h at ambient temperature before it was diluted with water (30 mL). The organic layer was washed with water (30 mL) and the combined aqueous layers were extracted with dichloromethane (60 mL). Drying over sodium sulfate and concentration afforded the title compound (7.94 g, 96%) as a brown oil. MS m/e: 345.3 [M-tert-butyl]+.

b) [(3S,4R)-4-(4-Chloro-phenyl)-pyrrolidin-3-yl]-methyl-carbamic acid tert-butyl ester In analogy to the procedure described for the synthesis of example 1 (step e), the title compound [(3S,4R)-4-(4-chlorophenyl)-pyrrolidin-3-yl]-methyl-carbamic acid tert-butyl ester was prepared from [(3S,4R)-1-benzyl-4-(4-chloro-phenyl)-pyrrolidin-3-yl]-methyl-carbamic acid tert-butyl ester instead of rac-[(3R,4S)-1-benzyl-4-(3,4-dichloro-phenyl)-pyrrolidin-3-yl]-methyl-carbamic acid tert-butyl ester and was obtained as an orange brown oil. MS m/e: 311.4 [M+H]+.

c) [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester In analogy to the procedure described for the synthesis of example 44 (step c), the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester was prepared from [(3S,4R)-4-(4-chloro-phenyl)-pyrrolidin-3-yl]-methyl-carbamic acid tert-butyl ester using 5'-cyano-3,4,5,6-tetrahydro-2H-[1,2']bipyridinyl-4-carboxylic acid instead of 1-methylcyclopropane-1-carboxylic acid and was obtained as an orange oil. MS m/e: 524.3 [M]+.

EXAMPLE 120 rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester

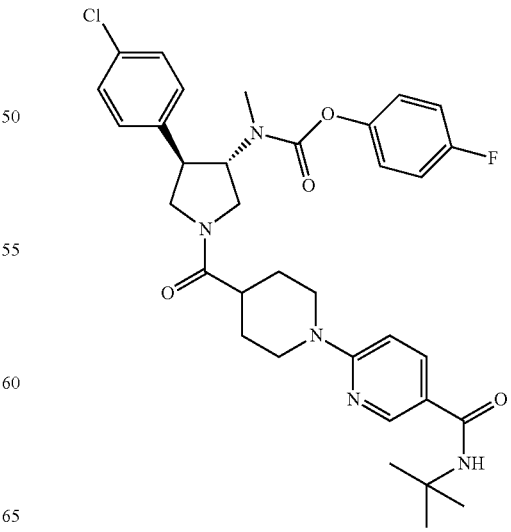

a) rac-[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester In analogy to the procedure described for the synthesis of example 1 (step f), the title compound rac-[(3S,4R)-4-(4-chloro-phenyl)-1-(5'-cyano-3,4,5,6-tetrahydro-2H-[1,2]bipyridinyl-4-carbonyl)-pyrrolidin-3-yl]-methyl-carbamic acid tert-butyl ester was prepared from rac-[(3R,4S)-4-(4-chloro-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester using 5'-cyano-3,4,5,6-tetrahydro-2H-[1,2']bipyridinyl-4-carboxylic acid instead of 141-methyl-cyclopropanecarbonyl)-piperidine-4-carboxylic acid and was obtained as an orange oil. MS m/e: 524.3 [M]$^+$.

b) rac-4-[(3R,4S)-3-(4-Chloro-phenyl)-4-methylamino-pyrrolidine-1-carbonyl]-3,4,5,6-tetrahydro-2H-[1,2']bipyridinyl-5'-carbonitrile In analogy to the procedure described for the synthesis of example 2 (step a), the title compound rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile was prepared from rac-[(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light yellow solid. MS m/e: 424.3 [M+H]$^+$.

c) rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester In analogy to the procedure described for the synthesis of example 2 (step b), the title compound rac-[(3S,4R)-1-(5'-tert-butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester was prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-fluorophenyl chloroformate and was obtained as a side product as a white solid. MS m/e: 635.2 [M−H]$^−$.

EXAMPLE 121 rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-trifluoromethyl-cyclohexyl ester

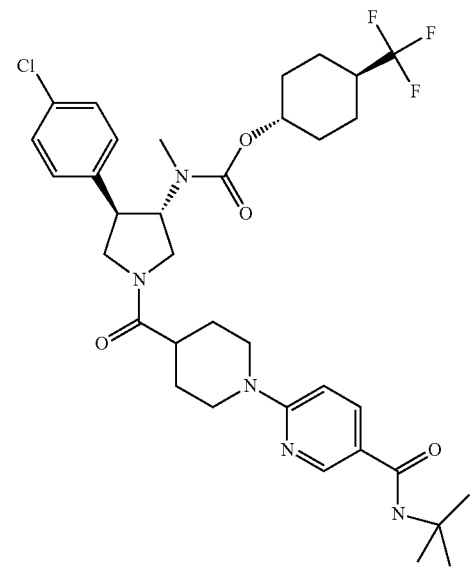 [SMILES: CN(C(=O)O[C@H]1CC[C@H](C(F)(F)F)CC1)[C@@H]1CN(C(=O)C2CCN(c3ccc(C(=O)NC(C)(C)C)cn3)CC2)C[C@H]1c1ccc(Cl)cc1]

a) rac-[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester In analogy to the procedure described for the synthesis of example 1 (step f), the title compound rac-[(3S,4R)-4-(4-Chloro-phenyl)-1-(5'-cyano-3,4,5,6-tetrahydro-2H-[1,2]bipyridinyl-4-carbonyl)-pyrrolidin-3-yl]-methyl-carbamic acid tert-butyl ester was prepared from rac-[(3R,4S)-4-(4-chloro-phenyl)-pyrrolidin-3-yl]-methyl-carbamic acid tert-butyl ester instead of rac-[(3R,4S)-4-(3,4-dichloro-phenyl)-pyrrolidin-3-yl]-methyl-carbamic acid tert-butyl ester using 5'-cyano-3,4,5,6-tetrahydro-2H-[1,2']bipyridinyl-4-carboxylic acid instead of 141-methyl-cyclopropanecarbonyl)-piperidine-4-carboxylic acid and was obtained as an orange oil. MS m/e: 524.3 [M]$^+$.

b) rac-4-[(3R,4S)-3-(4-Chloro-phenyl)-4-methylamino-pyrrolidine-1-carbonyl]-3,4,5,6-tetrahydro-2H-[1,2']bipyridinyl-5'-carbonitrile In analogy to the procedure described for the synthesis of example 2 (step a), the title compound rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile was prepared from rac-[(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light yellow solid. MS m/e: 424.3 [M+H]$^+$.

c) rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-trifluoromethyl-cyclohexyl ester In analogy to the procedure described for the synthesis of example 25, the title compound rac-[(3S,4R)-1-(5'-tert-butyl-carbamoyl-3,4,5,6-tetrahydro-2H-[1,2']bipyridinyl-4-carbonyl)-4-(4-chloro-phenyl)-pyrrolidin-3-yl]-methyl-carbamic acid 4-trifluoromethyl-cyclohexyl ester was prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-trifluoromethyl-cyclohexanol (cis/trans mixture) instead of 2-cyclopropylethanol and was obtained as a side product as an off-white foam. MS m/e: 692.3 [M]+.

EXAMPLE 122

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester

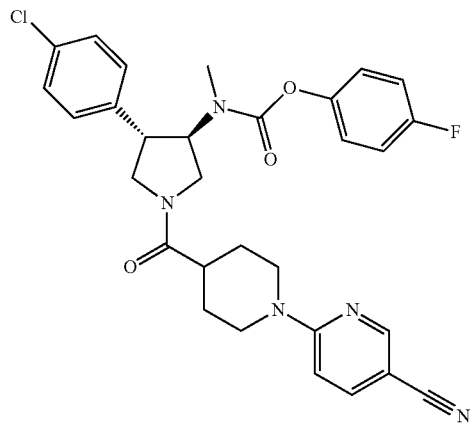 [SMILES: CN(C(=O)Oc1ccc(F)cc1)[C@H]1CN(C(=O)C2CCN(c3ccc(C#N)cn3)CC2)C[C@@H]1c1ccc(Cl)cc1]

rac-[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester was subjected to column chromatography on chiral phase to yield [(3R,4S)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester (MS (m/e): 562.2 [M]+) as an off-white foam.

EXAMPLE 123

{(3S,4R)-4-(3,4-Dichloro-phenyl)-1-[1-(tetrahydro-pyran-4-yl)-piperidine-4-carbonyl]-pyrrolidin-3-yl}-methyl-carbamic acid 4-trifluoromethyl-cyclohexyl ester

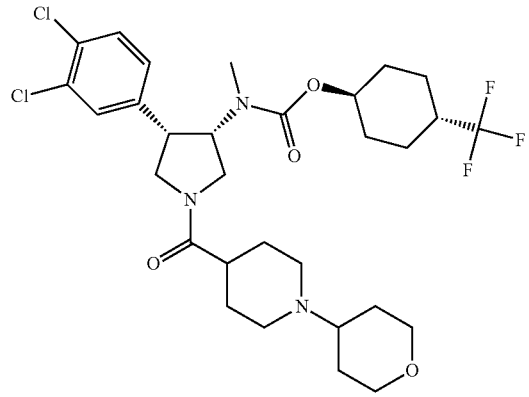 [SMILES: CN(C(=O)O[C@H]1CC[C@H](C(F)(F)F)CC1)[C@@H]1CN(C(=O)C2CCN(C3CCOCC3)CC2)C[C@@H]1c1ccc(Cl)c(Cl)c1]

In analogy to the procedure described for the synthesis of example 44 (step c), the title compound {(3S,4R)-4-(3,4-dichloro-phenyl)-1-[1-(tetrahydro-pyran-4-yl)-piperidine-4-carbonyl]-pyrrolidin-3-yl}-methyl-carbamic acid 4-trifluoromethyl-cyclohexyl ester was prepared from [(3S,4R)-4-(3,4-dichloro-phenyl)-pyrrolidin-3-yl]-methyl-carbamic acid 4-trifluoromethyl-cyclohexyl ester instead of [(3S,4R)-4-(3,4-dichloro-phenyl)-pyrrolidin-3-yl]-methyl-carbamic acid 4-fluoro-phenyl ester using 1-(tetrahydro-pyran-4-yl)-piperidine-4-carboxylic acid instead of 1-methylcyclopropane-1-carboxylic acid and was obtained as an off-white foam. MS m/e: 634.2 [M]+.

EXAMPLE 124 rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4,4,4-trifluoro-butyl ester

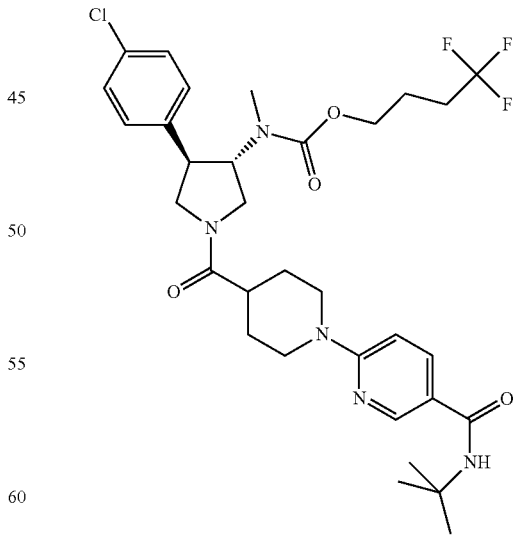

In analogy to the procedure described for the synthesis of example 25, the title compound rac-[(3S,4R)-1-(5'-tert-butyl-carbamoyl-3,4,5,6-tetrahydro-2H-[1,2']bipyridinyl-4-carbonyl)-4-(4-chloro-phenyl)-pyrrolidin-3-yl]-methyl-carbamic acid 4,4,4-trifluoro-butyl ester was prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,4-trifluoro-1-butanol instead of 2-cyclopropylethanol and was obtained as a side product as a brown oil. MS m/e: 651.2 [M−H]⁻.

EXAMPLE 125

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester

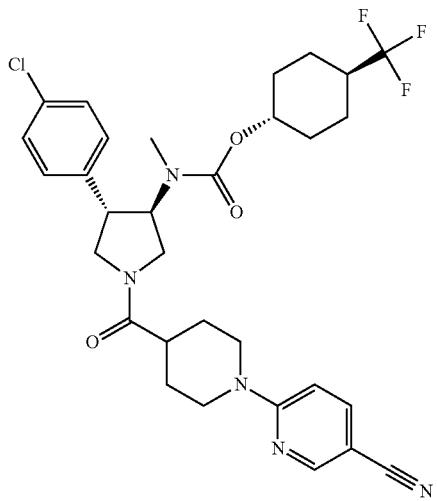 [SMILES: CN(C(=O)O[C@H]1CC[C@H](C(F)(F)F)CC1)[C@H]1CN(C(=O)C2CCN(c3ccc(C#N)cn3)CC2)C[C@@H]1c1ccc(Cl)cc1]

and

EXAMPLE 126

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester

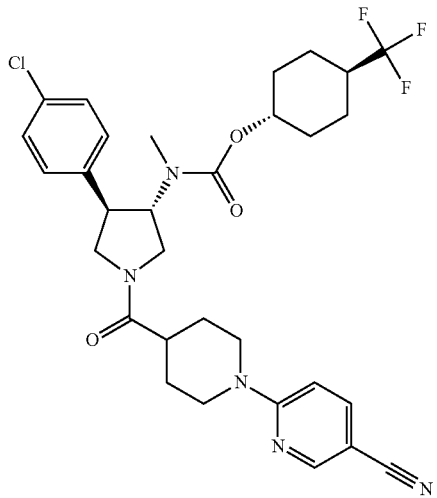 [SMILES: CN(C(=O)O[C@H]1CC[C@H](C(F)(F)F)CC1)[C@@H]1CN(C(=O)C2CCN(c3ccc(C#N)cn3)CC2)C[C@H]1c1ccc(Cl)cc1]

In analogy to the procedure described for the synthesis of example 25, the title compounds rac-[(3R,4S)-4-(4-Chloro-phenyl)-1-(5'-cyano-3,4,5,6-tetrahydro-2H-[1,2]bipyridinyl-4-carbonyl)-pyrrolidin-3-yl]-methyl-carbamic acid 4-trifluoromethyl-cyclohexyl ester were prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-trifluoromethyl-cyclohexanol (cis/trans mixture) instead of 2-cyclopropylethanol and were obtained as a colorless oil. MS m/e: 618.2 [M]⁺. It was subjected to column chromatography on chiral phase to yield [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester (MS (m/e): 617.4 [M]⁺) as a yellow solid and [(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester (MS (m/e): 617.4 [M]⁺) as a yellow solid.

EXAMPLE 127

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester

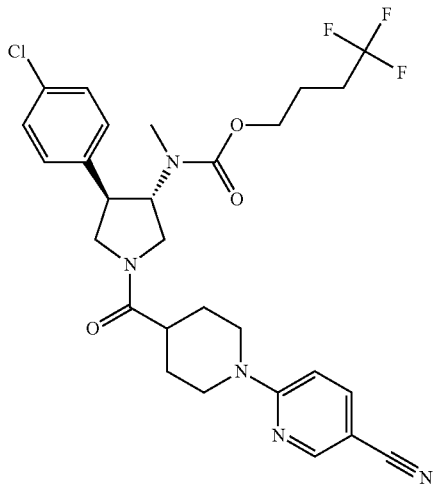 [SMILES: CN(C(=O)OCCCC(F)(F)F)[C@@H]1CN(C(=O)C2CCN(c3ccc(C#N)cn3)CC2)C[C@H]1c1ccc(Cl)cc1]

and

EXAMPLE 128

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester

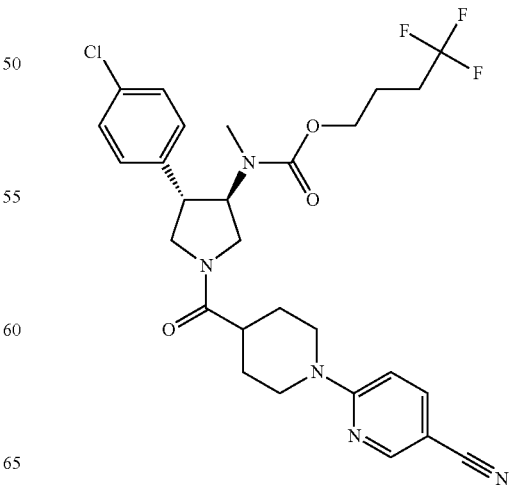

In analogy to the procedure described for the synthesis of example 25, the title compounds rac-[(3R,4S)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester were prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,4-trifluoro-1-butanol instead of 2-cyclopropylethanol and were obtained as a yellow solid. MS m/e: 578.4 [M+H]$^+$. It was subjected to column chromatography on chiral phase to yield [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester (MS (m/e): 577.2 [M]$^+$) as a yellow foam [(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester (MS (m/e): 577.2 [M]$^+$) as a yellow foam.

EXAMPLE 129

{(3S,4R)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester

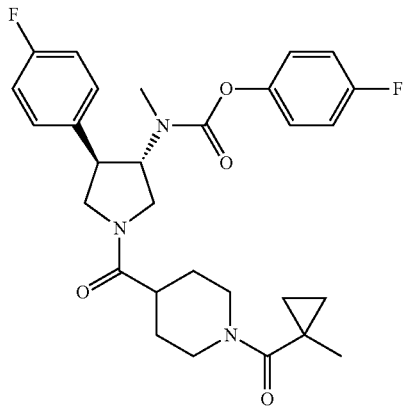 [SMILES: CN(C(=O)Oc1ccc(F)cc1)[C@@H]1CN(C(=O)C2CCN(C(=O)C3(C)CC3)CC2)C[C@H]1c1ccc(F)cc1]

a) rac-(3S,4R)-1-Benzyl-3-(4-fluoro-phenyl)-4-nitro-pyrrolidine

In analogy to the procedure described for the synthesis of example 1 (step a), the title compound rac-(3S,4R)-1-benzyl-3-(4-fluoro-phenyl)-4-nitro-pyrrolidine was prepared from 1-fluoro-4-((E)-2-nitro-vinyl)-benzene instead of 1,2-dichloro-4-((E)-2-nitro-vinyl)-benzene and was obtained as a light yellow oil. MS m/e: 301.2 [M+H]$^+$.

b) rac-(3R,4S)-1-Benzyl-4-(4-fluoro-phenyl)-pyrrolidin-3-ylamine

In analogy to the procedure described for the synthesis of example 1 (step b), the title compound rac-(3R,4S)-1-benzyl-4-(4-fluoro-phenyl)-pyrrolidin-3-ylamine was prepared from rac-(3S,4R)-1-benzyl-3-(4-fluoro-phenyl)-4-nitro-pyrrolidine instead of rac-(3R,4S)-1-Benzyl-3-(3,4-dichloro-phenyl)-4-nitro-pyrrolidine and was obtained as a dark brown oil. MS m/e: 271.3 [M+H]$^+$.

c) rac-[(3R,4S)-1-Benzyl-4-(4-fluoro-phenyl)-pyrrolidin-3-yl]-methyl-amine

In analogy to the procedure described for the synthesis of example 1 (step c), the title compound rac-[(3R,4S)-1-benzyl-4-(4-fluoro-phenyl)-pyrrolidin-3-yl]-methyl-amine was prepared from rac-(3R,4S)-1-benzyl-4-(4-fluoro-phenyl)-pyrrolidin-3-ylamine instead of rac-(3S,4R)-1-benzyl-4-(3,4-dichloro-phenyl)-pyrrolidin-3-ylamine and was obtained as a light brown oil. MS m/e: 285.2 [M+H]$^+$.

d) rac-[(3R,4S)-1-Benzyl-4-(4-fluoro-phenyl)-pyrrolidin-3-yl]-methyl-carbamic acid 4-fluoro-phenyl ester In analogy to the procedure described for the synthesis of example 2 (step b), the title compound rac-[(3R,4S)-1-benzyl-4-(4-fluoro-phenyl)-pyrrolidin-3-yl]-methyl-carbamic acid 4-fluoro-phenyl ester was prepared from rac-[(3R,4S)-1-benzyl-4-(4-fluoro-phenyl)-pyrrolidin-3-yl]-methyl-amine instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone and was obtained as a yellow oil. MS m/e: 423.2 [M+H]$^+$.

e) rac-[(3R,4S)-4-(4-Fluoro-phenyl)-pyrrolidin-3-yl]-methyl-carbamic acid 4-fluoro-phenyl ester In analogy to the procedure described for the synthesis of example 1 (step e), the title compound rac-[(3R,4S)-4-(4-fluoro-phenyl)-pyrrolidin-3-yl]-methyl-carbamic acid 4-fluoro-phenyl ester was prepared from rac-[(3R,4S)-1-benzyl-4-(4-fluoro-phenyl)-pyrrolidin-3-yl]-methyl-carbamic acid 4-fluoro-phenyl ester instead of rac-[(3R,4S)-1-benzyl-4-(3,4-dichloro-phenyl)-pyrrolidin-3-yl]-methyl-carbamic acid tert-butyl ester and was obtained as a dark brown oil which was used without further purification.

f) rac-{(3R,4S)-4-(4-Fluoro-phenyl)-1-[1-(1-methyl-cyclopropane carbonyl)-piperidine-4-carbonyl]-pyrrolidin-3-yl}-methyl-carbamic acid 4-fluoro-phenyl ester In analogy to the procedure described for the synthesis of example 1 (step f), the title compound rac-{(3R,4S)-4-(4-fluoro-phenyl)-1-[1-(1-methyl-cyclopropanecarbonyl)-piperidine-4-carbonyl]-pyrrolidin-3-yl}-methyl-carbamic acid 4-fluoro-phenyl ester was prepared from rac-[(3R,4S)-4-(4-fluoro-phenyl)-pyrrolidin-3-yl]-methyl-carbamic acid 4-fluoro-phenyl ester instead of rac-[(3R,4S)-4-(3,4-dichloro-phenyl)-pyrrolidin-3-yl]-methyl-carbamic acid tert-butyl ester and was obtained as a light brown semi-solid. MS m/e: 526.4 [M+H]$^+$.

g) {(3S,4R)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester rac-{(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester was subjected to column chromatography on chiral phase to yield {(3S,4R)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 526.4 [M+H]$^+$) as a white foam.

EXAMPLE 130

{(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester

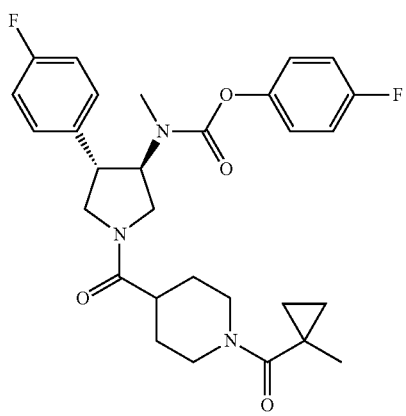 [SMILES: CN(C(=O)Oc1ccc(F)cc1)[C@H]1CN(C(=O)C2CCN(C(=O)C3(C)CC3)CC2)C[C@@H]1c1ccc(F)cc1]

rac-{(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester was subjected to column chromatography on chiral phase to yield {(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester (MS (m/e): 526.4 [M+H]$^+$) as a colorless waxy solid.

EXAMPLE 131

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester

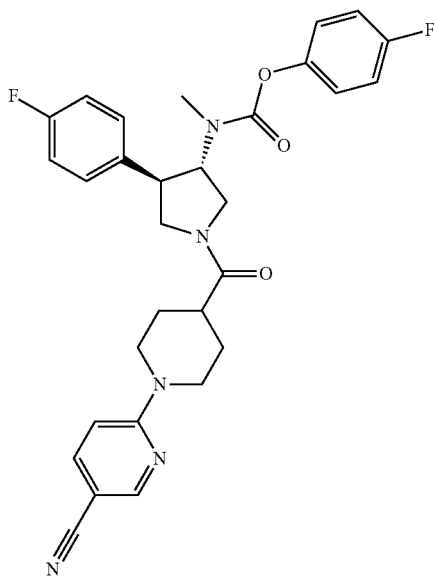 [SMILES: CN(C(=O)Oc1ccc(F)cc1)[C@@H]1CN(C(=O)C2CCN(c3ccc(C#N)cn3)CC2)C[C@H]1c1ccc(F)cc1]

and

EXAMPLE 132

[(3R,4S)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester

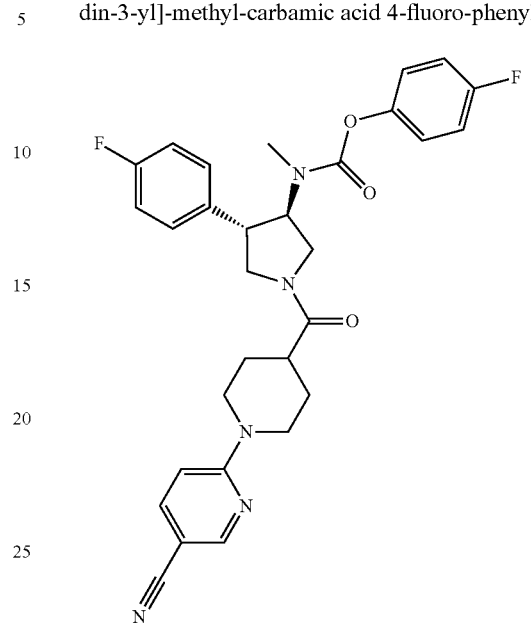

In analogy to the procedure described for the synthesis of example 44 (step c), the title compound rac-[(3R,4S)-1-(5'-cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester was prepared from rac-[(3R,4S)-4-(4-fluoro-phenyl)-pyrrolidin-3-yl]-methyl-carbamic acid 4-fluoro-phenyl ester using 5'-cyano-3,4,5,6-tetrahydro-2H-[1,2']bipyridinyl-4-carboxylic acid instead of 1-methylcyclopropane-1-carboxylic acid and was obtained as a brown semisolid. MS m/e: 562.1 [M]$^+$. The racemate was then subjected to column chromatography on chiral phase to yield -[(3S,4R)-1-(5'-cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester (MS (m/e): 546.3 [M+H]$^+$) as a yellow waxy solid and -[(3R,4S)-1-(5'-cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester (MS (m/e): 546.3 [M+H]$^+$) as a yellow waxy solid.

EXAMPLE 133

4-{(3R,4S)-3-(4-Chloro-phenyl)-4-[(4-fluoro-phenoxycarbonyl)-methyl-amino]-pyrrolidine-1-carbonyl}-piperidine-1-carboxylic acid tert-butyl ester

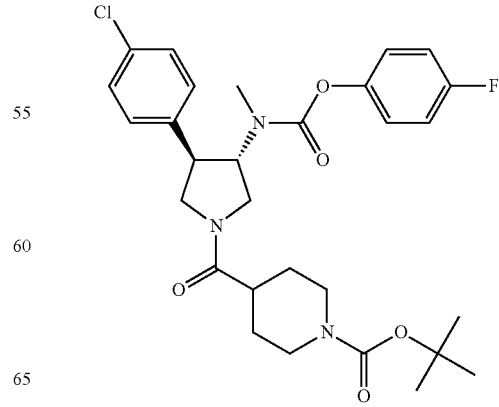

In analogy to the procedure described for the synthesis of example 44 (step c), the title compound 4-{(3R,4S)-3-(4-chloro-phenyl)-4-[(4-fluoro-phenoxycarbonyl)-methyl-amino]-pyrrolidine-1-carbonyl}-piperidine-1-carboxylic acid tert-butyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using piperidine-1,4-dicarboxylic acid mono-tert-butyl ester instead of 1-methylcyclopropane-1-carboxylic acid and was obtained as a light-brown gum. MS m/e: 560.3 [M]$^+$.

EXAMPLE 134

{(3S,4R)-4-(4-Chloro-phenyl)-1-[1-(5-methyl-[1,3,4]oxadiazol-2-yl)-piperidine-4-carbonyl]-pyrrolidin-3-yl}-methyl-carbamic acid 4-fluoro-phenyl ester

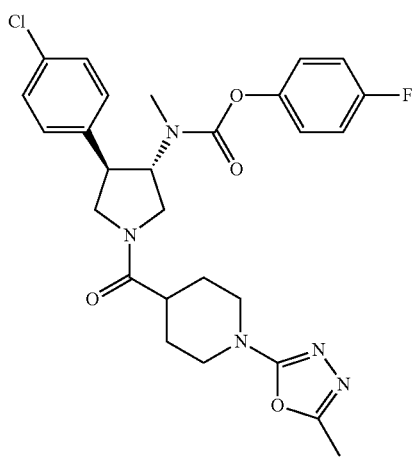 [SMILES: Cc1nnc(N2CCC(C(=O)N3C[C@@H](N(C)C(=O)Oc4ccc(F)cc4)[C@H](c4ccc(Cl)cc4)C3)CC2)o1]

In analogy to the procedure described for the synthesis of example 44 (step c), the title compound 4-{(3R,4S)-3-(4-chloro-phenyl)-4-[(4-fluoro-phenoxycarbonyl)-methyl-amino]-pyrrolidine-1-carbonyl}-piperidine-1-carboxylic acid tert-butyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 1-(5-methyl-[1,3,4]oxadiazol-2-yl)-piperidine-4-carboxylic acid instead of 1-methylcyclopropane-1-carboxylic acid and was obtained as an off-white foam. MS m/e: 542.3 [M]$^+$.

EXAMPLE 135

[(3S,4R)-4-(4-Chloro-phenyl)-1-(piperidine-4-carbonyl)-pyrrolidin-3-yl]-methyl-carbamic acid 4-fluoro-phenyl ester

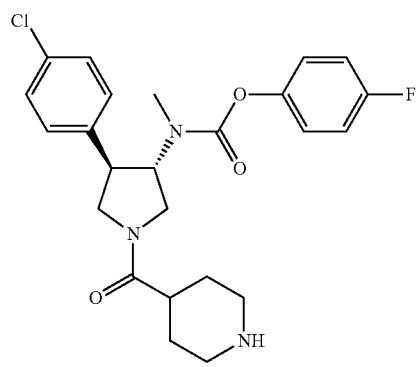 [SMILES: CN(C(=O)Oc1ccc(F)cc1)[C@@H]1CN(C(=O)C2CCNCC2)C[C@H]1c1ccc(Cl)cc1]

In analogy to the procedure described for the synthesis of example 2 (step a), the title compound [(3S,4R)-4-(4-chloro-phenyl)-1-(piperidine-4-carbonyl)-pyrrolidin-3-yl]-methyl-carbamic acid 4-fluoro-phenyl ester was prepared from 4-{(3R,4S)-3-(4-chloro-phenyl)-4-[(4-fluoro-phenoxycarbonyl)-methyl-amino]-pyrrolidine-1-carbonyl}-piperidine-1-carboxylic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light brown foam. MS m/e: 460.4 [M+H]$^+$.

EXAMPLE 136

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid ethyl ester

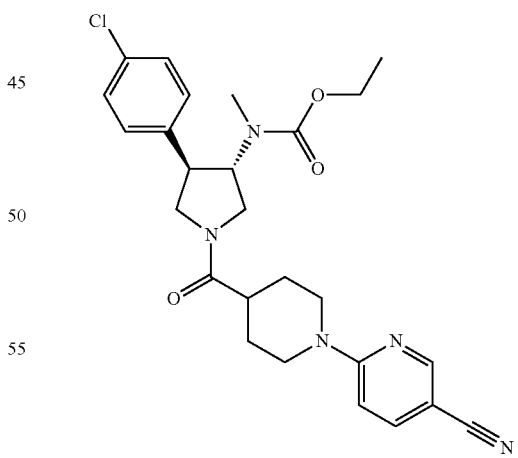

a) 4-[(3R,4S)-3-(4-Chloro-phenyl)-4-methylamino-pyrrolidine-1-carbonyl]-3,4,5,6-tetrahydro-2H-[1,2']bipyridinyl-5'-carbonitrile To a solution of [(3S,4R)-4-(4-Chloro-phenyl)-1-(5'-cyano-3,4,5,6-tetrahydro-2H-[1,2]bipyridinyl-4-carbonyl)- pyrrolidin-3-yl]-methyl-carbamic acid tert-butyl ester (3.20 g, 6.12 mmol) in acetonitrile (30 mL) was added at ambient temperature trifluoroacetic acid (4.7 mL, 61.2 mmol) and the reaction mixture was stirred for 4 h at this temperature. After concentration, the residue was dissolved in ethyl acetate and washed with aqueous sodium carbonate (20%). The organic layer was dried over sodium sulfate and concentrated affording the title compound (1.90 g, 73%) as a light yellow foam. MS m/e: 424.2 [M+H]+.

b) [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid ethyl ester To a solution of 4-[(3R,4S)-3-(4-Chloro-phenyl)-4-methylamino-pyrrolidine-1-carbonyl]-3,4,5,6-tetrahydro-2H-[1,2']bipyridinyl-5'-carbonitrile (30 mg, 0.07 mmol) in dichloromethane (1 mL) were added triethylamine (13 uL, 0.09 mmol) and ethyl chloroformate (9 uL, 0.09 mmol) and the reaction mixture was stirred at ambient temperature for 3 h. After concentration it was purified by chromatography affording the title compound (20 mg, 57%) as a colorless foam. MS m/e: 496.4 [M]+.

EXAMPLE 137

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid isopropyl ester

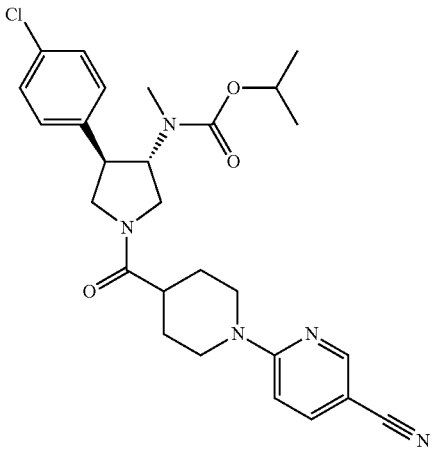 [SMILES: CC(C)OC(=O)N(C)[C@@H]1CN(C(=O)C2CCN(c3ccc(C#N)cn3)CC2)C[C@H]1c1ccc(Cl)cc1]

In analogy to the procedure described for the synthesis of example 136, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid isopropyl ester was prepared from 4-[(3R,4S)-3-(4-chloro-phenyl)-4-methylamino-pyrrolidine-1-carbonyl]-3,4,5,6-tetrahydro-2H-[1,2]bipyridinyl-5'-carbonitrile using isopropyl chloroformate instead of ethyl chloroformate and was obtained as a colorless foam. MS m/e: 510.4 [M]+.

EXAMPLE 138

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid propyl ester

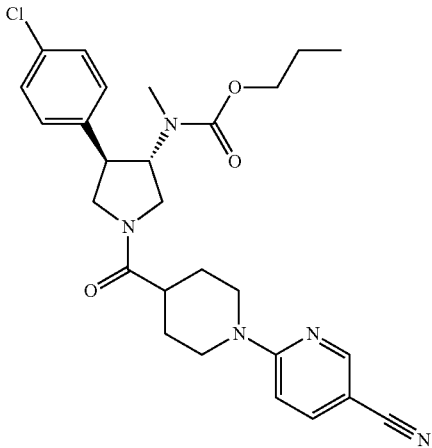 [SMILES: CCCOC(=O)N(C)[C@@H]1CN(C(=O)C2CCN(c3ccc(C#N)cn3)CC2)C[C@H]1c1ccc(Cl)cc1]

In analogy to the procedure described for the synthesis of example 136, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid propyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile using propyl chloroformate instead of ethyl chloroformate and was obtained as a colorless foam. MS m/e: 510.4 [M]+.

EXAMPLE 139

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid isobutyl ester

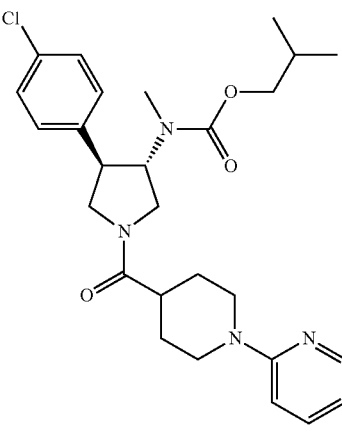

In analogy to the procedure described for the synthesis of example 136, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid isobutyl ester was prepared from 4-[(3R,4S)-3-(4-chloro-phenyl)-4-methylamino-pyrrolidine-1-carbonyl]-3,4,5,6-tetrahydro-2H-[1,2]bipyridinyl-5'-carbonitrile using isobutyl chloroformate instead of ethyl chloroformate and was obtained as a colorless foam. MS m/e: 524.5 [M]+.

EXAMPLE 140

{(3S,4R)-4-(4-Chloro-phenyl)-1-[1-(6-cyano-pyridazin-3-yl)-piperidine-4-carbonyl]-pyrrolidin-3-yl}-methyl-carbamic acid 4-fluoro-phenyl ester

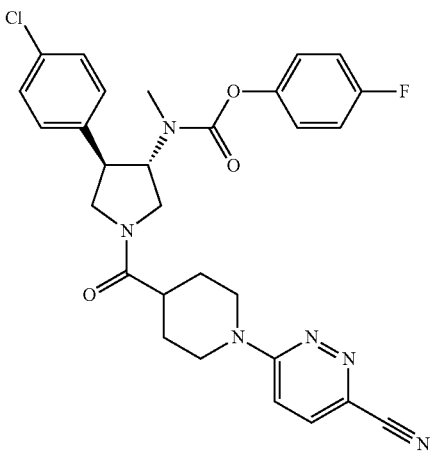 [SMILES: CN(C(=O)Oc1ccc(F)cc1)[C@@H]1CN(C(=O)C2CCN(c3ccc(C#N)nn3)CC2)C[C@H]1c1ccc(Cl)cc1]

To a solution of [(3S,4R)-4-(4-chloro-phenyl)-1-(piperidine-4-carbonyl)-pyrrolidin-3-yl]-methyl-carbamic acid 4-fluoro-phenyl ester (186 mg, 0.40 mmol) in DMF (2 mL) was added 6-chloro-3-pyridazinecarbonitrile (67 mg, 0.48 mmol) and N,N-diisopropyl ethyl amine (208, 1.21 mmol). The resulting dark brown solution was stirred for 3 h at 80° C. After cooling to ambient temperature the reaction mixture was diluted with ethyl acetate (15 mL) and washed with aqueous sodium carbonate (1M, 15 mL), water (15 mL) and brine (15 mL). The aqueous layers were extracted with ethyl acetate (15 mL) and the combined organic layers dried over sodium sulfate. Concentration and purification by chromatography (SiO$_2$, heptane:ethyl acetate=50:50 to 0:100) afforded the title compound (167 mg, 73%) as a white foam. MS m/e: 563.3 [M]$^+$.

EXAMPLE 141

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid isobutyl ester

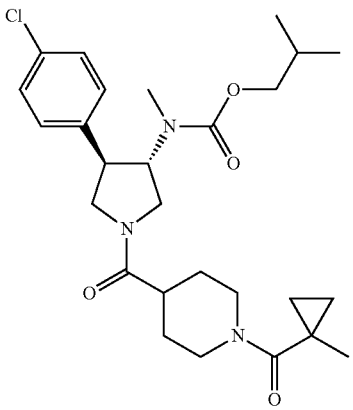 [SMILES: CC(C)COC(=O)N(C)[C@@H]1CN(C(=O)C2CCN(C(=O)C3(C)CC3)CC2)C[C@H]1c1ccc(Cl)cc1]

a) {(3S,4R)-4-(4-Chloro-phenyl)-1-[1-(1-methyl-cyclopropanecarbonyl)-piperidine-4-arbonyl]-pyrrolidin-3-yl}-methyl-carbamic acid tert-butyl ester In analogy to the procedure described for the synthesis of example 44 (step c), the title compound {(3S,4R)-4-(4-chloro-phenyl)-1-[1-(1-methyl-cyclopropane carbonyl)-piperidine-4-arbonyl]-pyrrolidin-3-yl}-methyl-carbamic acid tert-butyl ester was prepared from [(3S,4R)-4-(4-chloro-phenyl)-pyrrolidin-3-yl]-methyl-carbamic acid tert-butyl ester instead of [(3S,4R)-4-(4-chloro-phenyl)-pyrrolidin-3-yl]-methyl-carbamic acid 4-fluoro-phenyl ester using 1-methyl-cyclopropane-1-carboxylic acid and was obtained as an off-white foam. MS m/e: 504.2 [M]$^+$.

b) [(3R,4S)-3-(4-Chloro-phenyl)-4-methylamino-pyrrolidin-1-yl]-[1-(1-methyl-cyclopropanecarbonyl)-piperidin-4-yl]-methanone In analogy to the procedure described for the synthesis of example 2 (step a), the title compound [(3R,4S)-3-(4-chloro-phenyl)-4-methylamino-pyrrolidin-1-yl]-[1-(1-methyl-cyclopropanecarbonyl)-piperidin-4-yl]-methanone was prepared from {(3S,4R)-4-(4-chloro-phenyl)-1-[1-(1-methyl-cyclopropanecarbonyl)-piperidine-4-arbonyl]-pyrrolidin-3-yl}-methyl-carbamic acid tert-butyl ester instead of rac-{(3R,4S)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a light yellow foam. MS m/e: 403.9 [M]$^+$.

c) [(3S,4R)-4-(4-Chloro-phenyl)-1-[1-(1-methyl-cyclopropanecarbonyl)-piperidine-4-carbonyl]-pyrrolidin-3-yl]-methyl-carbamic acid isobutyl ester In analogy to the procedure described for the synthesis of example 136, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid isobutyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile using isobutyl chloroformate instead of ethyl chloroformate and was obtained as a colorless foam. MS m/e: 504.2 [M]$^+$.

EXAMPLE 142

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid propyl ester

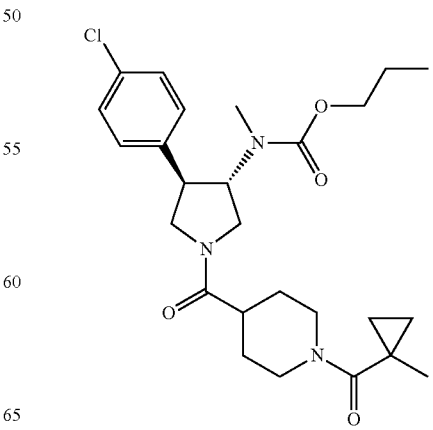

In analogy to the procedure described for the synthesis of example 136, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid propyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile using propyl chloroformate instead of ethyl chloroformate and was obtained as a colorless foam. MS m/e: 490.4 [M]⁺.

EXAMPLE 143

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclohexyl ester

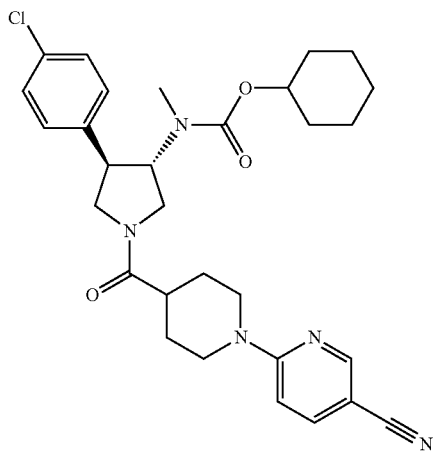 [SMILES: CN(C(=O)OC1CCCCC1)[C@@H]1CN(C(=O)C2CCN(c3ccc(C#N)cn3)CC2)C[C@H]1c1ccc(Cl)cc1]

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid cyclohexyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cyclohexanol instead of 2-cyclopropylethanol and was obtained as a colorless foam. MS m/e: 550.4 [M]⁺.

EXAMPLE 144

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester

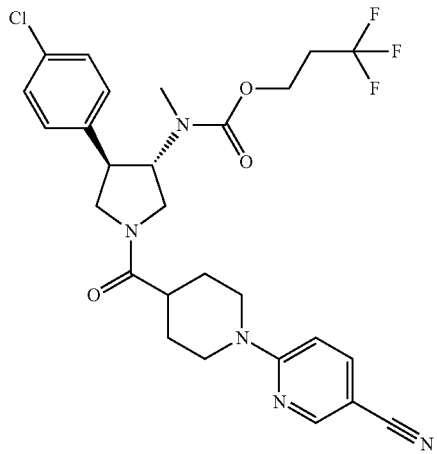 [SMILES: CN(C(=O)OCCC(F)(F)F)[C@@H]1CN(C(=O)C2CCN(c3ccc(C#N)cn3)CC2)C[C@H]1c1ccc(Cl)cc1]

and

EXAMPLE 145

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester

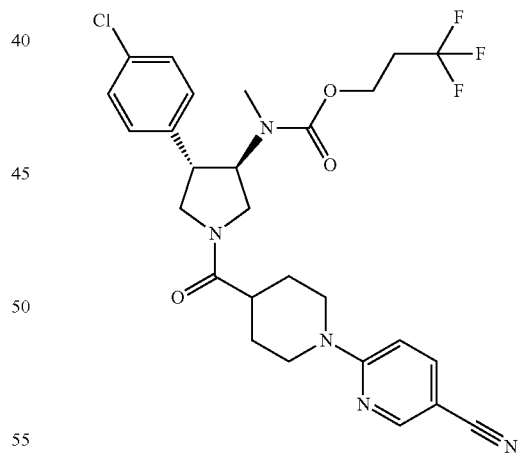

In analogy to the procedure described for the synthesis of example 25, the title compounds rac-[(3R,4S)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester were prepared from rac-4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 3,3,3- trifluoro-1-propanol instead of 2-cyclopropylethanol and were obtained as a colorless oil. MS m/e: 563.2 [M]+. It was subjected to column chromatography on chiral phase to yield [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester (MS (m/e): 563.2 [M]+) as a yellow solid and [(3R,4S)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester (MS (m/e): 563.2 [M]+) as a yellow foam.

EXAMPLE 146

[(3S,4R)-4-(4-Chloro-phenyl)-1-(2,2-dimethyl-tetrahydro-pyran-4-carbonyl)-pyrrolidin-3-yl]-methyl-carbamic acid 4-fluoro-phenyl ester

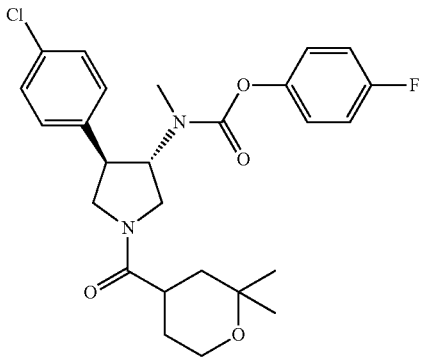 [SMILES: CN(C(=O)Oc1ccc(F)cc1)[C@@H]1CN(C(=O)C2CCOC(C)(C)C2)C[C@H]1c1ccc(Cl)cc1]

In analogy to the procedure described for the synthesis of example 44 (step c), the title compound [(3S,4R)-4-(4-chloro-phenyl)-1-(2,2-dimethyl-tetrahydro-pyran-4-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 2,2-dimethyl-tetrahydro-2H-pyrane-4-carboxylic acid instead of 1-methylcyclopropane-1-carboxylic acid and was obtained as an off-white foam. MS m/e: 489.3 [M+H]+.

EXAMPLE 147

[(3S,4R)-4-(4-Chloro-phenyl)-1-(tetrahydro-pyran-3-carbonyl)-pyrrolidin-3-yl]-methyl-carbamic acid 4-fluoro-phenyl ester

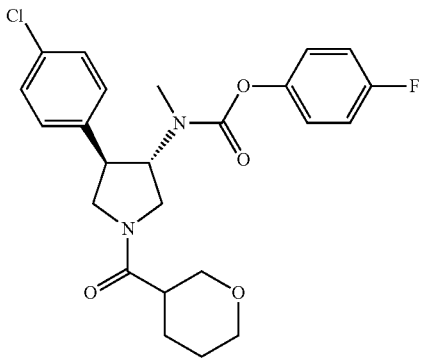 [SMILES: CN(C(=O)Oc1ccc(F)cc1)[C@@H]1CN(C(=O)C2CCCOC2)C[C@H]1c1ccc(Cl)cc1]

In analogy to the procedure described for the synthesis of example 44 (step c), the title compound [(3S,4R)-4-(4-chloro-phenyl)-1-(tetrahydro-pyran-3-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using rac-tetrahydro-pyran-3-carboxylic acid instead of 1-methylcyclopropane-1-carboxylic acid and was obtained as an off-white foam. MS m/e: 461.2 [M+H]+.

EXAMPLE 148

[(3S,4R)-4-(4-Chloro-phenyl)-1-(tetrahydro-furan-3-carbonyl)-pyrrolidin-3-yl]-methyl-carbamic acid 4-fluoro-phenyl ester

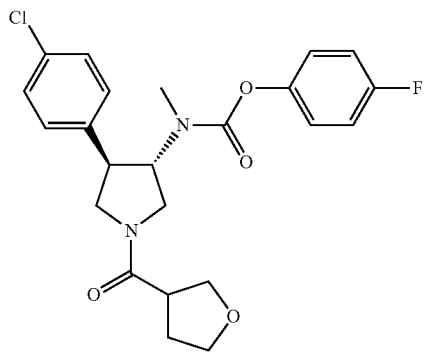 [SMILES: CN(C(=O)Oc1ccc(F)cc1)[C@@H]1CN(C(=O)C2CCOC2)C[C@H]1c1ccc(Cl)cc1]

In analogy to the procedure described for the synthesis of example 44 (step c), the title compound [(3S,4R)-4-(4-chloro-phenyl)-1-(tetrahydro-furan-3-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using rac-tetrahydro-3-furoic acid instead of 1-methylcyclopropane-1-carboxylic acid and was obtained as a light brown oil. MS m/e: 447.2 [M+H]+.

EXAMPLE 149

[(3S,4R)-4-(4-Chloro-phenyl)-1-(3-methoxy-cyclobutanecarbonyl)-pyrrolidin-3-yl]-methyl-carbamic acid 4-fluoro-phenyl ester

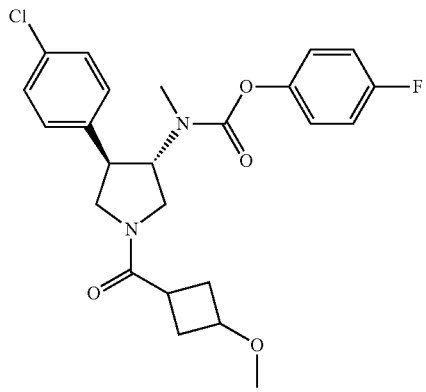 [SMILES: COC1CC(C(=O)N2C[C@@H](N(C)C(=O)Oc3ccc(F)cc3)[C@H](c3ccc(Cl)cc3)C2)C1]

In analogy to the procedure described for the synthesis of example 44 (step c), the title compound [(3S,4R)-4-(4- chloro-phenyl)-1-(3-methoxy-cyclobutanecarbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 3-methoxycyclobutanecarboxylic acid instead of 1-methylcyclopropane-1-carboxylic acid and was obtained as a light brown oil. MS m/e: 461.2 [M+H]$^+$.

EXAMPLE 150

[(3S,4R)-4-(4-Chloro-phenyl)-1-(1-cyclopropyl-piperidine-4-carbonyl)-pyrrolidin-3-yl]-methyl-carbamic acid 4-fluoro-phenyl ester

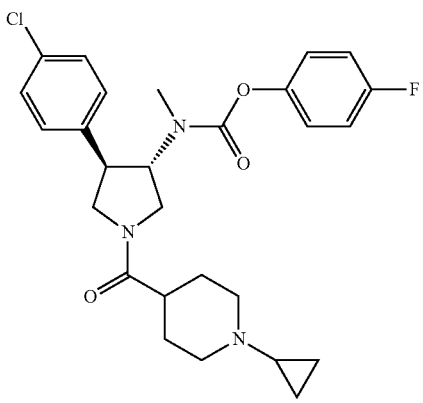 [SMILES: CN(C(=O)Oc1ccc(F)cc1)[C@@H]1CN(C(=O)C2CCN(C3CC3)CC2)C[C@H]1c1ccc(Cl)cc1]

In analogy to the procedure described for the synthesis of example 44 (step c), the title compound [(3S,4R)-4-(4-chloro-phenyl)-1-(1-cyclopropyl-piperidine-4-carbonyl)-pyrrolidin-3-yl]-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 1-cyclopropyl-piperidine-4-carboxylic acid instead of 1-methylcyclopropane-1-carboxylic acid and was obtained as a white foam. MS m/e: 500.3 [M]$^+$.

EXAMPLE 151

3-{(3R,4S)-3-(4-Chloro-phenyl)-4-[(4-fluoro-phenoxycarbonyl)-methyl-amino]-pyrrolidine-1-carbonyl}-pyrrolidine-1-carboxylic acid tert-butyl ester

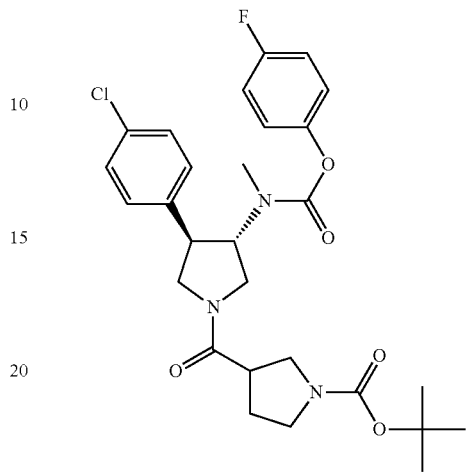

In analogy to the procedure described for the synthesis of example 44 (step c), the title compound 3-{(3R,4S)-3-(4-chloro-phenyl)-4-[(4-fluoro-phenoxycarbonyl)-methyl-amino]-pyrrolidine-1-carbonyl}-pyrrolidine-1-carboxylic acid tert-butyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using rac-pyrrolidine-1,3-dicarboxylic acid 1-tert-butyl ester instead of 1-methylcyclopropane-1-carboxylic acid and was obtained as a light yellow oil. MS m/e: 546.2 [M]$^+$.

EXAMPLE 152

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclohexyl ester

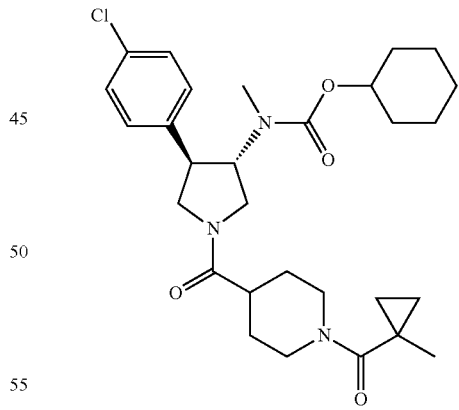

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid cyclohexyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidin-1-carbonyl]-piperidin-1-yl}-(1-methyl-cyclopropyl)-methanone using cyclohexanol instead of 2-cyclopropylethanol and was obtained as a colorless foam. MS m/e: 530.2 [M]$^+$.

EXAMPLE 153

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-cyclopropyl-ethyl ester

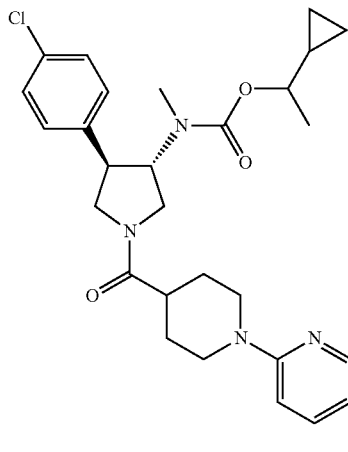

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 1-cyclopropyl-ethyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 1-cyclopropylethanol instead of 2-cyclopropylethanol and was obtained as a colorless foam. MS m/e: 536.3 [M]+.

EXAMPLE 154

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 1-cyclopropyl-ethyl ester

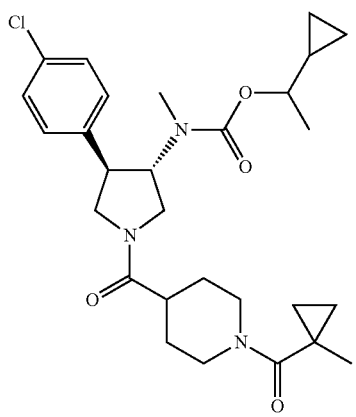 [SMILES: CC(OC(=O)N(C)[C@@H]1CN(C(=O)C2CCN(C(=O)C3(C)CC3)CC2)C[C@H]1c1ccc(Cl)cc1)C1CC1]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid 1-cyclopropyl-ethyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 1-cyclopropylethanol instead of 2-cyclopropylethanol and was obtained as a colorless foam. MS m/e: 516.5 [M]+.

EXAMPLE 155

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid oxetan-3-yl ester

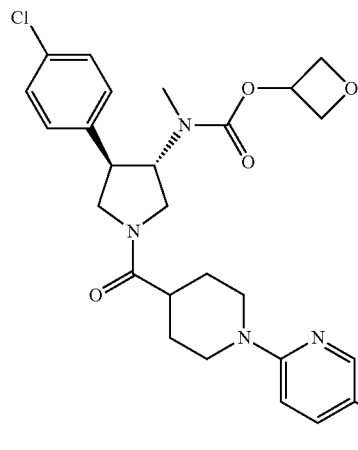

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid oxetan-3-yl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using oxetan-3-ol instead of 2-cyclopropylethanol and was obtained as a colorless foam. MS m/e: 524.4 [M]+.

EXAMPLE 156

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-yl ester

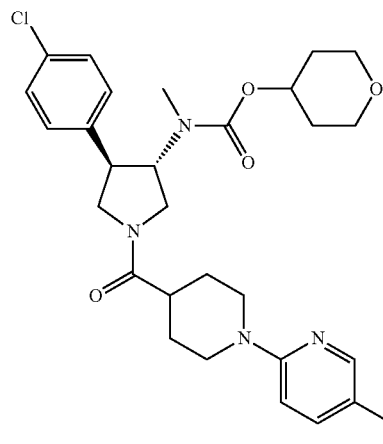

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid tetrahydropyran-4-yl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using tetrahydropyran-4-ol instead of 2-cyclopropylethanol and was obtained as a colorless foam. MS m/e: 552.4 [M]+.

EXAMPLE 157

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid sec-butyl ester

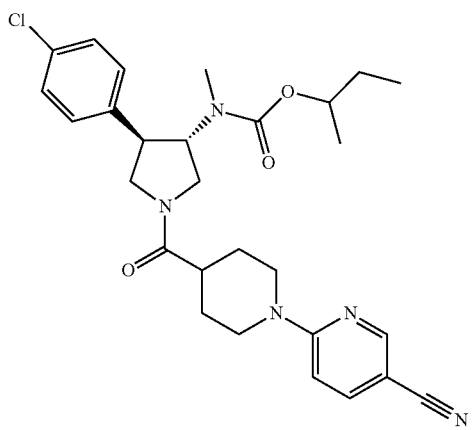 [SMILES: CCC(C)OC(=O)N(C)[C@@H]1CN(C(=O)C2CCN(c3ccc(C#N)cn3)CC2)C[C@H]1c1ccc(Cl)cc1]

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid sec-butyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2-butanol instead of 2-cyclopropylethanol and was obtained as a colorless foam. MS m/e: 524.4 [M]+.

EXAMPLE 158

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-ethyl ester

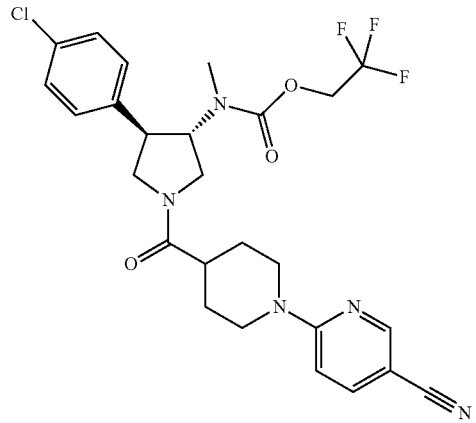 [SMILES: CN(C(=O)OCC(F)(F)F)[C@@H]1CN(C(=O)C2CCN(c3ccc(C#N)cn3)CC2)C[C@H]1c1ccc(Cl)cc1]

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-ethyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2,2,2-trifluoroethanol instead of 2-cyclopropylethanol and was obtained as a colorless foam. MS m/e: 550.4 [M]+.

EXAMPLE 159

[(3S,4R)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-trifluoromethyl-cyclohexyl ester

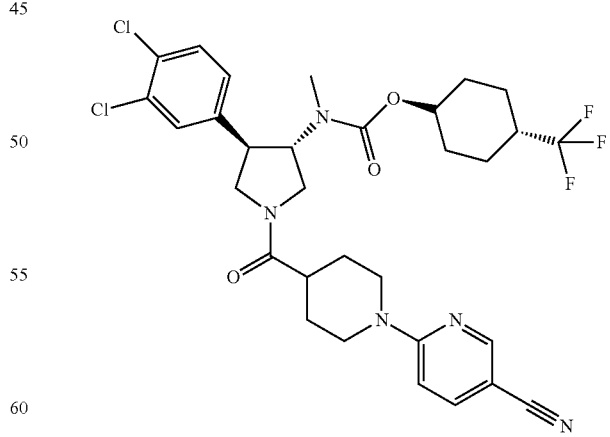

a) (3,4-Dichloro-phenyl)-propynoic acid ethyl ester

In analogy to the procedure described for the synthesis of example 89 (step a), the title compound (3,4-dichloro-phenyl)-propynoic acid ethyl ester was prepared from 3,4-dichloroiodobenzene instead of 1-chloro-4-iodobenzene and was obtained as a brown solid. MS m/e: 244.0 [M+H]+.

b) 1-Benzyl-4-(3,4-dichloro-phenyl)-2,5-dihydro-1H-pyrrole-3-carboxylic acid In analogy to the procedure described for the synthesis of example 89 (step b), the title compound I-benzyl-4-(3,4-dichloro-phenyl)-2,5-dihydro-1H-pyrrole-3-carboxylic acid was prepared from (3,4-dichloro-phenyl)-propynoic acid ethyl ester instead of (4-chloro-phenyl)-propynoic acid ethyl ester and was obtained as an off-white solid. MS m/e: 347.9 [M−H]−.

c) (3R,4R)-1-Benzyl-4-(3,4-dichloro-phenyl)-pyrrolidine-3-carboxylic acid

In analogy to the procedure described for the synthesis of example 89 (step c), the title compound (3R,4R)-1-benzyl-4-(3,4-dichloro-phenyl)-pyrrolidine-3-carboxylic acid was prepared from 1-benzyl-4-(3,4-dichloro-phenyl)-2,5-dihydro-1H-pyrrole-3-carboxylic acid instead of 1-benzyl-4-(4-chloro-phenyl)-2,5-dihydro-1H-pyrrole-3-carboxylic acid and was obtained as light grey crystals (e.e. >99.9% R,R (chiral HPLC)). MS m/e: 350.2 [M]+.

d) (3R,4R)-1-Benzyl-4-(3,4-dichloro-phenyl)-pyrrolidine-3-carboxylic acid methyl ester In analogy to the procedure described for the synthesis of example 89 (step d), the title compound (3R,4R)-1-benzyl-4-(3,4-dichloro-phenyl)-pyrrolidine-3-carboxylic acid methyl ester was prepared from (3R,4R)-1-benzyl-4-(3,4-dichloro-phenyl)-pyrrolidine-3-carboxylic acid instead of (3R,4R)-1-Benzyl-4-(4-chloro-phenyl)-pyrrolidine-3-carboxylic acid and was obtained as a brown oil. MS m/e: 366.2 [M+H]+.

e) (3S,4R)-1-Benzyl-4-(3,4-dichloro-phenyl)-pyrrolidine-3-carboxylic acid methyl ester In analogy to the procedure described for the synthesis of example 89 (step e), the title compound (3S,4R)-1-benzyl-4-(3,4-dichloro-phenyl)-pyrrolidine-3-carboxylic acid methyl ester was prepared from (3R,4R)-1-benzyl-4-(3,4-dichloro-phenyl)-pyrrolidine-3-carboxylic acid methyl ester instead of (3R,4R)-1-benzyl-4-(4-chloro-phenyl)-pyrrolidine-3-carboxylic acid methyl ester and was obtained as a light yellow oil. MS m/e: 366.2 [M+H]+.

f) (3S,4R)-1-Benzyl-4-(3,4-dichloro-phenyl)-pyrrolidine-3-carboxylic acid amide In analogy to the procedure described for the synthesis of example 89 (step f), the title compound (3S,4R)-1-benzyl-4-(3,4-dichloro-phenyl)-pyrrolidine-3-carboxylic acid amide was prepared from (3S,4R)-1-benzyl-4-(3,4-dichloro-phenyl)-pyrrolidine-3-carboxylic acid methyl ester instead of (3S,4R)-1-benzyl-4-(4-chloro-phenyl)-pyrrolidine-3-carboxylic acid methyl ester and was obtained as a white solid. MS m/e: 351.3 [M+H]+.

g) [(3S,4R)-1-Benzyl-4-(3,4-dichloro-phenyl)-pyrrolidin-3-yl]-carbamic acid methyl ester In analogy to the procedure described for the synthesis of example 89 (step g), the title compound [(3S,4R)-1-benzyl-4-(3,4-dichloro-phenyl)-pyrrolidin-3-yl]-carbamic acid methyl ester was prepared from (3S,4R)-1-benzyl-4-(3,4-dichloro-phenyl)-pyrrolidine-3-carboxylic acid amide instead of (3S,4R)-1-benzyl-4-(4-chloro-phenyl)-pyrrolidine-3-carboxylic acid amide and was obtained as a white solid. MS m/e: 381.3 [M+H]+.

h) (3S,4R)-1-benzyl-4-(3,4-dichlorophenyl)-N-methylpyrrolidin-3-amine

In analogy to the procedure described for the synthesis of example 89 (step h), the title compound [(3S,4R)-1-benzyl-4-(3,4-dichloro-phenyl)-pyrrolidin-3-yl]-methyl-amine was prepared from [(3S,4R)-1-benzyl-4-(3,4-dichloro-phenyl)-pyrrolidin-3-yl]-carbamic acid methyl ester instead of [(3S,4R)-1-benzyl-4-(4-chloro-phenyl)-pyrrolidin-3-yl]-carbamic acid methyl ester and was obtained as a light yellow liquid. MS m/e: 337.4 [M+H]+.

i) [(3S,4R)-1-Benzyl-4-(3,4-dichloro-phenyl)-pyrrolidin-3-yl]-methyl-carbamic acid 4-trifluoromethyl-cyclohexyl ester In analogy to the procedure described for the synthesis of example 25, the title compound [(3S,4R)-1-benzyl-4-(3,4-dichloro-phenyl)-pyrrolidin-3-yl]-methyl-carbamic acid 4-trifluoromethyl-cyclohexyl ester was prepared from [(3S,4R)-1-benzyl-4-(3,4-dichloro-phenyl)-pyrrolidin-3-yl]-methyl-amine instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4-(trifluoromethyl)cyclohexanol (cis/trans 1:3) instead of 2-cyclopropylethanol and was obtained as a white foam. MS m/e: 529.2 [M]+.

j) [(3S,4R)-4-(3,4-Dichloro-phenyl)-pyrrolidin-3-yl]-methyl-carbamic acid 4-trifluoromethyl-cyclohexyl ester In analogy to the procedure described for the synthesis of example 1 (step e), the title compound [(3S,4R)-4-(3,4-dichloro-phenyl)-pyrrolidin-3-yl]-methyl-carbamic acid 4-trifluoromethyl-cyclohexyl ester was prepared from [(3S,4R)-1-benzyl-4-(3,4-dichloro-phenyl)-pyrrolidin-3-yl]-methyl-carbamic acid 4-trifluoromethyl-cyclohexyl ester instead of rac-[(3R,4S)-1-benzyl-4-(3,4-dichloro-phenyl)-pyrrolidin-3-yl]-methyl-carbamic acid tert-butyl ester and was obtained as a light brown oil. MS m/e: 439.1 [M]+.

k) [(3S,4R)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-trifluoromethyl-cyclohexyl ester In analogy to the procedure described for the synthesis of example 44 (step c), the title compound [(3S,4R)-1-(5'-cyano-3,4,5,6-tetrahydro-2H-[1,2']bipyridinyl-4-carbonyl)-4-(3,4-dichloro-phenyl)-pyrrolidin-3-yl]-methyl-carbamic acid 4-trifluoromethyl-cyclohexyl ester was prepared from [(3S,4R)-4-(3,4-dichloro-phenyl)-pyrrolidin-3-yl]-methyl-carbamic acid 4-trifluoromethyl-cyclohexyl ester instead of [(3S,4R)-4-(3,4-dichloro-phenyl)-pyrrolidin-3-yl]-methyl-carbamic acid 4-fluoro-phenyl ester using 5'-cyano-3,4,5,6-tetrahydro-2H-[1,2']bipyridinyl-4-carboxylic acid instead of 1-methylcyclopropane-1-carboxylic acid and was obtained as an off-white foam. MS m/e: 652.3 [M]+.

EXAMPLE 160

{(3S,4R)-4-(3,4-Dichloro-phenyl)-1-[1-(6-methyl-pyridazin-3-yl)-piperidine-4-carbonyl]-pyrrolidin-3-yl}-methyl-carbamic acid 4-trifluoromethyl-cyclohexyl ester

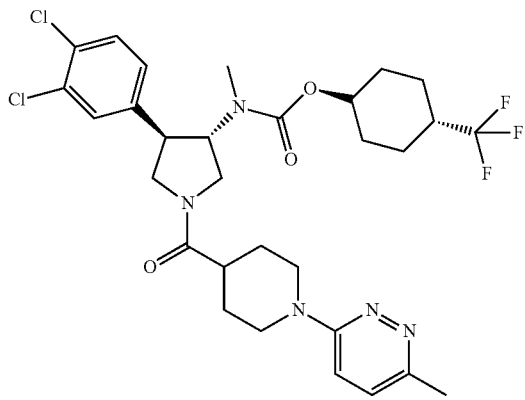

In analogy to the procedure described for the synthesis of example 44 (step c), the title compound {(3S,4R)-4-(3,4-dichloro-phenyl)-1-[1-(6-methyl-pyridazin-3-yl)-piperidine-4-carbonyl]-pyrrolidin-3-yl}-methyl-carbamic acid 4-trifluoromethyl-cyclohexyl ester was prepared from [(3S,4R)-4-(3,4-dichloro-phenyl)-pyrrolidin-3-yl]-methyl-carbamic acid 4-trifluoromethyl-cyclohexyl ester instead of [(3S,4R)-4-(3,4-dichloro-phenyl)-pyrrolidin-3-yl]-methyl-carbamic acid 4-fluoro-phenyl ester using 1-(6-methyl-pyridazin-3-yl)-piperidine-4-carboxylic acid instead of 1-methylcyclopropane-1-carboxylic acid and was obtained as an off-white foam. MS m/e: 642.4 [M]$^+$.

EXAMPLE 161

[(3S,4R)-4-(3,4-Dichloro-phenyl)-1-(tetrahydro-pyran-4-carbonyl)-pyrrolidin-3-yl]-methyl-carbamic acid 4-trifluoromethyl-cyclohexyl ester

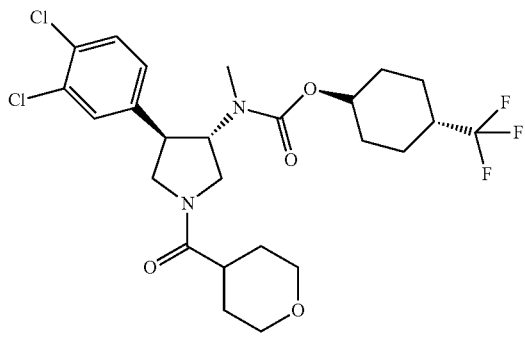

In analogy to the procedure described for the synthesis of example 44 (step c), the title compound [(3S,4R)-4-(3,4-dichloro-phenyl)-1-(tetrahydro-pyran-4-carbonyl)-pyrrolidin-3-yl]-methyl-carbamic acid 4-trifluoromethyl-cyclohexyl ester was prepared from [(3S,4R)-4-(3,4-dichloro-phenyl)-pyrrolidin-3-yl]-methyl-carbamic acid 4-trifluoromethyl-cyclohexyl ester instead of [(3S,4R)-4-(3,4-dichloro-phenyl)-pyrrolidin-3-yl]-methyl-carbamic acid 4-fluoro-phenyl ester using tetrahydropyran-4-yl-carboxylic acid instead of 1-methylcyclopropane-1-carboxylic acid and was obtained as an off-white foam. MS m/e: 551.4 [M]$^+$.

EXAMPLE 162

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid tetrahydro-pyran-4-yl ester

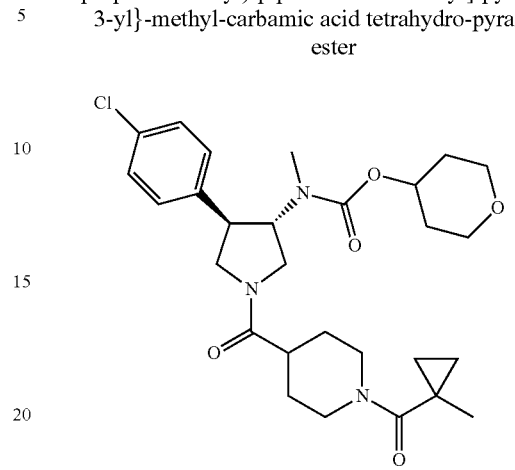

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid tetrahydro-pyran-4-yl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using tetrahydropyran-4-ol instead of 2-cyclopropylethanol and was obtained as a colorless foam. MS m/e: 532.4 [M]$^+$.

EXAMPLE 163

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid sec-butyl ester

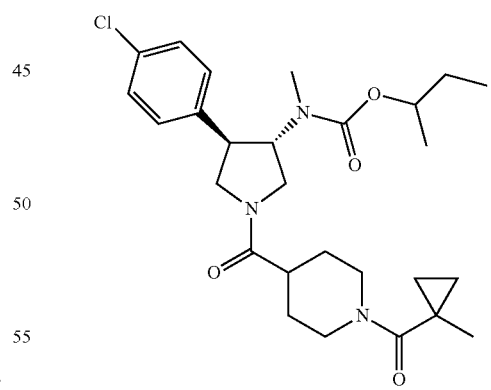

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid sec-butyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-

EXAMPLE 164

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro ethyl ester

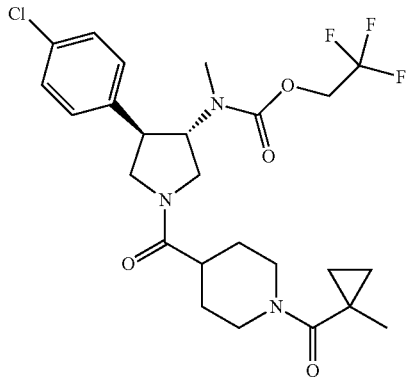 [SMILES: CN(C(=O)OCC(F)(F)F)[C@@H]1CN(C(=O)C2CCN(C(=O)C3(C)CC3)CC2)C[C@H]1c1ccc(Cl)cc1]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid 2,2,2-trifluoro ethyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2,2,2-trifluoroethanol instead of 2-cyclopropylethanol and was obtained as a colorless foam. MS m/e: 530.1 [M]$^+$.

EXAMPLE 165

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro-1-methyl-ethyl ester

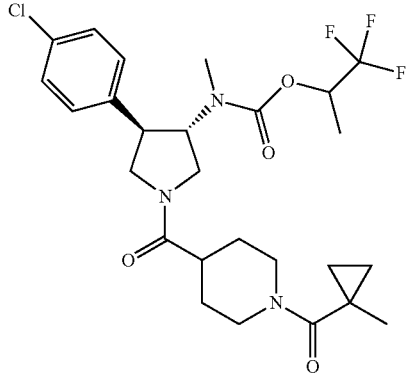 [SMILES: CC(OC(=O)N(C)[C@@H]1CN(C(=O)C2CCN(C(=O)C3(C)CC3)CC2)C[C@H]1c1ccc(Cl)cc1)C(F)(F)F]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid 2,2,2-trifluoro-1-methyl-ethyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 1,1,1-trifluoro-isopropanol instead of 2-cyclopropylethanol and was obtained as a colorless foam. MS m/e: 544.2 [M]$^+$.

EXAMPLE 166

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1-methyl-ethyl ester

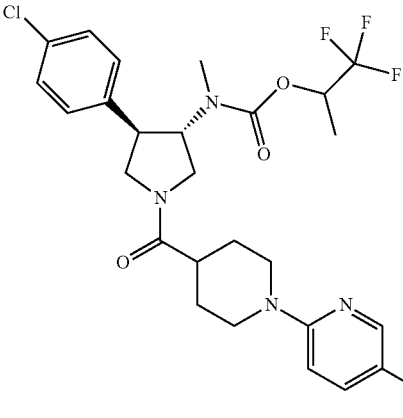

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1-methyl-ethyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 1,1,1-trifluoro-isopropanol instead of 2-cyclopropylethanol and was obtained as a colorless foam. MS m/e: 564.3 [M]$^+$.

EXAMPLE 167

{(3S,4R)-4-(4-Chloro-phenyl)-1-[1-(4-methyl-pyrimidin-2-yl)-piperidine-4-carbonyl]-pyrrolidin-3-yl}-methyl-carbamic acid 4-fluoro-phenyl ester

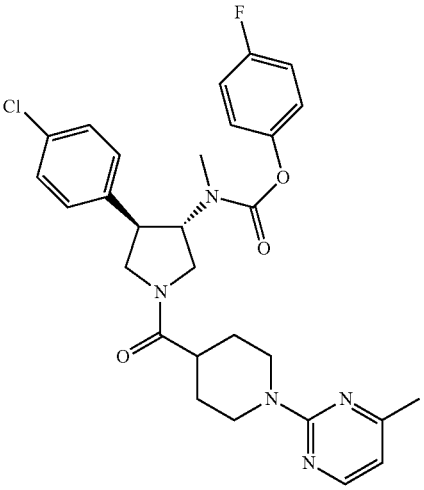 [SMILES: Cc1ccnc(N2CCC(C(=O)N3C[C@@H](N(C)C(=O)Oc4ccc(F)cc4)[C@H](c4ccc(Cl)cc4)C3)CC2)n1]

In analogy to the procedure described for the synthesis of example 44 (step c), the title compound {(3S,4R)-4-(4-chloro-phenyl)-1-[1-(4-methyl-pyrimidin-2-yl)-piperidine-4-carbonyl]-pyrrolidin-3-yl}-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 1-(4-methyl-pyrimidin-2-yl)-piperidine-4-carboxylic acid instead of 1-methylcyclopropane-1-carboxylic acid and was obtained as a yellow foam. MS m/e: 552.4 [M]$^+$.

EXAMPLE 168

[(3S,4R)-4-(4-Chloro-phenyl)-1-(pyrrolidine-3-carbonyl)-pyrrolidin-3-yl]-methyl-carbamic acid 4-fluoro-phenyl ester

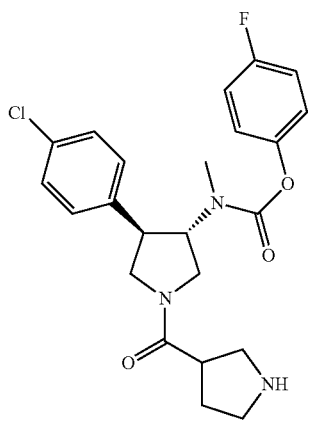 [SMILES: CN(C(=O)Oc1ccc(F)cc1)[C@@H]1CN(C(=O)C2CCNC2)C[C@H]1c1ccc(Cl)cc1]

To a solution of 3-{(3R,4S)-3-(4-chloro-phenyl)-4-[(4-fluoro-phenoxycarbonyl)-methyl-amino]-pyrrolidine-1-carbonyl}-pyrrolidine-1-carboxylic acid tert-butyl ester (1.17 g, 2.14 mmol) in dichloromethane (20 mL) was added at ambient temperature trifluoroacetic acid (1.64 mL, 21.4 mmol) and the reaction mixture was stirred for 3 h. It was treated with an aqueous solution of sodium carbonate (1M, 50 mL) and the organic layer was separated and washed with brine (40 mL). The aqueous layer was extracted with dichloromethane (40 mL) and the combined organic layers were dried over sodium sulfate. Concentration afforded the title compound (760 mg, 79%) as a white semi-solid. MS m/e: 446.1 [M+H]$^+$.

EXAMPLE 169

{(3S,4R)-4-(4-Chloro-phenyl)-1-[1-(5-fluoro-pyrimidin-2-yl)-piperidine-4-carbonyl]-pyrrolidin-3-yl}-methyl-carbamic acid 4-fluoro-phenyl ester

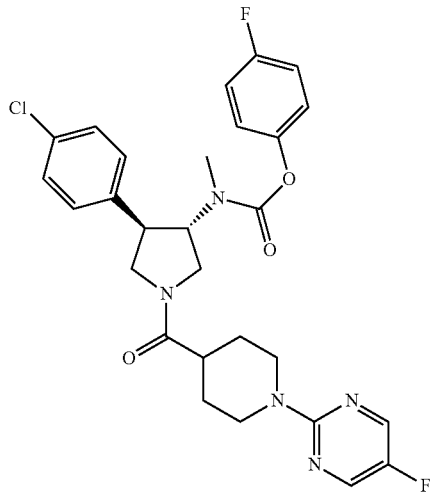 [SMILES: CN(C(=O)Oc1ccc(F)cc1)[C@@H]1CN(C(=O)C2CCN(c3ncc(F)cn3)CC2)C[C@H]1c1ccc(Cl)cc1]

In analogy to the procedure described for the synthesis of example 44 (step c), the title compound {(3S,4R)-4-(4-chloro-phenyl)-1-[1-(5-fluoro-pyrimidin-2-yl)-piperidine-4-carbonyl]-pyrrolidin-3-yl}-methyl-carbamic acid 4-fluoro-phenyl ester was prepared from [(3S,4R)-4-(4-chloro-phenyl)-pyrrolidin-3-yl]-methyl-carbamic acid 4-fluoro-phenyl ester instead of [(3S,4R)-4-(3,4-dichloro-phenyl)-pyrrolidin-3-yl]-methyl-carbamic acid 4-fluoro-phenyl ester using 145-fluoro-pyrimidin-2-yl)-piperidine-4-carboxylic acid instead of 1-methylcyclopropane-1-carboxylic acid and was obtained as a yellow foam. MS m/e: 556.2 [M]$^+$.

EXAMPLE 170

[(3S,4R)-4-(4-Chloro-phenyl)-1-(1-propionyl-pyrrolidine-3-carbonyl)-pyrrolidin-3-yl]-methyl-carbamic acid 4-fluoro-phenyl ester

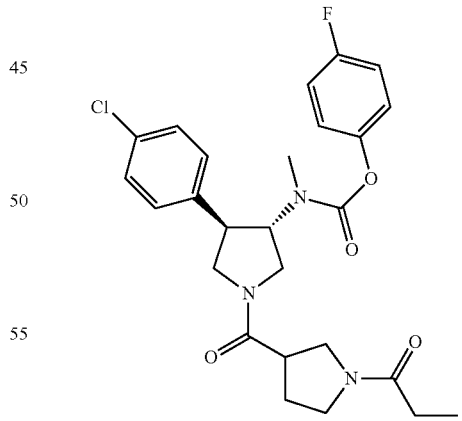

In analogy to the procedure described for the synthesis of example 73, the title [(3S,4R)-4-(4-chloro-phenyl)-1-(1-propionyl-pyrrolidine-3-carbonyl)-pyrrolidin-3-yl]-methyl-carbamic acid 4-fluoro-phenyl ester was prepared from [(3S,4R)-4-(4-chloro-phenyl)-1-(pyrrolidine-3-carbonyl)-pyrrolidin-3-yl]-methyl-carbamic acid 4-fluoro-phenyl ester instead of rac-[(3R,4S)-4-(3,4-dichloro-phenyl)-1-(piperidine-4-carbonyl)-pyrrolidin-3-yl]-methyl-carbamic acid 4-fluoro-phenyl ester using propionyl chloride and was obtained as a light yellow oil. MS m/e: 502.2 [M+H]+.

EXAMPLE 171

[(3S,4R)-4-(4-Chloro-phenyl)-1-(1-cyclopropanecarbonyl-pyrrolidine-3-carbonyl)-pyrrolidin-3-yl]-methyl-carbamic acid 4-fluoro-phenyl ester

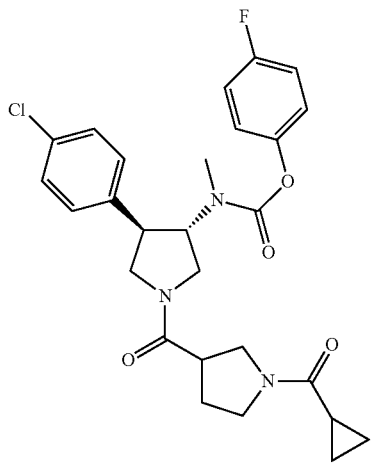 [SMILES: CN(C(=O)Oc1ccc(F)cc1)[C@@H]1CN(C(=O)C2CCN(C(=O)C3CC3)C2)C[C@H]1c1ccc(Cl)cc1]

In analogy to the procedure described for the synthesis of example 73, the title [(3S,4R)-4-(4-chloro-phenyl)-1-(1-cyclopropanecarbonyl-pyrrolidine-3-carbonyl)-pyrrolidin-3-yl]-methyl-carbamic acid 4-fluoro-phenyl ester was prepared from [(3S,4R)-4-(4-chloro-phenyl)-1-(pyrrolidine-3-carbonyl)-pyrrolidin-3-yl]-methyl-carbamic acid 4-fluoro-phenyl ester instead of rac-[(3R,4S)-4-(3,4-dichloro-phenyl)-1-(piperidine-4-carbonyl)-pyrrolidin-3-yl]-methyl-carbamic acid 4-fluoro-phenyl ester using cyclopropanecarbonyl chloride instead of propionyl chloride and was obtained as a colorless oil. MS m/e: 514.4 [M]+.

EXAMPLE 172

{(3S,4R)-4-(4-Chloro-phenyl)-1-[1-(2-methoxy-acetyl)-pyrrolidine-3-carbonyl]-pyrrolidin-3-yl}-methyl-carbamic acid 4-fluoro-phenyl ester

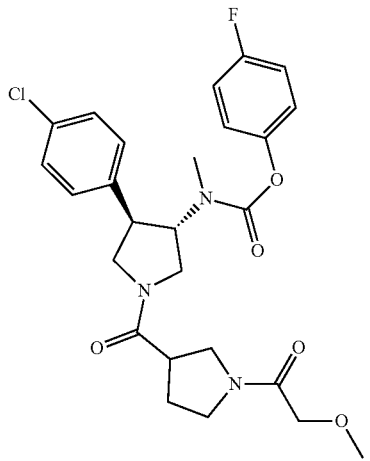 [SMILES: COCC(=O)N1CCC(C(=O)N2C[C@@H](N(C)C(=O)Oc3ccc(F)cc3)[C@H](c3ccc(Cl)cc3)C2)C1]

In analogy to the procedure described for the synthesis of example 73, the title [(3S,4R)-4-(4-chloro-phenyl)-1-(1-(2-methoxy-acetyl)-pyrrolidine-3-carbonyl)-pyrrolidin-3-yl]-methyl-carbamic acid 4-fluoro-phenyl ester was prepared from [(3S,4R)-4-(4-chloro-phenyl)-1-(pyrrolidine-3-carbonyl)-pyrrolidin-3-yl]-methyl-carbamic acid 4-fluoro-phenyl ester instead of rac-[(3R,4S)-4-(3,4-dichloro-phenyl)-1-(piperidine-4-carbonyl)-pyrrolidin-3-yl]-methyl-carbamic acid 4-fluoro-phenyl ester using methoxyacetyl chloride instead of propionyl chloride and was obtained as a light yellow oil. MS m/e: 518.3 [M+H]+.

EXAMPLE 173

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclobutyl ester

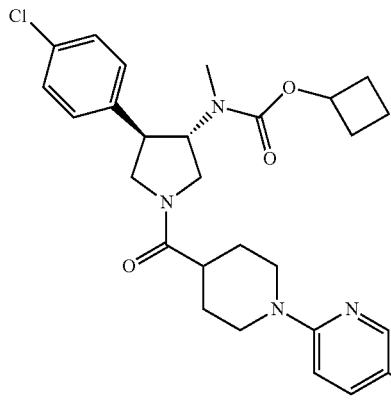

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid cyclobutyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cyclobutanol instead of 2-cyclopropylethanol and was obtained as a colorless foam. MS m/e: 522.4 [M]+.

EXAMPLE 174

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclobutyl ester

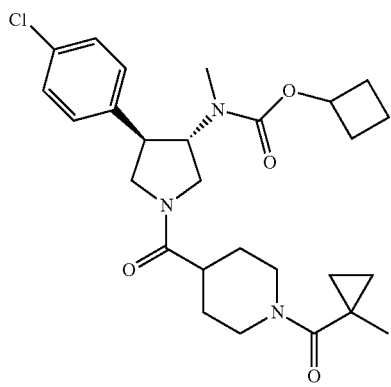 [SMILES: CN(C(=O)OC1CCC1)[C@@H]1CN(C(=O)C2CCN(C(=O)C3(C)CC3)CC2)C[C@H]1c1ccc(Cl)cc1]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid cyclobutyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using cyclobutanol instead of 2-cyclopropylethanol and was obtained as a colorless foam. MS m/e: 502.3 [M]⁺.

EXAMPLE 175

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,3,3-tetrafluorocyclobutyl ester

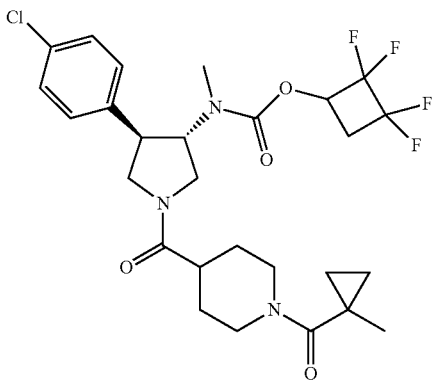 [SMILES: CN(C(=O)OC1CC(F)(F)C1(F)F)[C@@H]1CN(C(=O)C2CCN(C(=O)C3(C)CC3)CC2)C[C@H]1c1ccc(Cl)cc1]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid 2,2,3,3-tetrafluorocyclobutyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2,2,3,3-tetrafluorocyclobutanol instead of 2-cyclopropylethanol and was obtained as a colorless foam. MS m/e: 574.5 [M]⁺.

EXAMPLE 176

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,3,3-tetrafluorocyclobutyl ester

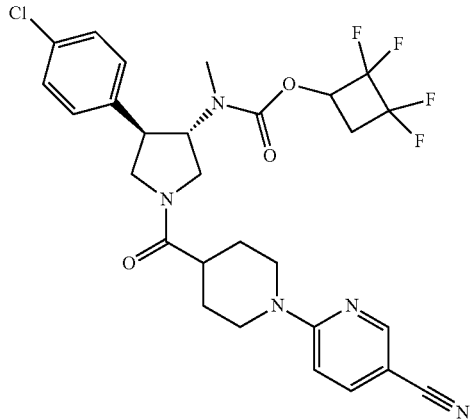 [SMILES: CN(C(=O)OC1CC(F)(F)C1(F)F)[C@@H]1CN(C(=O)C2CCN(c3ccc(C#N)cn3)CC2)C[C@H]1c1ccc(Cl)cc1]

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 2,2,3,3-tetrafluorocyclobutyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 2,2,3,3-tetrafluorocyclobutanol instead of 2-cyclopropylethanol and was obtained as a colorless foam. MS m/e: 594.4 [M]⁺.

EXAMPLE 177

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-1-methyl-propyl ester

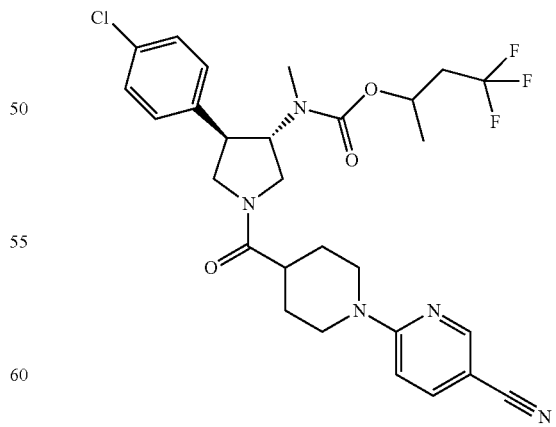

In analogy to the procedure described for the synthesis of example 25, the title compound [(3S,4R)-4-(4-chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-1-methyl-propyl ester was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,4-trifluorobutan-2-ol instead of 2-cyclopropylethanol and was obtained as a colorless foam. MS m/e: 578.4 [M]+.

EXAMPLE 178

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 3,3,3-trifluoro-1-methyl-propyl ester

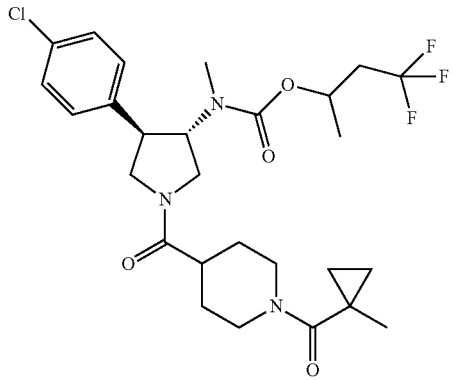 [SMILES: CC(CC(F)(F)F)OC(=O)N(C)[C@@H]1CN(C(=O)C2CCN(C(=O)C3(C)CC3)CC2)C[C@H]1c1ccc(Cl)cc1]

In analogy to the procedure described for the synthesis of example 25, the title compound {(3S,4R)-4-(4-chloro-phenyl)-1-[1-(1-methyl-cyclopropanecarbonyl)-piperidine-4-carbonyl]-pyrrolidin-3-yl}-methyl-carbamic acid 3,3,3-trifluoro-1-methyl-propyl ester was prepared from [(3R,4S)-3-(4-chloro-phenyl)-4-methylamino-pyrrolidin-1-yl]-[1-(1-methyl-cyclopropanecarbonyl)-piperidin-4-yl]-methanone instead of rac-{4-[(3S,4R)-3-(3,4-dichloro-phenyl)-4-methylamino-pyrrolidine-1-carbonyl]-piperidin-1-yl}-(1-methyl-cyclopropyl)-methanone using 4,4,4-trifluorobutan-2-ol instead of 2-cyclopropylethanol and was obtained as a colorless foam. MS m/e: 558.4 [M]+.

EXAMPLE 179

{(3S,4R)-4-(4-Chloro-phenyl)-1-[1-(tetrahydro-pyran-4-yl)-pyrrolidine-3-carbonyl]-pyrrolidin-3-yl}-methyl-carbamic acid 4-fluoro-phenyl ester

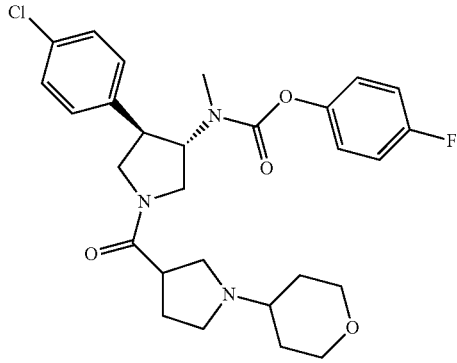 [SMILES: CN(C(=O)Oc1ccc(F)cc1)[C@@H]1CN(C(=O)C2CCN(C3CCOCC3)C2)C[C@H]1c1ccc(Cl)cc1]

To a solution of [(3S,4R)-4-(4-chloro-phenyl)-1-(pyrrolidine-3-carbonyl)-pyrrolidin-3-yl]-methyl-carbamic acid 4-fluoro-phenyl ester (408 mg, 0.92 mmol) in THF (4 mL) was added under an atmosphere of nitrogen tetrahydro-4H-pyran-4-one (25 mg, 0.25 mmol). After stirring for 15 min. at ambient temperature sodium triacetoxyborohydride (252 mg, 1.19 mmol) was added and stirred continued for 4 h at ambient temperature. The reaction mixture was diluted with ethyl acetate (10 mL) and washed with an aqeuous solution of sodium carbonate (10 mL). The aqueous layer was extracted with ethyl acetate (10 mL) and the combined organic layers were dried of sodium sulfate. Concentration and purification by chromatography (SiO$_2$, ethyl acetate:methanol=100:0 to 80:20) afforded the title compound (115 mg, 24%) as a light yellow oil. MS m/e: 530.3 [M]+.

EXAMPLE 180

[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester

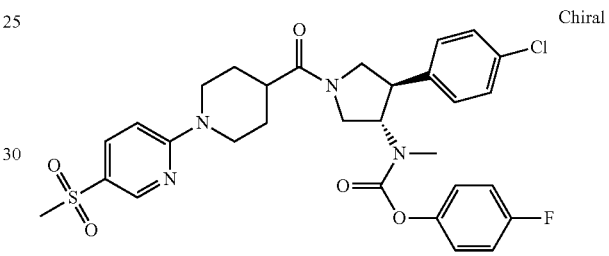

A mixture of 20 mg (0.043 mmol) [(3S,4R)-4-(4-Chloro-phenyl)-1-(piperidine-4-carbonyl)-pyrrolidin-3-yl]-methyl-carbamic acid 4-fluoro-phenyl ester, 11.2 uL (0.065 mmol) DIPEA and 12.8 mg (0.054 mmol) 2-bromo-5-(methylsulfonyl)pyridine in 1 mL DMF was heated to 60° C. over night. The mixture was subjected to purification by preparative HPLC on reversed phase eluting with a gradient formed from acetonitrile, water and NEt$_3$ to yield after evaporation of the product containing fractions the title compound as light yellow viscous oil. MS m/e: 615.3 [M]+.

EXAMPLE 181

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

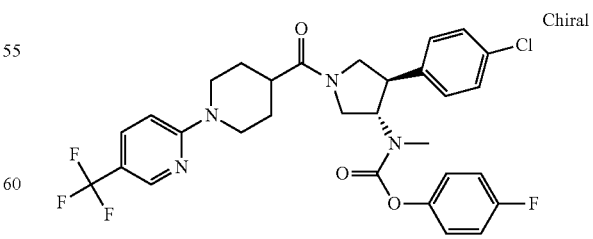

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-bromo-(trifluoromethyl)pyridine (commercially available) as light yellow viscous oil. MS m/e: 605.4 [M]±.

EXAMPLE 182

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester

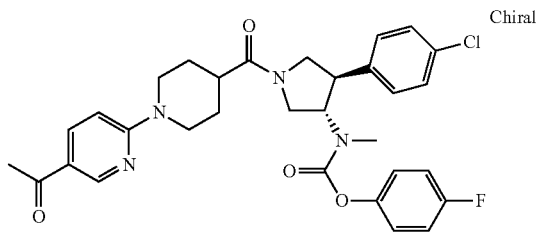 [SMILES: CC(=O)c1ccc(N2CCC(C(=O)N3C[C@@H](N(C)C(=O)Oc4ccc(F)cc4)[C@H](c4ccc(Cl)cc4)C3)CC2)nc1]

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-bromo-(trifluoromethyl)pyridine (commercially available) as light yellow viscous oil. MS m/e: 579.4 [M]+.

EXAMPLE 183

[(3S,4R)-4-(4-Chloro-phenyl)-1-(1-pyrimidin-2-yl-piperidine-4-carbonyl)-pyrrolidin-3-yl]-methyl-carbamic acid 4-fluoro-phenyl ester

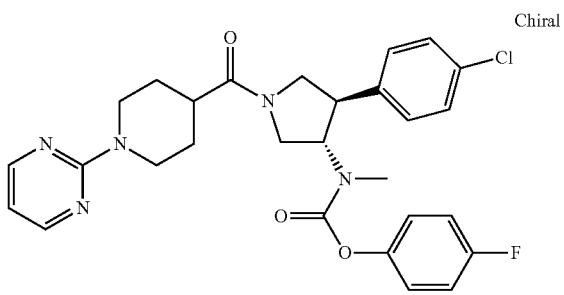 [SMILES: CN(C(=O)Oc1ccc(F)cc1)[C@@H]1CN(C(=O)C2CCN(c3ncccn3)CC2)C[C@H]1c1ccc(Cl)cc1]

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-bromo-pyrimidine (commercially available) as light yellow viscous oil. MS m/e: 538.4 [M]+.

EXAMPLE 184

{(3S,4R)-4-(4-Chloro-phenyl)-1-[1-(5-chloro-pyrimidin-2-yl)-piperidine-4-carbonyl]-pyrrolidin-3-yl}-methyl-carbamic acid 4-fluoro-phenyl ester

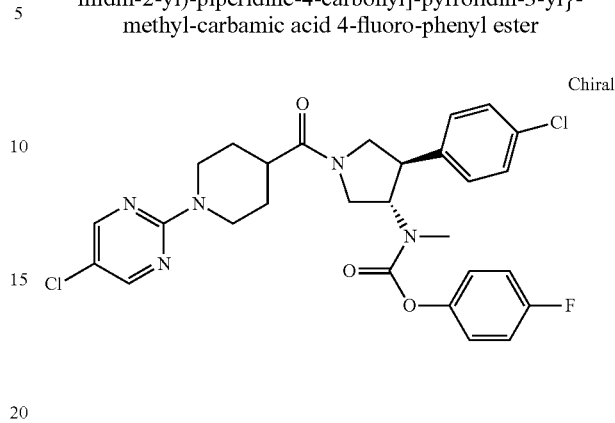

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 3,6-dichloropyrimidine (commercially available) as light yellow viscous oil. MS m/e: 572.2 [M]+.

EXAMPLE 185

[(3S,4R)-4-(4-Chloro-phenyl)-1-(4'-cyano-3,4,5,6-tetrahydro-2H-[1,2']bipyridinyl-4-carbonyl)-pyrrolidin-3-yl]-methyl-carbamic acid 4-fluoro-phenyl ester

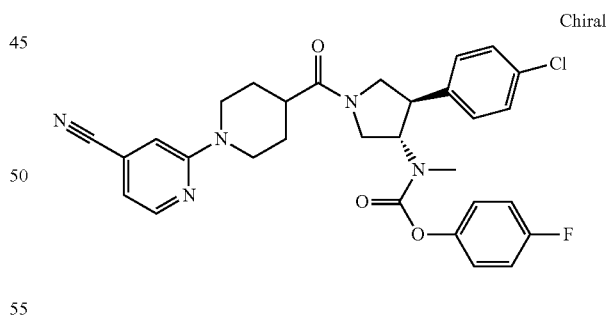

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloro-5cyano-pyridine (commercially available) as light yellow viscous oil. MS m/e: 562.4 [M]+.

EXAMPLE 186

[(3S,4R)-4-(4-Chloro-phenyl)-1-(3'-cyano-3,4,5,6-tetrahydro-2H-[1,2']bipyridinyl-4-carbonyl)-pyrrolidin-3-yl]-methyl-carbamic acid 4-fluoro-phenyl ester

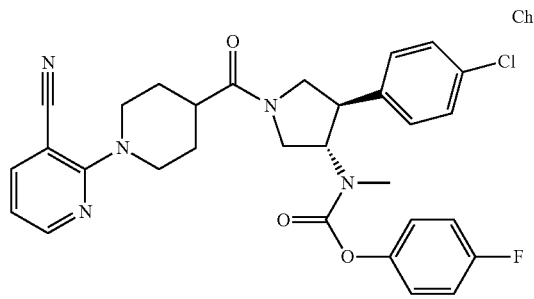

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloronicotinonitrile (commercially available) as light yellow viscous oil. MS m/e: 562.3 [M]$^+$.

EXAMPLE 187

{(3S,4R)-4-(4-Chloro-phenyl)-1-[1-(6-cyano-pyrazin-2-yl)-piperidine-4-carbonyl]-pyrrolidin-3-yl}-methyl-carbamic acid 4-fluoro-phenyl ester

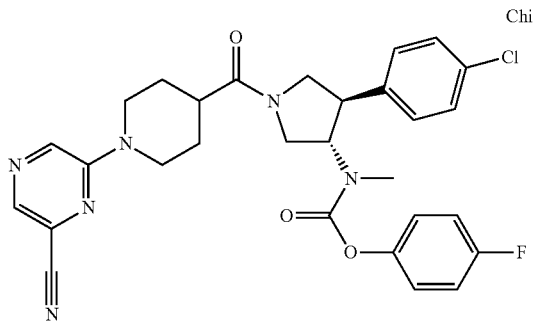

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 6-cyano-2-chloropyrazine (commercially available) as light yellow viscous oil. MS m/e: 563.3 [M]$^+$.

EXAMPLE 188

[(3S,4R)-4-(4-Chloro-phenyl)-1-(3'-chloro-5'-trifluoromethyl-3,4,5,6-tetrahydro-2H-[1,2]bipyridinyl-4-carbonyl)-pyrrolidin-3-yl]-methyl-carbamic acid 4-fluoro-phenyl ester

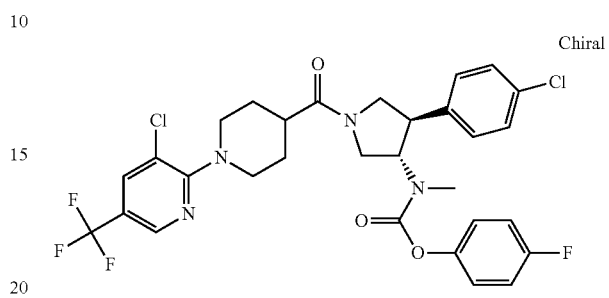

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2,3,-dichloro-5-(trifluoromethyl)pyridine (commercially available) as light yellow viscous oil. MS m/e: 639.3 [M]$^+$.

EXAMPLE 189

[(3S,4R)-4-(4-Chloro-phenyl)-1-(6'-cyano-3,4,5,6-tetrahydro-2H-[1,2']bipyridinyl-4-carbonyl)-pyrrolidin-3-yl]-methyl-carbamic acid 4-fluoro-phenyl ester

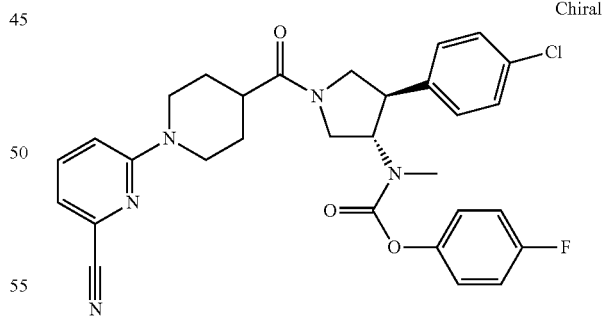

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloro-6-cyanopyridine (commercially available) as light yellow viscous oil. MS m/e: 562.3 [M]$^+$.

EXAMPLE 190

{(3S,4R)-4-(4-Chloro-phenyl)-1-[1-(5-methoxy-pyrimidin-2-yl)-piperidine-4-carbonyl]-pyrrolidin-3-yl}-methyl-carbamic acid 4-fluoro-phenyl ester

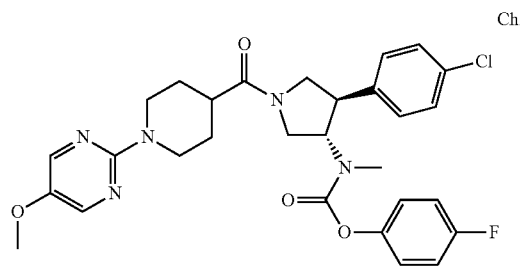

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloro-5-methoxy-pyrimidine (commercially available) as light brown viscous oil. MS m/e: 568.4 [M]$^+$.

EXAMPLE 191

[(3S,4R)-4-(4-Chloro-phenyl)-1-(1-pyrimidin-4-yl-piperidine-4-carbonyl)-pyrrolidin-3-yl]-methyl-carbamic acid 4-fluoro-phenyl ester

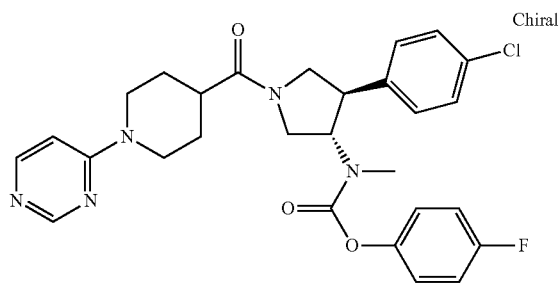 [SMILES: CN(C(=O)Oc1ccc(F)cc1)[C@@H]1CN(C(=O)C2CCN(c3ccncn3)CC2)C[C@H]1c1ccc(Cl)cc1]

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloro-pyrimidine (commercially available) as light yellow viscous oil. MS m/e: 538.4 [M]$^+$.

EXAMPLE 192

{(3S,4R)-4-(4-Chloro-phenyl)-1-[1-(5-cyano-pyrimidin-2-yl)-piperidine-4-carbonyl]-pyrrolidin-3-yl}-methyl-carbamic acid 4-fluoro-phenyl ester

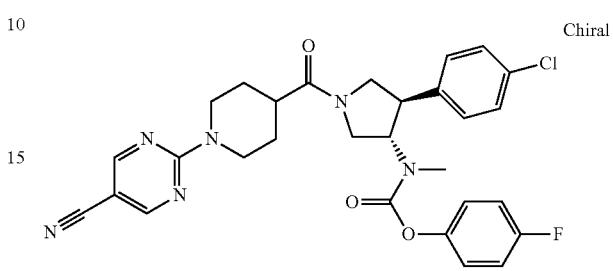

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 2-chloropyrimidine-5-carbonitrile (commercially available) as light yellow waxy solid. MS m/e: 563.4 [M]$^+$.

EXAMPLE 193

{(3S,4R)-4-(4-Chloro-phenyl)-1-[1-(5-cyano-pyrazin-2-yl)-piperidine-4-carbonyl]-pyrrolidin-3-yl}-methyl-carbamic acid 4-fluoro-phenyl ester

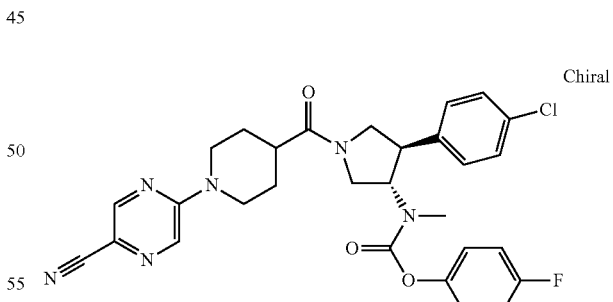

In analogy to the procedure described for the synthesis of [(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester (example 180) the title compound was prepared from [(3S,4R)-4-(4-Chloro-phenyl)-1-(piperidine-4-carbonyl)-pyrrolidin-3-yl]-methyl-carbamic acid 4-fluoro-phenyl ester and 5-bromopyrazine-2-carbonitrile (commercially available) as light yellow viscous oil. MS m/e: 563.3 [M]$^+$.

EXAMPLE 194

[(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester

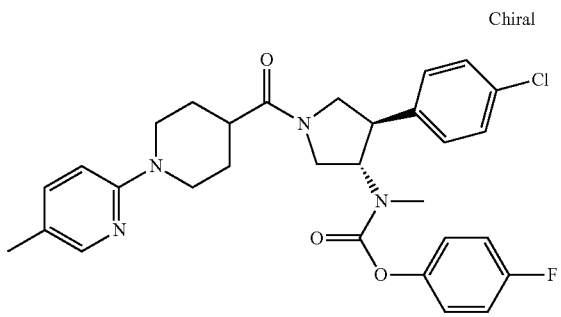 [SMILES: Cc1ccc(N2CCC(C(=O)N3C[C@@H](N(C)C(=O)Oc4ccc(F)cc4)[C@H](c4ccc(Cl)cc4)C3)CC2)nc1]

A mixture of 26.7 mg (0.085 mmol)[(3S,4R)-4-(4-chloro-phenyl)-pyrrolidin-3-yl]-methyl-carbamic acid 4-fluoro-phenyl ester, 15 mg (0.068 mmol) 1-(5-methyl-2-pyridinyl)-4-piperidinecarboxylic acid (commercially available), 31 mg (0.082 mmol) HATU and 70 uL (0.409 mmol) DIPEA in 2 mL DMF was shaken for 1 h at room temperature. The mixture was subjected to purification by preparative HPLC on reversed phase eluting with a gradient formed from acetonitrile, water and NEt₃ to yield after evaporation of the product containing fractions the title compound as off-white solid. MS m/e: 551.4 [M]⁺.

EXAMPLE 195

[(3S,4R)-4-(4-Chloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester

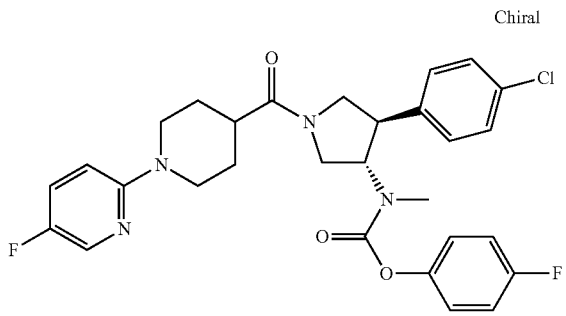 [SMILES: CN(C(=O)Oc1ccc(F)cc1)[C@@H]1CN(C(=O)C2CCN(c3ccc(F)cn3)CC2)C[C@H]1c1ccc(Cl)cc1]

a) 5'-Fluoro-3,4,5,6-tetrahydro-2H-[1,2']bipyridinyl-4-carboxylic acid ethyl ester

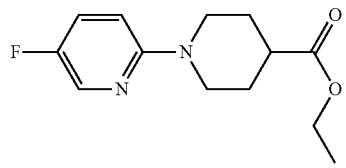

A mixture of 3.4 g (20 mmol) 2-bromo-5-fluoropyridine, 4.61 g (29 mmol) ethyl isonipecotate and 3.79 g (29 mmol) DIPEA in 5 mL NMP was heated for 15 min to 170° C. and 60 min to 200° C. After cooling to room temperature water was added and the mixture was extracted with ethyl acetate and heptane. The combined organic layers were washed with brine, dried with Na₂SO₄, filtered and evaporated to dryness. The residue was purified by column chromatography on silica eluting with a gradient formed from heptane and ethyl acetate. The product containing fractions were evaporated to yield 1.5 g (30%) of the title compound as light yellow oil. MS m/e: 253.3 [M]⁺.

b) 5'-Fluoro-3,4,5,6-tetrahydro-2H-[1,2']bipyridinyl-4-carboxylic acid

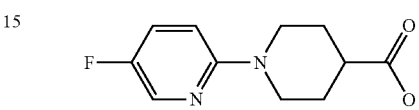

A mixture of 4 g (16 mmol) 5'-Fluoro-3,4,5,6-tetrahydro-2H-[1,2']bipyridinyl-4-carboxylic acid ethyl ester and 0.832 g (20 mmol) LiOH.H₂O in 50 mL THF, 50 mL water and 5 mL methanol was stirred for 2 h at 20° C. Acetic acid was added to pH 6 and water and ethyl acetate. The mixture was extracted with ethyl acetate and the combined organic layers were washed with brine, dried with Na₂SO₄, filtered and evaporated to dryness. The residue was purified by column chromatography on silica eluting with a gradient formed from heptane and ethyl acetate. The product containing fractions were evaporated to yield 3.1 g (87%) of the title compound as off-white solid. MS m/e: 223.1 [M−H].

c) [(3S,4R)-4-(4-Chloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester In analogy to the procedure described for the synthesis of [(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester (example 194) the title compound was prepared from [(3S,4R)-4-(4-chloro-phenyl)-pyrrolidin-3-yl]-methyl-carbamic acid 4-fluoro-phenyl ester and 5'-Fluoro-3,4,5,6-tetrahydro-2H-[1,2']bipyridinyl-4-carboxylic acid as off-white solid. MS m/e: 555.2 [M]⁺.

EXAMPLE 196

[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester

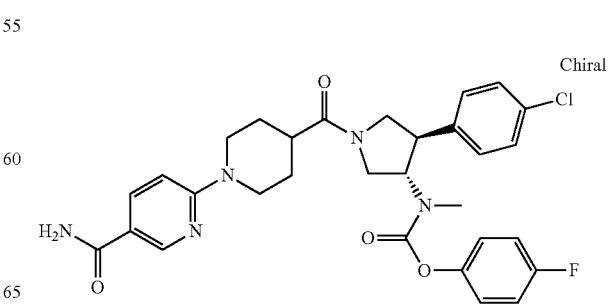

In analogy to the procedure described for the synthesis of [(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester (example 194) the title compound was prepared from [(3S,4R)-4-(4-chloro-phenyl)-pyrrolidin-3-yl]-methyl-carbamic acid 4-fluoro-phenyl ester and 5'-Carbamoyl-3,4,5,6-tetrahydro-2H-[1,2']bipyridinyl-4-carboxylic acid as light brown viscous oil. MS m/e: 580.4 [M]+.

EXAMPLE 197

{(3S,4R)-4-(4-Chloro-phenyl)-1-[1-(6-methoxy-pyridazin-3-yl)-piperidine-4-carbonyl]-pyrrolidin-3-yl}-methyl-carbamic acid 4-fluoro-phenyl ester

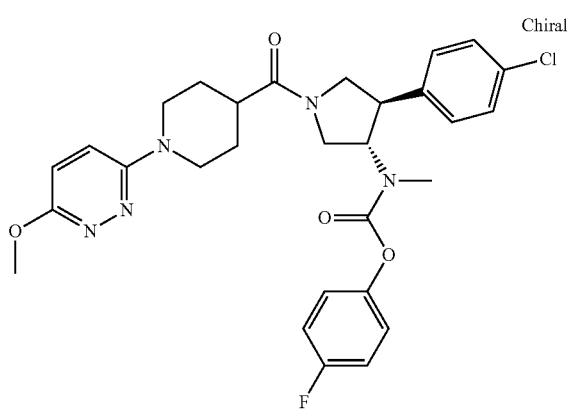 [SMILES: COc1ccc(N2CCC(C(=O)N3C[C@@H](N(C)C(=O)Oc4ccc(F)cc4)[C@H](c4ccc(Cl)cc4)C3)CC2)nn1]

a) 1-(6-Methoxy-pyridazin-3-yl)-piperidine-4-carboxylic acid ethyl ester

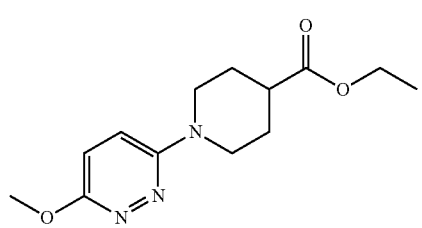 [SMILES: CCOC(=O)C1CCN(c2ccc(OC)nn2)CC1]

A mixture of 4.33 g (30 mmol) 3-chloro-6-methoxypyridazine, 5.66 g (36 mmol) ethyl isonipecotate, 3.46 g (36 mmol) sodium tert.-butylate, 0.56 g (0.9 mmol) BINAP amd 0.55 g (0.5 mmol) Pd$_2$ dba$_3$ in 60 mL toluene was heated to 100° C. for 90 min. After cooling to room temperature water was added and the mixture was extracted with ethyl acetate. The combined organic layers were washed with brine, dried with Na$_2$SO$_4$, filtered and evaporated to dryness. The residue was purified by column chromatography on silica eluting with a gradient formed from heptane and ethyl acetate. The product containing fractions were evaporated to yield 3.2 g (34%) of the title compound as orange solid. MS m/e: 266.3 [M+H]+.

b) 1-(6-Methoxy-pyridazin-3-yl)-piperidine-4-carboxylic acid

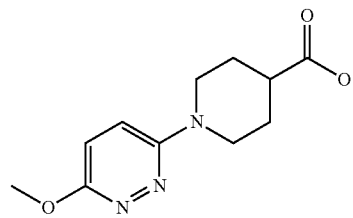 [SMILES: COc1ccc(N2CCC(C(=O)O)CC2)nn1]

In analogy to the procedure described for the synthesis of 5'-Fluoro-3,4,5,6-tetrahydro-2H-[1,2']bipyridinyl-4-carboxylic acid the title compound was prepared from 1-(6-Methoxy-pyridazin-3-yl)-piperidine-4-carboxylic acid ethyl ester through saponification with LiOH.H$_2$O. The title compound was isolated as orange solid. MS m/e: 236.2 [M−H].

c) {(3S,4R)-4-(4-Chloro-phenyl)-1-[1-(6-methoxy-pyridazin-3-yl)-piperidine-4-carbonyl]-pyrrolidin-3-yl}-methyl-carbamic acid 4-fluoro-phenyl ester In analogy to the procedure described for the synthesis of [(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester (example 194) the title compound was prepared from [(3S,4R)-4-(4-chloro-phenyl)-pyrrolidin-3-yl]-methyl-carbamic acid 4-fluoro-phenyl ester and 1-(6-Methoxy-pyridazin-3-yl)-piperidine-4-carboxylic acid as light yellow viscous oil. MS m/e: 568.5 [M+H]+.

EXAMPLE 198

[(3S,4R)-4-(4-Chloro-phenyl)-1-(6'-cyano-3,4,5,6-tetrahydro-2H-[1,3]bipyridinyl-4-carbonyl)-pyrrolidin-3-yl]-methyl-carbamic acid 4-fluoro-phenyl ester

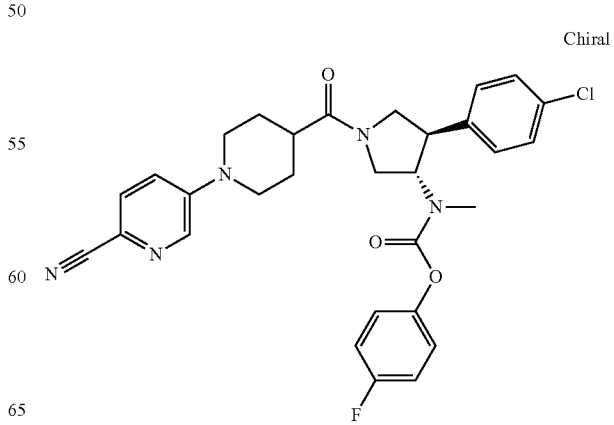

a) 6'-Cyano-3,4,5,6-tetrahydro-2H-[1,3']bipyridinyl-4-carboxylic acid ethyl ester

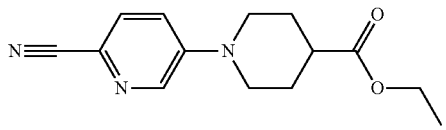

In analogy to the procedure described for the synthesis of 1-(6-Methoxy-pyridazin-3-yl)-piperidine-4-carboxylic acid ethyl ester the title compound was prepared from 5-bromo-cyanopyridine and ethyl isonipecotate as yellow viscous oil. MS m/e: 260.3 [M+H]+.

b) 6'-Cyano-3,4,5,6-tetrahydro-2H-[1,3]bipyridinyl-4-carboxylic acid

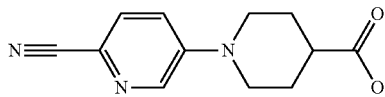

In analogy to the procedure described for the synthesis of 5'-Fluoro-3,4,5,6-tetrahydro-2H-[1,2']bipyridinyl-4-carboxylic acid the title compound was prepared from 6'-Cyano-3,4,5,6-tetrahydro-2H-[1,3']bipyridinyl-4-carboxylic acid ethyl ester through saponification with LiOH.H₂O. The title compound was isolated as yellow solid. MS m/e: 230 [M−H].

c) [(3S,4R)-4-(4-Chloro-phenyl)-1-(6'-cyano-3,4,5,6-tetrahydro-2H-[1,3']bipyridinyl-4-carbonyl)-pyrrolidin-3-yl]-methyl-carbamic acid 4-fluoro-phenyl ester In analogy to the procedure described for the synthesis of [(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester (example 194) the title compound was prepared from [(3S,4R)-4-(4-chloro-phenyl)-pyrrolidin-3-yl]-methyl-carbamic acid 4-fluoro-phenyl ester and 6'-Cyano-3,4,5,6-tetrahydro-2H-[1,3']bipyridinyl-4-carboxylic acid as light yellow viscous oil. MS m/e: 562.3 [M+H]+.

EXAMPLE 199

[(3S,4R)-4-(4-Chloro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester

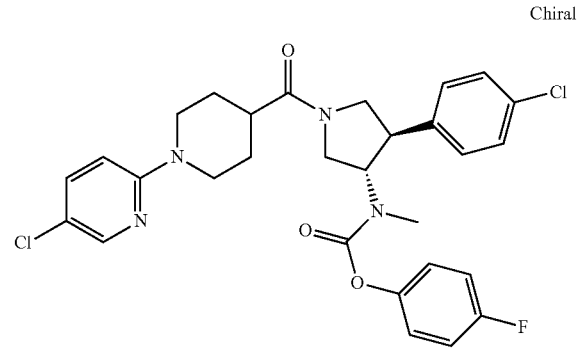 [SMILES: CN(C(=O)Oc1ccc(F)cc1)[C@@H]1CN(C(=O)C2CCN(c3ccc(Cl)cn3)CC2)C[C@H]1c1ccc(Cl)cc1]

In analogy to the procedure described for the synthesis of [(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester (example 194) the title compound was prepared from [(3S,4R)-4-(4-chloro-phenyl)-pyrrolidin-3-yl]-methyl-carbamic acid 4-fluoro-phenyl ester and 5'-Chloro-3,4,5,6-tetrahydro-2H-[1,2']bipyridinyl-4-carboxylic acid as light yellow viscous oil. MS m/e: 571.3 [M+H]+.

EXAMPLE 200

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester

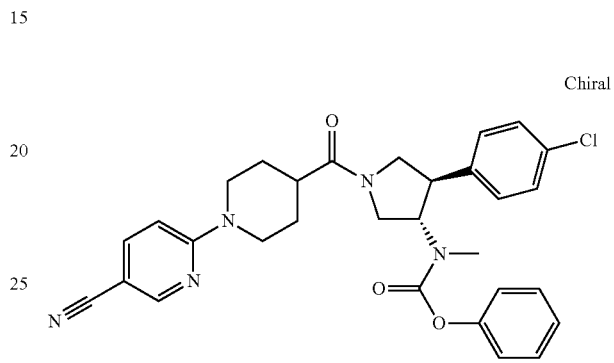

A mixture of 25 mg (0.059 mmol) 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile, 11.5 mg (0.074 mmol) phenyl chloroformate and 11.4 mg (0.088 mmol) DIPEA in 2 mL DCM was stirred for 15 min at 5° C. and over night at room temperature. Isolute was added and the mixture was evaporated to dryness and the residue was subjected to column chromatography on silica eluting with a gradient formed from DCM, methanol and NH₃. The product containing fractions were evaporated to yield 27 mg (84%) of the title compound as light yellow viscous oil. MS m/e: 544.4 [M+H]+.

EXAMPLE 201

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-phenyl ester

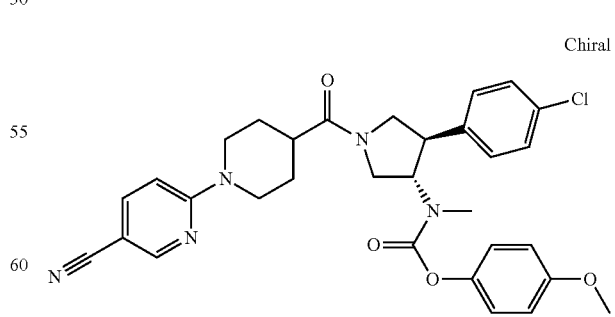

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-methoxyphenyl chloroformat as light yellow viscous oil. MS m/e: 574.5 [M+H]$^+$.

EXAMPLE 202

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid p-tolyl ester

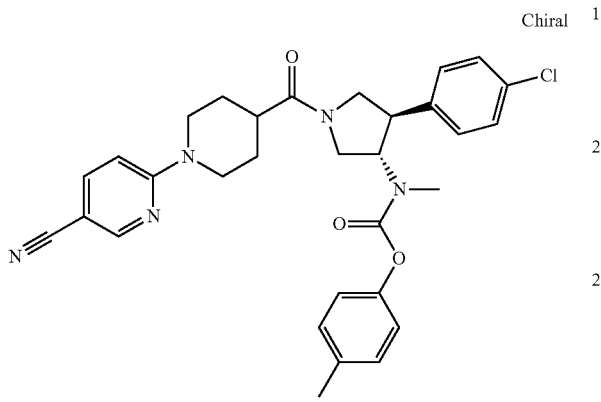

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and p-tolyl chloroformat as light yellow viscous oil. MS m/e: 558.4 [M+H]$^+$.

EXAMPLE 203

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-chloro-phenyl ester

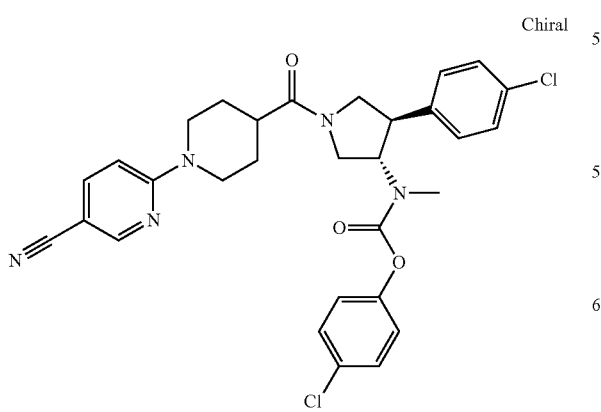

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-chlorophenyl chloroformat as light yellow viscous oil. MS m/e: 578.4 [M+H]$^+$.

EXAMPLE 204

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopentyl ester

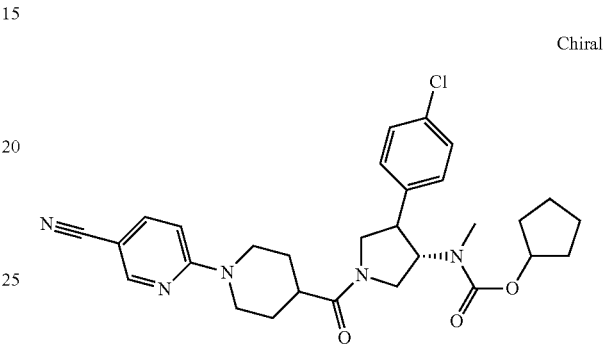

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and cyclopentyl chloroformat as colourless viscous oil. MS m/e: 536.3 [M+H]$^+$.

EXAMPLE 205

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2-dimethyl-propyl ester

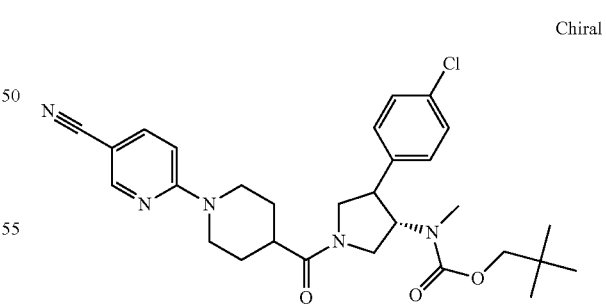

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and neopentyl chloroformat as colourless viscous oil. MS m/e: 538.4 [M+H]$^+$.

EXAMPLE 206

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-ethyl ester

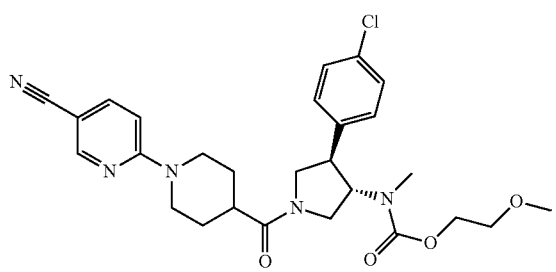

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and chloroformic acid 2-methoxyethyl ester as colourless viscous oil. MS m/e: 526.4 [M+H]$^+$.

EXAMPLE 207

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester

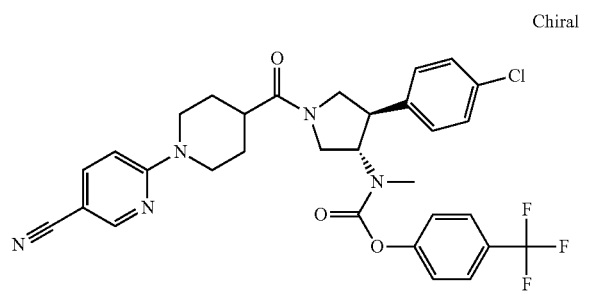

A solution of 243 mg (1.5 mmol) 4-hydroxybenzotrifluoride in 3 mL THF was treated with 1 mL (1.6 mmol) n-Buli (1.6M in hexane) at −70° C. and stirred for 15 min. 156 mg (0.526 mmol) triphosgene in 3 mL THF was added slowly and allowed to warm to room temperature. This mixture was added to a solution of 60 mg (0.142 mmol) 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 22.8 mg (0.177 mmol) DIPEA in 2 mL THF at 0° C. and stirred for 15 min Isolute was added and the mixture was evaporated to dryness and the residue was subjected to column chromatography on silica eluting with a gradient formed from DCM, methanol and NH$_3$ and subsequently to purification by preparative HPLC on reversed phase. The product containing fractions were evaporated to yield 30 mg (35%) of the title compound as light yellow viscous oil. MS m/e: 612.3 [M+H]$^+$.

EXAMPLE 208

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,4-difluoro-phenyl ester

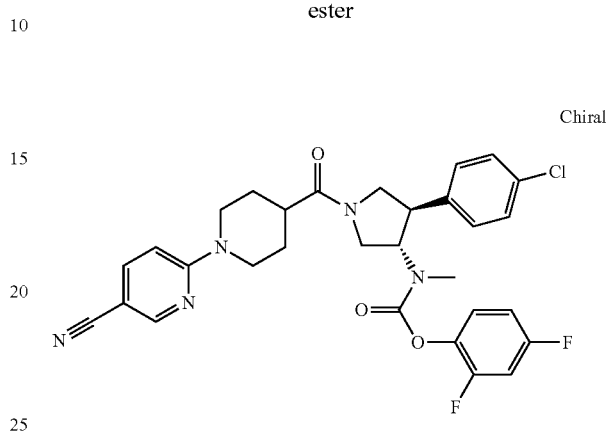

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2,4-difluorophenol as light yellow viscous oil. MS m/e: 580.4 [M+H]$^+$.

EXAMPLE 209

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,4-difluoro-phenyl ester

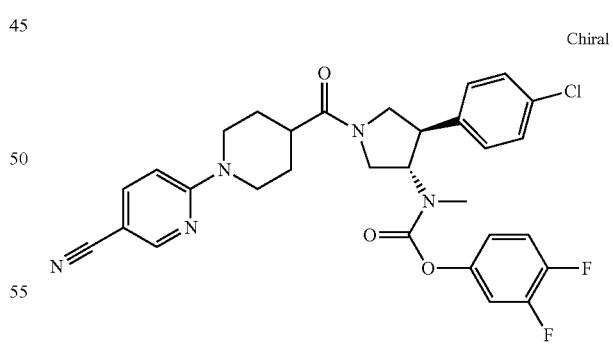

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3,4-difluorophenol as light yellow viscous oil. MS m/e: 580.3 [M+H]$^+$.

EXAMPLE 210

[(3S,4R)-4-(4-Chloro-phenyl)-1-(6'-cyano-3,4,5,6-tetrahydro-2H-[1,3]bipyridinyl-4-carbonyl)-pyrrolidin-3-yl]-methyl-carbamic acid 3,5-difluoro-phenyl ester

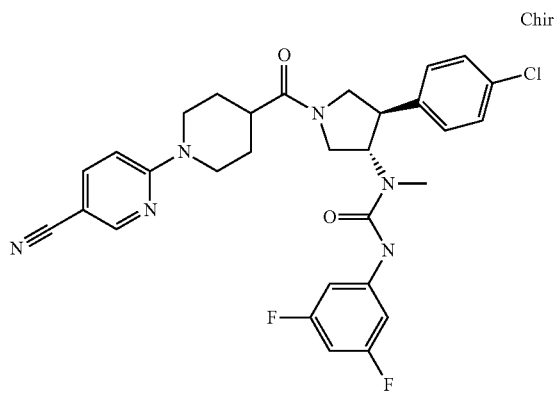 [SMILES: CN(C(=O)Oc1ccc(Cl)cc1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3,5-difluorophenol as colourless viscous oil. MS m/e: 580.3 [M+H]$^+$.

EXAMPLE 211

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,3-difluoro-phenyl ester

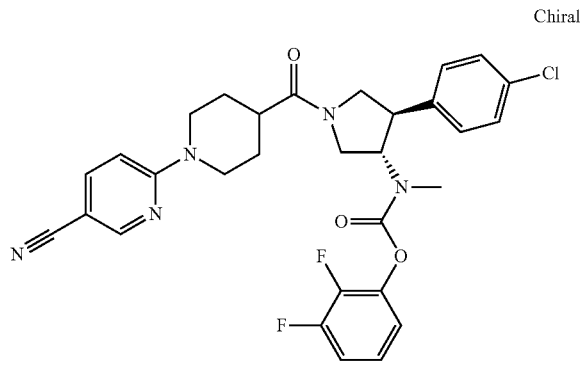 [SMILES: CN(C(=O)Oc1cccc(F)c1F)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2,4-difluorophenol as colourless viscous oil. MS m/e: 580.4 [M+H]$^+$.

EXAMPLE 212

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-phenyl ester

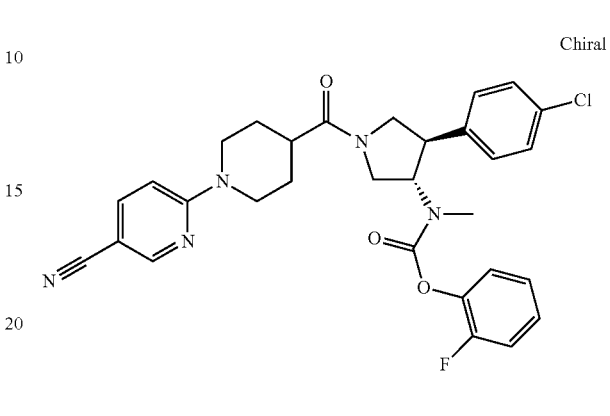

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-fluorophenol as colourless viscous oil. MS m/e: 562.3 [M+H]$^+$.

EXAMPLE 213

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-chloro-phenyl ester

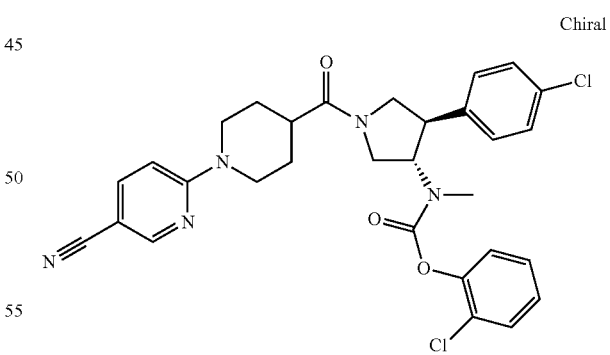

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-chlorophenol as colourless viscous oil. MS m/e: 578.3 [M+H]$^+$.

EXAMPLE 214

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-fluoro-propyl ester

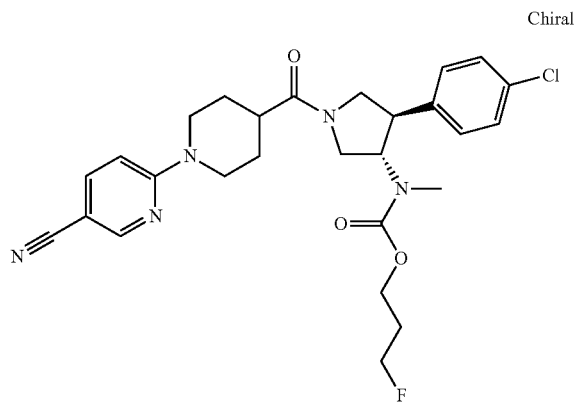 [SMILES: CN(C(=O)OCCCF)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3-fluoropropan-1ol as colourless viscous oil. MS m/e: 528.3 [M+H]+.

EXAMPLE 215

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropylmethyl ester

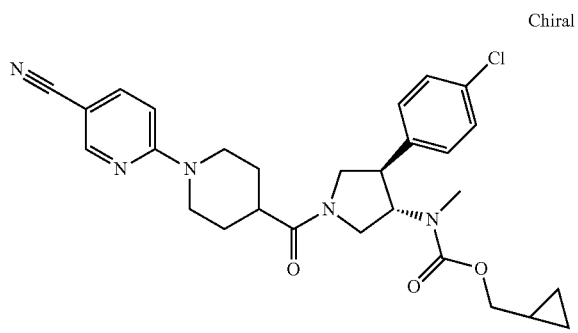 [SMILES: CN(C(=O)OCC1CC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and cyclopropyl-methanol as light yellow viscous oil. MS m/e: 522.4 [M+H]+.

EXAMPLE 216

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methoxy-propyl ester

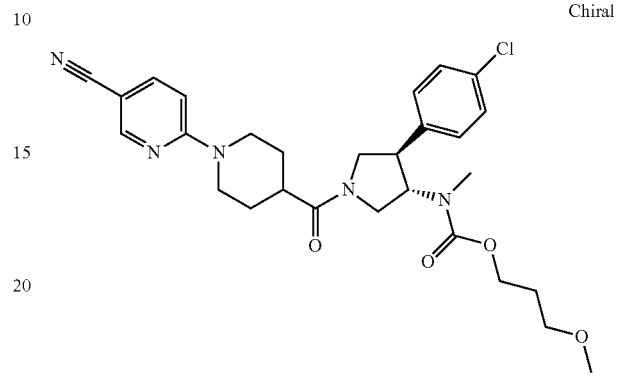

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3-methoxy-propan-1-ol as colourless yellow viscous oil. MS m/e: 540.4 [M+H]+.

EXAMPLE 217

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopropylmethyl ester

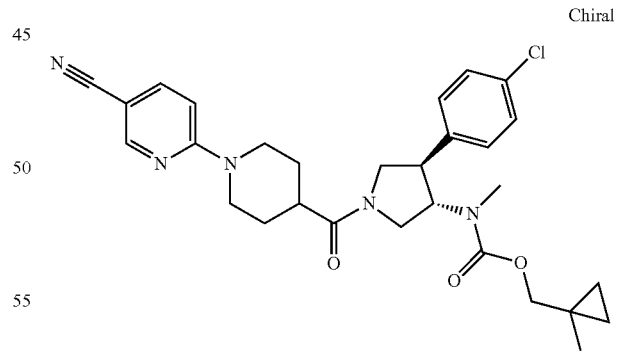

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2]bipyridinyl-5'-carbonitrile and (1-methyl-cyclopropyl)-methanol as colourless yellow viscous oil. MS m/e: 536.4 [M+H]+.

EXAMPLE 218

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methyl-oxetan-3-ylmethyl ester

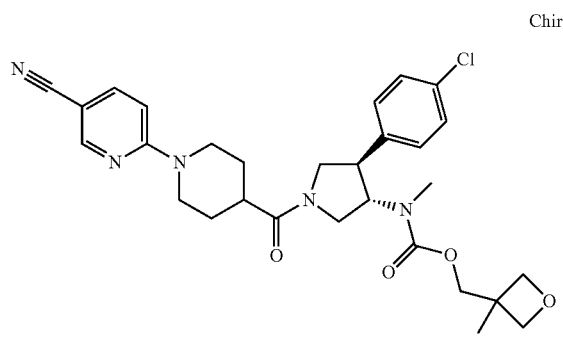

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and (3-methyl-oxetan-3-yl)-methanol as colourless yellow viscous oil. MS m/e: 552.5 [M+H]$^+$.

EXAMPLE 219

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-cyclopropyl-ethyl ester

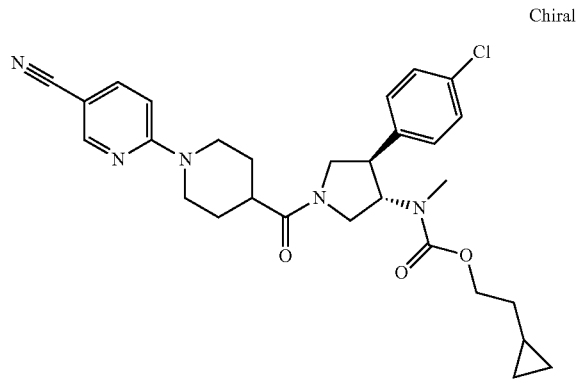 [SMILES: CN(C(=O)OCCC1CC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-cyclopropyl-ethanol as colourless viscous oil. MS m/e: 536.4 [M+H]$^+$.

EXAMPLE 220

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester

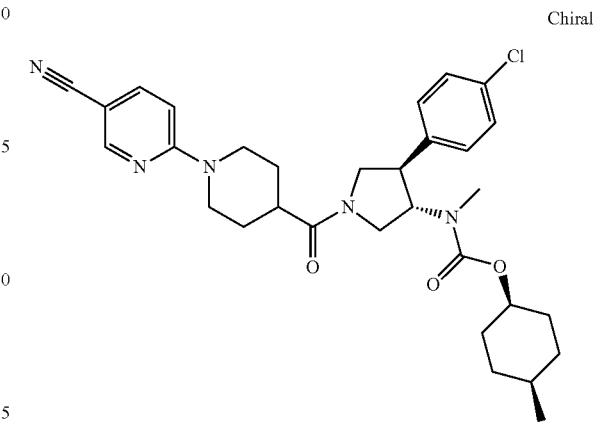

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-methylcyclohexanol as colourless viscous oil. MS m/e: 564.5 [M+H]$^+$.

EXAMPLE 221

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester

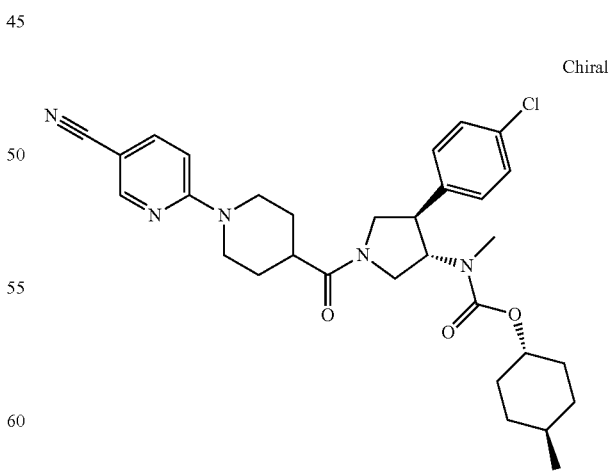

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-methylcyclohexanol as colourless viscous oil. MS m/e: 564.4 [M+H]+.

EXAMPLE 222

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-1-methyl-ethyl ester

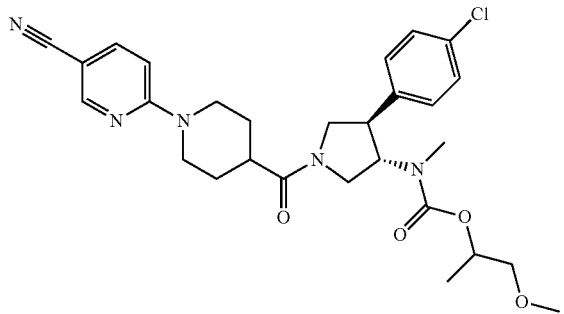 [SMILES: COCC(C)OC(=O)N(C)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1-methoxy-propan-2-ol as colourless viscous oil. MS m/e: 540.4 [M+H]+.

EXAMPLE 223

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-ethyl ester

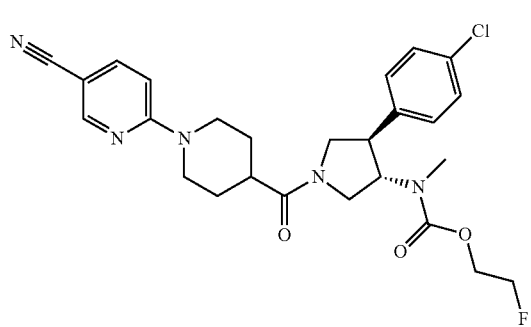

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-fluoro-ethanol as yellow viscous oil. MS m/e: 514.4 [M+H]+.

EXAMPLE 224

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methanesulfonyl-phenyl ester

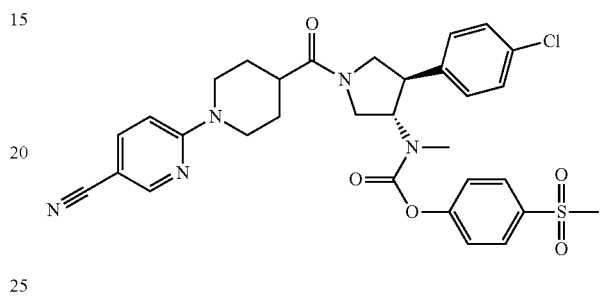

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-methanesulfonyl-phenol as yellow viscous oil. MS m/e: 622.4 [M+H]+.

EXAMPLE 225

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-cyano-phenyl ester

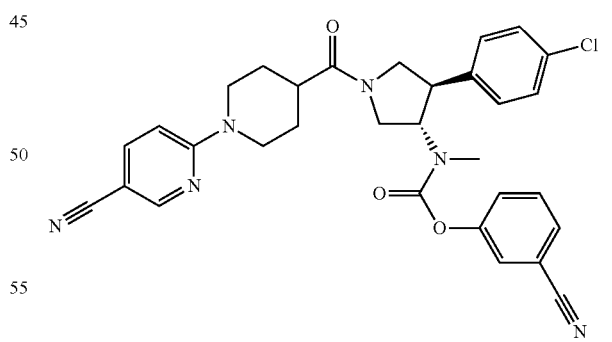

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3-hydroxy-benzonitrile as colourless viscous oil. MS m/e: 569.4 [M+H]+.

EXAMPLE 226

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-ethyl ester

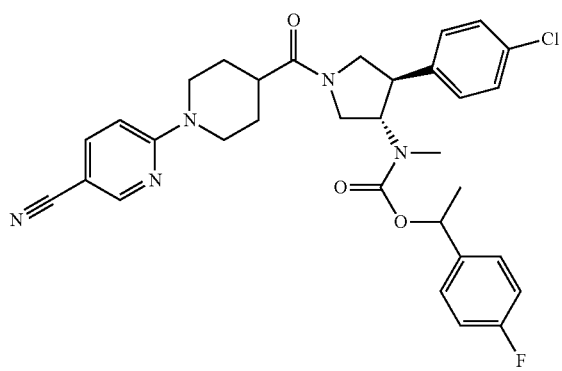 [SMILES: CC(OC(=O)N(C)[C@@H]1CN(C(=O)C2CCN(c3ccc(C#N)cn3)CC2)C[C@H]1c1ccc(Cl)cc1)c1ccc(F)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1-(4-fluoro-phenyl)-ethanol as colourless viscous oil. MS m/e: 590.4 [M+H]+.

EXAMPLE 227

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-1-fluoromethyl-ethyl ester

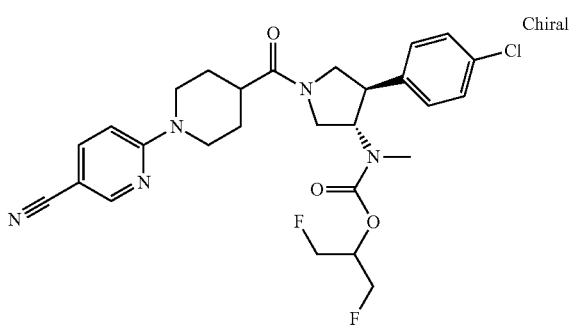 [SMILES: CN(C(=O)OC(CF)CF)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1,3-Difluoro-propan-2-ol as colourless viscous oil. MS m/e: 546.3 [M+H]+.

EXAMPLE 228

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-phenyl ester

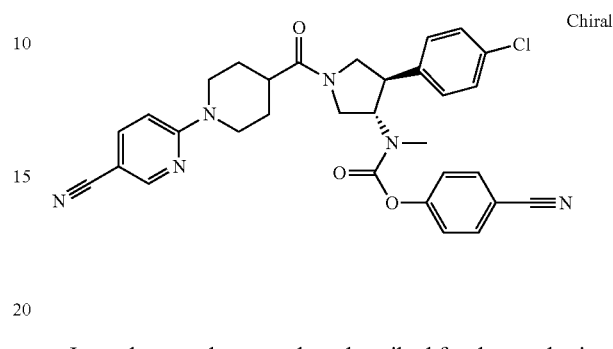

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-hydroxy-benzonitrile as colourless viscous oil. MS m/e: 569.4 [M+H]+.

EXAMPLE 229

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid o-tolyl ester

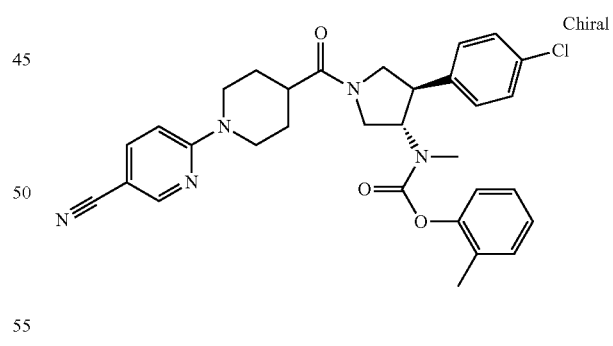

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-methyl-phenol as colourless viscous oil. MS m/e: 558.4 [M+H]+.

EXAMPLE 230

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid m-tolyl ester

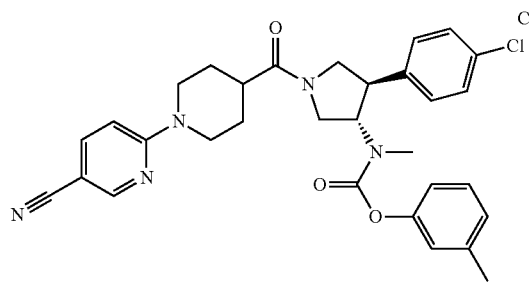

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3-methyl-phenol as colourless viscous oil. MS m/e: 558.4 [M+H]$^+$.

EXAMPLE 231

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-ylmethyl ester

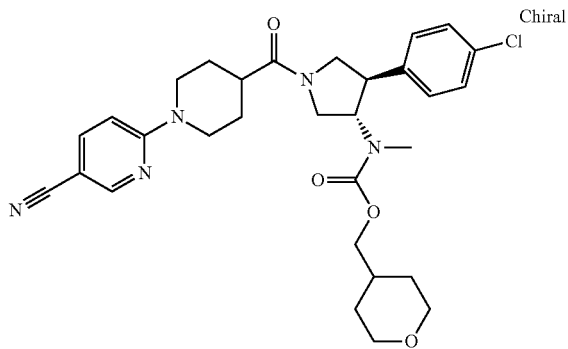 [SMILES: CN(C(=O)OCC1CCOCC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and (tetrahydro-pyran-4-yl)-methanol as colourless viscous oil. MS m/e: 566.5 [M+H]$^+$.

EXAMPLE 232

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-2-ylmethyl ester

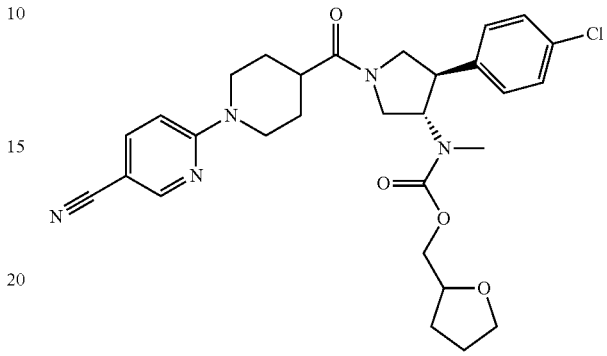

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and (tetrahydro-furan-2-yl)-methanol as colourless viscous oil. MS m/e: 552.5 [M+H]$^+$.

EXAMPLE 233

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-3-ylmethyl ester

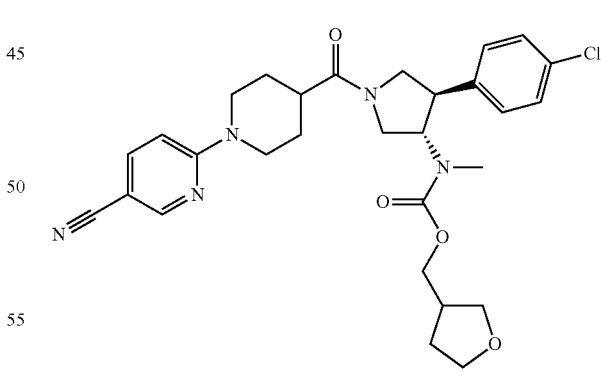

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and (tetrahydro-furan-3-yl)-methanol as colourless viscous oil. MS m/e: 552.5 [M+H]$^+$.

EXAMPLE 234

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,1-dimethyl-propyl ester

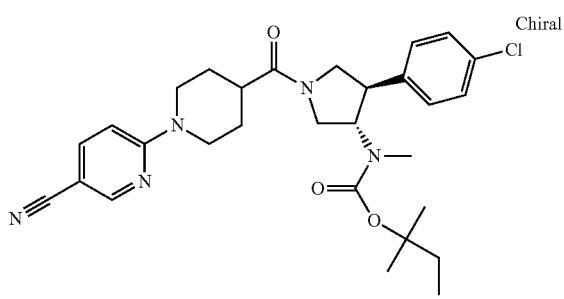 [SMILES: CCC(C)(C)OC(=O)N(C)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2]bipyridinyl-5'-carbonitrile and 2-methyl-butan-2-ol as colourless viscous oil. MS m/e: 538.4 [M+H]$^+$.

EXAMPLE 235

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1,1-dimethyl-ethyl ester

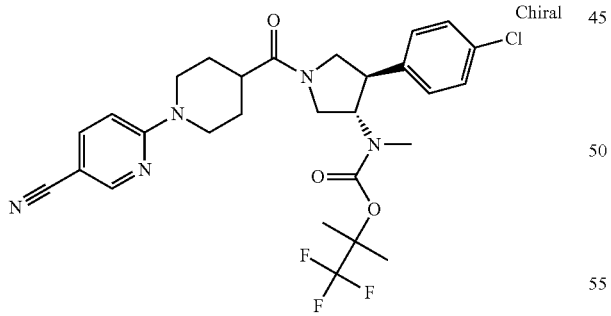

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1,1,1-trifluoro-2-methyl-propan-2-ol as colourless viscous oil. MS m/e: 578.4 [M+H]$^+$.

EXAMPLE 236

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-propyl ester

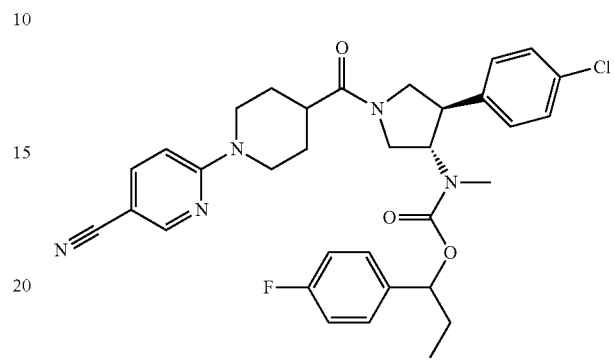

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1-(4-fluoro-phenyl)-propan-1-ol as light yellow viscous oil. MS m/e: 604.4 [M+H]$^+$.

EXAMPLE 237

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-2-fluoro-phenyl ester

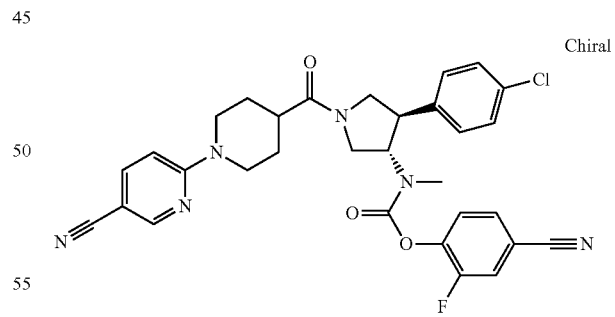

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 3-fluoro-4-hydroxy-benzonitrile as colourless viscous oil. MS m/e: 587.2 [M+H]$^+$.

EXAMPLE 238

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-cyclohexyl ester

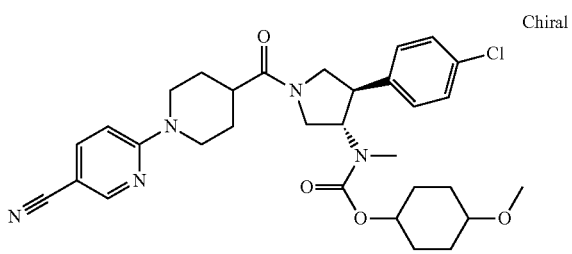 [SMILES: COC1CCC(OC(=O)N(C)[C@@H]2CN(C(=O)C3CCN(c4ccc(C#N)cn4)CC3)C[C@H]2c2ccc(Cl)cc2)CC1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2]bipyridinyl-5'-carbonitrile and 4-methoxy-cyclohexanol as colourless viscous oil. MS m/e: 580.4 [M+H]$^+$.

EXAMPLE 239

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropyl-(4-fluoro-phenyl)-methyl ester

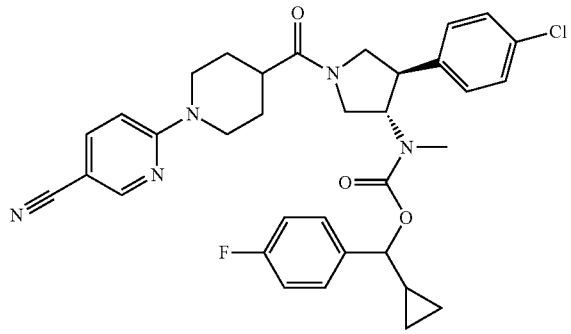 [SMILES: CN(C(=O)OC(c1ccc(F)cc1)C1CC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and cyclopropyl-(4-fluoro-phenyl)-methanol as colourless viscous oil. MS m/e: 616.4 [M+H]$^+$.

EXAMPLE 240

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-1-trifluoromethyl-cyclohexyl ester

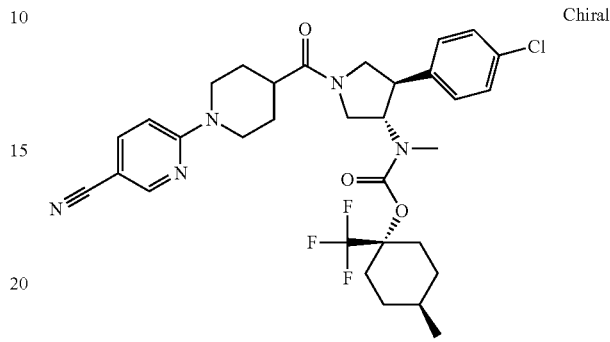

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 4-methyl-1-trifluoromethyl-cyclohexanol as light yellow viscous oil. MS m/e: 632.5 [M+H]$^+$.

EXAMPLE 241

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester

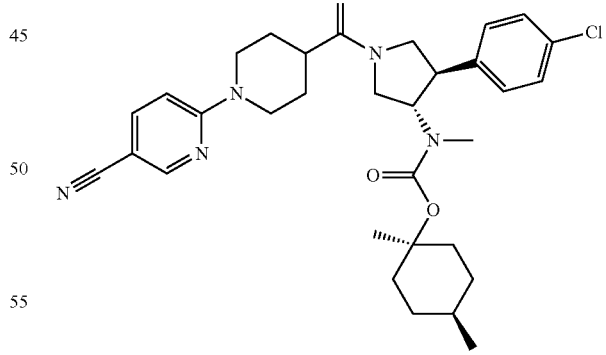

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1,4-dimethyl-cyclohexanol as light yellow viscous oil. MS m/e: 578.4 [M+H]$^+$.

EXAMPLE 242

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester

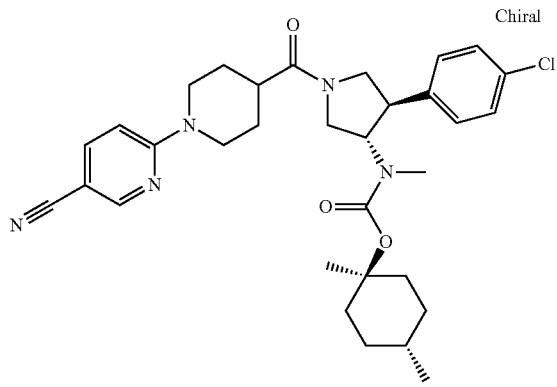 [SMILES: CN(C(=O)O[C@]1(C)CC[C@@H](C)CC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1,4-dimethyl-cyclohexanol as colourless viscous oil. MS m/e: 578.4 [M+H]+.

EXAMPLE 243

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopentyl ester

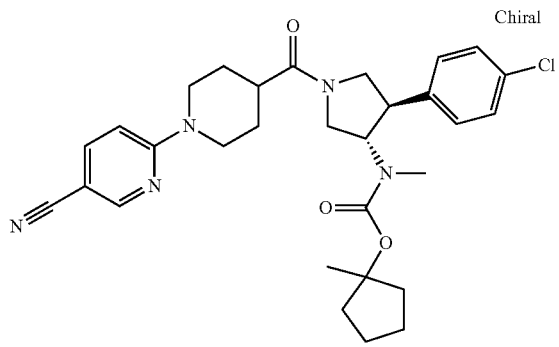 [SMILES: CN(C(=O)OC1(C)CCCC1)[C@@H]1CN(C(=O)C2CCN(c3ccc(C#N)cn3)CC2)C[C@H]1c1ccc(Cl)cc1]

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 1-methyl-cyclopentanol as colourless viscous oil. MS m/e: 550.4 [M+H]+.

EXAMPLE 244

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 5-chloro-pyridin-2-yl ester

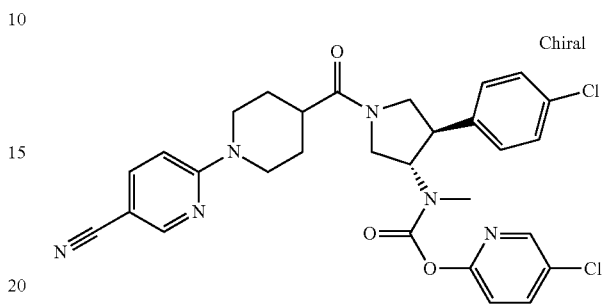

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 5-Chloro-pyridin-2-ol as colourless viscous oil. MS m/e: 579.3 [M+H]+.

EXAMPLE 245

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-3-fluoro-phenyl ester

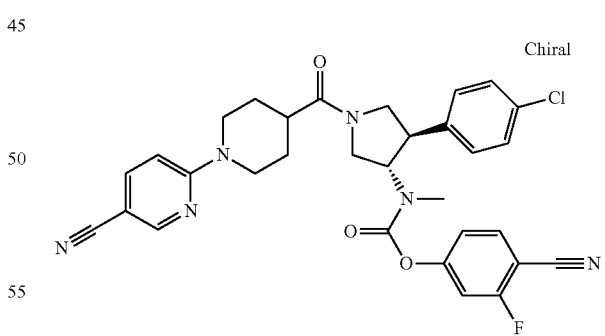

In analogy to the procedure described for the synthesis of [(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester (example 207) the title compound was prepared from 4-[(3R,4S)-3-(4-chloro-phenyl)-4-methylamino-pyrrolidine-1-carbonyl]-3,4,5,6-tetrahydro-2H-[1,2']bipyridinyl-5'-carbonitrile and 2-fluoro-4-hydroxy-benzonitrile as colourless viscous oil. MS m/e: 587.2 [M+H]+.

EXAMPLE 246

[(3S,4R)-1-(1-Acetyl-piperidine-4-carbonyl)-4-(4-chloro-phenyl)-pyrrolidin-3-yl]-methyl-carbamic acid 4-fluoro-phenyl ester

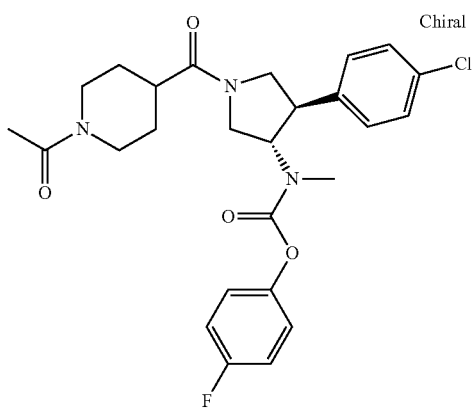 [SMILES: CC(=O)N1CCC(C(=O)N2C[C@@H](N(C)C(=O)Oc3ccc(F)cc3)[C@H](c3ccc(Cl)cc3)C2)CC1]

A mixture of 94 mg (0.204 mmol) 4-fluorophenyl (3S,4R)-4-(4-chlorophenyl)-1-(piperidine-4-carbonyl)pyrrolidin-3-yl(methyl)carbamate and 132 mg (1.02 mmol) DIPEA in 5 mL DCM was added 24.1 mg (0.3 mmol) acetyl chloride and stirred for 5 h. Methanol was added and stirred over night. The reaction mixture was extracted with sat NaHCO₃ and the aqueous layer extracted with DCM. The combined organic layers were dried with Na₂SO₄, filtered off and concentrated in vacuum. The residue was subjected to purification by column chromatography on silica eluting with a gradient formed from DCM, methanol and NH₃aq. The product containing fractions were evaporated to yield 53 mg (52%) of the title compound as light yellow foam. MS m/e: 502.2 [M+H]⁺.

EXAMPLE 247

[(3S,4R)-4-(4-Chloro-phenyl)-1-(1-cyclobutan e carbonyl-piperidine-4-carbonyl)-pyrrolidin-3-yl]-methyl-carbamic acid 4-fluoro-phenyl ester

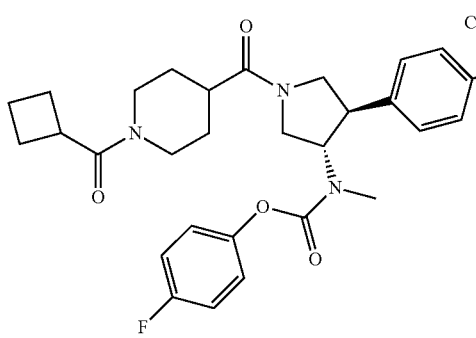

A mixture of 27.6 mg (0.06 mmol) 4-fluorophenyl (3S, 4R)-4-(4-chlorophenyl)-1-(piperidine-4-carbonyl)pyrrolidin-3-yl(methyl)carbamate, 0.52 mL (0.072 mmol) HATU (0.136 M in DMF), 12 mg (0.072 mmol) cyclobutanecarboxylic acid and 46.5 mg (0.36 mmol) DIPEA in 1.5 mL DMF was shaken at room temperature over night. The mixture was subjected to preparative HPLC chromatography on reversed phase eluting with a gradient formed from acetonitrile, water and NEt₃. The product containing fractions were evaporated to yield 12.5 mg (39%) of the title compounds as off-white solid. MS m/e: 542.3 [M+H]⁺.

EXAMPLE 248

{(3S,4R)-4-(4-Chloro-phenyl)-1-[1-(3-methyl-oxetane-3-carbonyl)-piperidine-4-carbonyl]-pyrrolidin-3-yl}-methyl-carbamic acid 4-fluoro-phenyl ester

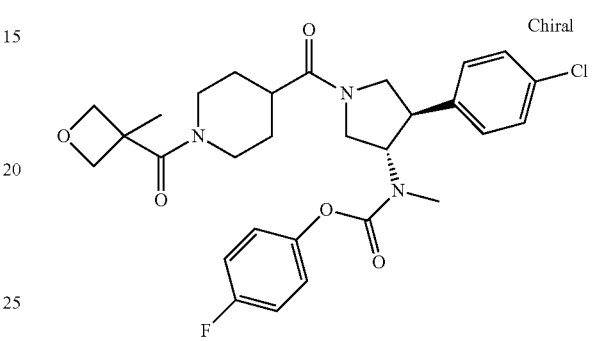

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 3-methyloxetane-3-carboxylic acid. MS m/e: 558.3 [M+H]F.

EXAMPLE 249

{(3S,4R)-4-(4-Chloro-phenyl)-1-[1-(3-fluoro-cyclobutanecarbonyl)-piperidine-4-carbonyl]-pyrrolidin-3-yl}-methyl-carbamic acid 4-fluoro-phenyl ester

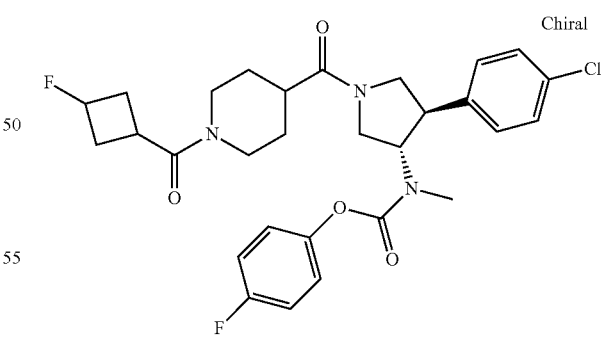

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 3-fluorocyclobutanecarboxylic acid. MS m/e: 560.2 [M+H]+.

EXAMPLE 250

{(3S,4R)-4-(4-Chloro-phenyl)-1-[1-(3,3-difluoro-cyclobutanecarbonyl)-piperidine-4-carbonyl]-pyrrolidin-3-yl}-methyl-carbamic acid 4-fluoro-phenyl Ester

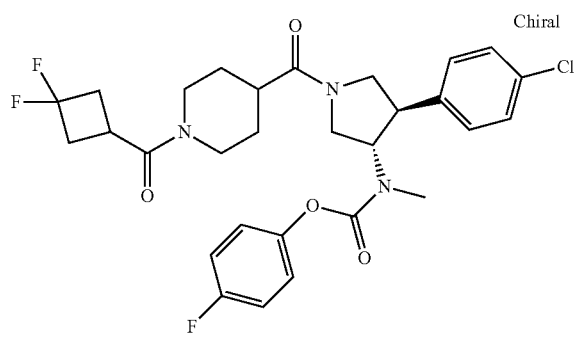 [SMILES: CN(C(=O)Oc1ccc(F)cc1)[C@@H]1CN(C(=O)C2CCN(C(=O)C3CC(F)(F)C3)CC2)C[C@H]1c1ccc(Cl)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 3,3-difluorocyclobutanecarboxylic acid. MS m/e: 578.3 [M+H]$^+$.

EXAMPLE 251

{(3S,4R)-4-(4-Chloro-phenyl)-1-[1-(3-methoxy-cyclobutanecarbonyl)-piperidine-4-carbonyl]-pyrrolidin-3-yl}-methyl-carbamic acid 4-fluoro-phenyl ester

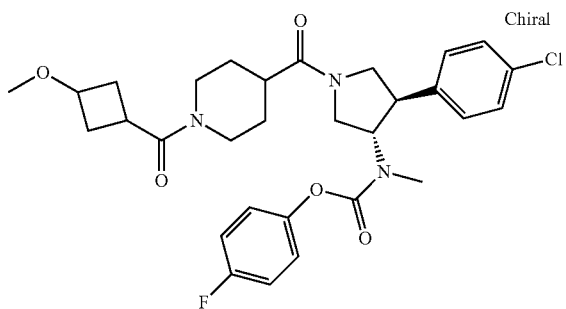 [SMILES: COC1CC(C(=O)N2CCC(C(=O)N3C[C@@H](N(C)C(=O)Oc4ccc(F)cc4)[C@H](c4ccc(Cl)cc4)C3)CC2)C1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 3-methoxycyclobutanecarboxylic acid. MS m/e: 572.2 [M+H]$^+$.

EXAMPLE 252

{(3S,4R)-4-(4-Chloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester

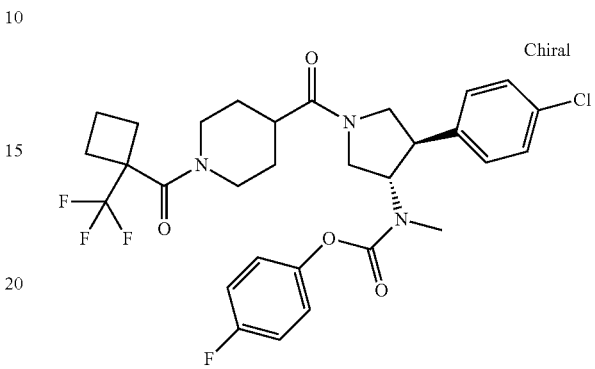

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 1-(trifluoromethyl)cyclobutanecarboxylic acid. MS m/e: 572.2 [M+H]$^+$.

EXAMPLE 253

{(3S,4R)-4-(4-Chloro-phenyl)-1-[1-(2-cyano-acetyl)-piperidine-4-carbonyl]-pyrrolidin-3-yl}-methyl-carbamic acid 4-fluoro-phenyl ester

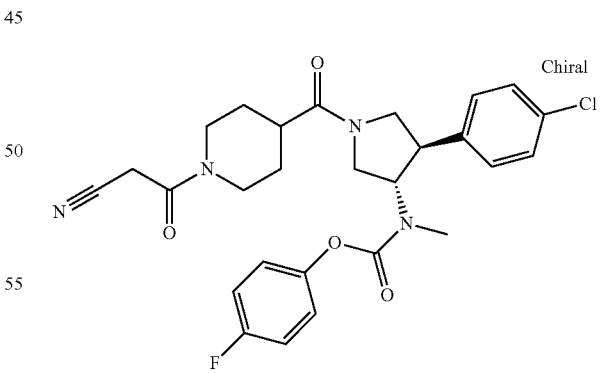

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 2-cyanoacetic acid. MS m/e: 572.2 [M+H]$^+$.

EXAMPLE 254

{(3S,4R)-4-(4-Chloro-phenyl)-1-[1-(1-cyano-cyclopropanecarbonyl)-piperidine-4-carbonyl]-pyrrolidin-3-yl}-methyl-carbamic acid 4-fluoro-phenyl ester

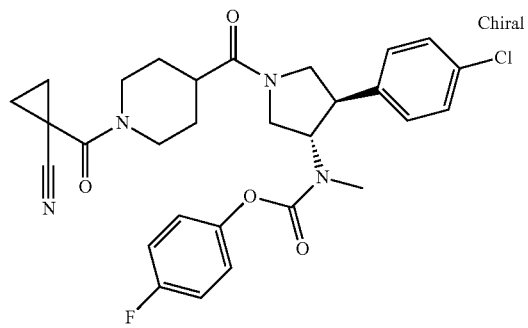 [SMILES: CN(C(=O)Oc1ccc(F)cc1)[C@@H]1CN(C(=O)C2CCN(C(=O)C3(C#N)CC3)CC2)C[C@H]1c1ccc(Cl)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 1-cyanocyclopropanecarboxylic acid. MS m/e: 553.3 [M+H]$^+$.

EXAMPLE 255

{(3S,4R)-4-(4-Chloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester

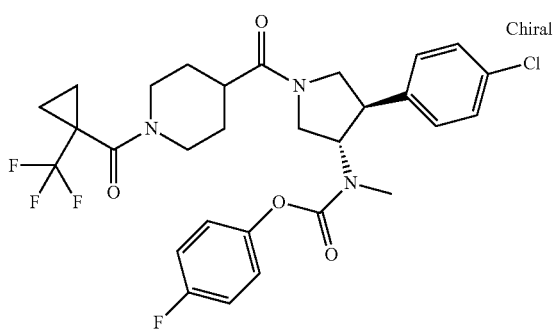 [SMILES: CN(C(=O)Oc1ccc(F)cc1)[C@@H]1CN(C(=O)C2CCN(C(=O)C3(C(F)(F)F)CC3)CC2)C[C@H]1c1ccc(Cl)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 1-(trifluoromethyl)cyclopropanecarboxylic acid. MS m/e: 596.3 [M+H]$^+$.

EXAMPLE 256

{(3S,4R)-4-(4-Chloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester

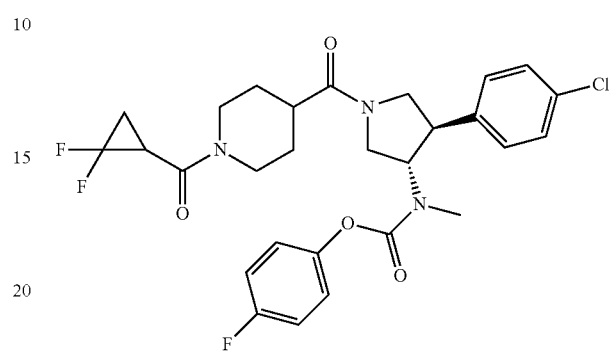

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 2,2-difluorocyclopropanecarboxylic acid. MS m/e: 564.3 [M+H]+.

EXAMPLE 257

{(3S,4R)-4-(4-Chloro-phenyl)-1-[1-(tetrahydro-pyran-4-carbonyl)-piperidine-4-carbonyl]-pyrrolidin-3-yl}-methyl-carbamic acid 4-fluoro-phenyl ester

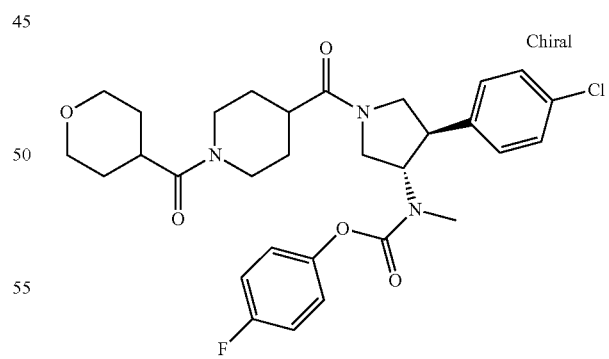

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and tetrahydro-2H-pyran-4-carboxylic acid. MS m/e: 572.2 [M+H]$^+$.

EXAMPLE 258

{(3S,4R)-4-(4-Chloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester

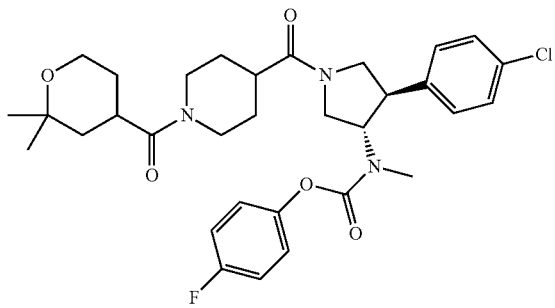 [SMILES: CN(C(=O)Oc1ccc(F)cc1)[C@@H]1CN(C(=O)C2CCN(C(=O)C3CCOC(C)(C)C3)CC2)C[C@H]1c1ccc(Cl)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 2,2-dimethyltetrahydro-2H-pyran-4-carboxylic acid. MS m/e: 600.3 [M+H]⁺.

EXAMPLE 259

{(3S,4R)-4-(4-Chloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester

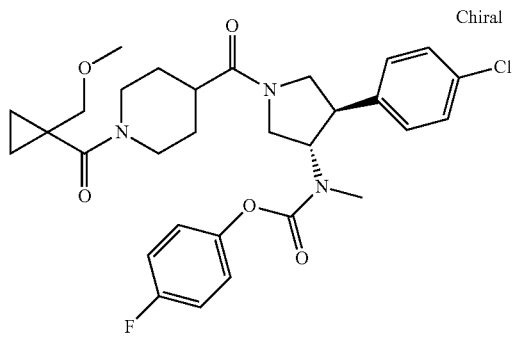 [SMILES: COCC1(C(=O)N2CCC(C(=O)N3C[C@@H](N(C)C(=O)Oc4ccc(F)cc4)[C@H](c4ccc(Cl)cc4)C3)CC2)CC1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 1-(methoxymethyl)cyclopropanecarboxylic acid. MS m/e: 572.2 [M+H]⁺.

EXAMPLE 260

{(3S,4R)-4-(4-Chloro-phenyl)-1-[1-(2,2-dimethyl-cyclopropanecarbonyl)-piperidine-4-carbonyl]-pyrrolidin-3-yl}-methyl-carbamic acid 4-fluoro-phenyl ester

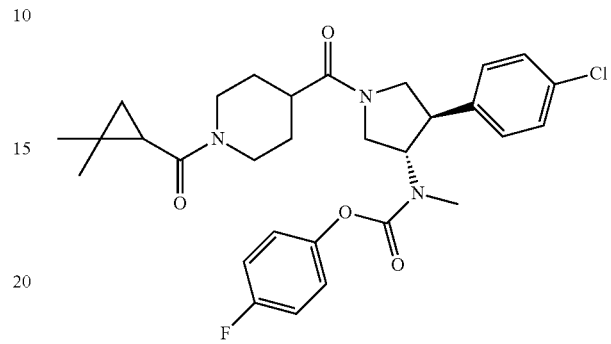

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 2,2-dimethylcyclopropanecarboxylic acid. MS m/e: 556.2 [M+H]+.

EXAMPLE 261

{(3S,4R)-4-(4-Chloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester

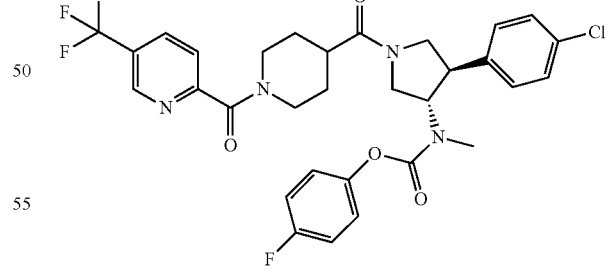

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 5-(trifluoromethyl)picolinic acid. MS m/e: 633.4 [M+H]⁺.

EXAMPLE 262

{(3S,4R)-4-(4-Chloro-phenyl)-1-[1-(5-fluoro-pyridine-2-carbonyl)-piperidine-4-carbonyl]-pyrrolidin-3-yl}-methyl-carbamic acid 4-fluoro-phenyl ester

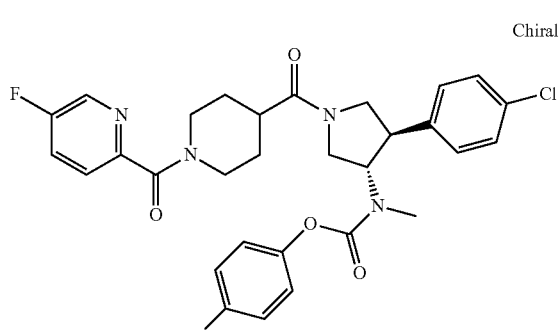

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 5-fluoropicolinic acid. MS m/e: 583.2 [M+H]⁺.

EXAMPLE 263

{(3S,4R)-4-(4-Chloro-phenyl)-1-[1-(6-oxo-piperidine-3-carbonyl)-piperidine-4-carbonyl]-pyrrolidin-3-yl}-methyl-carbamic acid 4-fluoro-phenyl ester

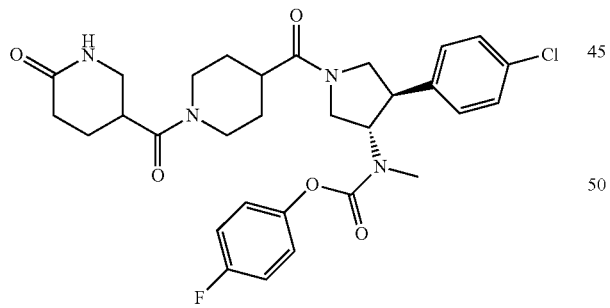

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 6-oxopiperidine-3-carboxylic acid. MS m/e: 585.3 [M+H]⁺.

EXAMPLE 264

{(3S,4R)-4-(4-Chloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester

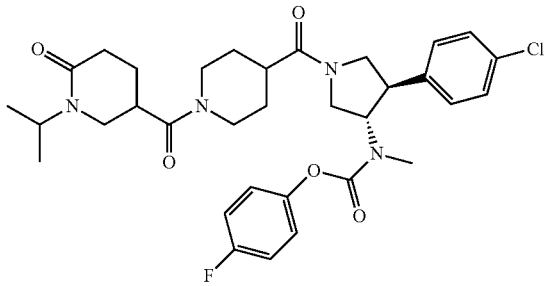 [SMILES: CC(C)N1CC(C(=O)N2CCC(C(=O)N3C[C@@H](N(C)C(=O)Oc4ccc(F)cc4)[C@H](c4ccc(Cl)cc4)C3)CC2)CCC1=O]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and 1-isopropyl-6-oxopiperidine-3-carboxylic acid. MS m/e: 627.4 [M+H]⁺.

EXAMPLE 265

[(3S,4R)-1-(1-Cyclobutanecarbonyl-piperidine-4-carbonyl)-4-(3,4-dichloro-phenyl)-pyrrolidin-3-yl]-methyl-carbamic acid 4-fluoro-phenyl ester

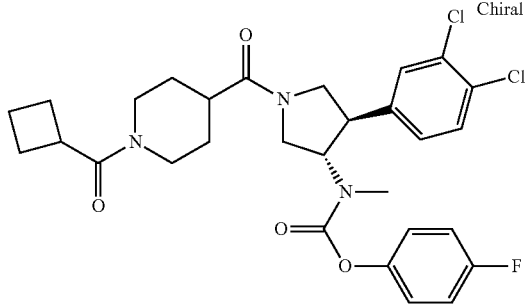 [SMILES: CN(C(=O)Oc1ccc(F)cc1)[C@@H]1CN(C(=O)C2CCN(C(=O)C3CCC3)CC2)C[C@H]1c1ccc(Cl)c(Cl)c1]

a) [(3S,4R)-1-Benzyl-4-(3,4-dichloro-phenyl)-pyrrolidin-3-yl]-methyl-carbamic acid 4-fluoro-phenyl ester

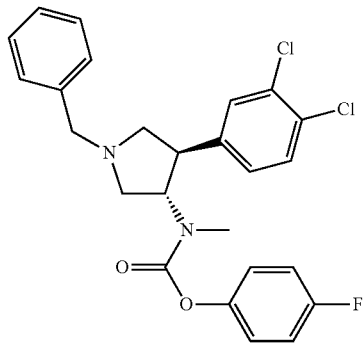 [SMILES: CN(C(=O)Oc1ccc(F)cc1)[C@@H]1CN(Cc2ccccc2)C[C@H]1c1ccc(Cl)c(Cl)c1]

A mixture of 3.35 g (10 mmol) (3S,4R)-1-benzyl-4-(3,4-dichlorophenyl)-N-methylpyrrolidin-3-amine (example 159, h), 1.61 g (12.5 mmol) DIPEA and 1.92 g (11 mmol) 4-fluorophenyl chloroformate in 50 mL DCM at 0-5° C. was stirred at 0° C. for 1 h and evaporated to dryness. The residue was subjected to column chromatography on silica eluting with a gradient formed from heptane and t-butyl-methylether to yield after evaporation of the product containing fractions 3.07 g (65%) of the title compound as colourless viscous oil. MS m/e: 473.1 [M+H]+.

b) [(3S,4R)-4-(3,4-Dichloro-phenyl)-pyrrolidin-3-yl]-methyl-carbamic acid 4-fluoro-phenyl ester

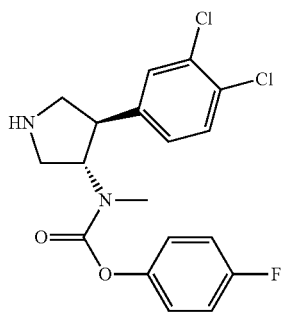 [SMILES: CN(C(=O)Oc1ccc(F)cc1)[C@@H]1CNC[C@H]1c1ccc(Cl)c(Cl)c1]

In analogy to the procedure described for the synthesis of rac-[(3R,4S)-4-(3,4-Dichloro-phenyl)-pyrrolidin-3-yl]-methyl-carbamic acid tert-butyl ester (example 1, e) the title compound was prepared from [(3S,4R)-1-Benzyl-4-(3,4-dichloro-phenyl)-pyrrolidin-3-yl]-methyl-carbamic acid 4-fluoro-phenyl ester and isolated as brown foam. MS m/e: 383.2 [M+H]+.

c) [(3S,4R)-4-(3,4-Dichloro-phenyl)-1-(piperidine-4-carbonyl)-pyrrolidin-3-yl]-methyl-carbamic acid 4-fluoro-phenyl ester

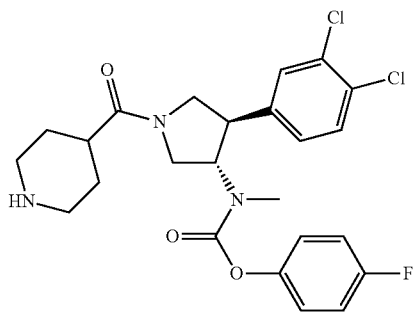 [SMILES: CN(C(=O)Oc1ccc(F)cc1)[C@@H]1CN(C(=O)C2CCNCC2)C[C@H]1c1ccc(Cl)c(Cl)c1]

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the Boc-protected title compound was prepared from [(3S,4R)-4-(3,4-Dichloro-phenyl)-pyrrolidin-3-yl]-methyl-carbamic acid 4-fluoro-phenyl ester and N-Boc-isonipecotic acid. The title compound was subsequently isolated after acidic cleavage of the Boc group with TFA. MS m/e: 494.2 [M+H]+.

d) [(3S,4R)-1-(1-Cyclobutanecarbonyl-piperidine-4-carbonyl)-4-(3,4-dichloro-phenyl)-pyrrolidin-3-yl]-methyl-carbamic acid 4-fluoro-phenyl ester In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and cyclobutanecarboxylic acid. MS m/e: 576.3 [M+H]+.

EXAMPLE 266

{(3S,4R)-4-(3,4-Dichloro-phenyl)-1-[1-(3-methyl-oxetane-3-carbonyl)-piperidine-4-carbonyl]-pyrrolidin-3-yl}-methyl-carbamic acid 4-fluoro-phenyl ester

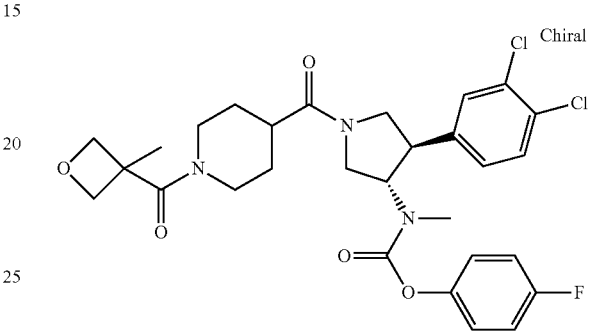

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 3-methyloxetane-3-carboxylic acid. MS m/e: 592.3 [M+H]+.

EXAMPLE 267

{(3S,4R)-4-(3,4-Dichloro-phenyl)-1-[1-(3-fluoro-cyclobutanecarbonyl)-piperidine-4-carbonyl]-pyrrolidin-3-yl}-methyl-carbamic acid 4-fluoro-phenyl ester

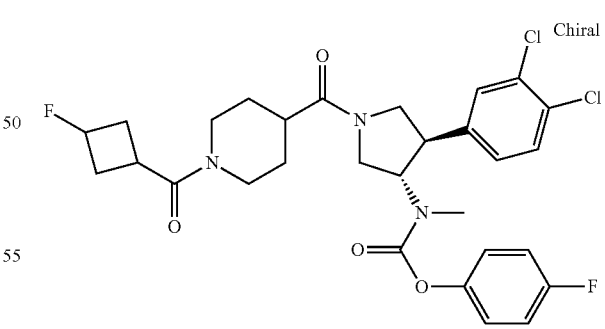

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 3-fluorocyclobutanecarboxylic acid. MS m/e: 594.3 [M+H]+.

EXAMPLE 268

{(3S,4R)-4-(3,4-Dichloro-phenyl)-1-[1-(3,3-difluoro-cyclobutanecarbonyl)-piperidine-4-carbonyl]-pyrrolidin-3-yl}-methyl-carbamic acid 4-fluoro-phenyl ester

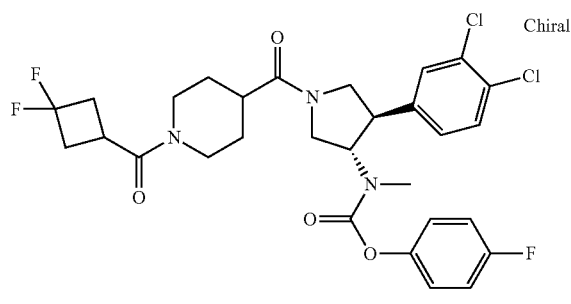 [SMILES: CN(C(=O)Oc1ccc(F)cc1)[C@@H]1CN(C(=O)C2CCN(C(=O)C3CC(F)(F)C3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 3,3-difluorocyclobutanecarboxylic acid. MS m/e: 612.2 [M+H]$^+$.

EXAMPLE 269

{(3S,4R)-4-(3,4-Dichloro-phenyl)-1-[1-(3-methoxy-cyclobutanecarbonyl)-piperidine-4-carbonyl]-pyrrolidin-3-yl}-methyl-carbamic acid 4-fluoro-phenyl ester

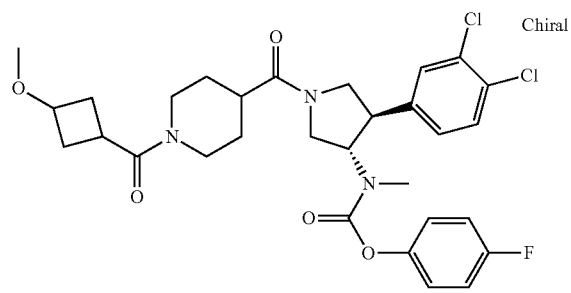 [SMILES: COC1CC(C(=O)N2CCC(C(=O)N3C[C@@H](N(C)C(=O)Oc4ccc(F)cc4)[C@H](c4ccc(Cl)c(Cl)c4)C3)CC2)C1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 3-methoxycyclobutanecarboxylic acid. MS m/e: 606.3 [M+H]$^+$.

EXAMPLE 270

{(3S,4R)-4-(3,4-Dichloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester

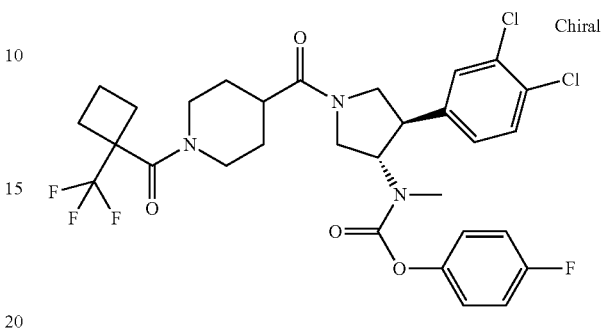

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 1-(trifluoromethyl)cyclobutanecarboxylic acid. MS m/e: 644.2 [M+H]$^+$.

EXAMPLE 271

[(3S,4R)-1-[1-(2-Cyano-acetyl)-piperidine-4-carbonyl]-4-(3,4-dichloro-phenyl)-pyrrolidin-3-yl]-methyl-carbamic acid 4-fluoro-phenyl ester

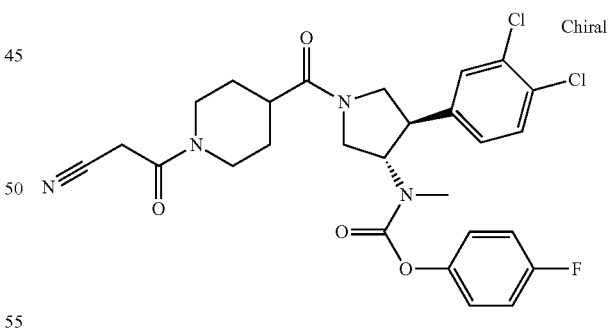

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 2-cyanoacetic acid. MS m/e: 561.1 [M+H]$^+$.

EXAMPLE 272

[(3S,4R)-1-[1-(1-Cyano-cyclopropanecarbonyl)-piperidine-4-carbonyl]-4-(3,4-dichloro-phenyl)-pyrrolidin-3-yl]-methyl-carbamic acid 4-fluoro-phenyl ester

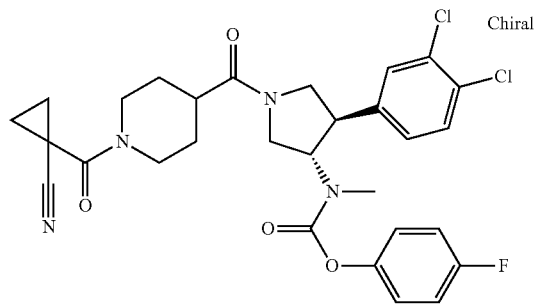 [SMILES: CN(C(=O)Oc1ccc(F)cc1)[C@@H]1CN(C(=O)C2CCN(C(=O)C3(C#N)CC3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 1-cyanocyclopropanecarboxylic acid. MS m/e: 587.1 [M+H]$^+$.

EXAMPLE 273

{(3S,4R)-4-(3,4-Dichloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester

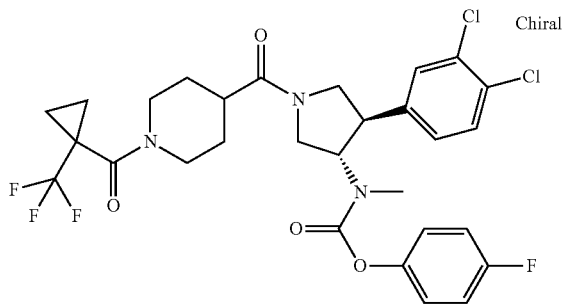 [SMILES: CN(C(=O)Oc1ccc(F)cc1)[C@@H]1CN(C(=O)C2CCN(C(=O)C3(C(F)(F)F)CC3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 1-(trifluoromethyl)cyclopropanecarboxylic acid. MS m/e: 630.4 [M+H]+.

EXAMPLE 274

{(3S,4R)-4-(3,4-Dichloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester

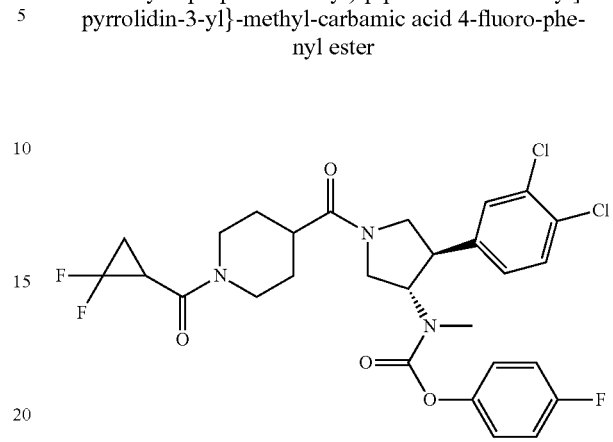

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 2,2-difluorocyclopropanecarboxylic acid. MS m/e: 598.1 [M+H]$^+$.

EXAMPLE 275

{(3S,4R)-4-(3,4-Dichloro-phenyl)-1-[1-(tetrahydropyran-4-carbonyl)-piperidine-4-carbonyl]-pyrrolidin-3-yl}-methyl-carbamic acid 4-fluoro-phenyl ester

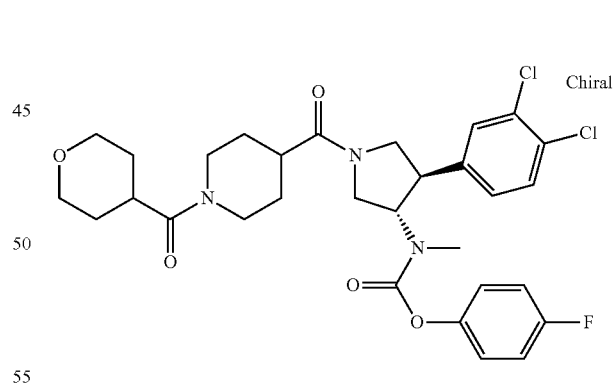

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and tetrahydro-2H-pyran-4-carboxylic acid. MS m/e: 606.2 [M+H]$^+$.

EXAMPLE 276

{(3S,4R)-4-(3,4-Dichloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester

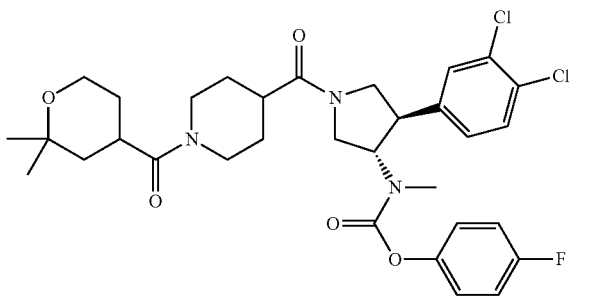 [SMILES: CN(C(=O)Oc1ccc(F)cc1)[C@@H]1CN(C(=O)C2CCN(C(=O)C3CCOC(C)(C)C3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 2,2-dimethyltetrahydro-2H-pyran-4-carboxylic acid. MS m/e: 634.2 [M+H]$^+$.

EXAMPLE 277

{(3S,4R)-4-(3,4-Dichloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester

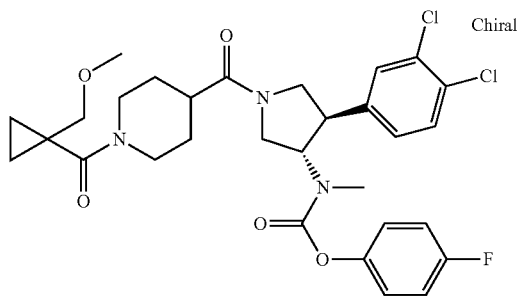 [SMILES: COCC1(C(=O)N2CCC(C(=O)N3C[C@@H](N(C)C(=O)Oc4ccc(F)cc4)[C@H](c4ccc(Cl)c(Cl)c4)C3)CC2)CC1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 1-(methoxymethyl)cyclopropanecarboxylic acid. MS m/e: 606.3 [M+H]$^+$.

EXAMPLE 278

{(3S,4R)-4-(3,4-Dichloro-phenyl)-1-[1-(2,2-dimethyl-cyclopropanecarbonyl)-piperidine-4-carbonyl]-pyrrolidin-3-yl}-methyl-carbamic acid 4-fluoro-phenyl ester

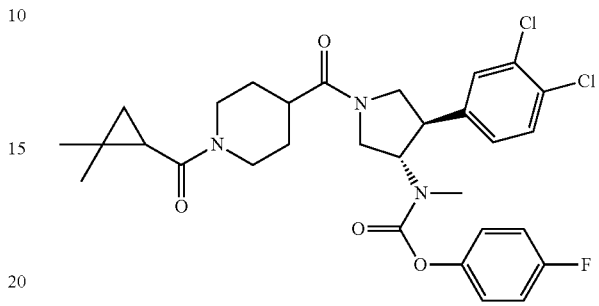

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 2,2-dimethylcyclopropanecarboxylic acid. MS m/e: 590.2 [M+H]$^+$.

EXAMPLE 279

{(3S,4R)-4-(3,4-Dichloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester

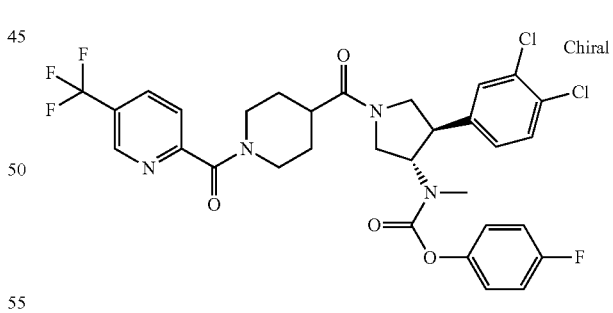

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 5-(trifluoromethyl)picolinic acid. MS m/e: 667.2 [M+H]$^+$.

EXAMPLE 280

{(3S,4R)-4-(3,4-Dichloro-phenyl)-1-[1-(5-fluoro-pyridine-2-carbonyl)-piperidine-4-carbonyl]-pyrrolidin-3-yl}-methyl-carbamic acid 4-fluoro-phenyl ester

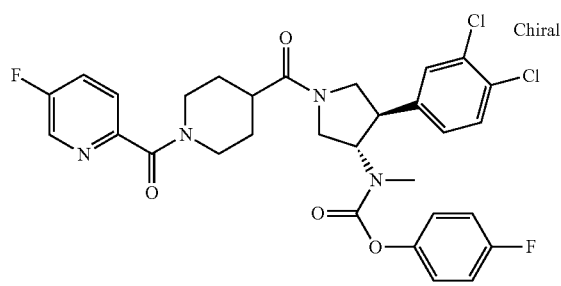 [SMILES: CN(C(=O)Oc1ccc(F)cc1)[C@@H]1CN(C(=O)C2CCN(C(=O)c3ccc(F)cn3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 5-fluoropicolinic acid. MS m/e: 617.3 [M+H]$^+$.

EXAMPLE 281

{(3S,4R)-4-(3,4-Dichloro-phenyl)-1-[1-(6-oxo-piperidine-3-carbonyl)-piperidine-4-carbonyl]-pyrrolidin-3-yl}-methyl-carbamic acid 4-fluoro-phenyl ester

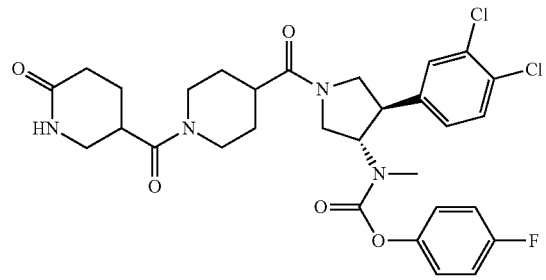 [SMILES: CN(C(=O)Oc1ccc(F)cc1)[C@@H]1CN(C(=O)C2CCN(C(=O)C3CCC(=O)NC3)CC2)C[C@H]1c1ccc(Cl)c(Cl)c1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 6-oxopiperidine-3-carboxylic acid. MS m/e: 619.4 [M+H]$^+$.

EXAMPLE 282

{(3S,4R)-4-(3,4-Dichloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester

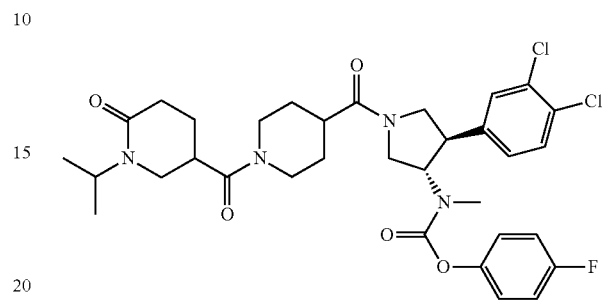

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and 1-isopropyl-6-oxopiperidine-3-carboxylic acid. MS m/e: 661.3 [M+H]$^+$.

EXAMPLE 283

[(3S,4R)-1-(1-Acetyl-piperidine-4-carbonyl)-4-(3,4-dichloro-phenyl)-pyrrolidin-3-yl]-methyl-carbamic acid 4-fluoro-phenyl ester

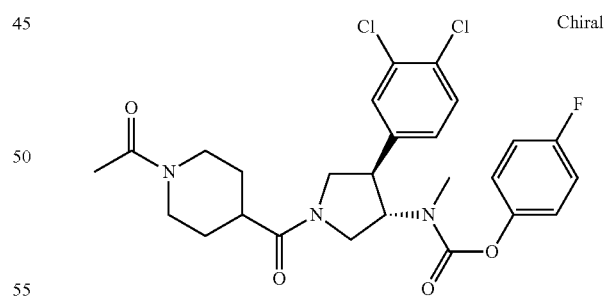

In analogy to the procedure described for the synthesis of [(3S,4R)-1-(1-Acetyl-piperidine-4-carbonyl)-4-(4-chloro-phenyl)-pyrrolidin-3-yl]-methyl-carbamic acid 4-fluoro-phenyl ester (example 246) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and acetyl chloride. MS m/e: 536.1 [M+H]$^+$.

EXAMPLE 284

[(3S,4R)-1-[1-(2-Cyano-acetyl)-piperidine-4-carbonyl]-4-(4-fluoro-phenyl)-pyrrolidin-3-yl]-methyl-carbamic acid 4-fluoro-phenyl ester

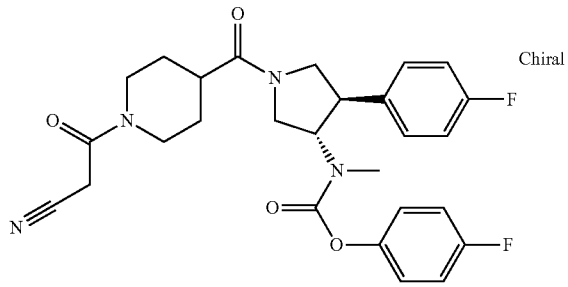 [SMILES: CN(C(=O)Oc1ccc(F)cc1)[C@@H]1CN(C(=O)C2CCN(C(=O)CC#N)CC2)C[C@H]1c1ccc(F)cc1]

a) [(3S,4R)-1-Benzyl-4-(4-fluoro-phenyl)-pyrrolidin-3-yl]-methyl-carbamic acid 4-fluoro-phenyl ester

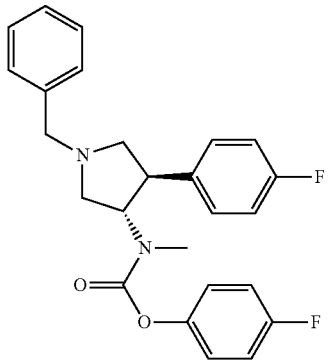 [SMILES: CN(C(=O)Oc1ccc(F)cc1)[C@@H]1CN(Cc2ccccc2)C[C@H]1c1ccc(F)cc1]

In analogy to the procedure described for the synthesis of [(3S,4R)-1-Benzyl-4-(3,4-dichloro-phenyl)-pyrrolidin-3-yl]-methyl-carbamic acid 4-fluoro-phenyl ester (example 265, a) the title compound was prepared from rac-[(3S,4R)-1-Benzyl-4-(4-fluoro-phenyl)-pyrrolidin-3-yl]-methyl-amine (WO2008128891) and 4-fluorophenyl chloroformate. MS m/e: 423.3 [M+H]⁺. This was followed by column chromatography on Chiralpak AD eluting with a gradient formed from ethanol and heptane. The product containing fractions were evaporated to yield the title compound as off-white solid. MS m/e: 423.3 [M+H]⁺.

b) [(3S,4R)-4-(4-Fluoro-phenyl)-1-(piperidine-4-carbonyl)-pyrrolidin-3-yl]-methyl-carbamic acid 4-fluoro-phenyl ester

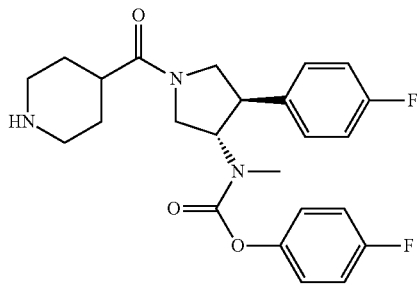 [SMILES: CN(C(=O)Oc1ccc(F)cc1)[C@@H]1CN(C(=O)C2CCNCC2)C[C@H]1c1ccc(F)cc1]

In analogy to the procedure described for the synthesis of rac-[(3R,4S)-4-(3,4-Dichloro-phenyl)-pyrrolidin-3-yl]-methyl-carbamic acid tert-butyl ester (example 1, e) the title compound was prepared from [(3S,4R)-1-Benzyl-4-(4-fluoro-phenyl)-pyrrolidin-3-yl]-methyl-carbamic acid 4-fluoro-phenyl ester through cleavage of the benzyl group. And, in analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the Boc-protected title compound was prepared from [(3S,4R)-4-(4-Fluoro-phenyl)-pyrrolidin-3-yl]-methyl-carbamic acid 4-fluoro-phenyl ester and N-Boc-isonipecotic acid. The title compound was subsequently isolated after acidic cleavage of the Boc group with TFA. MS m/e: 444.3 [M+H]⁺.

c) [(3S,4R)-1-[1-(2-Cyano-acetyl)-piperidine-4-carbonyl]-4-(4-fluoro-phenyl)-pyrrolidin-3-yl]-methyl-carbamic acid 4-fluoro-phenyl ester In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 2-cyanoacetic acid. MS m/e: 511.4 [M+H]⁺.

EXAMPLE 285

[(3S,4R)-1-(1-Acetyl-piperidine-4-carbonyl)-4-(4-fluoro-phenyl)-pyrrolidin-3-yl]-methyl-carbamic acid 4-fluoro-phenyl ester

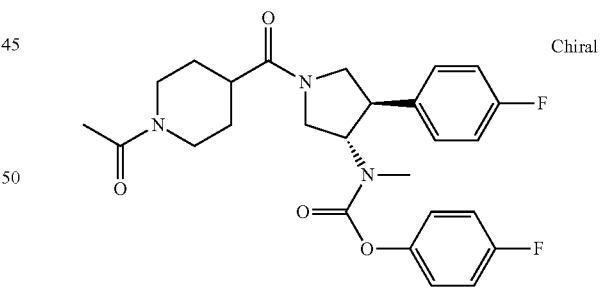

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and acetic acid. MS m/e: 486.4 [M+H]⁺.

EXAMPLE 286

{(3S,4R)-4-(4-Fluoro-phenyl)-1-[1-(3-methyl-oxetane-3-carbonyl)-piperidine-4-carbonyl]-pyrrolidin-3-yl}-methyl-carbamic acid 4-fluoro-phenyl ester

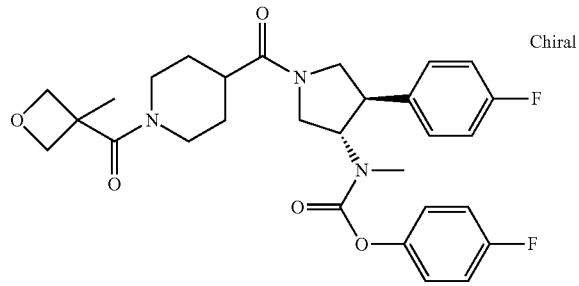 [SMILES: CN(C(=O)Oc1ccc(F)cc1)[C@@H]1CN(C(=O)C2CCN(C(=O)C3(C)COC3)CC2)C[C@H]1c1ccc(F)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 3-methyloxetane-3-carboxylic acid. MS m/e: 542.3 [M+H]⁺.

EXAMPLE 287

[(3S,4R)-1-[1-(3-Fluoro-cyclobutanecarbonyl)-piperidine-4-carbonyl]-4-(4-fluoro-phenyl)-pyrrolidin-3-yl]-methyl-carbamic acid 4-fluoro-phenyl ester

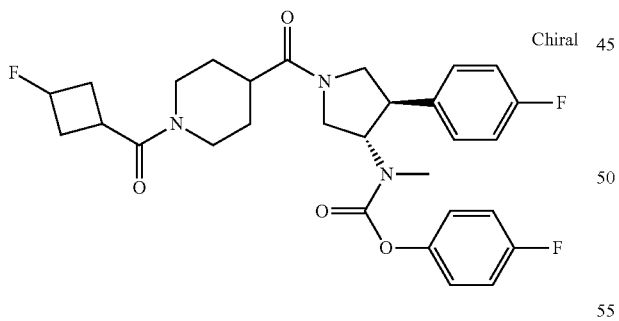

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 3-fluorocyclobutanecarboxylic acid. MS m/e: 544.4 [M+H]⁺.

EXAMPLE 288

[(3S,4R)-1-[1-(1-Cyano-cyclopropanecarbonyl)-piperidine-4-carbonyl]-4-(4-fluoro-phenyl)-pyrrolidin-3-yl]-methyl-carbamic acid 4-fluoro-phenyl ester

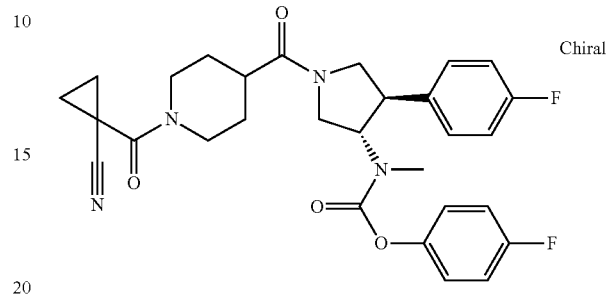

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 1-cyanocyclopropanecarboxylic acid. MS m/e: 537.3 [M+H]⁺.

EXAMPLE 289

{(3S,4R)-4-(4-Fluoro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester

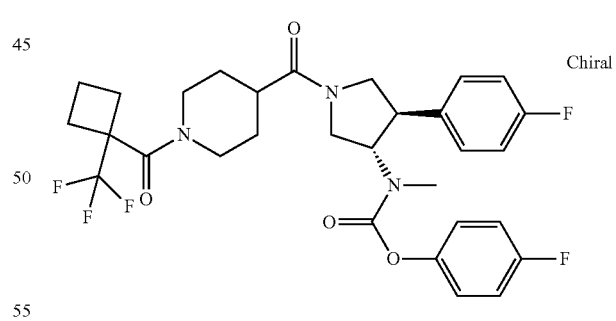

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 1-(trifluoromethyl)cyclobutanecarboxylic acid. MS m/e: 594.3 [M+H]+.

EXAMPLE 290

{(3S,4R)-4-(4-Fluoro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester

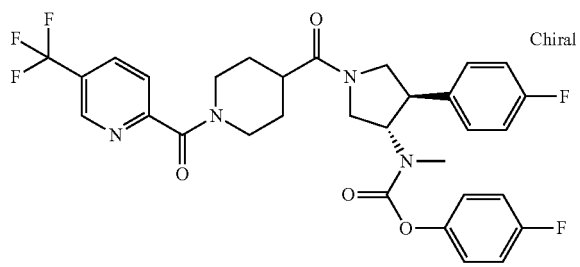 [SMILES: CN(C(=O)Oc1ccc(F)cc1)[C@@H]1CN(C(=O)C2CCN(C(=O)c3ccc(C(F)(F)F)cn3)CC2)C[C@H]1c1ccc(F)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 5-(trifluoromethyl)picolinic acid. MS m/e: 617.4 [M+H]$^+$.

EXAMPLE 291

{(3S,4R)-4-(4-Fluoro-phenyl)-1-[1-(6-oxo-piperidine-3-carbonyl)-piperidine-4-carbonyl]-pyrrolidin-3-yl}-methyl-carbamic acid 4-fluoro-phenyl ester

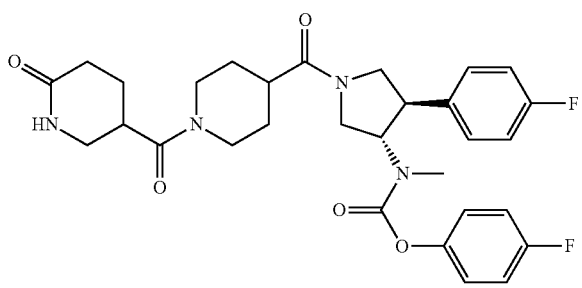 [SMILES: CN(C(=O)Oc1ccc(F)cc1)[C@@H]1CN(C(=O)C2CCN(C(=O)C3CCC(=O)NC3)CC2)C[C@H]1c1ccc(F)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(4-Fluoro-phenyl)-1-(piperidine-4-carbonyl)-pyrrolidin-3-yl]-methyl-carbamic acid 4-fluoro-phenyl ester and 6-oxopiperidine-3-carboxylic acid. MS m/e: 569.3 [M+H]$^+$.

EXAMPLE 292

{(3S,4R)-4-(3,4-Dichloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester

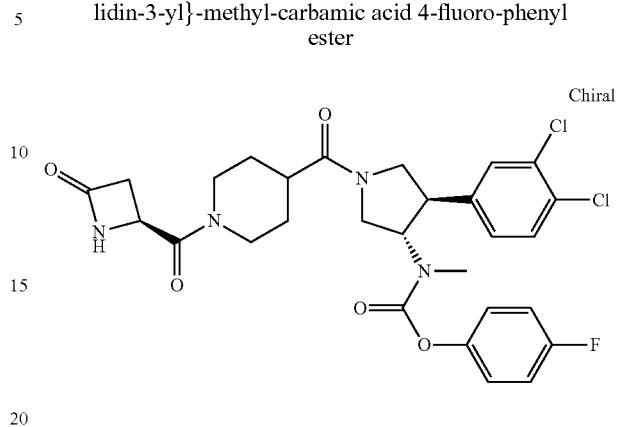

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester and (S)-4-oxoazetidine-2-carboxylic acid. MS m/e: 591.3 [M+H]$^+$.

EXAMPLE 293

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester

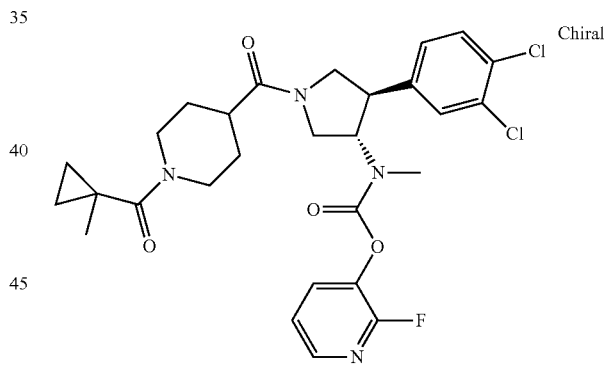

a) [(3S,4R)-1-Benzyl-4-(3,4-dichloro-phenyl)-pyrrolidin-3-yl]-methyl-carbamic acid tert-butyl ester

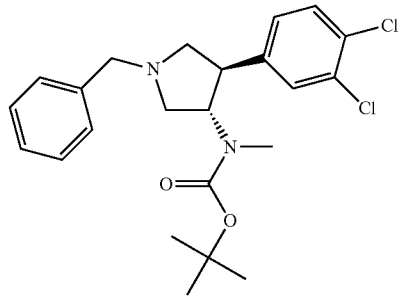 [SMILES: CN(C(=O)OC(C)(C)C)[C@@H]1CN(Cc2ccccc2)C[C@H]1c1ccc(Cl)c(Cl)c1]

A mixture of 5.96 g (17.8 mmol) (3S,4R)-1-benzyl-4-(3,4-dichlorophenyl)-N-methylpyrrolidin-3-amine (example 159, h), 4.27 g (19.6 mmol) di-tert.-butyloxy carbonyl and 21.7 mg (0.17 mmol) DMAP in THF was stirred at room temperature for 45 min and evaporated to dryness. The residue was subjected to column chromatography on silica eluting with a gradient formed from heptane and i-propanol to yield after evaporation of the product containing fractions 5.22 g (67%) of the title compound as yellow oil. MS m/e: 435.1 [M+H]+.

b) [(3R,4S)-3-(3,4-Dichloro-phenyl)-4-methylamino-pyrrolidin-1-yl]-[1-(1-methyl-cyclopropanecarbonyl)-piperidin-4-yl]-methanone

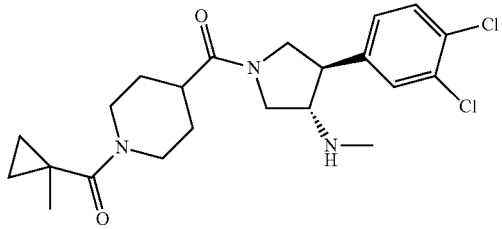 [SMILES: CN[C@@H]1CN(C(=O)C2CCN(C(=O)C3(C)CC3)CC2)C[C@H]1c1ccc(Cl)c(Cl)c1]

In analogy to the procedure described for the synthesis of rac-[(3R,4S)-4-(3,4-Dichloro-phenyl)-pyrrolidin-3-yl]-methyl-carbamic acid tert-butyl ester (example 1, e) the title compound was prepared from [(3S,4R)-1-Benzyl-4-(3,4-dichloro-phenyl)-pyrrolidin-3-yl]-methyl-carbamic acid tert-butyl ester through cleavage of the benzyl group. And, in analogy to the procedure described for the synthesis of rac-{(3R,4S)-4-(3,4-Dichloro-phenyl)-1-[1-(1-methyl-cyclo-propanecarbonyl)-piperidine-4-carbonyl]-pyrrolidin-3-yl}-methyl-carbamic acid tert-butyl ester (example 1, f) the Boc-protected title compound was prepared from the intermediately built [(3S,4R)-4-(3,4-Dichloro-phenyl)-pyrrolidin-3-yl]-methyl-carbamic acid tert-butyl ester and 1-(1-Methyl-cyclopropanecarbonyl)-piperidine-4-carboxylic acid. The title compound was subsequently isolated after acidic cleavage of the Boc group with TFA. MS m/e: 438.1 [M+H]+.

c) {(3S,4R)-4-(3,4-Dichloro-phenyl)-1-[1-(1-methyl-cyclopropanecarbonyl)-piperidine-4-carbonyl}-pyrrolidin-3-yl]-methyl-carbamic acid 2-fluoro-pyridin-3-yl ester A mixture of 50 mg (0.11 mmol) [(3R,4S)-3-(3,4-Dichloro-phenyl)-4-methylamino-pyrrolidin-1-yl]-[1-(1-methyl-cyclopropanecarbonyl)-piperidin-4-yl]-methanone, 16.2 mg (0.12 mmol) DIPEA and 11.8 mg (0.04 mmol) triphosgene in 5 mL THF at −78° C. was allowed to come to 0-5° C. during 2 h, concentrated under vacuum and dissolved in 1 mL DMF. A solution of 65.5 mg (0.57 mmol) 2-fluoropyridine-3-ol in 1 mL DMF was treated with 18.2 mg (0.45 mmol) NaH 55% in mineral oil and heated to 45° C. for 1 h. This solution was added to the activated amine in DMF and the mixture was shaken for 90 minutes at 80° C. The mixture was filtered and the filtrate was subjected to preparative HPLC on reversed phase eluting with a gradient formed from acetonitrile, water and NEt₃. The product containing fractions were evaporated to yield 42 mg (64%) of the title compound as off-white foam. MS m/e: 577.3 [M+H]+.

EXAMPLE 294

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-4-yl ester

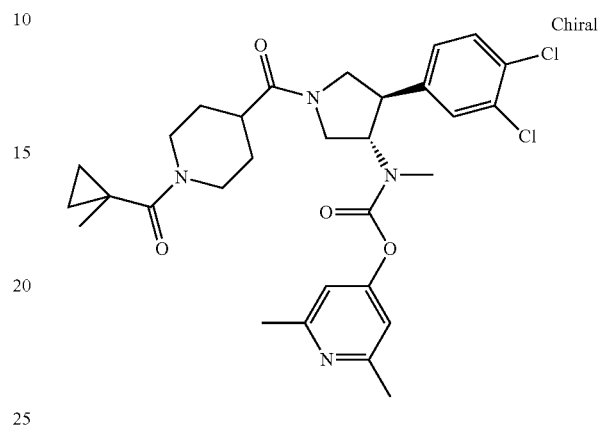

In analogy to the procedure described for the synthesis of {(3S,4R)-4-(3,4-Dichloro-phenyl)-1-[1-(1-methyl-cyclo-propanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 2,6-dimethylpyridin-4-ol. MS m/e: 587.2 [M+H]+.

EXAMPLE 295

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-3-yl ester

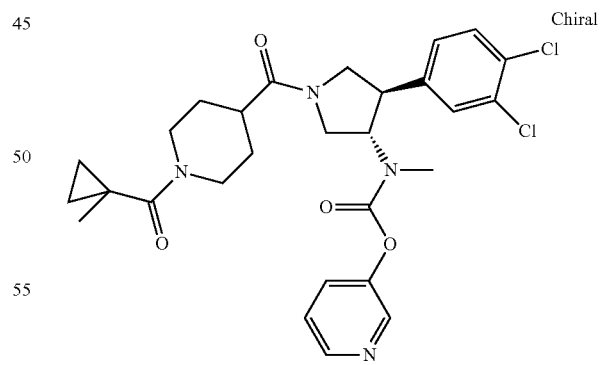

In analogy to the procedure described for the synthesis of {(3S,4R)-4-(3,4-Dichloro-phenyl)-1-[1-(1-methyl-cyclo-propanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and pyridin-3-ol. MS m/e: 559.3 [M+H]+.

EXAMPLE 296

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-methyl-pyridin-3-yl ester

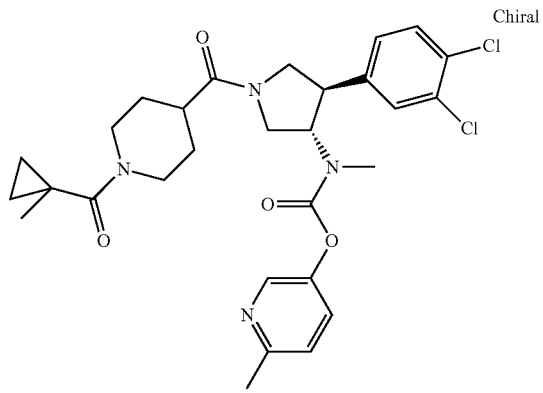 [SMILES: Cc1ccc(OC(=O)N(C)[C@@H]2CN(C(=O)C3CCN(C(=O)C4(C)CC4)CC3)C[C@H]2c2ccc(Cl)c(Cl)c2)cn1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 6-methylpyridin-3-ol. MS m/e: 573.2 $[M+H]^+$.

EXAMPLE 297

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-4-yl ester

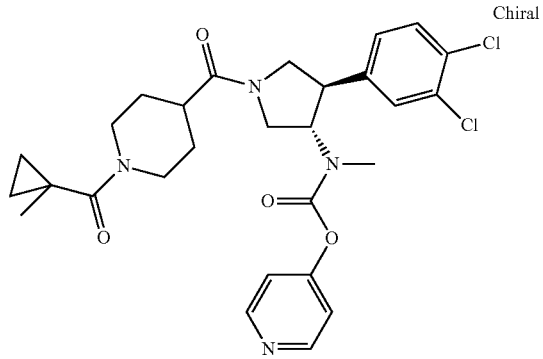 [SMILES: CN(C(=O)Oc1ccncc1)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and pyridin-4-ol. MS m/e: 559.3 $[M+H]^+$.

EXAMPLE 298

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-3-yl ester

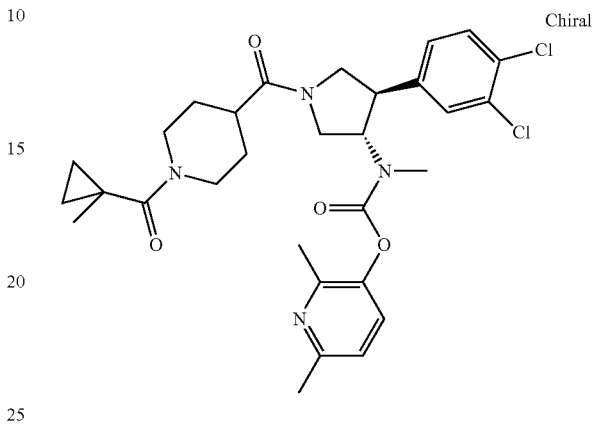

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 2,6-dimethylpyridin-3-ol. MS m/e: 587.2 $[M+H]^+$.

EXAMPLE 299

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 5-fluoro-pyridin-3-yl ester

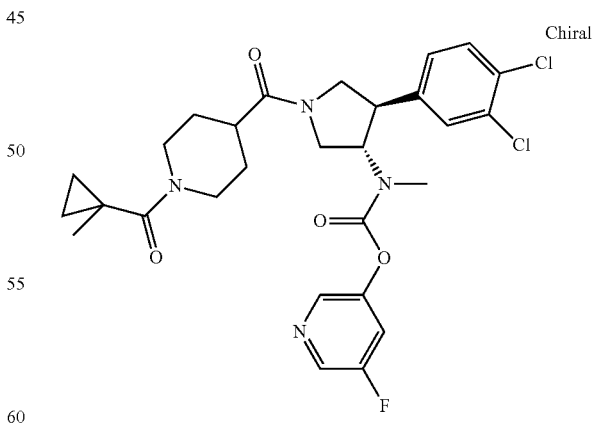

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1- methyl-cyclopropanecarbonyl)-piperidin-4-yl]-methanone, triphosgene and 5-fluoropyridin-3-ol. MS m/e: 577.3 [M+H]+.

EXAMPLE 300

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-2-yl ester

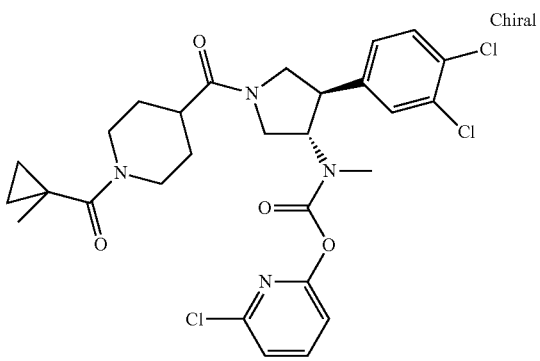 [SMILES: CN(C(=O)Oc1cccc(Cl)n1)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 6-chloropyridin-2-ol. MS m/e: 595.2 [M+H]+.

EXAMPLE 301

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-5-fluoro-pyridin-3-yl ester

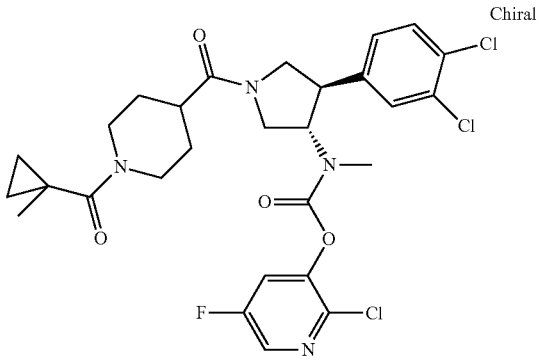 [SMILES: CN(C(=O)Oc1cc(F)cnc1Cl)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 2-chloro-5-fluoropyridin-3-ol. MS m/e: 613.1 [M+H]+.

EXAMPLE 302

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-pyridin-3-yl ester

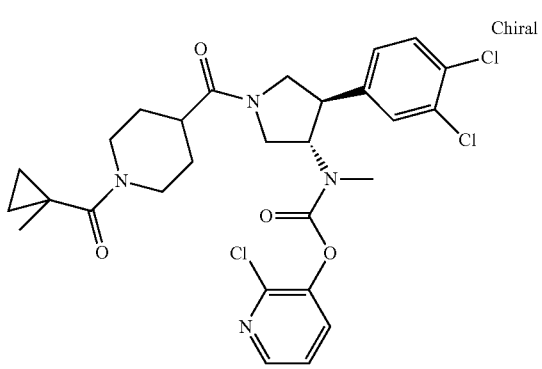 [SMILES: CN(C(=O)Oc1cccnc1Cl)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 2-chloropyridin-3-ol. MS m/e: 595.2 [M+H]+.

EXAMPLE 303

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester

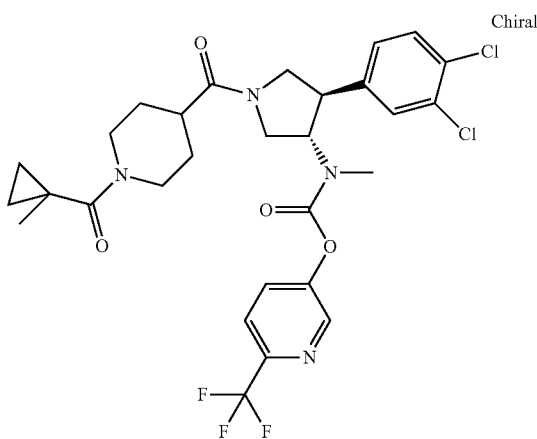 [SMILES: CN(C(=O)Oc1ccc(C(F)(F)F)nc1)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 6-(trifluoromethyl)pyridin-3-ol. MS m/e: 627.2 [M+H]⁺.

EXAMPLE 304

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-cyano-pyridin-3-yl ester

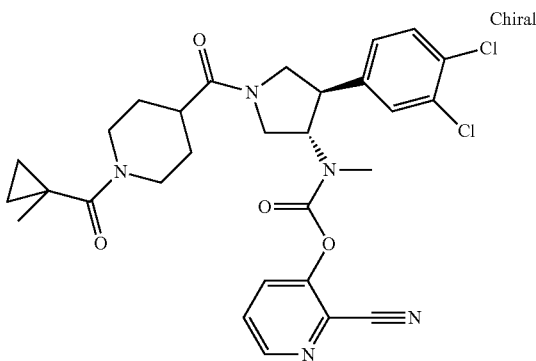 [SMILES: CN(C(=O)Oc1cccnc1C#N)[C@@H]1CN(C(=O)C2CCN(C(=O)C3(C)CC3)CC2)C[C@H]1c1ccc(Cl)c(Cl)c1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 3-hydroxypicolinonitrile. MS m/e: 584.2 [M+H]⁺.

EXAMPLE 305

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-6-methyl-pyridin-3-yl ester

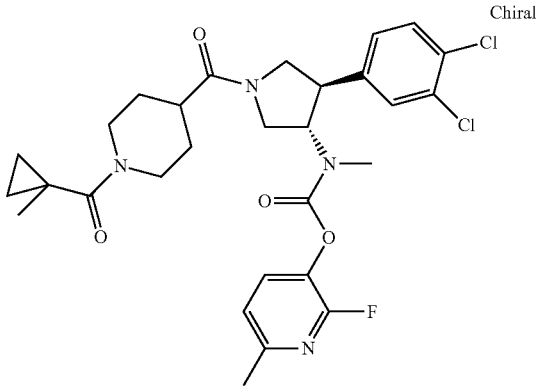 [SMILES: Cc1ccc(OC(=O)N(C)[C@@H]2CN(C(=O)C3CCN(C(=O)C4(C)CC4)CC3)C[C@H]2c2ccc(Cl)c(Cl)c2)c(F)n1]

In analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293) the title compound was prepared from [(3R,4S)-3-(3,4-Dichloro-phenyl)-4-methylamino-pyrrolidin-1-yl]-[1-(1-methyl-cyclopropanecarbonyl)-piperidin-4-yl]-methanone, triphosgene and 2-fluoro-6-methylpyridin-3-ol. MS m/e: 591.3 [M+H]⁺.

EXAMPLE 306

[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

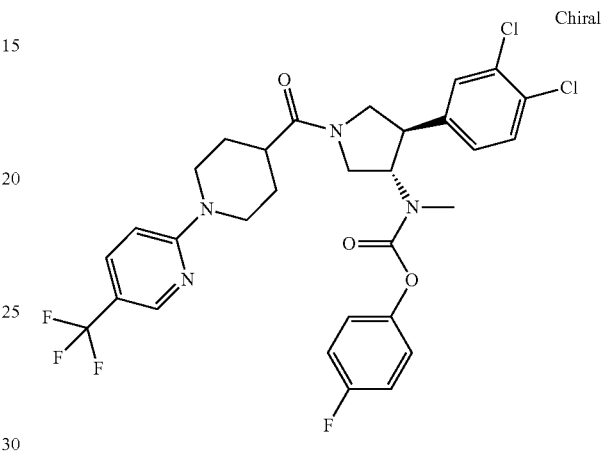

A mixture of 100 mg (0.2 mmol) [(3S,4R)-4-(3,4-Dichloro-phenyl)-1-(piperidine-4-carbonyl)-pyrrolidin-3-yl]-methyl-carbamic acid 4-fluoro-phenyl ester (example 265, c), 68 mg (0.3 mmol) 2-bromo-5-(trifluoromethyl)pyridine and 131 mg (1 mmol) DIPEA in 8 mL acetonitrile was heated to 80° C. for 18 h. The mixture was evaporated and the residue subjected to column chromatography on silica eluting with a gradient formed from ethyl acetate and heptane to yield after evaporation of the product containing fractions 70 mg (54%) of the title compounds as white foam. MS m/e: 639.1 [M+H]F.

EXAMPLE 307

[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester

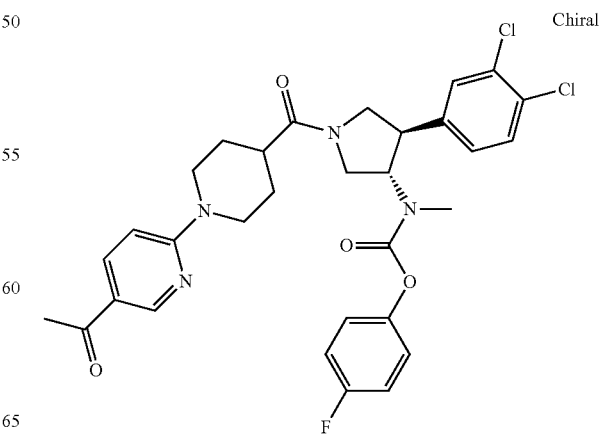

In analogy to the procedure described for the synthesis of [(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester (example 306) the title compound was prepared from [(3S,4R)-4-(3,4-Dichloro-phenyl)-1-(piperidine-4-carbonyl)-pyrrolidin-3-yl]-methyl-carbamic acid 4-fluoro-phenyl ester (example 265, c) and 1-(6-bromopyridin-3-yl)ethanone. MS m/e: 613.2 [M+H]F.

EXAMPLE 308

[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester

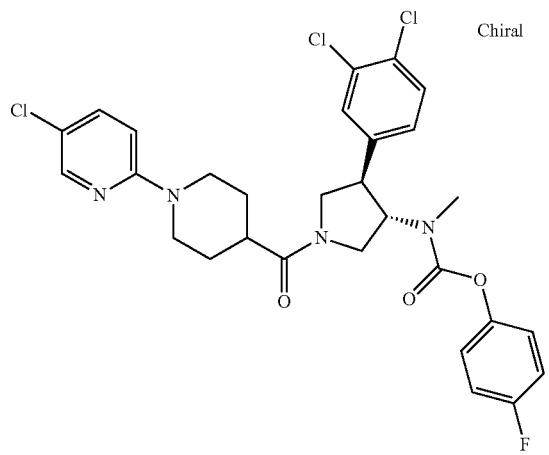 [SMILES: CN(C(=O)Oc1ccc(F)cc1)[C@@H]1CN(C(=O)C2CCN(c3ccc(Cl)cn3)CC2)C[C@H]1c1ccc(Cl)c(Cl)c1]

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Fluoro-phenyl)-pyrrolidin-3-yl]-methyl-carbamic acid 4-fluoro-phenyl ester and 1-(5-chloropyridin-2-yl)piperidine-4-carboxylic acid. MS m/e: 605.2 [M+H]+.

EXAMPLE 309

[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester

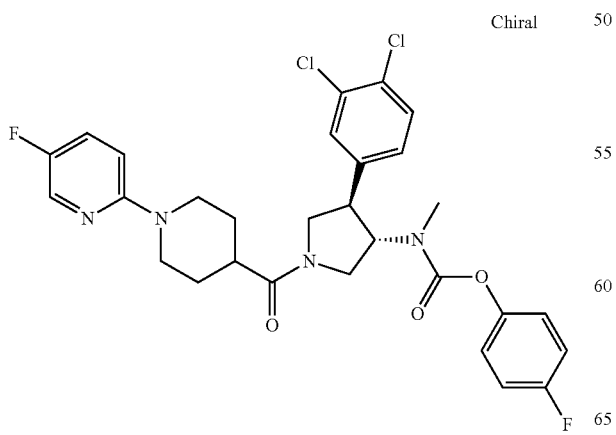

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Fluoro-phenyl)-pyrrolidin-3-yl]-methyl-carbamic acid 4-fluoro-phenyl ester and 5'-Fluoro-3,4,5,6-tetrahydro-2H-[1,2']bipyridinyl-4-carboxylic acid. MS m/e: 589.1 [M+H]+.

EXAMPLE 310

[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester

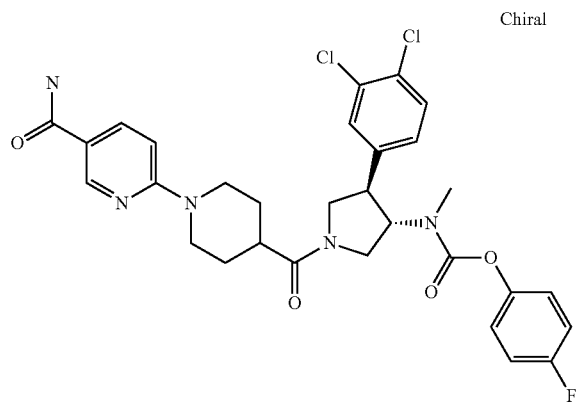 [SMILES: CN(C(=O)Oc1ccc(F)cc1)[C@@H]1CN(C(=O)C2CCN(c3ccc(C(N)=O)cn3)CC2)C[C@H]1c1ccc(Cl)c(Cl)c1]

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Fluoro-phenyl)-pyrrolidin-3-yl]-methyl-carbamic acid 4-fluoro-phenyl ester and 5'-Carbamoyl-3,4,5,6-tetrahydro-2H-[1,2']bipyridinyl-4-carboxylic acid. MS m/e: 614.1 [M+H]+.

EXAMPLE 311

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester

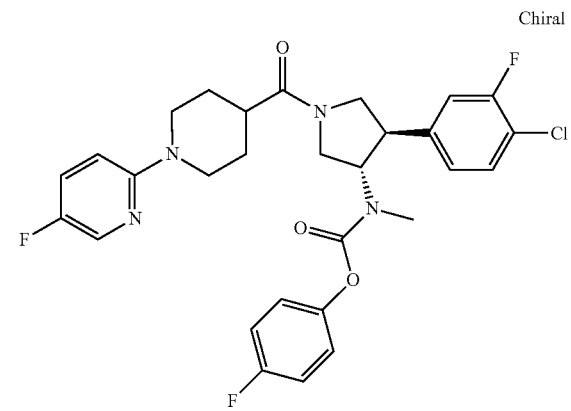 [SMILES: CN(C(=O)Oc1ccc(F)cc1)[C@@H]1CN(C(=O)C2CCN(c3ccc(F)cn3)CC2)C[C@H]1c1ccc(Cl)c(F)c1]

a) (3S,4R)-1-Benzyl-4-(4-chloro-3-fluoro-phenyl)-pyrrolidine-3-carboxylic acid methyl ester

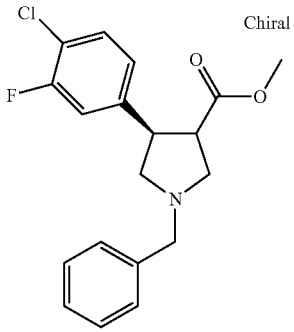 [SMILES: COC(=O)C1CN(Cc2ccccc2)C[C@H]1c1ccc(Cl)c(F)c1]

In analogy to the procedure described for the synthesis of (3S,4R)-1-Benzyl-4-(4-chloro-phenyl)-pyrrolidine-3-carboxylic acid methyl ester (example 89, e) the title compounds was prepared following steps a) through to e). MS m/e: 348.2 [M+H]$^+$.

b) (3S,4R)-1-Benzyl-4-(4-chloro-3-fluoro-phenyl)-pyrrolidine-3-carboxylic acid

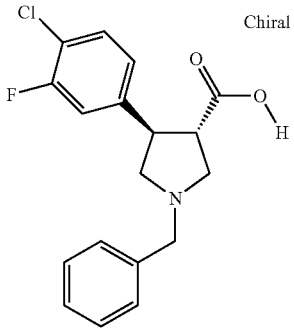 [SMILES: O=C(O)[C@@H]1CN(Cc2ccccc2)C[C@H]1c1ccc(Cl)c(F)c1]

A mixture of 19.5 g (56 mmol) (3S,4R)-1-Benzyl-4-(4-chloro-3-fluoro-phenyl)-pyrrolidine-3-carboxylic acid methyl ester and 14.1 g (337 mmol) LiOH.H$_2$O in water (100 mL) and methanol (10 mL) was heated to 80° C. for 45 min. The organic solvents were removed under vacuum and the aqueous phase acidified with 2N HCl tp pH=1-2. The precipitate was filtered off, washed with acetonitrile and dried to yield 15.1 g (73%) of the title compound as off-white solid. MS m/e: 334.1 [M+H]$^+$.

c) [(3S,4R)-1-Benzyl-4-(4-chloro-3-fluoro-phenyl)-pyrrolidin-3-yl]-carbamic acid tert-butyl ester

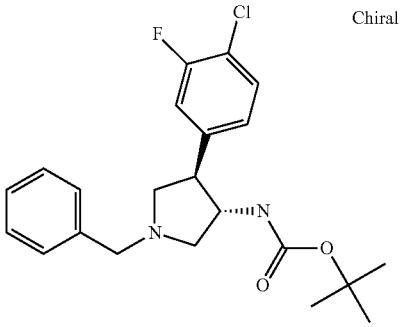 [SMILES: CC(C)(C)OC(=O)N[C@@H]1CN(Cc2ccccc2)C[C@H]1c1ccc(Cl)c(F)c1]

A mixture of 15.1 g (41 mmol) (3S,4R)-1-Benzyl-4-(4-chloro-3-fluoro-phenyl)-pyrrolidine-3-carboxylic acid and 11.6 g (90 mmol) DIPEA in 100 mL t-butanol was heated to 55° C. and 12.4 g (45 mmol) diphenylphosphoryl azide was added. The mixture was heated to 80° C. for 3 h and evaporated. The residue was subjected to column chromatography on silica eluting with a gradient formed from ethyl acetate and heptane to yield after evaporation of the product containing fractions 5.7 g (34%) of the title compound as off-white solid. MS m/e: 405.3 [M+H]$^+$.

d) [(3S,4R)-1-Benzyl-4-(4-chloro-3-fluoro-phenyl)-pyrrolidin-3-yl]-methyl-carbamic acid tert-butyl ester

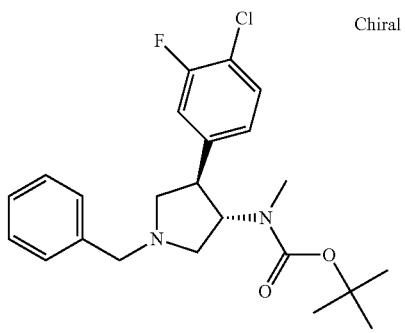 [SMILES: CN(C(=O)OC(C)(C)C)[C@@H]1CN(Cc2ccccc2)C[C@H]1c1ccc(Cl)c(F)c1]

A mixture of 5.7 g (14.1 mmol) [(3S,4R)-1-Benzyl-4-(4-chloro-3-fluoro-phenyl)-pyrrolidin-3-yl]-carbamic acid tert-butyl ester, 676 mg (17 mmol) NaH (55%) in DMF was stirred for 20 minutes at room temperature and 1 h at 60° C. 3 g (21 mmol) iodomethane in DMF was added and the mixture was stirred at 60° C. for 1 h and evaporated. The residue was taken up in ethyl acetate and water, the organic layer washed with brine and back-extracted with ethyl acetate. The combined organic layers were dried with Na$_2$SO$_4$, filtered off and evaporated. The residue was taken up on isolute and subjected to column chromatography on silica eluting with a gradient formed from ethyl acetate and heptane to yield after evaporation of the product containing fractions 2.67 g (45%) of the title compound as light yellow oil. MS m/e: 419.2 [M+H]$^+$.

e) [(3S,4R)-4-(4-Chloro-3-fluoro-phenyl)-pyrrolidin-3-yl]-methyl-carbamic acid 4-fluoro-phenyl ester

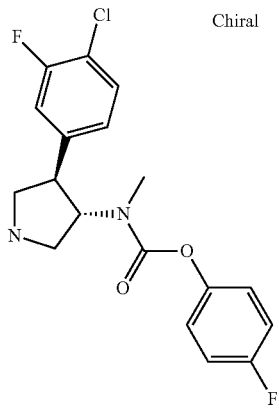 [SMILES: CN(C(=O)Oc1ccc(F)cc1)[C@@H]1CNC[C@H]1c1ccc(Cl)c(F)c1]

After acidic cleavage of the Boc-protecting group from [(3S,4R)-1-Benzyl-4-(4-chloro-3-fluoro-phenyl)-pyrrolidin-3-yl]-methyl-carbamic acid tert-butyl ester the intermediately built carbamate was prepared in analogy to the procedure described for the synthesis of {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester (example 293, c) with 4-fluorophenol. In analogy to the procedure described for the synthesis of rac-[(3R,4S)-4-(3,4-Dichloro-phenyl)-pyrrolidin-3-yl]-methyl-carbamic acid tert-butyl ester (example 1, e) the title compound was prepared from the intermediately built [(3S,4R)-1-Benzyl-4-(4-chloro-3-fluoro-phenyl)-pyrrolidin-3-yl]-methyl-carbamic acid 4-fluoro-phenyl ester through cleavage of the benzyl group. MS m/e: 367.0 [M+H]⁺.

f) [(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Chloro-3-fluoro-phenyl)-pyrrolidin-3-yl]-methyl-carbamic acid 4-fluoro-phenyl ester and 1-(5-fluoropyridin-2-yl)piperidine-4-carboxylic acid. MS m/e: 573.1 [M+H]⁺.

EXAMPLE 312

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester

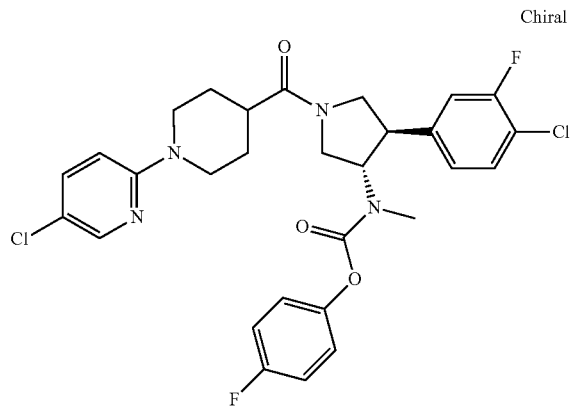 [SMILES: CN(C(=O)Oc1ccc(F)cc1)[C@@H]1CN(C(=O)C2CCN(c3ccc(Cl)cn3)CC2)C[C@H]1c1ccc(Cl)c(F)c1]

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Chloro-3-fluoro-phenyl)-pyrrolidin-3-yl]-methyl-carbamic acid 4-fluoro-phenyl ester and 1-(5-chloropyridin-2-yl)piperidine-4-carboxylic acid. MS m/e: 589.2 [M+H]⁺.

EXAMPLE 313

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

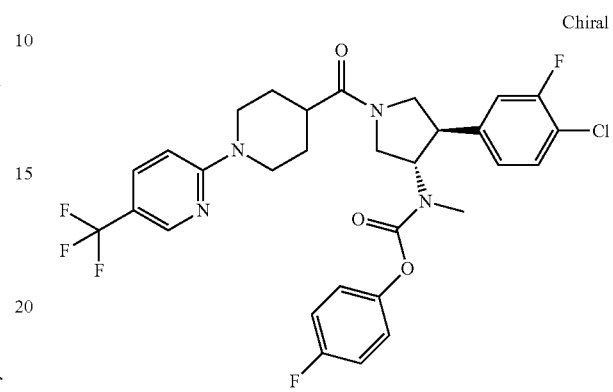

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Chloro-3-fluoro-phenyl)-pyrrolidin-3-yl]-methyl-carbamic acid 4-fluoro-phenyl ester and 1-(5-(trifluoromethyl)pyridin-2-yl)piperidine-4-carboxylic acid. MS m/e: 623.2 [M+H]⁺.

EXAMPLE 314

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-methyl-carbamic acid 4-fluoro-phenyl ester

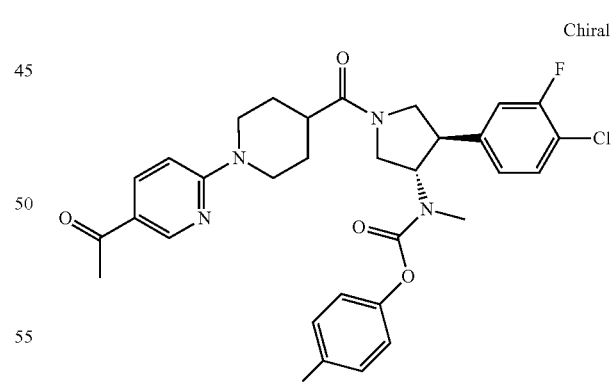

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Chloro-3-fluoro-phenyl)-pyrrolidin-3-yl]-methyl-carbamic acid 4-fluoro-phenyl ester and 1-(5-acetylpyridin-2-yl)piperidine-4-carboxylic acid. MS m/e: 597.2 [M+H]⁺.

EXAMPLE 315

[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester

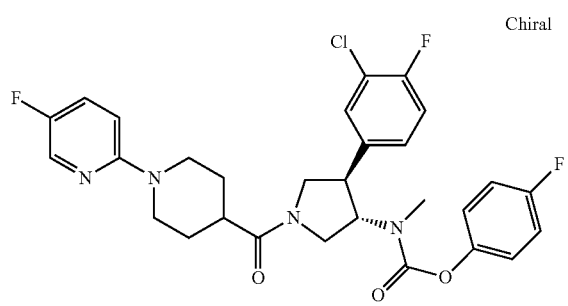 [SMILES: CN(C(=O)Oc1ccc(F)cc1)[C@@H]1CN(C(=O)C2CCN(c3ccc(F)cn3)CC2)C[C@H]1c1ccc(F)c(Cl)c1]

a) [(3S,4R)-4-(3-Chloro-4-fluoro-phenyl)-pyrrolidin-3-yl]-methyl-carbamic acid 4-fluoro-phenyl ester

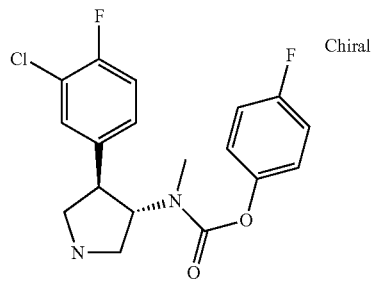 [SMILES: CN(C(=O)Oc1ccc(F)cc1)[C@@H]1CNC[C@H]1c1ccc(F)c(Cl)c1]

In analogy to the synthetic sequence described for [(3S,4R)-4-(4-Chloro-3-fluoro-phenyl)-pyrrolidin-3-yl]-methyl-carbamic acid 4-fluoro-phenyl ester (example 311, e) the title compound was prepared as an amorphous brown solid.

b) [(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(3-Chloro-4-fluoro-phenyl)-pyrrolidin-3-yl]-methyl-carbamic acid 4-fluoro-phenyl ester and 1-(5-fluoropyridin-2-yl)piperidine-4-carboxylic acid. MS m/e: 573.2 [M+H]$^+$.

EXAMPLE 316

[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester

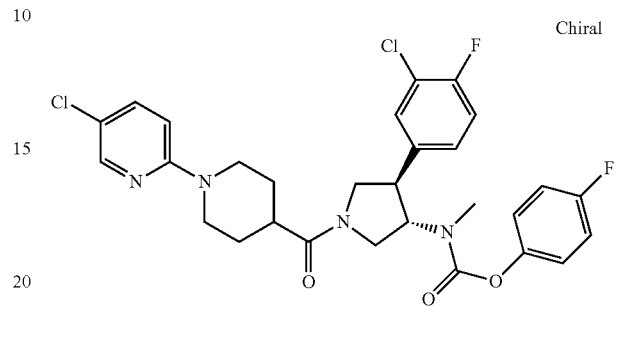

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(3-Chloro-4-fluoro-phenyl)-pyrrolidin-3-yl]-methyl-carbamic acid 4-fluoro-phenyl ester and 1-(5-chloropyridin-2-yl)piperidine-4-carboxylic acid. MS m/e: 589.2 [M+H]$^+$.

EXAMPLE 317

[(3S,4R)-4-(3-Chloro-4-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester

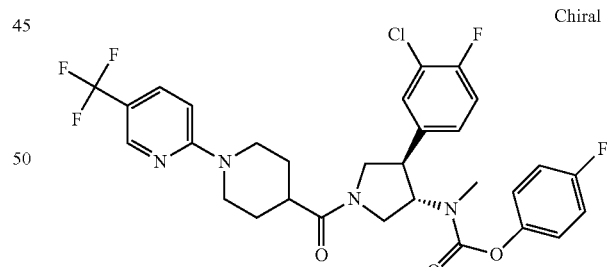

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(3-Chloro-4-fluoro-phenyl)-pyrrolidin-3-yl]-methyl-carbamic acid 4-fluoro-phenyl ester and 1-(5-(trifluoromethyl)pyridin-2-yl)piperidine-4-carboxylic acid. MS m/e: 623.3 [M+H]$^+$.

EXAMPLE 318

[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-methyl-carbamic acid 4-fluoro-phenyl ester

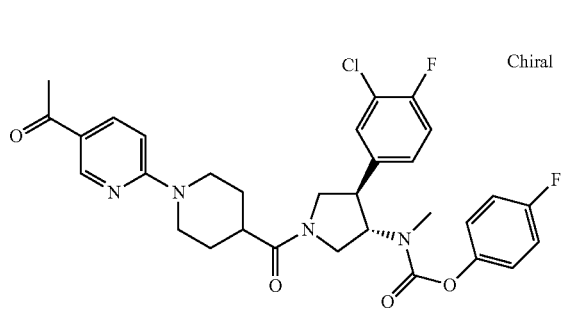 [SMILES: CC(=O)c1ccc(N2CCC(C(=O)N3C[C@@H](N(C)C(=O)Oc4ccc(F)cc4)[C@H](c4ccc(F)c(Cl)c4)C3)CC2)nc1]

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(3-Chloro-4-fluoro-phenyl)-pyrrolidin-3-yl]-methyl-carbamic acid 4-fluoro-phenyl ester and 1-(5-acetylpyridin-2-yl)piperidine-4-carboxylic acid. MS m/e: 597.3 [M+H]+.

EXAMPLE 319

{(3S,4R)-4-(4-Chloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester

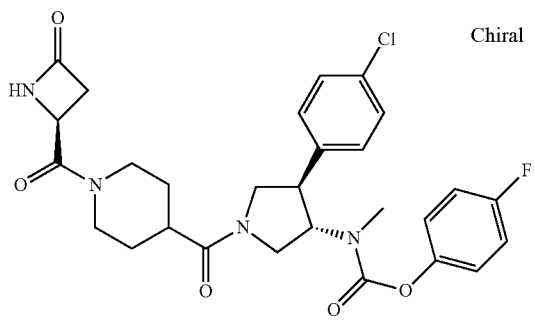 [SMILES: CN(C(=O)Oc1ccc(F)cc1)[C@@H]1CN(C(=O)C2CCN(C(=O)[C@@H]3CC(=O)N3)CC2)C[C@H]1c1ccc(Cl)cc1]

In analogy to the procedure described for the synthesis of [(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester (example 247) the title compound was prepared from 4-fluorophenyl (3S,4R)-4-(4-chlorophenyl)-1-(piperidine-4-carbonyl)pyrrolidin-3-yl(methyl)carbamate and (S)-4-oxoazetidine-2-carboxylic acid. MS m/e: 557.0 [M+H]+.

EXAMPLE 320

[(3S,4R)-4-(4-Chloro-phenyl)-1-(5'-hydroxy-3,4,5,6-tetrahydro-2H-[1,2']bipyridinyl-4-carbonyl)-pyrrolidin-3-yl]-methyl-carbamic acid 4-fluoro-phenyl ester

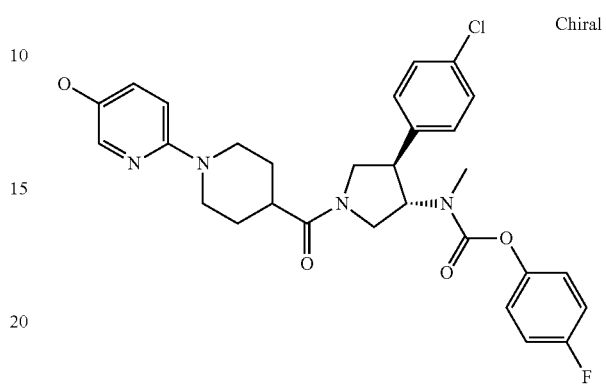

In analogy to the procedure described for the synthesis of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester (example 1, f) the title compound was prepared from [(3S,4R)-4-(4-Chloro-phenyl)-pyrrolidin-3-yl]-methyl-carbamic acid 4-fluoro-phenyl ester and 1-(5-hydroxypyridin-2-yl)piperidine-4-carboxylic acid. MS m/e: 553.2 [M+H]F.

EXAMPLE 321

Acetic acid 4-{(3R,4S)-3-(4-chloro-phenyl)-4-[(4-fluoro-phenoxycarbonyl)-methyl-amino]-pyrrolidine-1-carbonyl}-3,4,5,6-tetrahydro-2H-[1,2']bipyridinyl-5'-yl ester

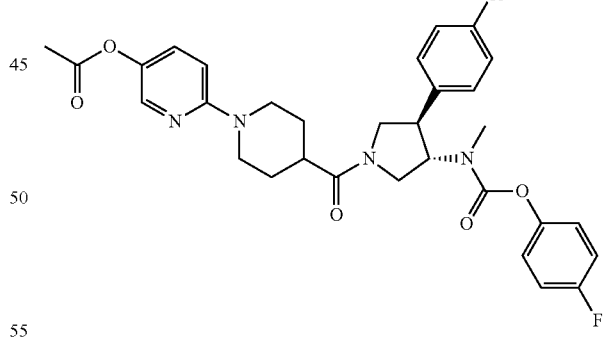

A mixture of [(3S,4R)-4-(4-Chloro-phenyl)-1-(5'-hydroxy-3,4,5,6-tetrahydro-2H-[1,2']bipyridinyl-4-carbonyl)-pyrrolidin-3-yl]-methyl-carbamic acid 4-fluoro-phenyl ester (example 320, crude) was treated with acetyl chloride and the mixture was purified by preparative HPLC on reversed phase eluting with a gradient formed from acetonitrile, water and NEt$_3$ to yield after evaporation of the product containing fractions the title compound as light yellow solid. MS m/e: 595.4 [M+H]+.

As mentioned earlier, the compounds of formula I and their pharmaceutically usable addition salts possess valuable pharmacological properties. Compounds of the present invention are antagonists of neurokinin 3 (NK-3) receptors. The compounds were investigated in accordance with the tests given hereinafter.

EXPERIMENTAL PROCEDURE

The compounds were investigated in accordance with the tests given hereinafter [$^3$H]SR142801 competition binding assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S.A., Ziirich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). $IC_{50}$ values were derived from the inhibition curve and the affinity constant (IQ values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

Results for some representative compounds with a hNK-3 receptor affinity <0.10 µM are shown in the following table 1.

TABLE 1

| Example | Data $K_i$ [µM] |
|---|---|
| 2 | 0.0004 |
| 4 | 0.0018 |
| 5 | 0.0562 |
| 6 | 0.0005 |
| 7 | 0.0096 |
| 8 | 0.004 |
| 9 | 0.0136 |
| 10 | 0.0015 |
| 11 | 0.0271 |
| 12 | 0.0006 |
| 13 | 0.002 |
| 14 | 0.0012 |
| 15 | 0.0025 |
| 17 | 0.0007 |
| 19 | 0.0002 |
| 20 | 0.0724 |
| 21 | 0.0104 |
| 22 | 0.0169 |

TABLE 1-continued

| Example | Data $K_i$ [µM] |
|---|---|
| 24 | 0.0335 |
| 25 | 0.0054 |
| 26 | 0.0029 |
| 27 | 0.0307 |
| 28 | 0.0034 |
| 29 | 0.0149 |
| 30 | 0.0103 |
| 31 | 0.0116 |
| 32 | 0.0014 |
| 34 | 0.0028 |
| 35 | 0.0811 |
| 36 | 0.033 |
| 37 | 0.0007 |
| 38 | 0.042 |
| 39 | 0.011 |
| 40 | 0.0042 |
| 42 | 0.0008 |
| 43 | 0.0034 |
| 44 | 0.0029 |
| 45 | 0.0032 |
| 47 | 0.0034 |
| 48 | 0.0294 |
| 49 | 0.0035 |
| 51 | 0.0018 |
| 52 | 0.0081 |
| 53 | 0.0047 |
| 54 | 0.0264 |
| 55 | 0.0861 |
| 56 | 0.0613 |
| 57 | 0.0076 |
| 60 | 0.0017 |
| 62 | 0.0314 |
| 64 | 0.0152 |
| 65 | 0.0007 |
| 66 | 0.0008 |
| 67 | 0.0004 |
| 68 | 0.0626 |
| 69 | 0.0076 |
| 70 | 0.0013 |
| 71 | 0.0018 |
| 72 | 0.0212 |
| 73 | 0.0008 |
| 74 | 0.0008 |
| 75 | 0.0006 |
| 76 | 0.0007 |
| 77 | 0.0015 |
| 78 | 0.0015 |
| 79 | 0.0004 |
| 80 | 0.0003 |
| 81 | 0.067 |
| 82 | 0.0014 |
| 83 | 0.0042 |
| 84 | 0.0183 |
| 85 | 0.0092 |
| 86 | 0.0604 |
| 87 | 0.0092 |
| 88 | 0.0083 |
| 89 | 0.0202 |
| 90 | 0.0079 |
| 91 | 0.0044 |
| 92 | 0.0023 |
| 93 | 0.0066 |
| 94 | 0.0002 |
| 95 | 0.0058 |
| 96 | 0.0537 |
| 97 | 0.031 |
| 98 | 0.048 |
| 99 | 0.0016 |
| 100 | 0.0122 |
| 102 | 0.004 |
| 103 | 0.0018 |
| 104 | 0.0074 |
| 105 | 0.0705 |
| 106 | 0.001 |
| 107 | 0.0586 |
| 108 | 0.0007 |
| 109 | 0.0002 |
| 110 | 0.0003 |

TABLE 1-continued

| Example | Data K$_i$ [μM] |
|---|---|
| 111 | 0.0044 |
| 112 | 0.0037 |
| 113 | 0.0003 |
| 114 | 0.083 |
| 115 | 0.0013 |
| 116 | 0.01 |
| 117 | 0.0174 |
| 118 | 0.0003 |
| 120 | 0.0016 |
| 121 | 0.0066 |
| 122 | 0.019 |
| 123 | 0.0028 |
| 124 | 0.0402 |
| 125 | 0.0509 |
| 126 | 0.0012 |
| 127 | 0.004 |
| 128 | 0.068 |
| 129 | 0.0137 |
| 131 | 0.001 |
| 132 | 0.0556 |
| 133 | 0.003 |
| 134 | 0.0036 |
| 135 | 0.0403 |
| 138 | 0.0371 |
| 139 | 0.0039 |
| 140 | 0.0009 |
| 141 | 0.0135 |
| 143 | 0.0032 |
| 144 | 0.0211 |
| 145 | 0.0569 |
| 146 | 0.0068 |
| 147 | 0.0737 |
| 149 | 0.0908 |
| 150 | 0.0156 |
| 151 | 0.0182 |
| 152 | 0.0147 |
| 153 | 0.0192 |
| 156 | 0.0183 |
| 157 | 0.0271 |
| 158 | 0.0125 |
| 159 | 0.0004 |
| 160 | 0.0005 |
| 161 | 0.0074 |
| 164 | 0.0814 |
| 166 | 0.0364 |
| 167 | 0.0049 |
| 168 | 0.0984 |
| 169 | 0.0041 |
| 170 | 0.0083 |
| 171 | 0.0095 |
| 172 | 0.0041 |
| 173 | 0.047 |
| 175 | 0.036 |
| 176 | 0.0046 |
| 177 | 0.0189 |
| 179 | 0.0566 |
| 180 | 0.0007 |
| 181 | 0.0028 |
| 182 | 0.002 |
| 183 | 0.016 |
| 184 | 0.0067 |
| 185 | 0.003 |
| 186 | 0.006 |
| 187 | 0.0026 |
| 188 | 0.0146 |
| 189 | 0.0035 |
| 190 | 0.0172 |
| 191 | 0.0012 |
| 192 | 0.0036 |
| 193 | 0.0011 |
| 194 | 0.0035 |
| 195 | 0.0014 |
| 196 | 0.0022 |
| 197 | 0.0026 |
| 198 | 0.0005 |
| 199 | 0.0009 |
| 200 | 0.0072 |
| 201 | 0.0033 |

TABLE 1-continued

| Example | Data K$_i$ [μM] |
|---|---|
| 202 | 0.0043 |
| 203 | 0.0003 |
| 204 | 0.0412 |
| 205 | 0.0057 |
| 206 | 0.0906 |
| 207 | 0.0006 |
| 208 | 0.0004 |
| 209 | 0.0008 |
| 210 | 0.0046 |
| 211 | 0.0024 |
| 212 | 0.0014 |
| 213 | 0.0072 |
| 214 | 0.0942 |
| 215 | 0.0084 |
| 216 | 0.0536 |
| 217 | 0.0077 |
| 218 | 0.0195 |
| 219 | 0.0036 |
| 220 | 0.0428 |
| 221 | 0.001 |
| 224 | 0.0228 |
| 225 | 0.0112 |
| 226 | 0.0792 |
| 228 | 0.0008 |
| 229 | 0.0168 |
| 230 | 0.0027 |
| 231 | 0.0057 |
| 232 | 0.0218 |
| 233 | 0.006 |
| 234 | 0.0794 |
| 236 | 0.0648 |
| 237 | 0.0004 |
| 238 | 0.048 |
| 239 | 0.0616 |
| 240 | 0.0228 |
| 242 | 0.0027 |
| 243 | 0.0472 |
| 244 | 0.0209 |
| 245 | 0.0011 |
| 246 | 0.0023 |
| 247 | 0.0009 |
| 248 | 0.0028 |
| 249 | 0.0019 |
| 250 | 0.0014 |
| 251 | 0.0022 |
| 252 | 0.0027 |
| 253 | 0.0018 |
| 254 | 0.002 |
| 255 | 0.0025 |
| 256 | 0.0026 |
| 257 | 0.0022 |
| 258 | 0.0029 |
| 259 | 0.0038 |
| 260 | 0.0015 |
| 261 | 0.0189 |
| 262 | 0.0039 |
| 263 | 0.0151 |
| 264 | 0.0088 |
| 265 | 0.0006 |
| 266 | 0.0005 |
| 267 | 0.0007 |
| 268 | 0.0006 |
| 269 | 0.0005 |
| 270 | 0.0006 |
| 271 | 0.0001 |
| 272 | 0.0008 |
| 273 | 0.0004 |
| 274 | 0.0009 |
| 275 | 0.0009 |
| 276 | 0.001 |
| 277 | 0.0005 |
| 278 | 0.0006 |
| 279 | 0.002 |
| 280 | 0.0008 |
| 281 | 0.0003 |
| 282 | 0.002 |
| 283 | 0.0007 |
| 284 | 0.0311 |

TABLE 1-continued

| Example | Data $K_i$ [μM] |
|---|---|
| 285 | 0.0191 |
| 286 | 0.0254 |
| 287 | 0.0072 |
| 288 | 0.0266 |
| 289 | 0.011 |
| 290 | 0.0998 |
| 291 | 0.1445 |
| 292 | 0.00004 |
| 293 | 0.0758 |
| 294 | 0.0112 |
| 295 | 0.0449 |
| 296 | 0.0084 |
| 297 | 0.0059 |
| 298 | 0.038 |
| 299 | 0.0228 |
| 300 | 0.0026 |
| 301 | 0.0215 |
| 302 | 0.0187 |
| 303 | 0.0026 |
| 304 | 0.2108 |
| 305 | 0.0055 |
| 306 | 0.0007 |
| 308 | 0.0002 |
| 309 | 0.0005 |
| 310 | 0.0006 |
| 311 | 0.0009 |
| 312 | 0.0004 |
| 313 | 0.0009 |
| 314 | 0.0006 |
| 315 | 0.0017 |
| 316 | 0.0009 |
| 317 | 0.0016 |
| 318 | 0.0007 |
| 319 | 0.0106 |
| 320 | 0.0067 |
| 321 | 0.0024 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

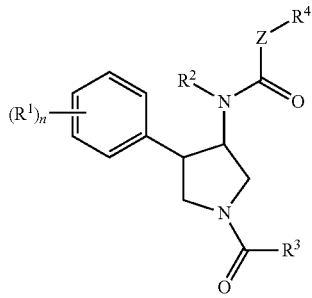

wherein
R¹ is hydrogen, halogen, cyano, lower alkyl or lower alkyl substituted by halogen;
n is 1, 2 or 3, wherein when n is 2 or 3, each R¹ is the same or different;
R² is hydrogen or methyl;
R³ is $(CH_2)_r$—$C(O)NH_2$ or $(CH_2)_r$—CN, wherein r is 1 or 2, or
is a non aromatic heterocyclic group

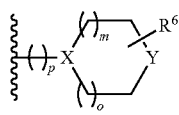

wherein
X is N or CH;
Y is —C(R)(R⁷)—; —N(R⁷')—, —S(O)₂ or O;
R⁶ is hydrogen, di-lower alkyl or =O;
o and m are each independently 0, 1 or 2;
p is 0, 1 or 2;
R is hydrogen, halogen, or lower alkyl;
R⁷ is hydrogen, halogen, hydroxy, lower alkyl substituted by hydroxy, cyano, or lower alkoxy;
R⁷' is hydrogen, —C(O)-lower alkyl, —C(O)O-lower alkyl, —C(O)CH₂O-lower alkyl, —C(O)CH₂CN, or is
—C(O)-cycloalkyl, cycloalkyl or —CH₂-cycloalkyl,
wherein the cycloalkyl groups are optionally substituted by halogen, lower alkoxy, lower alkyl substituted by halogen, cyano, —CH₂O-lower alkyl, or lower alkyl, or is
—C(O)-heterocycloalkyl, heterocycloalkyl, —C(O)-heteroaryl or heteroaryl,
which heterocycloalkyl or heteroaryl groups are optionally substituted by halogen, lower alkyl, =O, lower alkoxy, lower alkyl substituted by halogen, C(O)NH-lower alkyl, C(O)NH₂,C(O)-lower alkyl, S(O)₂— lower alkyl or cyano;
Z is —O—
R⁴ is
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q$CN, bicyclo[2.2.1]heptanyl,
$(CH_2)_q$-cycloalkyl optionally substituted by lower alkyl, lower alkyl substituted by halogen, lower alkoxy or by halogen, or is $(CH_2)_q$-heterocycloalkyl, $(CH_2)_q$-aryl, CH(lower alkyl)-aryl, CH(cycloalkyl)-aryl, or $(CH_2)_q$-heteroaryl,
which heterocycloalkyl, aryl or heteroaryl rings are optionally substituted by halogen, hydroxy, lower alkyl, lower alkyl substituted by halogen, S(O)₂-lower alkyl, cyano or by lower alkoxy;
q is 0, 1 or 2;
or a pharmaceutically active salt thereof.
2. The compound of claim 1 having formula Ia,

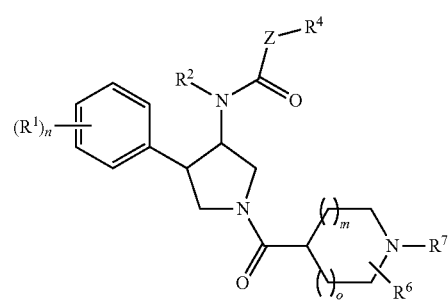

wherein
R¹ is hydrogen, halogen, cyano, lower alkyl or lower alkyl substituted by halogen;
n is 1, 2 or 3, wherein when n is 2 or 3, each R¹ is the same or different;
R² is hydrogen or methyl;
R⁶ is hydrogen, di-lower alkyl or =O;
o and m are each independently 0, 1 or 2;
R⁷' is hydrogen, —C(O)-lower alkyl, —C(O)O-lower alkyl, —C(O)CH₂O-lower alkyl, —C(O)CH₂CN, or is
—C(O)-cycloalkyl, cycloalkyl or —CH₂-cycloalkyl,
wherein the cycloalkyl groups are optionally substituted by halogen, lower alkoxy, lower alkyl substituted by halogen, cyano, —CH₂O-lower alkyl, or lower alkyl, or is
—C(O)-heterocycloalkyl, heterocycloalkyl, —C(O)-heteroaryl, or heteroaryl,
which heterocycloalkyl or heteroaryl groups are optionally substituted by halogen, lower alkyl, =O, lower alkoxy, lower alkyl substituted by halogen, C(O)NH-lower alkyl, C(O)NH₂,C(O)-lower alkyl, S(O)₂— lower alkyl or cyano;
Z is —O—
R⁴ is
lower alkyl substituted by halogen,
lower alkyl substituted by hydroxy,
lower alkyl substituted by cycloalkyl,
$(CH_2)_s$—O-lower alkyl, wherein s is 2 or 3,
$CH(CH_3)CH_2$—O-lower alkyl,
$(CH_2)_q$CN, bicyclo[2.2.1]heptanyl,
$(CH_2)_q$-cycloalkyl optionally substituted by lower alkyl, lower alkyl substituted by halogen, lower alkoxy or by halogen, or is
$(CH_2)_q$-heterocycloalkyl, $(CH_2)_q$-aryl, CH(lower alkyl)-aryl, CH(cycloalkyl)-aryl, or $(CH_2)_q$-heteroaryl,
which heterocycloalkyl, aryl or heteroaryl rings are optionally substituted by halogen, hydroxy, lower alkyl, lower alkyl substituted by halogen, S(O)₂-lower alkyl, cyano or by lower alkoxy;
q is 0, 1 or 2;
or a pharmaceutically active salt thereof.
3. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentyl ester;

rac-[(3R,4S)-1-(1-Cyclopropylmethyl-piperidine-4-carbonyl)-4-(3,4-dichloro-phenyl)-pyrrolidin-3-yl]-methyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-[(3R,4S)-1-(1-Cyclopropylmethyl-piperidine-4-carbonyl)-4-(3,4-dichloro-phenyl)-pyrrolidin-3-yl]-methyl-carbamic acid phenyl ester;

rac-[(3R,4S)-1-(1-Cyclopropylmethyl-piperidine-4-carbonyl)-4-(3,4-dichloro-phenyl)-pyrrolidin-3-yl]-methyl-carbamic acid p-tolyl ester;

rac-[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester; and rac-[(3R,4S)-1-(1-Cyclopropylmethyl-piperidine-4-carbonyl)-4-(3,4-dichloro-phenyl)-pyrrolidin-3-yl]-methyl-carbamic acid 4-chloro-phenyl ester.

4. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chloro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-methoxyphenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid p-tolyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-chlorophenyl ester; and

[(3R,4S)-1-(1-Cyclopropylmethyl-piperidine-4-carbonyl)-4-(3,4-dichloro-phenyl)-pyrrolidin-3-yl]-methyl-carbamic acid 4-methoxy-phenyl ester.

5. The compound of claim 2, selected from the group consisting of

[(3S,4R)-1-(1-Cyclopropylmethyl-piperidine-4-carbonyl)-4-(3,4-dichloro-phenyl)-pyrrolidin-3-yl]-methyl-carbamic acid 4-methoxy-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid prop-2-ynyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopropylmethyl ester;

rac-{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester; and rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,3-trifluoro-propyl ester.

6. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid tetrahydro-pyran-4-yl-methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid cyclopentylmethyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-methyl-oxetan-3-yl-methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester;

{(3R,4S)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

{(3S,4R)-4-(3,4-Dichloro-phenyl)-1-[1-(1-methyl-cyclopropanecarbonyl)-piperidine-4-arbonyl]-pyrrolidin-3-yl}-methyl-carbamic acid 2-cyclopropyl-ethyl ester;

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester; and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-3-yl ester.

7. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-carbamic acid 4-fluoro-phenyl ester;

rac-{(3R,4S)-4-(4-Chloro-phenyl)-1-[1-(1-methyl-cyclopropane carbonyl)-piperidine-4-carbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4-methyl-cyclohexyl ester;

{(3R,4R)-4-(3,4-Dichloro-phenyl)-1-[1-(1-methyl-cyclopropane carbonyl)-piperidine-4-carbonyl]-pyrrolidin-3-yl}-methyl-carbamic acid 4-fluoro-phenyl ester;

{(3S,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester;

rac-{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 2-cyclopropyl-ethyl ester;

rac-[(3R,4S)-1-(1-Acetyl-piperidine-4-carbonyl)-4-(3,4-dichloro-phenyl)-pyrrolidin-3-yl]-methyl-carbamic acid 4-fluoro-phenyl ester; and rac-4-{(3S,4R)-3-(3,4-Dichloro-phenyl)-4-[(4-fluoro-phenoxycarbonyl)-methyl-amino]-pyrrolidine-1-carbonyl}-piperidine-1-carboxylic acid tert-butyl ester.

8. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2S,4S)-bicyclo[2.2.1]hept-2-yl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid (1R,2R,4S)-bicyclo[2.2.1]hept-2-yl ester;

rac-{(3R,4S)-4-(3-Chloro-4-methyl-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-{(3R,4S)-4-(4-Chloro-3-methyl-phenyl)-1-[1-(1-methyl-cyclopropanecarbonyl)-piperidine-4-carbonyl]-pyrrolidin-3-yl}-methyl-carbamic acid 4-fluoro-phenyl ester;

rac-[(3R,4S)-4-(3,4-Dichloro-phenyl)-1-(piperidine-4-carbonyl)-pyrrolidin-3-yl]-methyl-carbamic acid 4-fluoro-phenyl ester;

rac-[(3R,4S)-4-(3,4-Dichloro-phenyl)-1-(1-propionyl-piperidine-4-carbonyl)-pyrrolidin-3-yl]-methyl-carbamic acid 4-fluoro-phenyl ester; and rac-[(3R,4S)-1-(1-Cyclopropanecarbonyl-piperidine-4-carbonyl)-4-(3,4-dichloro-phenyl)-pyrrolidin-3-yl]-methyl-carbamic acid 4-fluoro-phenyl ester.

9. The compound of claim 2, selected from the group consisting of rac-{(3R,4S)-4-(3,4-Dichloro-phenyl)-1-[1-(2-methoxy-acetyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(tetrahydro-pyran-4-carbonyl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(tetrahydro-pyran-4-yl)-piperidine-4-carbonyl]-pyrrolidin-3-yl}-methyl-carbamic acid 4-fluoro-phenyl ester;

rac-[(3R,4S)-4-(3,4-Dichloro-phenyl)-1-(1-[1,3,4]thiadiazol-2-yl-piperidine-4-carbonyl)-pyrrolidin-3-yl]-methyl-carbamic acid 4-fluoro-phenyl ester;

rac-[(3R,4S)-1-[1-(6-Chloro-pyridazin-3-yl)-piperidine-4-carbonyl]-4-(3,4-dichloro-phenyl)-pyrrolidin-3-yl]-methyl-carbamic acid 4-fluoro-phenyl ester;

rac-[(3R,4S)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3,4,4,4-pentafluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-2-yl)methyl ester;

and rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-2-yl)methyl ester.

10. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (S)-1-(tetrahydro-furan-3-yl)methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid (R)-1-(tetrahydro-furan-3-yl)methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carb amic acid 3,3,3-trifluoro-propyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carb amic acid 3,3,3-trifluoro-propyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4,5,5,5-pentafluoro-pentyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropyl-methyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 2-methyl-cyclopropyl-methyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester; and rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-fluoro-benzyl ester.

11. The compound of claim 2, selected from the group consisting of rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3-hydroxy-3-methyl-butyl ester;

rac {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexylmethyl ester;

{(3R,4S)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 4,4,4-trifluoro-butyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4,4-difluoro-cyclohexyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester;

{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 1-methyl-cyclopropylmethyl ester; and {(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester.

12. The compound of claim 2, selected from the group consisting of

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 4-trifluoromethyl-cyclohexyl ester;

{(3S,4R)-4-(4-Chloro-phenyl)-1-[1-(1,1-dioxo-hexahydro-1$\lambda^6$-thiopyran-4-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(6-chloro-pyridazin-3-yl)-piperidine-4-carbonyl]-pyrrolidin-3-yl}-methyl-carbamic acid 4-fluoro-phenyl ester;

rac-{(3R,4S)-4-(3,4-Dichloro-phenyl)-1-[1-(1-methyl-cyclopropanecarbonyl)-piperidine-4-carbonyl]-pyrrolidin-3-yl}-methyl-carbamic acid 3,3-difluoro-cyclopentylmethyl ester;

{(3S,4R)-4-(4-Chloro-phenyl)-1-[1-(tetrahydro-pyran-4-yl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 3-bromo-4-fluoro-phenyl ester;

{(3S,4R)-4-(4-Chloro-phenyl)-1-[1-(6-methyl-pyridazin-3-yl)-piperidine-4-carbonyl]-pyrrolidin-3-yl}-methyl-carbamic acid 4-fluoro-phenyl ester; and rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester.

13. The compound of claim 2, selected from the group consisting of rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4-trifluoromethyl-cyclohexyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-fluoro-phenyl ester;

{(3S,4R)-4-(3,4-Dichloro-phenyl)-1-[1-(tetrahydro-pyran-4-yl)-piperidine-4-carbonyl]-pyrrolidin-3-yl}-methyl-carbamic acid 4-trifluoromethyl-cyclohexyl ester;

rac-[(3S,4R)-1-(5'-tert-Butylcarbamoyl-3,4,5,6-tetrahydro-2H-[1,2']bipyridinyl-4-carbonyl)-4-(4-chloro-phenyl)-pyrrolidin-3-yl]-methyl-carbamic acid 4,4,4-trifluoro-butyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4,4,4-trifluoro-butyl ester;

{(3S,4R)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester; and {(3R,4S)-4-(4-Fluoro-phenyl)-1-[1-(1-methyl-cyclopropanecarbonyl)-piperidine-4-carbonyl]-pyrrolidin-3-yl}-methyl-carbamic acid 4-fluoro-phenyl ester.

14. The compound of claim 2, selected from the group consisting of

[(3S,4R)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester;

[(3R,4S)-1-(5'-Cyano-3,4,5,6-tetrahydro-2H-[1,2']bipyridinyl-4-carbonyl)-4-(4-fluoro-phenyl)-pyrrolidin-3-yl]-methyl-carbamic acid 4-fluoro-phenyl ester;

4-{(3R,4S)-3-(4-Chloro-phenyl)-4-[(4-fluoro-phenoxycarbonyl)-methyl-amino]-pyrrolidine-1-carbonyl}-piperidine-1-carboxylic acid tert-butyl ester;

{(3S,4R)-4-(4-Chloro-phenyl)-1-[1-(5-methyl-[1,3,4]oxadiazol-2-yl)-piperidine-4-carbonyl]-pyrrolidin-3-yl}-methyl-carbamic acid 4-fluoro-phenyl ester;

[(3S,4R)-4-(4-Chloro-phenyl)-1-(piperidine-4-carbonyl)-pyrrolidin-3-yl]-methyl-carbamic acid 4-fluoro-phenyl ester;

{(3S,4R)-4-(4-Chloro-phenyl)-1-[1-(6-cyano-pyridazin-3-yl)-piperidine-4-carbonyl]-pyrrolidin-3-yl}-methyl-carbamic acid 4-fluoro-phenyl ester.

15. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester;

[(3R,4S)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,3,3-trifluoro-propyl ester;

[(3S,4R)-4-(4-Chloro-phenyl)-1-(1-cyclopropyl-piperidine-4-carbonyl)-pyrrolidin-3-yl]-methyl-carbamic acid 4-fluoro-phenyl ester;

3-{(3R,4S)-3-(4-Chloro-phenyl)-4-[(4-fluoro-phenoxycarbonyl)-methyl-amino]-pyrrolidine-1-carbonyl}-pyrrolidine-1-carboxylic acid tert-butyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-cyclopropyl-ethyl ester; and {(3S,4R)-4-(4-Chloro-phenyl)-1-[1-(1-methyl-cyclopropanecarbonyl)-piperidine-4-carbonyl]-pyrrolidin-3-yl}-methyl-carbamic acid 1-cyclopropyl-ethyl ester.

16. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid oxetan-3-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-ethyl ester;

[(3S,4R)-1-(5'-Cyano-3,4,5,6-tetrahydro-2H-[1,2']bipyridinyl-4-carbonyl)-4-(3,4-dichloro-phenyl)-pyrrolidin-3-yl]-methyl-carbamic acid 4-trifluoromethyl-cyclohexyl ester;

{(3S,4R)-4-(3,4-Dichloro-phenyl)-1-[1-(6-methyl-pyridazin-3-yl)-piperidine-4-carbonyl]-pyrrolidin-3-yl}-methyl-carbamic acid 4-trifluoromethyl-cyclohexyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro ethyl ester; and {(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,2-trifluoro-1-methyl-ethyl ester.

17. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1-methyl-ethyl ester;

{(3S,4R)-4-(4-Chloro-phenyl)-1-[1-(4-methyl-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(pyrrolidine-3-carbonyl)-pyrrolidin-3-yl]-methyl-carbamic acid 4-fluoro-phenyl ester;

{(3S,4R)-4-(4-Chloro-phenyl)-1-[1-(5-fluoro-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(1-propionyl-pyrrolidine-3-carbonyl)-pyrrolidin-3-yl]-methyl-carbamic acid 4-fluoro-phenyl ester;

[(3S,4R)-4-(4-Chloro-phenyl)-1-(1-cyclopropanecarbonyl-pyrrolidine-3-carbonyl)-pyrrolidin-3-yl]-methyl-carbamic acid 4-fluoro-phenyl ester;

{(3S,4R)-4-(4-Chloro-phenyl)-1-[1-(2-methoxy-acetyl)-pyrrolidine-3-carbonyl]-pyrrolidin-3-yl}-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclobutyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid cyclobutyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 2,2,3,3-tetrafluorocyclobutyl ester; and

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,3,3-tetrafluorocyclobutyl ester.

18. The compound of claim 2, selected from the group consisting of

[(3S,4R)-4-(4-Chloro-phenyl)-1-(5'-cyano-3,4,5,6-tetrahydro-2H-[1,2']bipyridinyl-4carbonyl)-pyrrolidin-3-yl]-methyl-carbamic acid 3,3,3-trifluoro-1-methyl-propyl ester;

{(3S,4R)-4-(4-Chloro-phenyl)-1-[1-(1-methyl-cyclopropanecarbonyl)-piperidine-4-carbonyl]-pyrrolidin-3-yl}-methyl-carbamic acid 3,3,3-trifluoro-1-methyl-propyl ester;

{(3S,4R)-4-(4-Chloro-phenyl)-1-[1-(tetrahydro-pyran-4-yl)-pyrrolidine-3-carbonyl]-pyrrolidin-3-yl}-methyl-carbamic acid 4-fluoro-phenyl ester;

[(3S,4R)-4-(4-Chloro-phenyl)-1-(5'-methanesulfonyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester;

[(3S,4R)-4-(4-Chloro-phenyl)-1-(1-pyrimidin-2-yl-piperidine-4-carbonyl)-pyrrolidin-3-yl]-methyl-carbamic acid 4-fluoro-phenyl ester;

{(3S,4R)-4-(4-Chloro-phenyl)-1-[1-(5-chloro-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(4'-cyano-3,4,5,6-tetrahydro-2H-[1,2']bipyridinyl-4-carbonyl)-pyrrolidin-3-yl]-methyl-carbamic acid 4-fluoro-phenyl ester; and

[(3S,4R)-4-(4-Chloro-phenyl)-1-(3'-cyano-3,4,5,6-tetrahydro-2H-[1,2']bipyridinyl-4-carbonyl)-pyrrolidin-3-yl]-methyl-carbamic acid 4-fluoro-phenyl ester.

19. The compound of claim 2, selected from the group consisting of

{(3S,4R)-4-(4-Chloro-phenyl)-1-[1-(6-cyano-pyrazin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(3'-chloro-5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(6'-cyano-3,4,5,6-tetrahydro-2H-[1,2']bipyridinyl-4-carbonyl)-pyrrolidin-3-yl]-methyl-carbamic acid 4-fluoro-phenyl ester;

{(3S,4R)-4-(4-Chloro-phenyl)-1-[1-(5-methoxy-pyrimidin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(1-pyrimidin-4-yl-piperidine-4-carbonyl)-pyrrolidin-3-yl]-methyl-carbamic acid 4-fluoro-phenyl ester;

{(3S,4R)-4-(4-Chloro-phenyl)-1-[1-(5-cyano-pyrimidin-2-yl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-cyano-pyrazin-2-yl)-piperidine-4-carbonyl]-pyrrolidin-3-yl}-methyl-carbamic acid 4-fluoro-phenyl ester;

[(3S,4R)-4-(4-Chloro-phenyl)-1-(5'-methyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester; and

[(3S,4R)-1-(5'-Carbamoyl-3,4,5,6-tetrahydro-2H-[1,2']bipyridinyl-4-carbonyl)-4-(4-chloro-phenyl)-pyrrolidin-3-yl]-methyl-carbamic acid 4-fluoro-phenyl ester.

20. The compound of claim 2, selected from the group consisting of

{(3S,4R)-4-(4-Chloro-phenyl)-1-[1-(6-methoxy-pyridazin-3-yl)-piperidine-4-carbonyl]-pyrrolidin-3-yl}-methyl-carbamic acid 4-fluoro-phenyl ester;

[(3S,4R)-4-(4-Chloro-phenyl)-1-(6'-cyano-3,4,5,6-tetrahydro-2H-[1,3]bipyridinyl-4-carbonyl)-pyrrolidin-3-yl]-methyl-carbamic acid 4-fluoro-phenyl ester;

[(3S,4R)-4-(4-Chloro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid p-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-chloro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopentyl ester; and

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-ethyl ester.

21. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-trifluoromethyl-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,4-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3,4-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,3-difluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-chloro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-fluoro-propyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropylmethyl ester; and

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methoxy-propyl ester.

22. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopropylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-methyl-oxetan-3-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-cyclopropyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-methoxy-1-methyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methanesulfonyl-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 3-cyano-phenyl ester; and

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-ethyl ester.

23. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2-fluoro-1-fluoromethyl-ethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid o-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid m-tolyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-pyran-4-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-2-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid tetrahydro-furan-3-ylmethyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 2,2,2-trifluoro-1,1-dimethyl-ethyl ester; and

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-(4-fluoro-phenyl)-propyl ester.

24. The compound of claim 2, selected from the group consisting of

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-2-fluoro-phenyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methoxy-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid cyclopropyl-(4-fluoro-phenyl)-methyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-methyl-1-trifluoromethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1,4-dimethyl-cyclohexyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 1-methyl-cyclopentyl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 5-chloro-pyridin-2-yl ester;

[(3S,4R)-4-(4-Chloro-phenyl)-1-(5'-cyano-3,4,5,6-tetrahydro-2H-[1,2']bipyridinyl-4-carbonyl)-pyrrolidin-3-yl]-methyl-carbamic acid 4-cyano-3-fluoro-phenyl ester; and

[(3S,4R)-1-(1-Acetyl-piperidine-4-carbonyl)-4-(4-chloro-phenyl)-pyrrolidin-3-yl]-methyl-carbamic acid 4-fluoro-phenyl ester.

25. The compound of claim 2, selected from the group consisting of

[(3S,4R)-4-(4-Chloro-phenyl)-1-(1-cyclobutanecarbonyl-piperidine-4-carbonyl)-pyrrolidin-3-yl]-methyl-carbamic acid 4-fluoro-phenyl ester;

{(3S,4R)-4-(4-Chloro-phenyl)-1-[1-(3-methyl-oxetane-3-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3-fluoro-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3,3-difluoro-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(3-methoxy-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2-cyano-acetyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-cyano-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester; and {(3S,4R)-4-(4-Chloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester.

26. The compound of claim 2, selected from the group consisting of

{(3S,4R)-4-(4-Chloro-phenyl)-1-[1-(tetrahydro-pyran-4-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(2,2-dimethyl-cyclopropanecarbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(5-fluoro-pyridine-2-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(4-Chloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester;

[(3S,4R)-1-(1-Cyclobutanecarbonyl-piperidine-4-carbonyl)-4-(3,4-dichloro-phenyl)-pyrrolidin-3-yl]-methyl-carbamic acid 4-fluoro-phenyl ester; and {(3S,4R)-4-(3,4-Dichloro-phenyl)-1-[1-(3-methyl-oxetane-3-carbonyl)-piperidine-4-carbonyl]-pyrrolidin-3-yl}-methyl-carbamic acid 4-fluoro-phenyl ester.

27. The compound of claim 2, selected from the group consisting of

{(3S,4R)-4-(3,4-Dichloro-phenyl)-1-[1-(3-fluoro-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(3,3-difluoro-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(3-methoxy-cyclobutanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

[(3S,4R)-1-[1-(2-Cyano-acetyl)-piperidine-4-carbonyl]-4-(3,4-dichloro-phenyl)-pyrrolidin-3-yl]-methyl-carbamic acid 4-fluoro-phenyl ester;

[(3S,4R)-1-[1-(1-Cyano-cyclopropanecarbonyl)-piperidine-4-carbonyl]-4-(3,4-dichloro-phenyl)-pyrrolidin-3-yl]-methyl-carbamic acid 4-fluoro-phenyl ester;

{(3S,4R)-4-(3,4-Dichloro-phenyl)-1-[1-(1-trifluoromethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(2,2-difluoro-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(tetrahydro-pyran-4-carbonyl)-piperidine-4-carbonyl]-pyrrolidin-3-yl}-methyl-carbamic acid 4-fluoro-phenyl ester; and {(3S,4R)-4-(3,4-Dichloro-phenyl)-1-[1-(2,2-dimethyl-tetrahydro-pyran-4-carbonyl)-piperidine-4-carbonyl]-pyrrolidin-3-yl}-methyl-carbamic acid 4-fluoro-phenyl ester.

28. The compound of claim 2, selected from the group consisting of

{(3S,4R)-4-(3,4-Dichloro-phenyl)-1-[1-(1-methoxymethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(2,2-dimethyl-cyclopropanecarbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(5-fluoro-pyridine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-isopropyl-6-oxo-piperidine-3-carbonyl)-piperidine-4-carbonyl]-pyrrolidin-3-yl}-methyl-carbamic acid 4-fluoro-phenyl ester;

[(3S,4R)-1-(1-Acetyl-piperidine-4-carbonyl)-4-(3,4-dichloro-phenyl)-pyrrolidin-3-yl]-methyl-carbamic acid 4-fluoro-phenyl ester;

[(3S,4R)-1-[1-(2-Cyano-acetyl)-piperidine-4-carbonyl]-4-(4-fluoro-phenyl)-pyrrolidin-3-yl]-methyl-carbamic acid 4-fluoro-phenyl ester;

[(3S,4R)-1-(1-Acetyl-piperidine-4-carbonyl)-4-(4-fluoro-phenyl)-pyrrolidin-3-yl]-methyl-carbamic acid 4-fluoro-phenyl ester; and {(3S,4R)-4-(4-Fluoro-phenyl)-1-[1-(3-methyl-oxetane-3-carbonyl)-piperidine-4-carbonyl]-pyrrolidin-3-yl}-methyl-carbamic acid 4-fluoro-phenyl ester.

29. The compound of claim 2, selected from the group consisting of

[(3S,4R)-1-[1-(3-Fluoro-cyclobutanecarbonyl)-piperidine-4-carbonyl]-4-(4-fluoro-phenyl)-pyrrolidin-3-yl]-methyl-carbamic acid 4-fluoro-phenyl ester;

[(3S,4R)-1-[1-(1-Cyano-cyclopropanecarbonyl)-piperidine-4-carbonyl]-4-(4-fluoro-phenyl)-pyrrolidin-3-yl]-methyl-carbamic acid 4-fluoro-phenyl ester;

{(3S,4R)-4-(4-Fluoro-phenyl)-1-[1-(1-trifluoromethyl-cyclobutanecarbonyl)-piperidine-4-carbonyl]-pyrrolidin-3-yl}-methyl-carbamic acid 4-fluoro-phenyl ester;

{(3S,4R)-4-(4-Fluoro-phenyl)-1-[1-(5-trifluoromethyl-pyridine-2-carbonyl)-piperidine-4-carbonyl]-pyrrolidin-3-yl}-methyl-carbamic acid 4-fluoro-phenyl ester;

{(3S,4R)-4-(4-Fluoro-phenyl)-1-[1-(6-oxo-piperidine-3-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-4-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-methyl-pyridin-3-yl ester; and {(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid pyridin-4-yl ester.

30. The compound of claim 2, selected from the group consisting of

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2,6-dimethyl-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 5-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-chloro-pyridin-2-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-5-fluoro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-chloro-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 6-trifluoromethyl-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-cyano-pyridin-3-yl ester;

{(3S,4R)-4-(3,4-Dichloro-phenyl)-1-[1-(1-methyl-cyclopropanecarbonyl)-piperidine-4-carbonyl]-pyrrolidin-3-yl}-methyl-carbamic acid 2-fluoro-6-methyl-pyridin-3-yl ester;

[(3S,4R)-4-(3,4-Dichloro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

[(3S,4R)-1-(5'-Chloro-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester; and

[(3S,4R)-4-(3,4-Dichloro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester.

31. The compound of claim 2, selected from the group consisting of

[(3S,4R)-1-(5'-Carbamoyl-3,4,5,6-tetrahydro-2H-[1,2']bipyridinyl-4-carbonyl)-4-(3,4-dichloro-phenyl)-pyrrolidin-3-yl]-methyl-carbamic acid 4-fluoro-phenyl ester;

[(3S,4R)-4-(4-Chloro-3-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-3-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(4-Chloro-3-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(4-chloro-3-fluoro-phenyl)-pyrrolidin-3-yl]-methyl-carbamic acid 4-fluoro-phenyl ester;

[(3S,4R)-4-(3-Chloro-4-fluoro-phenyl)-1-(5'-fluoro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(3-Chloro-4-fluoro-phenyl)-1-(5'-chloro-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-4-(3-Chloro-4-fluoro-phenyl)-1-(5'-trifluoromethyl-3,4,5,6-tetrahydro-2H-[1,2']bipyridinyl-4-carbonyl)-pyrrolidin-3-yl]-methyl-carbamic acid 4-fluoro-phenyl ester;

[(3S,4R)-1-(5'-Acetyl-3,4,5,6-tetrahydro-2H-[1,2']bipyridinyl-4-carbonyl)-4-(3-chloro-4-fluoro-phenyl)-pyrrolidin-3-yl]-methyl-carbamic acid 4-fluoro-phenyl ester;

{(3S,4R)-4-(4-Chloro-phenyl)-1-[1-((S)-4-oxo-azetidine-2-carbonyl)-piperidine-4-carbonyl]-pyrrolidin-3-yl}-methyl-carbamic acid 4-fluoro-phenyl ester;

[(3S,4R)-4-(4-Chloro-phenyl)-1-(5'-hydroxy-3,4,5,6-tetrahydro-2H-[1,2']bipyridinyl-4-carbonyl)-pyrrolidin-3-yl]-methyl-carbamic acid 4-fluoro-phenyl ester; and Acetic acid 4-{(3R,4S)-3-(4-chloro-phenyl)-4-[(4-fluoro-phenoxycarbonyl)-methyl-amino]-pyrrolidine-1-carbonyl}-3,4,5,6-tetrahydro-2H-[1,2']bipyridinyl-5'-yl ester.

32. The compound of claim 1, having formula If

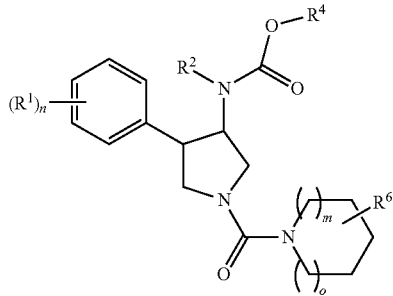

If wherein
R¹ is hydrogen, halogen, cyano, lower alkyl or lower alkyl substituted by halogen;
n is 1, 2 or 3, wherein when n is 2 or 3, each R¹ is the same or different;
R² is hydrogen or methyl;
R⁶ is hydrogen, di-lower alkyl or =O;
o and m are each independently 0, 1 or 2;
R⁴ is
 lower alkyl substituted by halogen,
 lower alkyl substituted by hydroxy,
 lower alkyl substituted by cycloalkyl,
 (CH₂)ₛ—O-lower alkyl, wherein when s is 2 or 3,
 CH(CH₃)CH₂—O-lower alkyl,
 (CH₂)_q CN, bicyclo[2.2.1]heptanyl,
 (CH₂)_q-cycloalkyl optionally substituted by lower alkyl, lower alkyl substituted by halogen, lower alkoxy or by halogen, or is
 (CH₂)_q-heterocycloalkyl, (CH₂)_q-aryl, CH(lower alkyl)-aryl, CH(cycloalkyl)-aryl, or (CH₂)_q-heteroaryl,
which heterocycloalkyl, aryl or heteroaryl rings are optionally substituted by halogen, hydroxy, lower alkyl, lower alkyl substituted by halogen, S(O)₂-lower alkyl, cyano or by lower alkoxy;
q is 0, 1 or 2;
or a pharmaceutically active salt thereof.

33. The compound of claim 32, which compound is
[(3R,4S)-4-(3,4-Dichloro-phenyl)-1-(cis-4-hydroxy-cyclohexanecarbonyl)-pyrrolidin-3-yl]-methyl-carbamic acid 4-fluoro-phenyl ester.

34. A pharmaceutical composition comprising a therapeutically effective amount of a compound of formula I

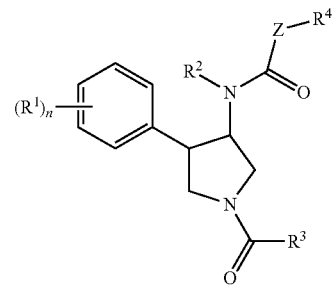

I wherein
R¹ is hydrogen, halogen, cyano, lower alkyl or lower alkyl substituted by halogen;
n is 1, 2 or 3, wherein when n is 2 or 3, each R¹ is the same or different;
R² is hydrogen or methyl;
R³ is (CH₂)_r—C(O)NH₂ or (CH₂)_r—CN, wherein r is 1 or 2, or
is a non aromatic heterocyclic group

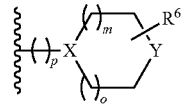

wherein
X is N or CH;
Y is —C(R)(R⁷)—; —N(R⁷)—, —S(O)₂ or O;
R⁶ is hydrogen, di-lower alkyl or =O;
o and m are each independently 0, 1 or 2;
p is 0, 1 or 2;
R is hydrogen, halogen, or lower alkyl;

$R^7$ is hydrogen, halogen, hydroxy, lower alkyl substituted by hydroxy, cyano, or lower alkoxy;

$R^{7'}$ is hydrogen, —C(O)-lower alkyl, —C(O)O-lower alkyl, —C(O)CH$_2$O-lower alkyl, —C(O)CH$_2$CN, or is —C(O)-cycloalkyl, cycloalkyl or —CH$_2$-cycloalkyl, wherein the cycloalkyl groups are optionally substituted by halogen, lower alkoxy, lower alkyl substituted by halogen, cyano, —CH$_2$O-lower alkyl, or lower alkyl, or is —C(O)-heterocycloalkyl, heterocycloalkyl, —C(O)-heteroaryl or heteroaryl, which heterocycloalkyl or heteroaryl groups are optionally substituted by halogen, lower alkyl, =O, lower alkoxy, lower alkyl substituted by halogen, C(O)NH-lower alkyl, C(O)NH$_2$,C(O)-lower alkyl, S(O)$_2$— lower alkyl or cyano;

Z is —O—;

$R^4$ lower alkyl substituted by halogen, lower alkyl substituted by hydroxy, lower alkyl substituted by cycloalkyl, (CH$_2$)$_s$—O-lower alkyl, wherein s is 2 or 3, CH(CH$_3$)CH$_2$—O-lower alkyl, (CH$_2$)$_q$CN, bicyclo[2.2.1]heptanyl, (CH$_2$)$_q$-cycloalkyl optionally substituted by lower alkyl, lower alkyl substituted by halogen, lower alkoxy or by halogen, or is (CH$_2$)$_q$-heterocycloalkyl, (CH$_2$)$_q$-aryl, CH(lower alkyl)-aryl, CH(cycloalkyl)-aryl, or (CH$_2$)$_q$-heteroaryl, which heterocycloalkyl, aryl or heteroaryl rings are optionally substituted by halogen, hydroxy, lower alkyl, lower alkyl substituted by halogen, S(O)$_2$-lower alkyl, cyano or by lower alkoxy;

q is 0, 1 or 2;

or a pharmaceutically active salt thereof and a pharmaceutically acceptable carrier.

\* \* \* \* \*